(12) United States Patent
Weaver et al.

(10) Patent No.: US 7,217,865 B2
(45) Date of Patent: May 15, 2007

(54) TRANSGENIC HIGH TRYPTOPHAN PLANTS

(75) Inventors: Lisa M Weaver, O'Fallon, MO (US); Jihong Liang, Chesterfield, MO (US); Ridong Chen, Maryland Heights, MO (US); Soon Seog Jeong, Maryland Heights, MO (US); Timothy Mitsky, Maryland Heights, MO (US); Steven Slater, Acton, MA (US); William Rapp, St. Louis, MO (US)

(73) Assignees: Monsanto Technology LLC, St. Louis, MO (US); Renessen LLC, Deerfield, IL (US)

( * ) Notice: Subject to any disclaimer, the term of this patent is extended or adjusted under 35 U.S.C. 154(b) by 323 days.

(21) Appl. No.: 10/138,927

(22) Filed: May 3, 2002

(65) Prior Publication Data

US 2003/0097677 A1 May 22, 2003

Related U.S. Application Data

(60) Provisional application No. 60/288,904, filed on May 4, 2001.

(51) Int. Cl.
*C12N 15/12* (2006.01)
*C12N 15/31* (2006.01)
*C12N 15/82* (2006.01)
*A01H 5/00* (2006.01)

(52) U.S. Cl. ................ 800/298; 435/320.1; 560/23.2; 560/23.7; 800/300; 800/302; 800/312; 800/320.1

(58) Field of Classification Search ............... 536/23.2; 435/320.1; 800/278, 287, 298, 320, 306
See application file for complete search history.

(56) References Cited

U.S. PATENT DOCUMENTS 4,581,847 A    4/1986  Hibberd et al. ............... 47/58
4,642,411 A    2/1987  Hibberd et al. ............... 800/1
6,118,047 A    9/2000  Anderson et al. ........... 800/278
6,271,016 B1   8/2001  Anderson et al. ........... 435/232
2003/0213010 A1  11/2003  Weaver et al. ............ 800/278

FOREIGN PATENT DOCUMENTS

WO    WO-97/26366    7/1997
WO    WO 99/06581  * 2/1999

OTHER PUBLICATIONS

Duggleby 1997, Gene 190:245-249.*
Bae et al 1989, Journal of Bacteriology 171(6):3471-3478.*
Knochel, T., et al., "The Crystal Structure of Anthranilate Synthase from Sulfolobus solfataricus: Functional Implications", *Proc. Natl. Acad. Sci. USA, 96*, (1999),9479-9484.
Bae et al., "Rhizobium meliloti Anthranilate Synthase Gene: Cloning, Sequence, and Expression in *Escherichia* coli", Journal of Bacteriology, 171(6):3471-3478 (1989).
The International Search Report for PCT/US02/14207.
Cho et al., "Increasing tryptophan synthesis in a forage legume astragalus sinicus by expressing the tobacco feedback-insensitive anthranilate synthase (ASA2) gene," *Plant Physiology*, 123:1069-1076, 2000.
EMBL-EBI Database AE09178.
Capela et al.; Accession No. GI-15966140 (NP 386493), 2003.
De Troch et al.; "Isolation and characterization of the azospirillum brasilense trp E(G) gene, encoding anthranilate synthase" *Current Microbiology*, 34:27-32, 1997.
De Troch et al.; Accession No. GI-1717765 (P50872), 2002.

* cited by examiner

*Primary Examiner*—David H Kruse
(74) *Attorney, Agent, or Firm*—Fulbright & Jaworski L.L.P.

(57) ABSTRACT

The present invention provides transgenic plants transformed with an isolated DNA encoding a monomeric anthranilate synthase. The present invention also provides an isolated DNA encoding a monomeric anthranilate synthase from *Agrobacterium tumefaciens*. Transformation vectors and transformed plants containing the isolated DNA and seeds derived therefrom, are also provided.

43 Claims, 53 Drawing Sheets

```
  1 MVTIIQDDGAETYETKGGIQVSRKRRPTDYANAIDNYIEKLDSHRGAVFS  50
    | :| :||||.| ||||| |.|:||   |..||  |:::||  ||||||
  1 MAAVILEDGAESYTTKGGIVVTRRREASYSDAIAGYVDRLDERRGAVFS  50

51 SNYEYPGRYTRWDTAIVDPPLGISCFGRKMWIEAYNGRGEVLLDFITEKL 100
    ||||||||||||||||:||||| || ||| :|||||| ||||||  | ||
 51 SNYEYPGRYTRWDTAVVDPPLAISSFGRSLWIEAYNERGEVLLALIAEDL 100

101 KATPDLTLGASSTRRLDLTVNEPDRVFTEEERSKIPTVFTALRAIVDLFY 150
    |.  |:|||.. ||||||:|||||||||||||||.|||| |||: .||:
101 KSVADITLGSLAARRLDLTINEPDRVFTEEERSKMPTVFTVLRAVTNLFH 150

151 SSADSAIGLFGAFGYDLAFQFDAIKLSLARPEDQRDMVLFLPDEILVVDH 200
    |  || :||:|||||||||||||||.| |.||:||||||||||||||||
151 SEEDSNLGLYGAFGYDLAFQFDAIELKLSRPDDQRDMVLFLPDEILVVDH 200

201 YSAKAWIDRYDFEKDGMTTDGKSSDITPDPFKTTDTIPPKGDHRPGEYSE 250
    |.|||||||||| ::  :.|:||..|| |:||:. |.||| ||||||.|
201 YAAKAWIDRYDFARENLSTEGKAADIAPEPFRSVDSIPPHGDHRPGEYAE 250

251 LVVKAKESFRRGDLFEVVPGQKFMERCESNPSAISRRLKAINPSPYSFFI 300
    |||||||||||||||||||||||| ||| || || |||||||||||||||
251 LVVKAKESFRRGDLFEVVPGQKFYERCESRPSEISNRLKAINPSPYSFFI 300

301 NLGDQEYLVGASPEMFVRVSGRRIETCPISGTIKRGDDPIADSEQILKLL 350
    |||.|||||||||||||||||||||||||||||||||||||||||||||
301 NLGNQEYLVGASPEMFVRVSGRRIETCPISGTIKRGDDPIADSEQILKLL 350

351 NSKKDESELTMCSDVDRNDKSRVCEPGSVKVIGRRQIEMYSRLIHTVDHI 400
    ||||||||||||||||||||||||| |||||||||||||||||||||||
351 NSKKDESELTMCSDVDRNDKSRVCVPGSVKVIGRRQIEMYSRLIHTVDHI 400

401 EGRLRDDMDAFDGFLSHAWAVTVTGAPKLWAMRFIEGHEKSPRAWYGGAI 450
    ||||||||||||||||||||||||||||||||||||| |||||||||||
401 EGRLRDDMDAFDGFLSHAWAVTVTGAPKLWAMRFIESHEKSPRAWYGGAI 450

451 GMVGFNGDMNTGLTLRTIRIKDGIAEVRAGATLLNDSNPQEEEAETELKA 500
    |||||||||||||||||||||||||||||||||||:|||||||||||||
451 GMVGFNGDMNTGLTLRTIRIKDGIAEVRAGATLLYDSNPEEEEAETELKA 500

501 SAMISAIRDAKGTNSAATKRDAAKVGTGVKILLVDHEDSFVHTLANYFRQ 550
    ||||.||||||  |||  . ||  || || ||||||||||||||||||||
501 SAMIAAIRDAKSANSAKSARDVAAVGAGVSILLVDHEDSFVHTLANYFRQ 550

551 TGATVSTVRSPVAADVFDRFQPDLVVLSPGPGSPTDFDCKATIKAARARD 600
    |||.|.|||.||| ::|||  .||||||||||.| |||||||| |||||
551 TGASVTTVRTPVAEEIFDRVKPDLVVLSPGPGTPKDFDCKATIKKARARD 600

601 LPIFGVCLGLQALAEAYGGELRQLAVPMHGKPSRIRVLEPGLVFSGLGKE 650
    |||||||||||||||||||:||||:|||||||||||||||:||||||||
601 LPIFGVCLGLQALAEAYGGDLRQLAIPMHGKPSRIRVLEPGIVFSGLGKE 650

651 VTVGRYHSIFADPATLPRDFIITAESEDGTIMGIEHAKEPVAAVQFHPES 700
    |||||||||||||. |||:|:||||||||||||||.|||||||||||||
651 VTVGRYHSIFADPSNLPREFVITAESEDGTIMGIEHSKEPVAAVQFHPES 700

701 IMTLGQDAGMRMIENVVVHLTRKAKTKAA 729
    ||||| ||||||||||| ||  ::||||||
701 IMTLGGDAGMRMIENVVAHLAKRAKTKAA 729
```

*Fig. 2*

Agrobacterium_TrpEG  MVTIIQDDGAETYETKGGIQVSRKRRPTDYANAIDNYIEKLDSHRGAVFSSNYEYPGRYT
Sulfolobus_TrpE      ------------------------MEVHPISEFASPFEVFKCIERDFKVAGLLES----

Agrobacterium_TrpEG  R-WDTAIVDPPLGISCFGRKMWIEAYNGRGEVLLDFITEKLKATPDLTLGASSTRRLDLT
Sulfolobus_TrpE      ---------IGGPQYKARYSVIAWSTNG------YLKIHDDP---------VNIL Agrobacterium_TrpEG  VNEPDRVFTEEERSKIPTVFTALRAIVDLFYSSADSAIGLFGAFGYDLAFQFDAIKLSLA
Sulfolobus_TrpE      NG----YLKDLKLADIPGLFKG---------------GMIGYISYDAVRFWEKIRDLKP Agrobacterium_TrpEG  RPEDQRDMVLFLPDEILVVDHYSAKAWIDRYDFEKDGMTTDGKSSDITPDPFKTTDTIPP
Sulfolobus_TrpE      AAEDWPYAEFFTPDNIIIYDHNEGKVYVN-----ADLSSVGGCGDIGEFKVSFYDESLN Agrobacterium_TrpEG  KGDHRPGEYSELVVKAKESFRRGDLFEVVPGQKFMERCESNPSAISRRLKAINPSYSFF
Sulfolobus_TrpE      K--N---S-YERIVSESLEYIRSGYIFQVVLSRFYRYIFSGDPLRIYNLRRINPSPYMFY Agrobacterium_TrpEG  INLGDQEYLVGASPEMFVRVSGRRIETCPISGTIKRGDDPIADSEQILKLLNSKKDESEL
Sulfolobus_TrpE      LKF-DEKYLIGSSPELLFRVQDNIVETYPIAGTRPRGADQEEDLKLELELMNSEKDKAEH Agrobacterium_TrpEG  TMCSDVDRNDKSRVCEPGSVKVIGRRQIEMYSRLIHTVDHIEGRLRDDMDAFDGFLSHAW
Sulfolobus_TrpE      LMLVDLARNDLGKVCVPGTVKVPELMYVEKYSHVQHIVSKVIGTLKKKYNALNVLSATFP

Fig. 6A

```
Agrobacterium_TrpEG    AVTVTGAPKLWAMRFIEGHEKSPRAWYGGAIGMVGFNGDMNTGLTLRTIRIKDGIAEVRA
Sulfolobus_TrpE        AGTVSGRPKPMAMNIETLEEYKRGPYAGAVGFISADGNAEFAIAIRTAFLNKELLRIHA Agrobacterium_TrpEG    GATLLNDSNPQEEEAETELKASAMISAIRDAKGTNSAATKRDAAKVGTGVKILLVDHEDS
Sulfolobus_TrpE        GAGIVYDSNPESEYFETEHKLKALKTAIGVR------------------------------

Agrobacterium_TrpEG    FVHTLANYFRQTGATVSTVRSPVAADVFDRFQPDLVVLSPGPGSPTDFDCKATIKAARAR
Sulfolobus_TrpE        ------------------------------------------------------------

Agrobacterium_TrpEG    DLPIFGVCLGLQALAEAYGGELRQLAVPMHGKPSRIRVLEPGLVFSGLGKEVTVGRYHSI
Sulfolobus_TrpE        ------------------------------------------------------------

Agrobacterium_TrpEG    FADPATLPRDFIITAESEDGTIMGIEHAKEPVAAVQFHPESIMTLGQDAGMRMIENVVH
Sulfolobus_TrpE        ------------------------------------------------------------

Agrobacterium_TrpEG    LTRKAKTKAA
Sulfolobus_TrpE        ----------
```

*Fig. 6B*

```
V48F-F:  CCATCGCGGCGCGtTTTTTTCGTCCAACTATG       (SEQ ID NO:9)
V48F-R:  CATAGTTGGACGAAAAAaCGCGCCGCGATGG        (SEQ ID NO:10)

V48Y-F:  CCATCGCGGCGCGtaTTTTTCGTCCAACTATGAATATCC (SEQ ID NO:11)
V48Y-R:  GGATATTCATAGTTGGACGAAAAAtaCGCGCCGCGATGG (SEQ ID NO:12)

V48W-F:  CCATCGCGGCGCGtggTTTTTCGTCCAACTATGAATATCC (SEQ ID NO:13)
V48W-R:  GGATATTCATAGTTGGACGAAAAAccaCGCGCCGCGATGG (SEQ ID NO:14)

S50K-F:  CCATCGCGGCGCGGTTTTaaGTCCAACTATGAATATCC  (SEQ ID NO:15)
S50K-R:  GGATATTCATAGTTGGACTtAAAAACCGCGCCGCGATGG (SEQ ID NO:16)

S51C-F:  GCGCGGTTTTTCGTgCAACTATGAATATCCGGG        (SEQ ID NO:17)
S51C-F:  CCCGGATATTCATAGTTGCACGAAAAACCGCGC        (SEQ ID NO:18)

S51F-F:  CGGCGGTTTTTTCGTtCAACTATGAATATCCGGGC      (SEQ ID NO:19)
S51F-R:  GCCCGGATATTCATAGTTGaACGAAAAAACCGCG       (SEQ ID NO:20)

S51I-F:  CGGCGGTTTTTTCGatCAACTATGAATATCCGGGC      (SEQ ID NO:21)
S51I-R:  GCCCGGATATTCATAGTTGatCGAAAAAACCGCGCCG    (SEQ ID NO:22)

S51L-F:  GGGCGGTTTTTTCGctCAACTATGAATATCCGGGC      (SEQ ID NO:23)
S51L-R:  GCCCGGATATTCATAGTTGagCGAAAAAACCGCGCC     (SEQ ID NO:24)

S51M-F   CGGCGGTTTTTTCGatgAACTATGAATATCCGGGCCG   (SEQ ID NO:25)
S51M-R   CGGCCCGGATATTCATAGTTCatCGAAAAACCGCGCCG  (SEQ ID NO:26)
```

Fig. 7A

```
S51T-F:  CGCGGTTTTTCGaCCAACTATGAATATCCGGGC  (SEQ ID NO:27)
S51T-R:  GCCCGGATATTCATAGTTGGtCGAAAAACCGCG  (SEQ ID NO:28)

S51V-F:  GGCGCGGTTTTTCGgtCAACTATGAATATCCGGGC  (SEQ ID NO:29)
S51V-R:  GCCCGGATATTCATAGTTGacCGAAAAACCGCGCC  (SEQ ID NO:30)

S51Y-F   GCGCGGTTTTTCGTaCAACTATGAATATCCGGGC  (SEQ ID NO:31)
S51Y-R   GCCCGGATATTCATAGTTGtACGAAAAACCGCGC  (SEQ ID NO:32)

N52F-F:  CGGCGCGGTTTTTCGTCCttCTATGAATATCCGGG  (SEQ ID NO:33)
N52F-R:  CCCGGATATTCATAGaaGGACGAAAAACCGCGCCG  (SEQ ID NO:34)

P293A-F:  CTGAAGGCGATCAACgCGTCGCCCTATTC  (SEQ ID NO:35)
P293A-R:  GAATAGGGCGACGCGTTGATCGCCTTCAG  (SEQ ID NO:36)

P293G-F:  CCTGAAGGCGATCAACggGTCGCCCTATTCC  (SEQ ID NO:37)
P293G-R:  GGAATAGGGCGACccGTTGATCGCCTTCAGG  (SEQ ID NO:38)

F298A-F:  CGTCGCCCTATTCCgcCTTCATCAATCTCGGCG  (SEQ ID NO:39)
F298A-R:  CGCCGAGATTGATGAAGgcGGAATAGGGCGACG  (SEQ ID NO:40)

F298W-F:  CGTCGCCCTATTCCTggTTCATCAATCTCGGCG  (SEQ ID NO:41)
F298W-R:  CGCCGAGATTGATGAAccAGGAATAGGGCGACG  (SEQ ID NO:42)
```

Fig. 7B

```
TRPEG_AGRTU_MONSANTO_  MVTIIQDDGAETYETKGGIQVSRKRRP---------------------------------  27
TRPEG_RHIME_A30904_    MAAVILEDGAESYTTKGGIVVTRRRRE---------------------------------  27
TRPE_SULSO_Q06128_     MEVHPISEFASPFEVFKCIER---------------------------------------  21
TRPE_ARATH_S27752_     MSAVSISAVKSDFFTVEAIAVTHHRTPHPHFPSLRFPLSLKSPPATSLN            50
                       *   .       .                             .

TRPEG_AGRTU_MONSANTO_  TDYANAIDNYIEKLDSHRGAVFSSNYEYPGRYTRWDTAIVDPPLGISCFG            77
TRPEG_RHIME_A30904_    ASYSDAIAGYVDRLDERRGAVFSSNYEYPGRYTRWDTAVVDPPLAISSFG            77
TRPE_SULSO_Q06128_     ---------------------------DFKVAG---------------             27
TRPE_ARATH_S27752_     LVAGSKLLHFSRRLPSIKCSYTPSLDLSEEQFTKFKKASEKGNLVPLFRC           100
                                                  *                 .  .  ..

TRPEG_AGRTU_MONSANTO_  ----------RKMWIEAYNGRGEVLLDFITEKLKATPDLTLGASSTRR              115
TRPEG_RHIME_A30904_    ----------RSLWIEAYNERGEVLLALIAEDLKSVADITLGSLAARR              115
TRPE_SULSO_Q06128_     -------------------LLESIG-GPQ--YKARYSVIAWST                   48
TRPE_ARATH_S27752_     VFSDHLTPILAYRCLVKEDDRDAPSLFESVEPGSQSSNIGRYSVVGAQP             150
                                          *  .         ..  .  .

TRPEG_AGRTU_MONSANTO_  LDLTVNEPDRVFTE----------EERSKIPTVFTALRAIVDLFYSSA              153
TRPEG_RHIME_A30904_    LDLTINEPDRVFTE----------EERSKMPTVFTVTVLRAVTNLFHSEE            153
TRPE_SULSO_Q06128_     NGYLKIH----------DDPVNILNGYLKDLK---LADIPG                     76
TRPE_ARATH_S27752_     TIEIVAKGNVVTVMDHGASLRTEEEVDDPMMVPQKIMEEWNPQGIDELPE            200
                                                                    ..

TRPEG_AGRTU_MONSANTO_  DSAIGLFGAFGYDLAFQFDAIKLSLARPEDQ----RDMVLFLPDEILVVD            199
TRPEG_RHIME_A30904_    DSNLGLYGAFGYDLAFQFDAIELKLSRPDDQ----RDMVLFLPDEILVVD            199
TRPE_SULSO_Q06128_     LFKGGMIGYISYDAVRFWEKIR-DLKPAAED---WPYAEFFTPDNIIIYD            122
TRPE_ARATH_S27752_     AFCGGWVGYFSYDTVRYVEKKKLPFSNAPEDDRSLPDVNLGLYDDVIVFD            250
                        *     .  * **  .     *     .         ..  ::.
```

Fig. 21A

```
TRPEG_AGRTU_MONSANTO   HYSAKAWIDRYDFEKDGMTTDG----KSSDITP-------------------------  228
TRPEG_RHIME_A30904     HYAAKAWIDRYDFDFARENLSTEG----KAADIAP-------------------------  228
TRPE_SULSO_Q06128      HNEGKVYVN------ADLSSVG---GCGDIG----------------------------  144
TRPE_ARATH_S27752      HVEKKAYVIHWVRIDKDRSVEENFREGMNRLESLTSRIQDQKPPKMPTGF           300
                       *      :    .

TRPEG_AGRTU_MONSANTO   ---DPFKTTDTIPPKGDHRPGEYSELVVKAKESFRRGDLFEVVPGQKFMER           276
TRPEG_RHIME_A30904     --EPFRSVDSIPPHGDHRPGEYAELVVKAKESFRRGDLFEVVPGQKFYER           276
TRPE_SULSO_Q06128      -EFKVSFYDESLNK-----NSYERIVSESLEYIRSGYIFQVVLSRFYRYI           188
TRPE_ARATH_S27752      IKLRTQLFGPKLEKSTMTSEAYKEAVVEAKEHILAGDIFQIVLSQRFERR           350
                         :   .         * ::* :   :  *:   . .*::*..:*: :

TRPEG_AGRTU_MONSANTO   CESNPSAISRRLKAINPSYSFFINLGDQEYLVGASPEMFVRVSGRRIET            326
TRPEG_RHIME_A30904     CESRPSEISNRLKAINPSYSFFINLGNQEYLVGASPEMFVRVSGRRIET            326
TRPE_SULSO_Q06128      FSGDPLRIYNLRRINPSPYMFYLKFD-EKYLIGSSPELLFRVQDNIVET            237
TRPE_ARATH_S27752      TFADPFEIYRALRIVNPSPYMAYLQVR-GCILVASSPEILLRSKNRKITN           399
                         . * * :  *:*:**.::  :        ::.:**::: *     : *

TRPEG_AGRTU_MONSANTO   CPISGTIKRGDDPIADSEQILKLLNSKKDESELTMCSDVDRNDKSRVCEP           376
TRPEG_RHIME_A30904     CPISGTIKRGDDPIADSEQILKLLNSKKDESELTMCSDVDRNDKSRVCVP           376
TRPE_SULSO_Q06128      YPIAGTRPRGADQEEDLKLELELMNSEKDKAEHLMLVDLARNDLGKVCVP           287
TRPE_ARATH_S27752      RPLAGTVRRGKTPKEDLMLEKELLSDEKQCAEHIMLVDLGRNDVGKVSKP           449
                        *:.*  **.   : ::  :   : .:::.*:  :::*  **. ..* *

TRPEG_AGRTU_MONSANTO   GSVKVIGRRQIEMYSRLIHTVDHIEGRLRDDMDAFDGFLSHAWAVTVTGA           426
TRPEG_RHIME_A30904     GSVKVIGRRQIEMYSRLIHTVDHIEGRLRDDMDAFDGFLSHAWAVTVTGA           426
TRPE_SULSO_Q06128      GTVKVPELMYVEKYSHVQHIVSKVIGTLKKYNALNVLSATFPAGTVSGR           337
TRPE_ARATH_S27752      GSVEVKKLKDIEWFSHVMHISSTVVGELLDHLTSWDALRAVLPVGTVSGA           499
                       *:*:*      :  *::  *   .     :     .: . * :*.
```

Fig. 21B

```
TRPEG_AGRTU_MONSANTO    PKLWAMRFIEGHEKSPRAWYGGAIGMVGFNGDMNTGLTLRTIRIKDG---      473
TRPEG_RHIME_A30904      PKLWAMRFIESHEKSPRAWYGGAIGMVGFNGDMNTGLTLRTIRIKDG---      473
TRPE_SULSO_Q06128       PKPMAMNIIETLEEYKRGPYAGAVGFISADGNAEFAIAIRTAFLN-----      382
TRPE_ARATH_S27752       PKVKAMELIDELEVTRRGPYSGGFGGISFNGDMDIALALRTMVFPTNTRY      549
                        ** ***.::*:    * .: :. *  .. ::*. : ..::.**  :

TRPEG_AGRTU_MONSANTO    ---------IAEVRAGATLLNDSNPQEEEAETELKASAMISAIR         508
TRPEG_RHIME_A30904      ---------IAEVRAGATLLYDSNPEEEEAETELKASAMIAAIR         508
TRPE_SULSO_Q06128       ---------IHAGAGIVYDSNPESEYFETEHKLKALKTAIG           419
TRPE_ARATH_S27752       DTLYSYKHPQRRREWIAHIQAGAGIVADSNPDDEHRECENKAAALARAID  599
                               :: *****:: .* *    *:  *

TRPEG_AGRTU_MONSANTO    DAKGTNSAATKRDAAKVGTGVKILLVDHEDSFVHTLANYFRQTGATVSTV  558
TRPEG_RHIME_A30904      DAKSANSANSAKSARDVAAVGAGVSILLVDHEDSFVHTLANYFRQTGASVTTV 558
TRPE_SULSO_Q06128       VR--------------------------------------------      421
TRPE_ARATH_S27752       LAESSFLEAPEFTTITPHINNI--------------------------    621

TRPG_AGRTU_MONSANTO     GMVGFNGDMNTGLTLRTIRIKDGIAEVRAGATLLNDSNPQEEEAETELKA   500
TRPG_RHIME_A30904       GMVGFNGDMNTGLTLRTIRIKDGIAEVRAGATLLYDSNPEEEEAETELKA   500
TRPG_SULSO_B40635       -------------------------------------------------   -
TRPG_ARATH_AAA32742     ----MAASTLYKSCLLQPKSGSTTRRLNPSLVNPLTNPTRVSVLGKSR     44

TRPG_AGRTU_MONSANTO     SAMISAIRDAKGTNSAATKRDAAKVGTGVKILLVDHEDSFVHTLANYFRQ   550
TRPG_RHIME_A30904       SAMIAAIRDAKSANSAKSARDVAAVGAGVSILLVDHEDSFVHTLANYFRQ   550
TRPG_SULSO_B40635       ------MDLT--------------LIIDNYDSFVNIAQIVGE          23
TRPG_ARATH_AAA32742     RDVFAKASIEMAESNSIPSVVVNSSKQHGPIIVDNYDSFTYNLCQYMGE   94
                                                         *** .:..:: .  :
```

*Fig. 21C*

```
TRPEG_AGRTU_MONSANTO    TGATVSTVRSP-VAADVFDRFQPDLVVLSPGPGSPT---DFDCKATIKAA  596
TRPEG_RHIME_A30904      TGASVTTVRTP-VAEEIFDRVKPDLVVLSPGPGTPK---DFDCKATIKKA  596
TRPG_SULSO_B40635       LGSYPIVIRNDEISIKGIERIDPDRLIISPGPGTPEKREDIGVSLDVIKY   73
TRPG_ARATH_AAA32742     LGCHFEVYRNDELTVEELKKKNPRGVLISPGPGTPQ---DSGISLQTVLE  141
                         *    . ::   :  :.. .*  ::::::******.*

TRPEG_AGRTU_MONSANTO    RARDLPIFGVCLGLQALAEAYGGELR-QLAVPMHGKPSRIRVLEPG--LV  643
TRPEG_RHIME_A30904      RARDLPIFGVCLGLQALAEAYGGDLR-QLAIPMHGKPSRIRVLEPG--IV  643
TRPG_SULSO_B40635       LGKRTPILGVCLGHQAIGYAFGAKIRRARK-VFHGKISNIILVNNSPLSL  122
TRPG_ARATH_AAA32742     LGPLVPLFGVCMGLQCIGEAFGGKIVRSPFGVMHGKSSMVHYDEKGEEGL  191
                          : :*:**:* *   .*   :  .   . :**  .: :

TRPEG_AGRTU_MONSANTO    FSGLGKEVTVGRYHSIFADPATLPR-DFIITAES-EDGTIMGIEHAKEP-  690
TRPEG_RHIME_A30904      FSGLGKEVTVGRYHSIFADPSNLPR-EFVITAES-EDGTIMGIEHSKEP-  690
TRPG_SULSO_B40635       YYGIAKEFKATRYHSLVVDEVHRP---LIVDAISAEDNEIMAIHHEEYP-  168
TRPG_ARATH_AAA32742     FSGLSNPFIVGRYHSLVIEKDTFPSDELEVTAWT-EDGLVMAARHRKYKH  240
                        : *:   :  ***:.   .  *     :  :     :   : : :

TRPEG_AGRTU_MONSANTO    VAAVQFHPESIMTLGQDAGMRMIENVVHLTRKAKTKAA  729  (SEQ ID NO:4)
TRPEG_RHIME_A30904      VAAVQFHPESIMTLGGDAGMRMIENVVAHLAKRAKTKAA 729  (SEQ ID NO:43)
TRPG_SULSO_B40635       IYGVQFHPESVGTS---LGYKILYNFLNRV-------  195  (SEQ ID NO:44)
TRPG_ARATH_AAA32742     IQGVQFHPESIITT---EGKTIVRNFIKIVEKKESEKLT 276  (SEQ ID NO:45)
                          .:*****:               :

Fig.21D
```

```
atgcaaacacaaaaaccgactctcgaactggaattcctggtgtggaaaacggtatcgccaccgt
gcaagcgggtgctggtgtactgtccttgattctgttccgcagtcggaagccgacgaaacccgta
acaaagcccgcgctgtactgcgcgctattgccaccgcatcatgccacgcacaggagactttctga
tggctggacattctgctgctcgataatatcgactcttttacgtacaacctggcagatcagtt
gcgca
```

Fig. 30

```
  1 - ATGGTAACGATCATTCAGGATGACGGAGCGGAGACCTACGAGACGAAAGGCGGCATCCAG -  60
      M  V  T  I  I  Q  D  D  G  A  E  T  Y  E  T  K  G  G  I  Q
 61 - GTCAGCCGAAAGCGCCGGCCCACCGATTATGCCAACGCCATCGATAATTACATCGAAAAG - 120
      V  S  R  K  R  R  P  T  D  Y  A  N  A  I  D  N  Y  I  E  K
121 - CTTGATTCCCATCGCGGCGCGGTTTTTCGTCCAACTATGAATATCCGGGCCGTTACACC - 180
      L  D  S  H  R  G  A  V  F  S  N  Y  E  Y  P  G  R  Y  T
181 - CGCTGGGATACGGCCATCGTCGGCCATTCCTGTTTTGGCCGCAAGATG - 240
      R  W  D  T  A  I  V  D  P  P  L  G  I  S  C  F  G  R  K  M
241 - TGGATCGAAGCCTATAATGGCCGGCGAAGTGCTGTCGATTTCATTACGAAAAGCTG - 300
      W  I  E  A  Y  N  G  R  G  E  V  L  L  D  F  I  T  E  K  L
301 - AAGGCGACACCCGATCTCACCCTCGGCGCTTCCTCGACCCGCCGGCTCGATCTTACCGTC - 360
      K  A  T  P  D  L  T  L  G  A  S  S  T  R  R  L  D  L  T  V
361 - AACGAACCGGACCGTGTCTTCACCGAAGAAGAACGCTCGAAATCCCGACGGTCTTCACC - 420
      N  E  P  D  R  V  F  T  E  E  E  R  S  K  I  P  T  V  F  T
421 - GCTCTCAGAGCCATCGTCGACATCTCGCCCTTCGCCAGTTGCTTTCCAGTTTCGATCAC - 480
      A  L  R  A  I  V  D  L  F  Y  S  S  A  D  S  A  I  G  L  F
481 - GGTGCCTTCGGTTACGATCTGGACATGGTCTTGCCCGATGAAATCCTCGTTGATCAC - 540
      G  A  F  G  Y  D  L  A  F  D  M  V  L  F  P  D  E  I  L  V  D  H
541 - CCGGAAGACCAGCGCAAGGCCTGTGACATTCGAGATTTCGAGAAGGACGCATGACGACGGAC - 600
      P  E  D  Q  R  D  M  V  L  F  P  D  F  E  K  D  G  M  T  D
601 - TATTCCGCAAATCCTCCGGATATCCCCGGCTTGAAGCTTGTGTTGAAGGCCAAGGAAAGCTTCCGC - 660
      Y  S  A  K  A  W  I  D  R  Y  D  F  E  K  T  D  T  I  P  P  K
661 - GGCAAATCCTCCGGATATTCCCGGGCTTGAAGCTTGTGGTGAAGGCCAAGGAAAGCTTCCGC - 720
      G  K  S  S  D  I  T  P  D  P  F  K  T  D  T  I  P  P  K
721 - GGCGATCACCCGTCCCGGCGAATATTCGAGCTTGTGGTGAAGGCCAAGGAAAGCTTCCGC - 780
      G  D  H  R  P  G  E  Y  S  E  L  V  V  K  A  K  E  S  F  R
781 - CGCGGCGACCTGTTCGAGGTCGTTCCCGGCCAGAAATTCATGGAGCGTTGCGAAAGCAAT - 840
      R  G  D  L  F  E  V  V  P  G  Q  K  F  M  E  R  C  E  S  N
```

*Fig. 32A*

```
 841 - CCGTCGGCGATTTCCCGCCGCCTGAAGGCGATCAACCCGTCGCCCTATTCCTTCTTCATC -  900
        P  S  A  I  S  R  R  L  K  A  I  N  P  S  P  Y  S  F  F  I
 901 - AATCTCGGCGATCAGGAATATCTGGTCGGCGCCTCGCCGGAAATGTTCGTGCGCGTCTCC -  960
        N  L  G  D  Q  E  Y  L  V  G  A  S  P  E  M  F  V  R  V  S
 961 - GGCCGTCGCATCGAGACCTGCCCGATATCAGGCACCATCAAGCGCGGCGACGATCCGATT - 1020
        G  R  R  I  E  T  C  P  I  S  G  T  I  K  R  G  D  D  P  I
1021 - GCCGACAGCGAGCAGATTTTGAAACTGCTCAACTCGAAAAAGGACGAATCCGAACTGACC - 1080
        A  D  S  E  Q  I  L  K  L  L  N  S  K  K  D  E  S  E  L  T
1081 - ATGTGCTCGGACGTGGACCGCAACGACAAGAGCCGTGTCTGCGAGCCGGGTTCGGTGAAG - 1140
        M  C  S  D  V  D  R  N  D  K  S  R  V  C  E  P  G  S  V  K
1141 - GTCATTGGCCGCCAGATCGAGATGTATTCACGGCCCTCATCCACCGTCGATCACATC - 1200
        V  I  G  R  Q  I  E  M  Y  S  R  L  I  H  T  V  D  H  I
1201 - GAAGGCCGCCTGCGCGACGATATGGACGCCTTTGACGGTTTCCTCAGCCACGCCTGGGCC - 1260
        E  G  R  L  R  D  D  M  D  A  F  D  G  F  L  S  H  A  W  A
1261 - GTCACCGTCACCGGTGCGCCTAAGCTGTGGGGCGCCATCGGCATGGTCGGCTTCAACGGC - 1320
        V  T  V  T  G  A  P  K  L  W  A  M  R  F  I  E  G  H  E  K
1321 - AGCCCGCGCGCCTGGTATGGCGCCATCCGGGATCAAGGACGGTATTGCCGAAGTGCGCGGC - 1380
        S  P  R  A  W  Y  G  G  A  I  G  M  V  G  F  N  G  D  M  N
1381 - ACCGGCCTGCTCAATGATTCCAACCCGAACGAAGCCGAAACTGAAACCGAACTGAAGGCC - 1440
        T  G  L  L  R  T  I  R  I  K  D  G  I  A  E  V  R  A  G
1441 - GCGACCCTGCTCAATGATTCCAACCCGAACGAAGCCGAAACTGAACTGAAGGCC - 1500
        A  T  L  L  N  D  S  N  P  Q  E  E  A  E  T  E  L  K  A
1501 - TCCGCCATGATATCAGCGCGCGTCGACGAGATCCGTCGACGAAGACAGCTTC - 1560
        S  A  M  I  S  A  I  R  D  A  K  G  T  N  S  A  T  K  R
1561 - GATGCCGCAAAGTCGGCACCGGGTCAAGATCCTCGTCGACCACGAAGACAGCTTC - 1620
        D  A  K  V  G  T  G  V  K  I  L  L  V  D  H  E  D  S  F
1621 - GTGCACACGCTGGCGAATTATTTCCGCCAGACGGGCGCTCGACCGTCAGATCA - 1680
        V  H  T  L  A  N  Y  F  R  Q  T  G  A  T  V  S  T  V  R  S
```

Fig. 32B

```
1681 - CCGGTCGCAGCCGACGTGTTCGATCGCTTCCAGCCGGACCTCGTTGTCCTGTCGCCCGGA - 1740
       P  V  A  A  D  V  F  D  R  F  Q  P  D  L  V  V  L  S  P  G
1741 - CCCGGCAGCCCGACTTCGACTGCAAGGCAACGATCAAGGCCGCGCCCGCGCGCGAT - 1800
       P  G  S  P  T  D  F  D  C  K  A  T  I  K  A  A  R  A  R  D
1801 - CTGCCGATCTTCGGCGTTTGCCTGGTCGCAGGCATTGGCAGAAGCCTATGGCGGCGAG - 1860
       L  P  I  F  G  V  C  L  G  L  Q  A  L  A  E  A  Y  G  G  E
1861 - CTGCCGCCAGCTTGCTGTGCCCATGCACGGCCAAGCCTTCGCGCATCCGCGTGCTGGAACCC - 1920
       L  R  Q  L  A  V  P  M  H  G  K  P  S  R  I  R  V  L  E  P
1921 - GGCCTCGTCTTCTCCGGTCTCGGCAAGGAAGTCACGGTCGGTTCGTTACCATTCGATCTTC - 1980
       G  L  V  F  S  G  L  G  K  E  V  T  V  G  R  Y  H  S  I  F
1981 - GCCGATCCCGCCACCCTGCCGCGTGATTTCATCACCGCAGAAAGCGAGGACGGCACG - 2040
       A  D  P  A  T  L  P  R  D  F  I  I  T  A  E  S  E  D  G  T
2041 - ATCATGGGCATCGAACACGCCAAGGAACCGGTGGCCGCCGTTCAGTTCCACCCCGGAATCG - 2100
       I  M  G  I  E  H  A  K  E  P  V  A  A  V  Q  F  H  P  E  S
2101 - ATCATGACGCTCGGGACACAGGACGCGGGCATGCGGATGATCGAGAATGTCGTGGTGCATCTG - 2160
       I  M  T  L  G  Q  D  A  G  M  R  M  I  E  N  V  V  V  H  L
2161 - ACCCGCAAGGCGAAGACCAAGGCCGCGTGA - 2190
       T  R  K  A  K  T  K  A  A  *
```

Fig. 32C

```
  1  ATGGAATCCC TAGCCGCCAC CTCCGTGTTC GCGCCCTCCC GCGTCGCCGT
 51  CCCGGCGGCG CGGGCCCTGG TTAGGGCGGG GACGGTGGTA CCAACCAGGC
101  GGACGAGCAG CCGGAGCGGA ACCAGCGGGG TGAAATGCTC TGCTGCCGTG
151  ACGCCGCAGG CGAGCCCAGT GATTAGCAGG AGCCGCTGCG CGGCGAAGGC
201  GGCGGGAGGA GACAAGAGGC GGTTCTTCGA GGCGGGGGCG CGGGGGAGCG
251  GGAAGGGGAA CCTGGTGCCC ATGTGGGAGT CCGTCGAGCA ACGTCGACGC
301  ACCCCCGTGC TCGCCTACCG CTGCCTCGTC CCCGAGGACA ACGTCGACGC
351  CCCCAGCTTC CTCTTCGAGT CCGTCGAGCA GGGCCCCAG GGCACCACCA
401  ACGTCGGCCG CTATAGCATG GTGGGAGCCC ACCCAGTGAT GGAGATTGTG
451  GCCAAAGACC ACAAGGTTAC GATCATGGAC CACGAGAAGA GCCAAGTGAC
501  AGAGCAGGTA GTGGACGACC CGATGCAGAT CCCGAGGACC ATGATGGAGG
551  GATGGCACCC ACAGCAGATC GACGAGCTCC CTGAATCCTT CTCCGGTGGA
601  TGGGTTGGGT TCTTTTCCTA TGATACGGTT AGGTATGTTG AGAAGAAGAA
```

*Fig. 33A*

```
 651  GCTACCGTTC TCCAGTGCTC CTCAGGACGA TAGGAACCTT CCTGATGTGC
 701  ACTTGGGACT CTATGATGAT GTTCTAGTCT TCGATAATGT TGAGAAGAAA
 751  GTATATGTTA TCCATTGGGT CAATGTGGAC CGGCATGCAT CTGTTGAGGA
 801  AGCATACCAA GATGGCAGGT CCCGACTAAA CATGTTGCTA TCTAAAGTGC
 851  ACAATTCCAA TGTCCCCACA CTCTCTCCTG GATTTGTGAA GCTGCACACA
 901  CGCAAGTTTG GTACACCTTT GAACAAGTCG ACCATGACAA GTGATGAGTA
 951  TAAGAATGCT GTTCTGCAGG CTAAGGAACA TATTATGGCT GGGATATCT
1001  TCCAGATTGT ATCGAGCATT AGGTTCGAGA GACGAACATA TGCCAACCCA
1051  TTTGAGGTTT GCAAGAGGCT ACGGATTGTG AATCCTAGCC CATACATGGC
1101  GTATGTACAG CAGTAAGGGG GTGTATTGGT TGCGTCTAGT CCTGAAATTC
1151  TTACACGAGT CAGTAAGGGG AAGATTATTA ATCGACCACT TGCTGGAACT
1201  GTTCGAAGGG GCAAGACAGA GAAGGAAGAT CAAATGCAAG AGCAGCAACT
1251  GTTAAGTGAT GAAAAACAGT GTGCCGAGCA CATAATGCTT GTGGACTTGG
```

*Fig. 33B*

```
1301 GAAGGAATGA TGTTGGCAAG GTATCCAAAC CAGGATCAGT GAAGGTGGAG
1351 AAGTTGATGA ACATTGAGAG ATACTCCCAT GTTATGCACA TCAGCTCAAC
1401 GGTTAGTGGA CAGTTGGATG ATCATCTCCA GAGTTGGGAT GCCTTGAGAG
1451 CTGCCCTTGCC CGTTGGAACA GTCAGTGGTG CACCAAAGGT GAAGGCCATG
1501 GAGTTGATTG ATAAGTTGGA AGTTACGAGG CGAGGACCAT ATAGTGGTGG
1551 TCTAGGAGGA ATATCGTTTG ATGGTGACAT GCAAATTGCA CTTTCTCTCC
1601 GCACCATCGT ATTCTCAACA GCGCCGAGCC ACAACACGAT GTACTCATAC
1651 AAAGACGCAG ATAGGCGTCG GGAGTGGGTC GCTCATCTTC AGGCTGGTGC
1701 AGGCATTGTT GCCGACAGTA GCCCAGATGA CGAACAACGT GAATGCGAGA
1751 ATAAGGCTGC TGCACTAGCT CGGGCCATCG ATCTTGCAGA GTCAGCTTTT
1801 GTAGACAAAG AATAG
```

*Fig. 33C*

1    MESLAATSVF APSRVAVPAA RALVRAGTVV PTRRTSSRSG TSGVKCSAAV
51   TPQASPVISR SAAAAKAAEE DKRRFFEAAA RGSGKGNLVP MWECIVSDHL
101  TPVLAYRCLV PEDNVDAPSF LFESVEQGPQ GTTNVGRYSM VGAHPVMEIV
151  AKDHKVTIMD HEKSQVTEQV VDDPMQIPRT MMEGWHPQQI DELPESFSGG
201  WVGFFSYDTV RYVEKKKLPF SSAPQDDRNL PDVHLGLYDD VLVFDNVEKK
251  VYVIHWVNVD RHASVEEAYQ DGRSRLNMLL SKVHNSNVPT LSPGFVKLHT
301  RKFGTPLNKS TMTSDEYKNA VLQAKEHIMA GDIFQIVLSQ RFERRTYANP
351  FEVYRALRIV NPSPYMAYVQ ARGCVLVASS PEILTRVSKG KIINRPLAGT
401  VRRGKTEKED QMQEQLLSD EKQCAEHIML VDLGRNDVGK VSKPGSVKVE
451  KLMNIERYSH VMHISSTVSG QLDDHLQSWD ALRAALPVGT VSGAPKVKAM
501  ELIDKLEVTR RGPYSGGLGG ISFDGDMQIA LSLRTIVFST APSHNTMYSY
551  KDADRRREWV AHLQAGAGIV ADSSPDDEQR ECENKAAALA RAIDLAESAF
601  VDKE*

Fig. 33D

```
AgrTu_158889565    -----MVTIIQDDGAETYETKGGIQVSRKRRPTDYANAIDNYIEKLDSHRGAVFSSNYEY   55
RhiMe_136328       -----MAAVILEDGAESYTTKGIVVTRRREASYSDAIAGYVDRLDERRGAVFSSNYEY     55
MesLo_13472468     -METAMTMKVLENGAESFVTAGGITITRERHDRPYAGAIDAYVDGLNSRRGAVFSSNYEY   59
AzoBr_1717765      MYPADLLASPDLLEPLRFQTRGGVTVTRRATALDPRTALDPVIDALDRRRGLLLSSGVEA   60
BruMe_179867 32    -----MNAKTADSEIFQHETAGGIIVERVRHLTAYKGAIESYIDVLNEWRGAVFSSNYEY   55
Nostoc_17227910    ---------MIADSHSYRTNGNVRVSRSITQVKMETALEEILFYLNSQRGGLLTSSYEY    50
Nostoc_17230725    --------------MRVSRSTTEVKMDTALDEILFHLNQVRGGLLTSSYEY           37
RhoPa_TrpEG        ----MNRTVFSLPATSDYKTAAGLAVTRSAQPFAGGQALDELIDLLDHRRGVMLSSGTTV  56
                                                 *    *          **  :::*

AgrTu_158889565    PGRYTRWDTAIVDPPLGISCFGRKMWIEAYNGRGEVLLDFITEKLKATPDLTLGASSTRR  115
RhiMe_136328       PGRYTRWDTAVVDPPLAISSFGRSLWIEAYNERGEVLLALIAEDLKSVADITLGSLAARR  115
MesLo_13472468     PGRYTRWDTAIIDPPLVISARGRAMRIEALNRRGEALLPVIGKTLGGLADITIAETTKTL  119
AzoBr_1717765      PGRYTRWDTAIVDPPVALTARGRTLRIDALNGRGQVLLPAVAEALRGLEALAGLEEAPSR  120
BruMe_17986732     PGRYTRWDTAIVDPPVVITSRARTMRIEALNARGVILLRPILDTVKALSEVKIDQSGENR  115
Nostoc_17227910    PGRYKRWAIGFVNPPVELSTSGNTFLTALNERGYVLLPVIFECLSKSEQLQKLTEHHHK   110
Nostoc_17230725    PGRYKRWAIGFINPPLQLTTRENAFTISSLNPRGQVLLPTLFQHLSAQSQLQQISLNHDY   97
RhoPa_TrpEG        PGRYESFDLGFADPPLALTTRAEKFTIEALNPRGRVLIAFLSDKLEEPCVVVEQACATKI  116
                   ****      .  **:    ..     ::*  **  * :

AgrTu_158889565    LDLTVNEPDRVFTEEERSKIPTVFTALRAIVDLFYSSADSAIGLFGAFGYDLAFQFDAIK  175
RhiMe_136328       LDLTINEPDRVFTEEERSKMPTVFTVFTVLRAVTNLFHSEEDSNLGLYGAFGYDLAFDAIE  175
MesLo_13472468     IRLDVAKPGRVFTEEERSRVPSVFTVLRAITALFKTDEDANLGLYGAFGYDLSFQFDPVD  179
AzoBr_1717765      VTASSASPAPL-PGEERSRQPSVFSVLRAVLDLFAAPDDPLLGLYGAFQFEPIR        179
BruMe_17986732     IDLTIVEPVGTFTEEERSRMPSVFTVLRAIVGLFFSEEDANLGLYGAFGYDLAFQFDPIQ  175
Nostoc_17227910    ITGLVKSTPEFFAEEERSKQPSTFTVIREILHIFSSQEDEHLGLYGAFGYDLVFQFEQIT  170
Nostoc_17230725    ITGEIRPTKQLFTEEQRSKQPSAFTVIREILQIFASDEDEHLGLYGAFGYDLVFQFEPIP  157
RhoPa_TrpEG        RGHIVRGEAPV-DEEQRTRRASAISLVRAVIAAFASPADPMLGLYGAFAYDLVFQFEDLK  175
                        .                :  :*:  :  * :       **:*** :**.*** 
```

Fig. 35A

```
AgrTu_158889565    LSLARPEDQRDMVLFLPDEILVVDHYSAKAWIDRYDFEKDGMTTDGKSSDITPDPFKTTD  235
RhiMe_136328       LKLSRPDDQRDMVLFLPDEILVVDHYAAKAWIDRYDFARENLSTEGKAADIAPEPFRSVD  235
MesLo_13472468     YKLERKPSQRDLVLFLPDEILVVDHYSAKAWTDRYDYSGEGFSTEGLPRDAIAEPFKTAD  239
AzoBr_1717765      QRLERPDDQRDLLLYLPDRLVALDPIAGLARLVAYEFITAAGSTEGLECGGRDHPYRPDT  239
BruMe_179867732    YKLKRPDDQRDLVLFIPDEIFVADHYAARAWVDRYEFRCGGSSTHGLDRATPVVPFKPSE  235
Nostoc_17227910    QCLERPQDQRDLVLYLPDELIVVDYYQQQAFRLEYDFITAHGSTYDLPRTGESVDYRGQC  230
Nostoc_17230725    QKIARPADQRDLVLYLPDELIVVDYYLQKAYRHQYEFATEHGNTEHLPRTGQSIDYQGKH  217
RhoPa_TrpEG        QKRAREADQRDIVLYVPDRLLAYDRATGRGVDISYEFAWKGQSTAGLPNETAESVT-QT   234
                    :  :..** .::::*:  : .:*::.:                                
                      .                         .      *

AgrTu_158889565    TIPPK-GDHRPGEYSELVVKAKESFRRGDLFEVVPGQKFMERCESNPSAISRRLKAINPS  294
RhiMe_136328       SIPPH-GDHRPGEYAELVVKAKESFRRGDLFEVVPGQKFYERCESRPSEISNRLKAINPS  294
MesLo_13472468     RIPPR-GDHEPGEYANLVRRAMDSFKRGDLFEVVPGQMFYERCETQPSDISRKLKSINPS  298
AzoBr_1717765      NAEAG-CDHAPGDYQRVESAKAAFRRGDLFEVVPGQTFAEPCADAPSSVFRRLRAANPA  298
BruMe_179867732    RKLAR-GDHNPGEYARLVERAKESFKRGDLFEVVPGQTFYERCHTAPSEIFRRLKSINPS  294
Nostoc_17227910    LTPPQNADHKIGEYAKLVEFALDYFRRGDLFEVVPSQNFFTACEAPPSQLFETLKQINPS  290
Nostoc_17230725    LLPNQTADHQPGEYANLVEQALDYFRRGDLFEVVPSQNFFTACEQSPSQLFQTLRQINPS  277
RhoPa_TrpEG        GRQGF-ADHAPGDYPKVVEKARAAFARGDLFEAVPGQLFGEPCERSPAEVFKRLCRINPS  293
                        .*: **:  :* :    * **** * **::*  *      :.:*: : * **:
                                                                         *

AgrTu_158889565    PYSFFINLGDQEYLVGASPEMFVRVSGRRIETCPISGTIKRGDDPIADSEQILKLLNSKK  354
RhiMe_136328       PYSFFINLGNQEYLVGASPEMFVRVSGRRIETCPISGTIKRGDDPIADSEQILKLLNSKK  354
MesLo_13472468     PYSFFINLGENEYLIGASPEMFVRVNGRRVETCPISGTIKRGDDAISDSEQILKLLNSKK  358
AzoBr_1717765      PYEAFVNLGRGEFLVGASPEMYVRVAGGRVETCPISGTVARGADALGDAAQVLRLLTSAK  358
BruMe_179867732    PYSFFINLGESEYLVGASPEMFVRVNGRRIETCPISGTIKRGEDAISDSEQILKLLNSKK  354
Nostoc_17227910    PYGFIFNLG-GEYIIGASPEMFVRVEGRRVETCPISGTITRGHDAIDDAVQIRQLLNSHK  349
Nostoc_17230725    PYGFLINLG-GEYLIGASPEMFVRVDGRRVETCPISGTIRRGEDALGDAVQIRQLLNSHK  336
RhoPa_TrpEG        PYGGLLNLGDGEFLVSASPEMFVRSDGRRIETCPISGTIARGVDAISDAEQIQKLLNSEK  353
                   **  ::***  *::.:*****:**  **:********: **.** .*  *:  **.*
                   **                     *****                        *
```

Fig. 35B

```
AgrTu_15889565    DESELTMCSDVDRNDKSRVCEPGSVKVIGRRQIEMYSRLIHTVDHIEGRLRDDMDAFDGF  414
RhiMe_136328      DESELTMCSDVDRNDKSRVCEPGSVKVIGRRQIEMYSRLIHTVDHIEGRLRDDMDAFDGF  414
MesLo_13472468    DESELTMCSDVDRNDKSRVCVPGSVRVIGRRQIEMYSRLIHTVDHIEGRLREGMDAFDAF  418
AzoBr_1717765     DAAELTMCTDVDRNDKARVCEPGSVRVIGRRMIELYSRLIHTVDHVEGRLRSGMDALDAF  418
BruMe_17986732    DESELTMCSDVDRNDKSRVCEPGSVRVIGRRQIEMYSRLIHTVDHIEGRLRDGMDAFDGF  414
Nostoc_17227910   DEAELTMCTDVDRNDKSRICEPGSVKVIGRRQIELYSHLIHTVDHVEGILRPEFDALDAF  409
Nostoc_17230725   DEAELTMCTDVDRNDKSRICEPGSVRVIGRRQIELYSHLIHTVDHVEGILRPEFDALDAF  396
RhoPa_TrpEG       DEFELNMCTDVDRNDKARVCVPGTIKVLARRQIETYSKLFHTVDHVEGMLRPGFDALDAF  413
                    *  *** *******  * ****.:*:*** ** :: ::******.::** ** ** *

AgrTu_15889565    LSHAWAVTVTGAPKLWAMRFIEGHEKSPRAWYGGAIGMVGFNGDMNTGLTLRTIRIKDGI  474
RhiMe_136328      LSHAWAVTVTGAPKLWAMRFIESHEKSPRAWYGGAIGMVGFNGDMNTGLTLRTIRIKDGI  474
MesLo_13472468    LSHAWAVTVTGAPKLWAMRFIEQNEKSPRAWYGGAIGMVNFNGDMNTGLTLRTIRIKDGI  478
AzoBr_1717765     LTHSWAVTVTGAPKRWAMQFLEDTEQSPRRWYGGAFGRLGFDGGMDTGLTLRTIRMAEGV  478
BruMe_17986732    LSHAWAVTVTGAPKLWAMRFLEENERSPRAWYGGAIGMHFNGDMNTGLTLRTIRIKDGV  474
Nostoc_17227910   LSHTWAVTVTGAPKRAAIQFIEKNERSVRRWYGGAVGYLNFNGNLNTGLILRTIRLQDSI  469
Nostoc_17230725   LSHTWAVTVTGAPKRAAMQFIEQHERSARRWYGGAVGYLGFNGNLNTGLTLRTIRLQDSI  456
RhoPa_TrpEG       LTHAWAVTVTGAPKLWAMQFVEDHERSPRRWYAGAFGVVGFDGSINTGLTIRTIRMKDGL  473
                  *:::******** .: * : .::* * **.** *   *:*.  *** ::**** .

AgrTu_15889565    AEVRAGATLLNDSNPQEEEAETELKASAMISAIRDAKGTNSAATKRDAAK------VGT  527
RhiMe_136328      AEVRAGATLLYDSNPEEEEAETELKASAMIAAIRDAKSANSAKSARDVAA------VGA  527
MesLo_13472468    AEVRAGATLLFDSIPEEEEAETELKASAMLSAIRDAKTGNSASTERTTAR------VGD  531
AzoBr_1717765     AYVRAGATLLSDSDPDAEDAECRLKAAAFRDAIRGTAAGAAPTLPAAPRG------GE   530
BruMe_17986732    AEIRAGATLFDSNPDEEEAETELKASAMIAAVRDAQKSNQIAEESVAAK------VGE   527
Nostoc_17227910   AEVRAGATLLYDSIPQAEEQETITKAAAAFETIRRAKQIDPQIEESSTRKLSKYLPDGQS  529
Nostoc_17230725   AEVRVGATVLYDSIPSAEEETITKATALFETIRRHTTANKTQGNDSHRP-----GDIAH  511
RhoPa_TrpEG       AEVRVGATCLFDSNPVAEDKECQVKAAALFQALRGDPAKPLSAV-APDAT-------GS  524
                  * :*.***  ** *     * ::**:* : :*   .

Fig.35C
```

```
AgrTu_15889565    GVKILLVDHEDSFVHTLANYFRQTGATVSTVRSPVAADVEDRFQPDLVVLSPGPGSPTDF  587
RhiMe_136328      GVSILLVDHEDSFVHTLANYFRQTGASVTTVRTPVAEEIFDRVKPDLVVLSPGPGTPKDF  587
MesLo_13472468    GVNILLVDHEDSFVHTLANYFRQTGANVSTVRTPVPDEVFERLKPDLVVLSPGPGTPKDF  591
AzoBr_1717765     GRRVLLVDHDDSFVHTLADYLRQTGASVTTLRHSHARAALAERRPDLVVLSPGPGRPADF  590
BruMe_17986732    GVSILLVDHEDSFVHTLANYFRQTGAKVSTVRSPVAEEIFDRVNPDLVVLSPGPGSPQDF  587
Nostoc_17227910   GKHILLIDHEDSFVHTLANYIRSTGATVTTLRHGFSESLFDTERPDLVVLSPGPGRPSEF  589
Nostoc_17230725   NKRILLIDYEDSFVHTLANYIRTTGATVTTLRHGFAESYFDAERPDLVVLSPGPGRPSDF  571
RhoPa_TrpEG       GKKVLLVDHDDSFVHMLADYFRQVGAQVTVRYVHGLKMLAENSYDLLVLSPGPGRPEDF   584
                     :*::*::*.***** :**.* ::.:.*:.          **:**:******* . *

AgrTu_15889565    DCKATIKAARARDLPIFGVCLGLQALAEAYGGELRQLAVPMHGKPSRIRVLEP-GLVFSG  646
RhiMe_136328      DCKATIKKARARDLPIFGVCLGLQALAEAYGGDLRQLAIPMHGKPSRIRVLEP-GIVFSG  646
MesLo_13472468    DCAATIRRARARDLPIFGVCLGLQALAEAYGGELRQLHIPMHGKPSRIRVSKP-GIIFSG  650
AzoBr_1717765     DVAGTIDAALALGLPVFGVCLGLQGMVERFGGAIDVLPEPVHGKATEVRVLGG--ALFAG  648
BruMe_17986732    DCKATIDKARKRQLPIFGVCLGLQALAEAYGGALRQLRVPVHGKPSRIRVSKP-ERIFSG  646
Nostoc_17227910   KVQETVAACVRRQIPLFGVCLGLQGIVEAFGGELGVLNYPQHGKSSRIFVTAPDSVMFQD  649
Nostoc_17230725   RVPQTVAALVGREIPIFGVCLGLQGIVEAFGGELGVLDYPQHGKPARISVTAPDSVLFQN  631
RhoPa_TrpEG       KIKDTIDAALAKKLPIFGVCLGVQAMGEYFGGTLGQLAQPAHGRPSRIQVRGG--ALMRG  642
                    :  :     .:*:*****:*.     **    *   . ::*   .:  :

AgrTu_15889565    LGKEVTVGRYHSIFADPATLPRDFIITAESEDGTIMGIEHAKEPVAAVQFHPESIMTLGQ  706
RhiMe_136328      LGKEVTVGRYHSIFADPSNLPREFVITAESEDGTIMGIEHSKEPVAAVQFHPESIMTLGG  706
MesLo_13472468    LPKEVTVGRYHSIFADPVRLPDDFIVTAETEDGIIMAFEHRKEPIAAVQFHPESIMTLGH  710
AzoBr_1717765     LPERLTVGRYHSLVARRDRLPADLTVTAETADGLVMAVEHRRLPLAAVQFHPESILSLDG  708
BruMe_17986732    LPEEVTVGRYHSIFADPERLPDDFLVTAETEDGIIMAFEHKHEPVAAVQFHPESIMTLGH  706
Nostoc_17227910   LPESFTVGRYHSLFALSQRLPKELKVTAISDDEVIMAIEHQTLPIAAVQFHPESIMTLAG  709
Nostoc_17230725   LPASFIVGRYHSLFAQPQTIPGELKVTAISEDNVIMAIEHQTLPIAAVQFHPESIMTLAG  691
RhoPa_TrpEG       LPNEVTIGRYHSLYVDMRDMPKELTVTASTDDGIAMAIEHKTLPVGGVQFHPESLMSLGG  702
                  *     :*****::       :    ** . .  :* ::     .:*******:::*
```

Fig. 35D

```
AgrTu_158889565    DAGMRMIENVVVHLTRKAKTKAA----    729
RhiMe_136328       DAGMRMIENVVAHLAKRAKTKAA----    729
MesLo_13472468     NAGMRIIENIVAHLPRKAKEKAA----    733
AzoBr_1717765      GAGLALLGNVMDRLAAGALTDAAA----   732
BruMe_17986732     NAGMRMIENIVTHLAGKHKARRTNY-     731
Nostoc_17227910    EVGLMMIKNVVQKYTQSQQSTVPIYD     735
Nostoc_17230725    EVGQTIKNVVQTYTQTLETSIYS---     715
RhoPa_TrpEG        EVGLRIVENAFRLGQAA--------      719
                     *   :: *
```

*Fig. 35E*

```
   1 ATGGTGACCA TCATTCAGGA TGACGGTGCC GAGACCTACG AGACCAAGGG CGGCATCCAG
  61 GTGAGCCGCA AGCGCCGCCC CACCGATTAC GCCAACGCCA TCGATAACTA CATCGAAAAG
 121 CTTGATTCCC ATCGCGGTGC CGTGTTCTCC TCCAACTACG AATACCCAGG CCGCTACACC
 181 CGCTGGGATA CCGCCATCGT CGATCCACCA CTCGGCATTT CCTGCTTCGG CCGCAAGATG
 241 TGGATCGAAG CCTACAACGG CCGCGGCGAA GTGCTGCTCG ATTTCATTAC CGAAAAGCTG
 301 AAGGCCACAC CCGATCTCAC CCTCGGCGCT TCCTCCACCC GCCGCCTCA TCTTACCGTC
 361 AACGAACCAG ACCGCGTCTT CACCGAAGAA GAACGCTCCA AAATCCCAAC CGTCTTCACC
 421 GCTCTCAGGG CCATCGTCGA CCTCTTCTAC TCCAGCGCCG ATTCCGCCAT CGGCCTGTTC
 481 GGTGCCTTCG GTTACGATCT CGCCCTTCCAG TTCGACGCCA TCAAGCTTTC CCTGGCCCGC
 541 CCAGAAGACC AGCGCGACAT CGCCCCGATG AAATCCTCGT CGTTGATCAC GACCACCGAC
 601 TACTCCGCCA AGGCCTGGAT CGACCGCTAC GATTTCGAGA AGGACGGCAT CCACCCCAAG
 661 GGCAAATCCT CCGACATTAC CCCCGATCCC TTCAAGACCA AGGCCAAGGA AGCTTCCGC
 721 GGCGATCACC GCCCCGGCGA ATACTCCGAG CTTGTGGTGA TGGAGCGCTG CGAAAGCAAC
 781 CGCGGCGACC TGTTCGAGGT CGTTCCCGGC CAGAAAATTCA CCCCCTACTC CTTCTTCATC
 841 CCATCCGCCA TTTCCCGCCG CCTGAAGGCC ATCAACCCAT GCCTCCCCAG AAATGTTCGT GCGCGTCTCC
 901 AACCTCGGCG ATCAGGAATA CCTGGTCGCC GCCACCATCA AGCGCGGCGA CGATCCAATT
 961 GGCCGCCGCA TCGAGACCTG CCCAATCTCA GGCACCATCA AGCGCGGGCGA CGAACTGACC
1021 GCCGACAGCG AGCAGATTTT GAAACTGCTC AACTCCAAAA AGCCGCGTCT TTCCGTGAAG
1081 ATGTGCTCCG ACGTGGACCG CAACGACAAG AGCCGCCTTCA TCCACACCGT CGATCACATC
1141 GTCATTGGCC GCCGCCAGAT CGAGATGTAC TTCGACGGTT TCCTCAGCCA CGCCTGGGCC
1201 GAAGGCCCGC TGCGCGACGA TATGGACGCC AAAGCTGTGG GCCATCGCGCT TCATCGAAGG TCATGAAAAG
1261 GTCACCGTCA CCGGTGCACC AAAGCTGTGG GCCATGGTCG GCATGGTTCG GCTTCAAGCG TCATGAAAAG
1321 AGCCCACGCG CCTGGTACGG CATCCGCCAT AAGGACGGTA TTGCCGAAGT GCGCGCCGGC
1381 ACCGGCCTGA CCCTGCGCAC CAACCCACAG AAGGAAGAAG AAAGGCACCA ACTGAAGGCC
1441 GCCACCCTGC TCAACGATTC TCGCGACGCA AAAGGCACCA ACTCTGCCGC CACCAAGCGC
1501 TCCGCCATGA TCTCAGCCAT TCGCGACGCA ACTCTGCCGC CACCAAGCGC
1561 GATGCCGCCA AAGTCGGCCA CGGCGTCAAG ATCCTGCTCG TCGACCACGA AGACAGCTTC
```

Fig. 36A

```
1621  GTGCACACCC  TGGCCAACTA  CTTCCGCCAG  ACCGGGCGCCA  CCGTCTCCAC  CGTCAGGTCA
1681  CCAGTCGCAG  CCGACGTGTT  CGATCGCTTC  CAGCCAGACC  TCGTTGTCCT  GTCCCCCGGT
1741  CCCGGCAGCC  CAACCGATTT  CGACTGCAAG  GCAACCATCA  AGGCCGCCCG  CGCCCGCGAT
1801  CTGCCAATCT  TCGGCGTTTG  CCTCGGTCTG  CAGGCATTGG  CAGAAGCCTA  CGGCGGCGAG
1861  CTGCGCCAGC  TTGCTGTGCC  CATGCACGGC  AAGCCTTCCC  GCATCCGCGT  GCTGGAACCC
1921  GGCCTCGTCT  TCTCCGGTCT  CGGCAAGGAA  GTCACCGTCG  GTCGCTACCA  TTCCATCTTC
1981  GCCGATCCCG  CCACCCTGCC  ACGCGATTTC  ATCATCACCG  CAGAAAGCGA  GGACGGCACC
2041  ATCATGGGCA  TCGAACACGC  CAAGGAACCA  GTGGCCGCCG  TTCAGTTCCA  CCCAGAATCC
2101  ATCATGACCC  TCGGTCAGGA  CGCCCGGCATG  CGCATGATCG  AGAACGTCGT  GGTGCATCTG
2161  ACCCGCAAGG  CCAAGACCAA  GGCCGCCTGA
```

```
                |1550      |1560      |1570      |1580      |1590      |1600      |1610      |1620      |1630      |1640      |1650
ACTCTGCCGCCACCAAGCGTGATGCCGCCAAAGTCGGCACCGGGCGTCAAGATCCTGCTCGTCGACCACGAAGACAGCTTCGTGCACACGCTGGCACACCCTGGAATTATTTCCGCCAG
                °1550      °1560      °1570      °1580      °1590      °1600      °1610      °1620      °1630      °1640      °1650

|1660      |1670      |1680      |1690      |1700      |1710      |1720      |1730      |1740      |1750      |1760
ACGGGCGCGACGGTCTCGACCGTCAGATCACCGTCGCAGTGTTCGACGCGTGTTCGACGCGTTCCAGCCGGACCTCGTTGTCCTCGTTGTCCTGTCCCGGACCGCAGCCGCCAACCGATTT
ACCGGCGCGCCACCGTCTCCACCGTCAGTGTCCACCGGGCCAATCAAGGCCGCGCCGCCGCCGCCGCCGCCGCCGCCGGCGCCAATCAAGGCGCCGCGCCGCCGCGCCAGCCGCCAGC
                °1660      °1670      °1680      °1690      °1700      °1710      °1720      °1730      °1740      °1750      °1760
```

Fig. 37C

TRANSGENIC HIGH TRYPTOPHAN PLANTS

CROSS-REFERENCE TO RELATED APPLICATION

This application claims benefit under 35 U.S.C. 119(e) from U.S. Provisional Application Ser. No. 60/288,904, filed May 4, 2001, which application is incorporated herein by reference.

BACKGROUND OF THE INVENTION

The seeds of a number of important crops, including soybean and maize do not contain sufficient quantities of several amino acids to be nutritionally complete. These amino acids include, but are not limited to: tryptophan, isoleucine, valine, arginine, lysine, methionine and threonine. Therefore, the biosynthetic pathways for these amino acids, and/or biosynthetic pathways for metabolites that feed into those pathways, are potential targets for manipulation in order to increase the amino acid content of these plants.

Anthranilate synthase (AS, EC 4.1.3.27) catalyzes the first reaction branching from the aromatic amino acid pathway to the biosynthesis of tryptophan in plants, fungi, and bacteria.

The most common form of anthranilate synthase (for example, the maize anthranilate synthase) is a heterotetrameric enzyme consisting of two subunits, the α or TrpE subunit and the β or TrpG subunit. Two α subunits and two β subunits assemble to form the heterotetrameric anthranilate synthases. "Monomeric" forms of AS have also been discovered that comprise a single polypeptide chain having the activities of both TrpE and TrpG subunits (for example *Rhizobium meliloti*). While monomeric anthranilate synthases comprise just one type of polypeptide, the enzymatically active form of a monomeric anthranilate synthase is typically a homodimer consisting of two such monomeric polypeptides. Both heterotetrameric and monomeric anthranilate synthases catalyze the formation of anthranilate in a reaction utilizing glutamine and chorismate. The domain found on the α subunit (referred to herein as the "α domain") binds chorismate and eliminates the enolpyruvate side chain, and the domain found on the β-subunit (referred to herein as the "β domain") transfers an amino group from glutamine to the position on the chorismate phenyl ring that resides between the carboxylate and the enolpyruvate moieties.

The next reaction in the synthesis of tryptophan is the transfer of the phosphoribosyl moiety of phosphoribosyl pyrophosphate to anthranilate. The indole ring is formed in two steps involving an isomerization converting the ribose group to a ribulose followed by a cyclization reaction to yield indole glycerol phosphate. The final reaction in the pathway is catalyzed by a single enzyme that may contain either one or two subunits. The reaction accomplishes the cleavage of indole glyceraldehyde-3-phosphate and condensation of the indole group with serine (Umbarger, *Ann. Rev. Biochem*, 47, 555 (1978)).

Metabolite flow in the tryptophan pathway in higher plants and microorganisms is apparently regulated through feedback inhibition of anthranilate synthase by tryptophan. Tryptophan may block the conformational rearrangement that is required to activate the β-domain and to create a channel for passage of ammonia toward the active site of the α-domain. Such feedback inhibition by tryptophan is believed to depress the production of tryptophan by anthranilate synthase. See Li J. & Last, R. L. The *Arabidopsis thaliana* trp5 mutant has a feedback-resistant anthranilate synthase and elevated soluble tryptophan. *Plant Physiol.* 110, 51–59 (1996).

Several amino acid residues have been identified as being involved in the feedback regulation of the anthranilate synthase complex from *Salmonella typhimurium*. Such information provides evidence of an amino-terminal regulatory site. *J. Biol. Chem.* 266, 8328–8335 (1991). Niyogi et al. have further characterized the anthranilate synthase from certain plants employing a molecular approach. See Niyogi and Fink (*Plant Cell*, 4, 721 (1992)) and Niyogi et al. (*Plant Cell*, 5, 1011 (1993)). They found that the α-subunits of the *Arabidopsis* anthranilate synthase are encoded by two closely related, nonallelic genes that are differentially regulated. One of these α-subunit genes, ASA1, is induced by wounding and bacterial pathogen infiltration, implicating its involvement in a defense response, whereas the other α-subunit gene, ASA2, is expressed at constitutive basal levels. Both predicted proteins share regions of homology with bacterial and fungal anthranilate synthase proteins, and contain conserved amino acid residues at positions that have been shown to be involved in tryptophan feedback inhibition in bacteria (Caligiuri et al., *J. Biol. Chem.*, 266, 8328 (1991)).

Amino acid analogs of tryptophan and analogs of the intermediates in the tryptophan biosynthetic pathway (e.g., 5-methyltryptophan, 4-methyltryptophan, 5-fluorotryptophan, 5-hydroxytryptophan, 7-azatryptophan, 3β-indoleacrylic acid, 3-methylanthranilic acid), have been shown to inhibit the growth of both prokaryotic and eukaryotic organisms. Plant cell cultures can be selected for resistance to these amino acid analogs. For example, cultured tobacco, carrot, potato, corn and *Datura innoxia* cell lines have been selected that are resistant to growth inhibition by 5-methyltryptophan (5-MT), an amino acid analog of tryptophan, due to expression of an altered anthranilate synthase.

Ranch et al. (*Plant Physiol.*, 71, 136 (1983)) selected for 5-MT resistance in cell cultures of *Datura innoxia*, a dicot weed, and reported that the resistant cell cultures contained increased tryptophan levels (8 to 30 times higher than the wild type level) and an anthranilate synthase with less sensitivity to tryptophan feedback inhibition. Regenerated plants were also resistant to 5-MT, contained an altered anthranilate synthase, and had greater concentrations of free tryptophan (4 to 44 times) in the leaves than did the leaves of the control plants. In contrast to the studies with *N. tabacum*, where the altered enzyme was not expressed in plants regenerated from resistant cell lines, these results indicated that the amino acid overproduction phenotype could be selected at the cellular level and expressed in whole plants regenerated from the selected cells in *Datura innoxia*.

Hibberd et al. (U.S. Pat. No. 4,581,847, issued Apr. 15, 1986) described 5-MT resistant maize cell lines that contained an anthranilate synthase that was less sensitive to feedback inhibition than wild-type anthranilate synthase. One 5-MT resistant cell line accumulated free tryptophan at levels almost twenty-fold greater than that of non-transformed cell lines.

P. C. Anderson et al. (U.S. Pat. No. 6,118,047) disclose the use of a tryptophan-insensitive α-domain of anthranilate synthase from C28 maize in a transgene to prepare transgenic maize plants (*Zea mays*) exhibiting elevated levels of free tryptophan in the seed(s).

Although it is possible to select for 5-MT resistance in certain cell cultures and plants, this characteristic does not necessarily correlate with the overproduction of free tryptophan in whole plants. Additionally, plants regenerated from 5-MT resistant lines frequently do not express an altered form of the enzyme. Nor is it predictable that this characteristic will be stable over a period of time and will be passed along as a heritable trait.

Anthranilate synthase has also been partially purified from crude extracts of cell cultures of higher plants (Hankins et al., *Plant Physiol.*, 57, 101 (1976); Widholm, *Biochim. Biophys. Acta*, 320, 217 (1973)). However, it was found to be very unstable. Thus, there is a need to provide plants with a source of anthranilate synthase that can increase the tryptophan content of plants.

SUMMARY OF THE INVENTION

The present invention provides nucleic acids encoding an anthranilate synthase (AS) that can be used to generate transgenic plants. When such anthranilate synthase nucleic acids are expressed in a transgenic plant, elevated levels of tryptophan can be achieved within the cells of the plant. In one embodiment, the invention is directed to DNA molecules that encode a monomeric anthranilate synthase, where such a monomeric anthranilate synthase is a natural or genetically engineered chimeric fusion of the α- and β-domains of an anthranilate synthase. The anthranilate synthase gene from a few species (e.g., some bacteria and other microbes) naturally gives rise to a monomeric anthranilate synthase that constitutes a single polypeptide chain. However, most species have a heterotetrameric anthranilate synthase composed of two α and two β domains found on separate subunits. The invention also contemplates formation of chimeric anthranilate synthase fusion proteins comprising any anthranilate synthase α-domain linked to any β-domain.

In general, the sequence identity of naturally occurring monomeric anthranilate synthases with most plant anthranilate synthases is quite low. However, according to the invention, such monomeric anthranilate synthases can provide high levels of tryptophan when expressed in a plant, despite a low sequence identity with the plant's endogenous anthranilate synthase enzyme. Accordingly, the invention provides monomeric anthranilate synthases that can have divergent sequences and that are capable of efficiently providing high levels of tryptophan in a plant host. For example, transgenic soybean plants containing the monomeric *Agrobacterium tumefaciens* anthranilate synthase can produce from up to about 10,000 to about 12,000 ppm tryptophan in seeds, with average trp levels ranging up to about 7,000 to about 8,000 ppm. In contrast, non-transgenic soybean plants normally have up to only about 100 to about 200 ppm tryptophan in seeds.

Accordingly, the invention provides an isolated DNA sequence encoding a monomeric anthranilate synthase, wherein the monomeric anthranilate synthase has an anthranilate α-domain and an anthranilate β-domain and wherein the monomeric anthranilate synthase is expressed in a plant. Such expression can elevate the level of L-tryptophan in the plant.

The monomeric anthranilate synthase can be naturally monomeric. Examples of organisms from which naturally monomeric anthranilate synthase nucleic acids may be isolated, include but are not limited to organisms such as *Agrobacterium tumefaciens, Rhizobium meliloti* (e.g., Genbank Accession No. GI 95177), *Mesorhizobium loti* (e.g., Genbank Accession No. GI 13472468), *Brucella melitensis* (e.g., Genbank Accession No. GI 17982357), *Nostoc sp.* PCC7120 (e.g., Genbank Accession Nos. GI 17227910 or GI 17230725), *Azospirillum brasilense* (e.g., Genbank Accession No. GI 1174156) and *Anabaena* M22983 (e.g., Genbank Accession No. GI 152445). In some embodiments, the isolated DNA encodes an *Agrobacterium tumefaciens* anthranilate synthase having, for example, an amino acid sequence having SEQ ID NO:4 or a nucleotide sequence having any one of SEQ ID NO:1 or 75.

Alternatively, the monomeric anthranilate synthase can be a fusion of any available anthranilate synthase α and β domain. Such α and β domains can be derived from from *Zea mays, Ruta graveolens, Sulfolobus solfataricus, Salmonella typhimurium, Serratia marcescens, Escherichia coli, Agrobacterium tumefaciens, Arabidopsis thaliana, Rhizobium meliloti* (e.g., Genbank Accession No. GI 95177), *Mesorhizobium loti* (e.g., Genbank Accession No. GI 13472468), *Brucella melitensis* (e.g., Genbank Accession No. GI 17982357), *Nostoc sp.* PCC7120 (e.g., Genbank Accession No. GI 17227910 or GI 17230725), *Azospirillum brasilense* (e.g., Genbank Accession No. GI 1174156) and *Anabaena* M22983 (e.g., Genbank Accession No. GI 152445)), soybean, rice, cotton, wheat, tobacco or any gene encoding a subunit or domain of anthranilate synthase. For example, nucleic acids encoding such an α or β domain can be obtained by using the sequence information in any of SEQ ID NO:1–70, 75–103.

In another embodiment, the invention provides an isolated DNA encoding an α domain of anthranilate synthase from *Zea mays* that comprises SEQ ID NO:5, or SEQ ID NO:66. Such an isolated DNA can have nucleotide sequence SEQ ID NO:2, 67 or 68. The isolated DNA can be operably linked to a promoter and, when expressed in a plant can provide elevated levels of L-tryptophan in the plant.

The isolated DNA can also encode a mutant anthranilate synthase, or a mutant anthranilate synthase domain. Such a mutant anthranilate synthase, or domain thereof, can have one or more mutations. As is known to one of skill in the art, mutations can be silent, can give rise to variant gene products having enzymatic activity similar to wild type or can give rise to derivative gene products that have altered enzymatic acitivity. The invention contemplates all such mutations.

The mutated isolated DNA can be generated from a wild type anthranilate synthase nucleic acid either in vitro or in vivo and can encode, for example, one or more amino acid substitutions, deletions or insertions. Mutant isolated DNAs that generate a mutant anthranilate synthase having increased activity, greater stability, or less sensitivity to feedback inhibition by tryptophan or tryptophan analogs are desirable. In one embodiment, the anthranilate synthase, or a domain thereof, is resistant to inhibition by endogenous L-tryptophan or by tryptophan analogs. For example, the anthranilate synthase can have one or more mutations in the tryptophan-binding pocket or elsewhere that reduces the sensitivity of the anthranilate synthase, or the domain thereof, to tryptophan inhibition. Among the amino acid residues contemplated for mutation are residues, for example, at about positions 48, 51, 52, 293 and 298. For example, the mutation can be:

a) at about position 48 replace Val with Phe;
b) at about position 48 replace Val with Tyr;
c) at about position 51 replace Ser with Phe;
d) at about position 51 replace Ser with Cys;
e) at about position 52 replace Asn with Phe;
f) at about position 293 replace Pro with Ala;
g) at about position 293 replace Pro with Gly; or
h) at about position 298 replace Phe with Trp;

wherein the position of the mutation is determined by alignment of the amino acid sequence of the selected anthranilate synthase with an *Agrobacterium tumefaciens* anthranilate synthase amino acid sequence. Examples of anthranilate synthases having such mutations include those with SEQ ID NO:58–65, 69, 70, 84–94.

The isolated DNA can encode other elements and functions. Any element or function contemplated by one of skill in the art can be included. For example, the isolated DNA can also include a promoter that can function in a plant cell that is operably linked to the DNA encoding the anthranilate synthase. The isolated DNA can further encode a plastid transit peptide. The isolated DNA can also encode a selectable marker or a reporter gene. Such a selectable marker gene can impart herbicide resistance to cells of said plant, high protein content, high oil content, high lysine content, high isoleucine content, high tocopherol content and the like. The DNA sequence can also comprise a sequence encoding one or more of the insecticidal proteins derived from *Bacillus thuringiensis*.

The invention further provides vectors comprising an isolated DNA of the invention. Such vectors can be used to express anthranilate synthase polypeptides in prokaryotic and eukaryotic cells, to transform plant cells and to generate transgenic plants.

The invention also provides a transgenic plant comprising an isolated DNA of the invention. Expression of these isolated DNAs in the transgenic plant can result in an elevated level of L-tryptophan, preferably free L-tryptophan, in the transgenic plant, e.g., in the seeds or other parts of the plant. The level is increased above the level of L-tryptophan in the cells of a plant that differ from the cells of the transgenic soybean plant by the absence of the DNA, e.g., the corresponding untransformed cells or an untransformed plant with the same genetic background. The DNA is preferably heritable in that it is preferably transmitted through a complete normal sexual cycle of the fertile plant to its progeny and to further generations.

Transgenic plants that can have such an isolated DNA include dicotyledonous plants (dicots), for example, soybean or canola. Alternatively, the transgenic plants can be monocotyledonous plants (monocots), for example, maize, rice, wheat, barley or sorghum.

The invention also provides a seed of any of the transgenic plants containing any of the isolated DNAs, anthranilate synthase polypeptides, transgenes or vectors of the invention.

The invention further provides an animal feed or human food that contains at least a portion of a plant having an isolated DNA of the invention. Portions of plants that can be included in the animal feed or human food include, for example, seeds, leaves, stems, roots, tubers, or fruits. Desirable portions of plants have increased levels of tryptophan provided by expression of an anthranilate synthase encoded by an isolated DNA of the invention.

The invention further provides a method for altering, preferably increasing, the tryptophan content of a plant (dicot or a monocot) by introducing an isolated DNA of the invention into regenerable cells of the plant. The DNA sequence is preferably operably linked to at least one promoter operable in the plant cells. The transformed cells are identified or selected, and then regenerated to yield a plant comprising cells that can express a functional anthranilate synthase polypeptide. In some embodiments, the DNA encoding the anthranilate synthase, or domain thereof, is a mutant DNA. The introduced DNA is preferably heritable and the plant is preferably a fertile plant. For example, the introduced DNA preferably can be passed by a complete sexual cycle to progeny plants, and can impart the high tryptophan phenotype to subsequent generations of progeny.

The anthranilate synthase-encoding DNAs, are preferably incorporated into vectors or "transgenes" that can also include DNA sequences encoding transit peptides, such as plastid transit peptides, and selectable marker or reporter genes, operably linked to one or more promoters that are functional in cells of the target plant. The promoter can be, for example, an inducible promoter, a tissue specific promoter, a strong promoter or a weak promoter. Other transcription or translation regulatory elements, e.g., enhancers or terminators, can also be functionally linked to the anthranilate synthase-encoding DNA segment.

Cells in suspension culture or as embryos, intact tissues or organs can be transformed by a wide variety of transformation techniques, for example, by microprojectile bombardment, electroporation and *Agrobacterium tumefaciens*-mediated transformation, and other procedures available to the art.

Thus, the cells of the transformed plant comprise a native anthranilate synthase gene and a transgene or other DNA segment encoding an exogenous anthranilate synthase. The expression of the exogenous anthranilate synthase in the cells of the plant can lead to increased levels of tryptophan and its secondary metabolites. In some embodiments, such expression confers tolerance to an amount of endogenous L-tryptophan analogue, for example, so that at least about 10% more anthranilate synthase activity is present than in a plant cell having a wild type or tryptophan-sensitive anthranilate synthase.

The invention also provides a method for altering the tryptophan content in a plant comprising: (a) introducing into regenerable cells of a plant a transgene comprising an isolated DNA encoding an anthranilate synthase domain and a plastid transit peptide, operably linked to a promoter functional in the plant cell to yield transformed cells; and (b) regenerating a transformed plant from said transformed plant cells wherein the cells of the plant express the anthranilate synthase domain encoded by the isolated DNA in an amount effective to increase the tryptophan content in said plant relative to the tryptophan content in an untransformed plant of the same gentic background. The domain can be an anthranilate synthase α-domain. The anthranilate synthase domain can have one or more mutations, for example, mutations that reduce the sensitivity of the domain to tryptophan inhibition. Such mutations can be, for example, in the tryptophan-binding pocket. Such a domain can be, for example, an anthranilate synthase domain from *Agrobacterium tumefaciens*, *Anabaena* M22983, *Arabidopsis thaliana*, *Azospirillum brasilense*, *Brucella melitensis*, *Escherichia coli*, *Euglena gracilis*, *Mesorhizobium loti*, *Nostoc* sp. PCC7120, *Rhizobium meliloti*, *Ruta graveolens*, *Rhodopseudomonas palustris*, *Salmonella typhimurium*, *Serratia marcescens*, *Sulfolobus solfataricus*, soybean, rice, cotton or *Zea mays*. *Ruta graveolens* has its own chloroplast transport sequence that may be used with the anthranilate synthase transgene. Accordingly, one of skill in the art may not need to add a plastid transport sequence when using a *Ruta graveolens* DNA.

The present invention also provides novel isolated and purified DNA molecules comprising a DNA encoding a monomeric anthranilate synthase, or a domain thereof. Such an anthranilate synthase DNA can provide high levels of tryptophan when expressed within a plant. In some embodiments, the anthranilate synthase is substantially resistant to inhibition by free L-tryptophan or an analog thereof. Examples of novel DNA sequences contemplated by the invention include but are not limited to DNA molecules isolated from *Agrobacterium tumefaciens, Anabaena* M22983, *Arabidopsis thaliana, Azospirillum brasilense, Brucella melitensis, Escherichia coli, Euglena gracilis, Mesorhizobium loti, Nostoc* sp. PCC7120, *Rhizobium meliloti, Ruta graveolens, Rhodopseudomonas palustris, Salmonella typhimurium, Serratia marcescens, Sulfolobus solfataricus*, or *Zea mays* (maize) or other such anthranilate synthases.

These DNA sequences include synthetic or naturally-occurring monomeric forms of anthranilate synthase that have the α-domain of anthranilate synthase linked to at least one other anthranilate synthase domain on a single polypeptide chain. The monomeric anthranilate synthase can, for example, be a fusion of an anthranilate synthase α or β domain. Such an anthranilate synthase α or β domain can be derived from *Agrobacterium tumefaciens, Anabaena* M22983, *Arabidopsis thaliana, Azospirillum brasilense, Brucella melitensis, Escherichia coli, Euglena gracilis, Mesorhizobium loti, Nostoc* sp. PCC7120, *Rhizobium meliloti, Ruta graveolens, Rhodopseudomonas palustris, Salmonella typhimurium, Serratia marcescens, Sulfolobus solfataricus*, soybean, rice, cotton, wheat, tobacco or *Zea mays* (maize) or any gene encoding a subunit or domain of anthranilate synthase. Such anthranilate synthases and domains thereof are also exemplified herein by the anthranilate synthase nucleic acids isolated from *Agrobacterium tumefaciens*, (SEQ ID NO:1, 75, 84–94), *Zea mays*, (SEQ ID NO:2, 67, 68, 96), *Ruta graveolens* (SEQ ID NO:3), *Anabaena* M22983, *Arabidopsis thaliana* (SEQ ID NO:45), *Azospirillum brasilense* (SEQ ID NO:78), *Brucella melitensis* (SEQ ID NO:79), *Mesorhizobium loti* (SEQ ID NO:77), *Nostoc* sp. PCC7120 (SEQ ID NO:80 or 81), *Rhizobium meliloti* (SEQ ID NO:7), *Rhodopseudomonas palustris* (SEQ ID NO:57), *Sulfolobus solfataricus* (SEQ ID NO:8), rice (SEQ ID NO:94 or 95), wheat (SEQ ID NO:97), or tobacco (SEQ ID NO:98). These nucleotide sequences encode anthranilate synthases or a-domains thereof from *Agrobacterium tumefaciens* (SEQ ID NO:4, 58–65, 69, 70,); *Zea mays* (SEQ ID NO:5, 66 or 101) and *Ruta graveolens* (SEQ ID NO:6), *Anabaena* M22983, *Azospirillum brasilense* (SEQ ID NO:78), *Brucella melitensis* (SEQ ID NO:79), *Mesorhizobium loti* (SEQ ID NO:77), *Nostoc* sp. PCC7120 (SEQ ID NO:80 or 81), *Rhizobium meliloti* (SEQ ID NO:7 or 43), *Rhodopseudomonas palustris* (SEQ ID NO:57 or 82), *Sulfolobus solfataricus* (SEQ ID NO:8 or 44), rice (SEQ ID NO:99 or 100), wheat (SEQ ID NO:102), or tobacco (SEQ ID NO:103).

The invention also provides an isolated DNA molecule comprising a DNA sequence encoding an *Agrobacterium tumefaciens* anthranilate synthase or a domain thereof having enzymatic activity. Such a DNA molecule can encode an anthranilate synthase having SEQ ID NO:4, 58–65, 69 or 70, a domain or variant thereof having anthranilate synthase activity. The DNA molecule can also have a sequence comprising SEQ ID NO:1, 75, 84–94, or a domain or variant thereof. Coding regions of any DNA molecule provided herein can also be optimized for expression in a selected organism, for example, a selected plant or microbe. An example of a DNA molecule having optimized codon usage for a selected plant is an *Agrobacterium tumefaciens* anthranilate synthase DNA molecule having SEQ ID NO:75.

The invention also provides an isolated and purified DNA molecule comprising a DNA sequence encoding a *Zea mays* anthranilate synthase domain. Such a DNA molecule can encode an anthranilate synthase domain having SEQ ID NO:5, 66 or a variant or derivative thereof having anthranilate synthase activity. The DNA molecule can also have a sequence comprising SEQ ID NO:2, 67 or 68, or a domain or variant thereof.

The invention further provides an isolated DNA molecule of at least 8 nucleotides that hybridizes to the complement of a DNA molecule comprising any one of SEQ ID NO:1, 75 or 84–94 under stringent conditions. Such a DNA molecule can be a probe or a primer, for example, a nucleic acid having any one of SEQ ID NO:9–42 or 47–56. Alternatively, the DNA it can include up to an entire coding region for a selected anthranilate synthase, or a domain thereof. Such a DNA can also include a DNA sequence encoding a promoter operable in plant cells and/or a DNA sequence encoding a plastid transit peptide. The invention further contemplates vectors for transformation and expression of these types of DNA molecules in plants and/or microbes.

Functional anthranilate synthase DNA sequences and functional anthranilate synthase polypeptides that exhibit 50%, preferably 60%, more preferably 70%, even more preferably 80%, most preferably 90%, e.g., 95% to 99%, sequence identity to the DNA sequences and amino acid sequences explicitly described herein are also within the scope of the invention. For example, 85% identity means that 85% of the amino acids are identical when the two sequences are aligned for maximum matching. Gaps (in either of the two sequences being matched) are allowed in maximizing matching; gap lengths of 5 or less are preferred with 2 or less being more preferred.

Alternatively and preferably, two polypeptide sequences are homologous, as this term is used herein, if they have an alignment score of more than 5 (in standard deviation units) using the program ALIGN with the mutation data matrix and a gap penalty of 6 or greater. See Dayhoff, M. O., in Atlas of Protein Sequence and Structure, 1972, volume 5, National Biomedical Research Foundation, pp. 101–110, and Supplement 2 to this volume, pp. 1–10. The two sequences or parts thereof are more preferably homologous if their amino acids are greater than or equal to 50% identical when optimally aligned using the ALIGN program.

The invention further provides expression vectors for generating a transgenic plant with high seed levels of tryptophan comprising an isolated DNA sequence encoding a monomeric anthranilate synthase comprising an anthranilate synthase α-domain linked to an anthranilate synthase β-domain and a plastid transit peptide, operably linked to a promoter functional in a plant cell. Such a monomeric anthranilate synthase can, for example, be an *Agrobacterium tumefaciens, Rhizobium meliloti, Mesorhizobium loti, Brucella melitensis, Nostoc* sp. PCC7120, *Azospirillum brasilense* or *Anabaena* M22983 anthranilate synthase. The monomeric anthranilate synthase can also be a fusion of anthranilate synthase α and β domains derived from *Agrobacterium tumefaciens, Anabaena* M22983, *Arabidopsis thaliana, Azospirillum brasilense, Brucella melitensis, Mesorhizobium loti, Nostoc* sp. PCC7120, *Rhizobium meliloti, Rhodopseudomonas palustris, Ruta graveolens, Sulfolobus solfataricus, Salmonella typhimurium, Serratia marcescens*, soybean, rice, cotton, wheat, tobacco *Zea mays*, or any gene encoding a subunit or domain of anthranilate synthase.

The transmission of the isolated and purified anthranilate synthase DNA providing increased levels of tryptophan can be evaluated at a molecular level, e.g., Southern or Northern blot analysis, PCR-based methodologies, the biochemical or immunological detection of anthranilate synthase, or by phenotypic analyses, i.e., whether cells of the transformed progeny can grow in the presence of an amount of an amino acid analog of tryptophan that inhibits the growth of untransformed plant cells.

The invention also provides a method of producing anthranilate synthase in a prokaryotic or eukaryotic host cell, such as a yeast, insect cell, or bacterium, which can be cultured, preferably on a commercial scale. The method includes the steps of introducing a transgene comprising a DNA segment encoding an anthranilate synthase, or a domain thereof, such as a monomeric anthranilate synthase, comprising at least the α and β anthranilate synthase domains, or functional variant thereof, into a host cell and expressing anthranilate synthase in the host cell so as to yield functional anthranilate synthase or domain thereof. A transgene generally includes transcription and translation regulatory elements, e.g., a promoter, functional in host cell, either of eukaryotic or prokaryotic origin. Preferably, the transgene is introduced into a prokaryotic cell, such as *Escherichia coli*, or a eukaryotic cell, such as a yeast or insect cell, that is known to be useful for production of recombinant proteins. Culturing the transformed cells can lead to enhanced production of tryptophan and its derivatives, which can be recovered from the cells or from the culture media. Accumulation of tryptophan may also lead to the increased production of secondary metabolites in microbes and plants, for example, indole containing metabolites such as simple indoles, indole conjugates, indole alkaloids, indole phytoalexins and indole glucosinalates in plants.

Anthranilate synthases insensitive to tryptophan have the potential to increase a variety of chorismate-derived metabolites, including those derived from phenylalanine due to the stimulation of phenylalanine synthesis by tryptophan via chorismate mutase. See Siehl, D. The biosynthesis of tryptophan, tyrosine, and phenylalanine from chorismate in Plant Amino Acids: Biochemistry and Biotechnology, ed. B K Singh, pp 171–204. Other chorismate-derived metabolites that may increase when feedback insensitive anthranilate synthase s are present include phenylpropanoids, flavonoids, and isoflavonoids, as well as those derived from anthranilate, such as indole, indole alkaloids, and indole glucosinolates. Many of these compounds are important plant hormones, plant defense compounds, chemopreventive agents of various health conditions, and/or pharmacologically active compounds. The range of these compounds whose synthesis might be increased by expression of anthranilate synthase depends on the organism in which the anthranilate synthase is expressed. The invention contemplates synthesis of tryptophan and other useful compounds in a variety of prokaryotic and eukaryotic cells or organisms, including plant cells, microbes, fungi, yeast, bacteria, insect cells, and mammalian cells.

Hence, the invention provides a method for producing tryptophan comprising: culturing a prokaryotic or eukaryotic host cell comprising an isolated DNA under conditions sufficient to express a monomeric anthranilate synthase encoded by the isolated DNA, wherein the monomeric anthranilate synthase comprises an anthranilate synthase α domain and a anthranilate synthase β domain, and wherein the conditions sufficient to express a monomeric anthranilate synthase comprise nutrients and precursors sufficient for the host cell to synthesize tryptophan utilizing the monomeric anthranilate synthase.

Examples of useful compounds that may be generated upon expression in a variety of host cells and/or organisms include indole acetic acid and other auxins, isoflavonoid compounds important to cardiovascular health found in soy, volatile indole compounds which act as signals to natural enemies of herbivorous insects in maize, anticarcinogens such as indole glucosinolates (indole-3-carbinol) found in the Cruciferae plant family, as well as indole alkaloids such as ergot compounds produced by certain species of fungi. (Barnes et al., *Adv Exp Med Biol*, 401, 87 (1996); Frey et al., *Proc Natl Acad Sci*, 97, 14801 (2000); Muller et al., *Biol Chem*, 381, 679 (2000); Mantegani et al., *Farmaco*, 54, 288 (1999); Zeligs, *J Med Food*, 1, 67 (1998); Mash et al., *Ann NY Acad Sci*, 844, 274 (1998); Melanson et al., *Proc Natl Acad Sci*, 94, 13345 (1997); Broadbent et al., *Curr Med Chem*, 5, 469 (1998)).

The present invention also provides an isolated and purified DNA molecule of at least seven nucleotide bases that hybridizes under moderate, and preferably, high stringency conditions to the complement of an anthranilate synthase encoding DNA molecule. Such isolated and purified DNA molecules comprise novel DNA segments encoding anthranilate synthase or a domain or mutant thereof. The mutant DNA can encode an anthranilate synthase that is substantially resistant to inhibition by free L-tryptophan or an amino acid analog of tryptophan. Such anthranilate synthase DNA molecules can hybridize, for example, to an *Agrobacterium tumefaciens, Rhodopseudomonas palustris* or *Ruta graveolens* anthranilate synthase, or an α-domain thereof, including functional mutants thereof When these DNA molecules encode a functional anthranilate synthase or an anthranilate synthase domain, they are termed "variants" of the primary DNA molecules encoding anthranilate synthase, anthranilate synthase domains or mutants thereof. Shorter DNA molecules or oligonucleotides can be employed as primers for amplification of target DNA sequences by PCR, or as intermediates in the synthesis of full-length genes.

Also provided is a hybridization probe comprising a novel isolated and purified DNA segment of at least seven nucleotide bases, which is detectably labeled or which can bind to a detectable label, which DNA segment hybridizes under moderate or, preferably, high stringency conditions to the non-coding strand of a DNA molecule comprising a DNA segment encoding an anthranilate synthase such as a monomeric anthranilate synthase, or a domain thereof, such as the α-domain, including functional mutants thereof, that are substantially resistant to inhibition by an amino acid analog of tryptophan. Moderate and stringent hybridization conditions are well known to the art, see, for example sections 0.47–9.51 of Sambrook et al., Molecular Cloning: A Laboratory Manual, $2^{nd}$ Edition (1989); see also, Sambrook and Russell, Molecular Cloning: A Laboratory Manual, $3^{rd}$ Edition (Jan. 15, 2001). For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5×SSC (0.75 M NaCl, 0.075 M sodium citrate), 50 mM sodium phosphate (pH 6.8), 0.1% sodium pyrophosphate, 5×Denhardt's solution, sonicated salmon sperm DNA (50 μg/ml), 0.1% sodium dodecylsulfate (SDS), and 10% dextran sulfate at 42° C., with washes at 42° C. in 0.2×SSC and 0.1% SDS.

BRIEF DESCRIPTION OF THE FIGURES

FIG. 2 depicts the translated sequence of the *Agrobacterium tumefaciens* anthranilate synthase DNA sequence (upper sequence) (SEQ ID NO:4) and the translated sequence of the anthranilate synthase DNA sequence from *Rhizobium meliloti* (lower sequence) (SEQ ID NO:7).

FIG. 6(A–B) depicts an anthranilate synthase amino acid sequence alignment comparing the *Agrobacterium tumefaciens* α-domain sequence (SEQ ID NO:4) and the *Sulfolobus solfataricus* α-domain sequence (SEQ ID NO:8).

FIG. 7(A–B) depicts the sequences of the 34 primers (SEQ ID NOs 9–42) used to mutate SEQ ID NO:1. The mutated codons are underlined and the changed bases are in lower case.

FIG. 21(A–D) depicts a multiple sequence alignment of monomeric "TrpEG" anthranilate synthases having SEQ ID NO:4 and 43 (derived from *Agrobacterium tumefaciens* and *Rhizobium meliloti*, respectively) with the TrpE (α) and TrpG (β) domains of heterotetrameric anthranilate synthases from *Sulfolobus solfataricus* (SEQ ID NO:44) and *Arabidopsis thaliana* (SEQ ID NO:45). Linker regions are underlined.

FIG. 30 depicts the sequence of the truncated trpE gene of *Escherichia coli* EMG2 (K-12 wt F+) (SEQ ID NO:46). The first 30 bp and the last 150 bp of this trpE nucleic acid are connected by an EcoR1 restriction site. The beginning of the trpG gene follows the trpE stop codon.

FIG. 32(A–C) depicts the DNA (SEQ ID NO:1) and amino acid (SEQ ID NO:4) sequences of the α-domain of the anthranilate synthase gene isolated from *Agrobacterium tumefaciens*.

FIG. 33 (A–C) depicts the DNA (SEQ ID NO:2) sequence of the α-domain of the anthranilate synthase gene isolated from *Zea mays*. FIG. 33(D) depicts the amino acid (SEQ ID NO:5) sequence of the α-domain of the anthranilate synthase gene isolated from *Zea mays*.

FIG. 35(A–E) provides a sequence comparison of anthranilate synthase amino acid sequences from *Agrobacterium tumefaciens* (AgrTu__15889565) (SEQ ID NO:4), *Rhizobium meliloti* (RhiMe__136328) (SEQ ID NO:7), *Mesorhizobium loti* (MesLo__13472468) (SEQ ID NO:77), *Azospirillum brasilense* (AzoBr__717765) (SEQ ID NO:78), *Brucella melitensis* (BruMe__17986732) (SEQ ID NO:79), *Nostoc* sp. (Nostoc__17227910) (SEQ ID NO:80), *Nostoc* sp. (Nostoc__17230725) (SEQ ID NO:81), and *Rhodopseudomonas palustris* (RhoPa_TrpEG) (SEQ ID NO:82).

FIG. 36(A–B) provides an optimized nucleotide sequence for *Agrobacterium tumefaciens* anthranilate synthase (SEQ ID NO:75).

FIG. 37 (A–C) provides an alignment of the wild type (top strand) and optimized (bottom strand) *Agrobacterium tumefaciens* anthranilate synthase nucleotide sequences (SEQ ID NO:1 and 75). These two sequences are 94% identical.

DETAILED DESCRIPTION OF THE INVENTION

Figure 1:
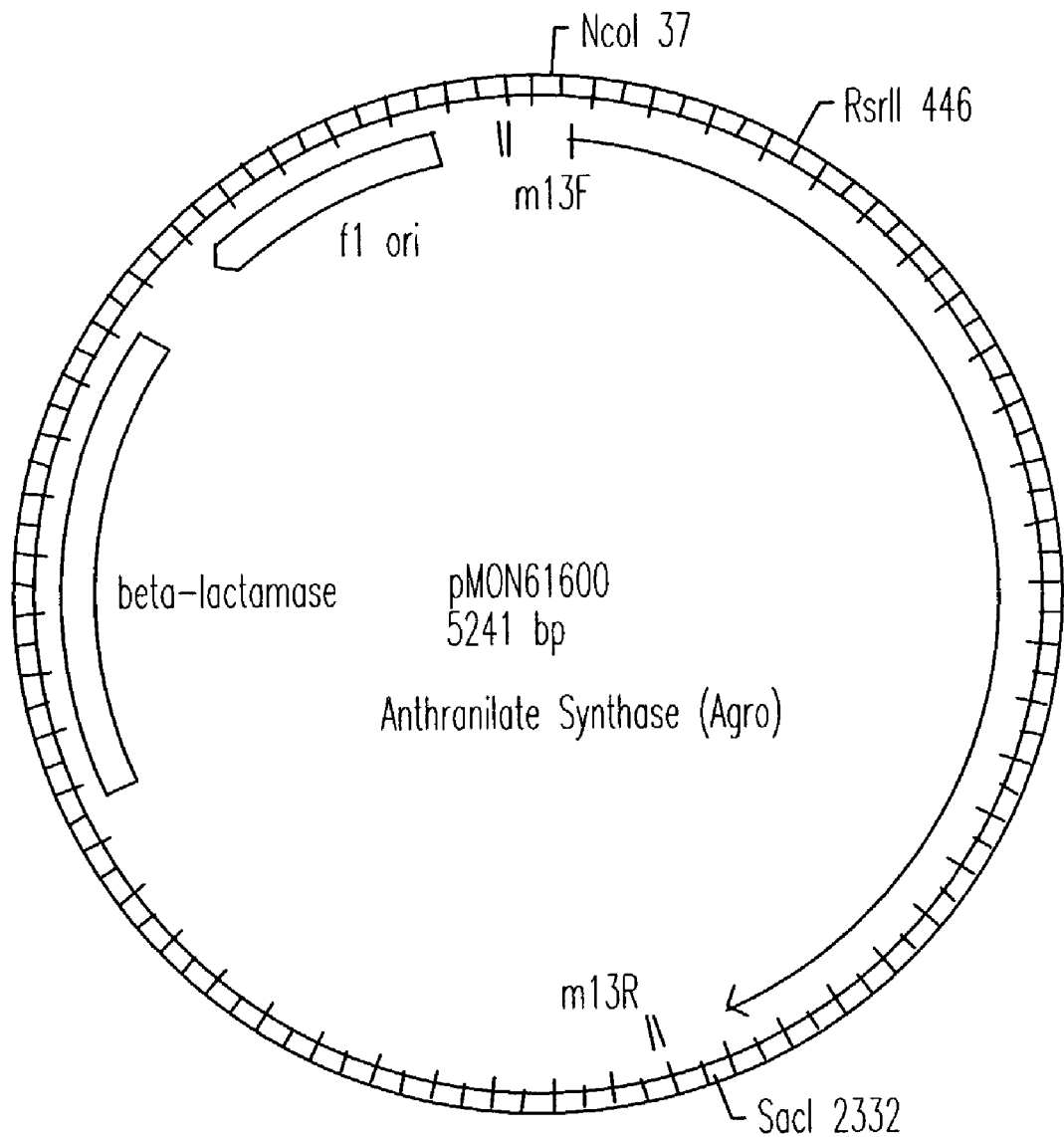
FIG. 1 is a restriction map of pMON61600.

The present invention provides isolated DNAs, vectors, host cells and transgenic plants comprising an isolated nucleic acid encoding an anthranilate synthase capable of providing high levels of tryptophan upon expression within the plant. In one embodiment, the isolated nucleic acid encodes a monomeric anthranilate synthase (AS). In other embodiments, the isolated nucleic acid encodes an anthranilate synthase, or a domain thereof, that is substantially resistant to inhibition by free L-tryptophan or an amino acid analog of tryptophan. Expression of the anthranilate synthase, or domain thereof, elevates the level of tryptophan, e.g., free tryptophan in the seed, over the level present in the plant absent such expression.

Methods are also provided for producing transgenic plants having nucleic acids associated with increased anthranilate synthase activity, and producing cultured cells, plant tissues, plants, plant parts and seeds that produce high levels of tryptophan. Such transgenic plants can preferably sexually transmit the ability to produce high levels of tryptophan to their progeny. Also described are methods for producing isolated DNAs encoding mutant anthranilate synthases, and cell culture selection techniques to select for novel genotypes that overproduce tryptophan and/or are resistant to tryptophan analogs. For example, to produce soybean lines capable of producing high levels of tryptophan, transgenic soybean cells that contain at least on of the isolated DNAs of the invention, are prepared and characterized, then regenerated into plants. Some of the isolated DNAs are resistant to growth inhibition by the tryptophan analog. The methods provided in the present invention may also be used to produce increased levels of free tryptophan in dicot plants, such as other legumes, as well as in monocots, such as the cereal grains.

Definitions

As used herein, "altered" levels of tryptophan in a transformed plant, plant tissue, plant part or plant cell are levels which are greater or lesser than the levels found in the corresponding untransformed plant, plant tissue, plant part or plant cell.

As used herein, a "α-domain" is a portion of an enzyme or enzymatic complex that binds chorismate and eliminates the enolpyruvate side chain. Such an α-domain can be encoded by a TrpE gene. In some instances, the α-domain is a single polypeptide that functions only to bind chorismate and to eliminate the enolpyruvate side chain from chorismate. In other instances, the α-domain is part of a larger polypeptide that can carry out other enzymatic functions in addition to binding chorismate and eliminating the enolpyruvate side chain from chorismate.

The term "β-domain" refers to a portion of an enzyme or enzymatic complex that transfers an amino group from glutamine to the position on the chorismate ring that resides between the carboxylate and the enolpyruvate moieties. Such a β-domain can be encoded by a TrpG gene. In some instances, the β-domain is a single polypeptide that functions only to transfer an amino group from glutamine to the position on the chorismate ring that resides between the carboxylate and the enolpyruvate moieties. In other instances, the β-domain is part of a larger polypeptide that can carry out other enzymatic functions in addition to transferring an amino group from glutamine to the position on the chorismate ring that resides between the carboxylate and the enolpyruvate moieties.

As used herein, "an amino acid analog of tryptophan" is an amino acid that is structurally related to tryptophan and that can bind to the tryptophan-binding site in a wild type anthranilate synthase. These analogs include, but are not limited to, 6-methylanthranilate, 5-methyltryptophan, 4-methyltryptophan, 5-fluorotryptophan, 5-hydroxytryptophan, 7-azatryptophan, 3β-indoleacrylic acid, 3-methylanthranilic acid, and the like.

The term "consists essentially of" as used with respect to the present DNA molecules, sequences or segments is defined to mean that a major portion of the DNA molecule, sequence or segment encodes an anthranilate synthase. Unless otherwise indicated, the DNA molecule, sequence or segment generally does not encode proteins other than an anthranilate synthase.

The term "complementary to" is used herein to mean that the sequence of a nucleic acid strand could hybridize to all, or a portion, of a reference polynucleotide sequence. For illustration, the nucleotide sequence "TATAC" has 100% identity to a reference sequence 5'-TATAC-3' but is 100% complementary to a reference sequence 5'-GTATA-3'.

As used herein, an "exogenous" anthranilate synthase is an anthranilate synthase that is encoded by an isolated DNA that has been introduced into a host cell, and that is preferably not identical to any DNA sequence present in the cell in its native, untransformed state. An "endogenous" or "native" anthranilate synthase is an anthranilate synthase that is naturally present in a host cell or organism.

As used herein, "increased" or "elevated" levels of free L-tryptophan in a plant cell, plant tissue, plant part or plant are levels that are about 2 to 200 times, preferably about 5 to 150 times, and more preferably about 10–100 times, the levels found in an untransformed plant cell, plant tissue, plant part or plant, i.e., one where the genome has not been altered by the presence of an exogenous anthranilate synthase nucleic acid or domain thereof. For example, the levels of free L-tryptophan in a transformed plant seed are compared with those in an untransformed plant seed ("the starting material").

DNA molecules encoding an anthranilate synthase, and DNA molecules encoding a transit peptide or marker/reporter gene are "isolated" in that they were taken from their natural source and are no longer within the cell where they normally exist. Such isolated DNA molecules may have been at least partially prepared or manipulated in vitro, e.g., isolated from a cell in which they are normally found, purified, and amplified. Such isolated DNA molecules can also be "recombinant" in that they have been combined with exogenous DNA molecules or segments. For example, a recombinant DNA can be an isolated DNA that is operably linked to an exogenous promoter, or to a promoter that is endogenous to the host cell.

As used herein with respect to anthranilate synthase, the term "monomeric" means that two or more anthranilate synthase domains are incorporated in a functional manner into a single polypeptide chain. The monomeric anthranilate synthase may be assembled in vivo into a dimeric form. Monomeric anthranilate synthase nucleic acids and polypeptides can be isolated from various organisms such as *Agrobacterium tumefaciens*, *Anabaena* M22983, *Azospirillum brasilense*, *Brucella melitensis*, *Euglena gracilis*, *Mesorhizobium loti*, *Nostoc sp.* PCC7120 or *Rhizobium meliloti*. Alternatively, monomeric anthranilate synthase nucleic acids and polypeptides can be constructed from a combination of domains selected from any convenient monomeric or multimeric anthranilate synthase gene. Such organisms include, for example, *Agrobacterium tumefaciens*, *Anabaena* M22983, *Arabidopsis thaliana*, *Azospirillum brasilense*, *Brucella melitensis*, *Mesorhizobium loti*, *Nostoc sp.* PCC7120, *Rhizobium meliloti*, *Rhodopseudomonas palustris*, *Ruta graveolens*, *Sulfolobus solfataricus*, *Salmonella typhimurium*, *Serratia marcescens*, soybean, rice, cotton *Zea mays*, or any gene encoding a subunit or domain of anthranilate synthase. Nucleic acids encoding the selected domains can be linked recombinantly. For example, a nucleic acid encoding the C-terminus of an α-domain can be linked to a nucleic acid encoding the N-terminus of the β-domain, or vice versa, by forming a phosphodiester bond. As an alternative, such single domain polypeptides can be linked chemically. For example, the α-domain can be linked via its C-terminus to the N-terminus of the β-domain, or vice versa, by forming a peptide bond.

As used herein, a "native" gene means a gene that has not been changed in vitro, i.e., a "wild-type" gene that has not been mutated in vitro.

The term "plastid" refers to the class of plant cell organelles that includes amyloplasts, chloroplasts, chromoplasts, elaioplasts, eoplasts, etioplasts, leucoplasts, and proplastids. These organelles are self-replicating, and contain what is commonly referred to as a "chloroplast genome," a circular DNA molecule that ranges in size from about 120 to about 217 kb, depending upon the plant species, and which usually contains an inverted repeat region.

As used herein, "polypeptide" means a continuous chain of amino acids that are all linked together by peptide bonds, except for the N-terminal and C-terminal amino acids that have amino and carboxylate groups, respectively, and that are not linked in peptide bonds. Polypeptides can have any length and can be post-translationally modified, for example, by glycosylation or phosphorylation.

As used herein, a plant cell, plant tissue or plant that is "resistant or tolerant to inhibition by an amino acid analog of tryptophan" is a plant cell, plant tissue, or plant that retains at least about 10% more anthranilate synthase activity in the presence of an analog of L-tryptophan, than a corresponding wild type anthranilate synthase. In general, a plant cell, plant tissue, or plant that is "resistant or tolerant to inhibition by an amino acid analog of tryptophan" can grow in an amount of an amino acid analog of tryptophan that normally inhibits growth of the untransformed plant cell, plant tissue, or plant, as determined by methodologies known to the art. For example, a homozygous backcross converted inbred plant transformed with a DNA molecule that encodes an anthranilate synthase that is substantially resistant or tolerant to inhibition by an amino acid analog of tryptophan grows in an amount of an amino acid analog of tryptophan that inhibits the growth of the corresponding, i.e., substantially isogenic, recurrent inbred plant.

As used herein, an anthranilate synthase that is "resistant or tolerant to inhibition by tryptophan or an amino acid analog of tryptophan" is an anthranilate synthase that retains greater than about 10% more activity than a corresponding "wild-type" or native susceptible anthranilate synthase, when the tolerant/resistant and wild type anthranilate synthases are exposed to equivalent amounts of tryptophan or an amino acid analog of tryptophan. Preferably the resistant or tolerant anthranilate synthase retains greater than about 20% more activity than a corresponding "wild-type" or native susceptible anthranilate synthase.

As used herein with respect to anthranilate synthase, the term "a domain thereof," includes a structural or functional segment of a full-length anthranilate synthase. A structural domain includes an identifiable structure within the anthranilate synthase. An example of a structural domain includes an alpha helix, a beta sheet, an active site, a substrate or inhibitor binding site and the like. A functional domain includes a segment of an anthranilate synthase that performs an identifiable function such as a tryptophan binding pocket, an active site or a substrate or inhibitor binding site. Functional domains of anthranilate synthase include those portions of anthranilate synthase that can catalyze one step in the biosynthetic pathway of tryptophan. For example, an α-domain is a domain that can be encoded by trpE and that can transfer $NH_3$ to chorismate and form anthranilate. A β-domain can be encoded by trpG and can remove an amino group from glutamine to form ammonia. Hence, a functional domain includes enzymatically active fragments and domains of an anthranilate synthase. Mutant domains of anthranilate synthase are also contemplated. Wild type anthranilate synthase nucleic acids utilized to make mutant domains include, for example, any nucleic acid encoding a domain of *Agrobacterium tumefaciens, Anabaena* M22983, *Arabidopsis thaliana, Azospirillum brasilense, Brucella melitensis, Mesorhizobium loti, Nostoc* sp. PCC7120, *Rhizobium meliloti, Rhodopseudomonas palustris, Rula graveolens, Sulfolobus solfataricus, Salmonella typhimurium, Serratia marcescens,* soybean, rice, cotton, wheat, tobacco *Zea mays*, or any gene encoding a subunit or domain of anthranilate synthase that can comprise at least one amino acid substitution in the coding region thereof. Domains that are mutated or joined to form a monomeric anthranilate sysnthase having increased tryptophan biosynthetic activity, greater stability, reduced sensitivity to tryptophan or an analog thereof, and the like, are of particular interest.

General Concepts

The present invention relates to novel nucleic acids and methods for obtaining plants that produce elevated levels of free L-tryptophan. The overproduction results from the introduction and expression of a nucleic acid encoding anthranilate synthase, or a domain thereof. Such anthranilate synthase nucleic acids include wild type or mutant α-domains, or monomeric forms of anthranilate synthase. A monomeric form of anthranilate synthase comprises at least two anthranilate synthase domains in a single polypeptide chain, e.g., an α-domain linked to a β-domain.

Native plant anthranilate synthases are generally quite sensitive to feedback inhibition by L-tryptophan and analogs thereof. Such inhibition constitutes a key mechanism for regulating the tryptophan synthetic pathway. Therefore, an anthranilate synthase or a domain thereof that is highly active, more efficient or that is inhibited to a lesser extent by tryptophan or an analog thereof will likely produce elevated levels of tryptophan. According to the invention, the *Agrobacterium tumefaciens* anthranilate synthase is particularly useful for producing high levels of tryptophan.

To generate high levels of tryptophan in a plant or a selected host cell, the selected anthranilate synthase nucleic acid is isolated and may be manipulated in vitro to include regulatory signals required for gene expression in plant cells or other cell types. Because the tryptophan biosynthetic pathway in plants is reported to be present within plastids, the exogenous anthranilate synthase nucleic acids are either introduced into plastids or are modified by adding a nucleic acid segment encoding an amino-terminal plastid transit peptide. Such a plastid transit peptide can direct the anthranilate synthase gene product into plastids. In some instances the anthranilate synthase may already contain a plastid transport sequence, in which case there is no need to add one.

In order to alter the biosynthesis of tryptophan, the nucleic acid encoding an anthranilate synthase activity must be introduced into plant cells or other host cells and these transformed cells identified, either directly or indirectly. An entire anthranilate synthase or a useful portion or domain thereof can be used. The anthranilate synthase is stably incorporated into the plant cell genome. The transcriptional signals controlling expression of the anthranilate synthase must be recognized by and be functional within the plant cells or other host cells. That is, the anthranilate synthase must be transcribed into messenger RNA, and the mRNA must be stable in the plant cell nucleus and be transported intact to the cytoplasm for translation. The anthranilate synthase mRNA must have appropriate translational signals to be recognized and properly translated by plant cell ribosomes. The polypeptide gene product must substantially escape proteolytic attack in the cytoplasm, be transported into the correct cellular compartment (e.g. a plastid) and be able to assume a three-dimensional conformation that will confer enzymatic activity. The anthranilate synthase must further be able to function in the biosynthesis of tryptophan and its derivatives; that is, it must be localized near the native plant enzymes catalyzing the flanking steps in biosynthesis (presumably in a plastid) in order to obtain the required substrates and to pass on the appropriate product.

Even if all these conditions are met, successful overproduction of tryptophan is not a predictable event. The expression of some transgenes may be negatively affected by nearby chromosomal elements. If the high level of tryptophan is achieved by mutation to reduce feedback inhibition, there may be other control mechanisms compensating for the reduced regulation at the anthranilate synthase step. There may be mechanisms that increase the rate of breakdown of the accumulated amino acids. Tryptophan and related amino acids must be also overproduced at levels that are not toxic to the plant. Finally, the introduced trait must be stable and heritable in order to permit commercial development and use.

Isolation and Identification of DNA Coding for an Anthranilate Synthase Nucleic acids encoding an anthranilate synthase can be identified and isolated by standard methods, for eample, as described by Sambrook et al., Molecular Cloning: A Laboratory Manual, $2^{nd}$ Edition (1989); Sambrook and Russell, Molecular Cloning: A Laboratory Manual, $3^{rd}$ Edition (Jan. 15, 2001). For example, a DNA sequence encoding an anthranilate synthase or a domain thereof can be identified by screening of a DNA or cDNA library generated from nucleic acid derived from a particular cell type, cell line, primary cells, or tissue. Examples of libraries useful for identifying and isolating an anthranilate synthase include, but are not limited to, a cDNA library derived from *Agrobacterium tumefaciens* strain A348, maize inbred line B73 (Stratagene, La Jolla, Calif., Cat. #937005, Clontech, Palo Alto, Calif., Cat. #FL1032a, #FL1032b, and FL1032n), genomic library from maize inbred line Mo17 (Stratagene, Cat. #946102), genomic library from maize inbred line B73 (Clontech, Cat. #FL1032d), genomic DNA from *Anabaena* M22983 (e.g., Genbank Accession No. GI 152445), *Arabidopsis thaliana, Azospirillum brasilense* (e.g., Genbank Accession No. GI 1174156), *Brucella melitensis* (GI 17982357), *Escherichia coli, Euglena gracilis, Mesorhizobium loti* (e.g., Genbank Accession No. GI 13472468), *Nostoc sp.* PCC7120 (e.g., Genbank Accession No. GI 17227910 or GI 17230725), *Rhizobium meliloti* (e.g., Genbank Accession No. GI 95177), *Ruta graveolens, Rhodopseudomonas palustris, Salmonella typhimurium, Serratia marcescens, Sulfolobus solfataricus,* soybean, rice, cotton, wheat, tobacco *Zea mays* (maize) or other species. Moreover, anthranilate synthase nucleic acids can be isolated by nucleic acid amplification procedures using genomic DNA, mRNA or cDNA isolated from any of these species.

Screening for DNA fragments that encode all or a portion of the sequence encoding an anthranilate synthase can be accomplished by screening plaques from a genomic or cDNA library for hybridization to a probe of an anthranilate synthase gene from other organisms or by screening plaques from a cDNA expression library for binding to antibodies that specifically recognize anthranilate synthase. DNA fragments that hybridize to anthranilate synthase probes from other organisms and/or plaques carrying DNA fragments that are immunoreactive with antibodies to anthranilate synthase can be subcloned into a vector and sequenced and/or used as probes to identify other cDNA or genomic sequences encoding all or a portion of the desired anthranilate synthase gene. Preferred cDNA probes for screening a maize or plant library can be obtained from plasmid clones pDPG600 or pDPG602.

A cDNA library can be prepared, for example, by random oligo priming or oligo dT priming. Plaques containing DNA fragments can be screened with probes or antibodies specific for anthranilate synthase. DNA fragments encoding a portion of an anthranilate synthase gene can be subcloned and sequenced and used as probes to identify a genomic anthranilate synthase gene. DNA fragments encoding a portion of a bacterial or plant anthranilate synthase can be verified by determining sequence homology with other known anthranilate synthase genes or by hybridization to anthranilate synthase-specific messenger RNA. Once cDNA fragments encoding portions of the 5', middle and 3' ends of an anthranilate synthase are obtained, they can be used as probes to identify and clone a complete genomic copy of the anthranilate synthase gene from a genomic library.

Portions of the genomic copy or copies of an anthranilate synthase gene can be sequenced and the 5' end of the gene identified by standard methods including either by DNA sequence homology to other anthranilate synthase genes or by RNAase protection analysis, for example, as described by Sambrook et al., Molecular Cloning: A Laboratory Manual, $2^{nd}$ Edition (1989); Sambrook and Russell, Molecular Cloning: A Laboratory Manual, $3^{rd}$ Edition (Jan. 15, 2001). The 3' and 5' ends of the target gene can also be located by computer searches of genomic sequence databases using known AS coding regions. Once portions of the 5' end of the gene are identified, complete copies of the anthranilate synthase gene can be obtained by standard methods, including cloning or polymerase chain reaction (PCR) synthesis using oligonucleotide primers complementary to the DNA sequence at the 5' end of the gene. The presence of an isolated full-length copy of the anthranilate synthase gene can be verified by hybridization, partial sequence analysis, or by expression of a maize anthranilate synthase enzyme.

Exemplary isolated DNAs of the invention include DNAs having the following nucleotide SEQ ID NO:

SEQ ID NO:1—*Agrobacterium tumefaciens* (wild type)
SEQ ID NO:2—*Zea mays* (wild type)
SEQ ID NO:3—*Ruta graveolens*
SEQ ID NO:46—truncated TrpE gene of *E. coli* EMG2 (K-12 wt F+)
SEQ ID NO:67—*Zea mays* (C28 mutant)
SEQ ID NO:68—*Zea mays* (C28+ terminator)
SEQ ID NO:71—Chloroplast Targeting Peptide (g)
SEQ ID NO:73—Chloroplast Targeting Peptide (a)
SEQ ID NO:75—*Agrobacterium tumefaciens* (optimized)
SEQ ID NO:76—*Rhodopseudomonas palustris*
SEQ ID NO:83—*Rhodopseudomonas palustris (RhoPa_TrpEG)*
SEQ ID NO:84—*Agrobacterium tumefaciens* V48F mutant
SEQ ID NO:85—*Agrobacterium tumefaciens* V48Y mutant
SEQ ID NO:86—*Agrobacterium tumefaciens* S51F mutant
SEQ ID NO:87—*Agrobacterium tumefaciens* S51C mutant
SEQ ID NO:88—*Agrobacterium tumefaciens* N52F mutant
SEQ ID NO:89—*Agrobacterium tumefaciens* P293A mutant
SEQ ID NO:90—*Agrobacterium tumefaciens* P293G mutant
SEQ ID NO:91—*Agrobacterium tumefaciens* F298W mutant
SEQ ID NO:92—*Agrobacterium tumefaciens* S50K mutant
SEQ ID NO:93—*Agrobacterium tumefaciens* F298A mutant
SEQ ID NO:94—rice
SEQ ID NO:95—rice isozyme
SEQ ID NO:96—maize (U.S. Pat. No. 6,118,047 to Anderson)
SEQ ID NO:97—wheat
SEQ ID NO:98—tobacco Certain primers are also useful for the practise of the invention, for example, primers having SEQ ID NO:9–42, 47–56.

The invention also contemplates any isolated nucleic acid encoding an anthranilate synthase having, for example, any one of the following amino acid sequences.

SEQ ID NO:4 *Agrobacterium tumefaciens* (wild type)
SEQ ID NO:5 *Zea mays* (wild type)
SEQ ID NO:6 *Ruta graveolens*
SEQ ID NO:7 *Rhizobium meliloti*
SEQ ID NO:8 *Sulfolobus solfataricus*
SEQ ID NO:43 *Rhizobium meliloti*
SEQ ID NO:44 *Sulfolobus solfataricus*
SEQ ID NO:45 *Arabidopsis thaliana*
SEQ ID NO:57 *Rhodopseudomonas palustris*
SEQ ID NO:58 *Agrobacterium tumefaciens* V48F mutant
SEQ ID NO:59 *Agrobacterium tumefaciens* V48Y mutant
SEQ ID NO:60 *Agrobacterium tumefaciens* S51F mutant
SEQ ID NO:61 *Agrobacterium tumefaciens* S51C mutant
SEQ ID NO:62 *Agrobacterium tumefaciens* N52F mutant
SEQ ID NO:63 *Agrobacterium tumefaciens* P293A mutant
SEQ ID NO:64 *Agrobacterium tumefaciens* P293G mutant
SEQ ID NO:65 *Agrobacterium tumefaciens* F298W mutant
SEQ ID NO:66 *Zea mays* C28 mutant
SEQ ID NO:69 *Agrobacterium tumefaciens* S50K mutant
SEQ ID NO:70 *Agrobacterium tumefaciens* F298A mutant
SEQ ID NO:74 Chloroplast Targeting Peptide (a)
SEQ ID NO:72 Chloroplast Targeting Peptide (g)
SEQ ID NO:77 *Mesorhizobium loti* (MesLo__13472468)
SEQ ID NO:78 *Azospirillum brasilense* (AzoBr__1717765)
SEQ ID NO:79 *Brucella melitensis* (BruMe__17986732)
SEQ ID NO:80 *Nostoc* sp. (Nostoc__17227910)
SEQ ID NO:81 *Nostoc* sp. (Nostoc__17230725)
SEQ ID NO:82 *Rhodopseudomonas palustris* RhoPa_TrpEG
SEQ ID NO:99—rice
SEQ ID NO:100—rice isozyme
SEQ ID NO:101—maize (U.S. Pat. No. 6,118,047 to Anderson)
SEQ ID NO:102—wheat
SEQ ID NO:103—tobacco Any of these nucleic acids and polypeptides can be utilized in the practice of the invention, as well as any mutant, variant or derivative thereof.

Monomeric Anthranilate Synthases

According to the invention, monomeric anthranilate synthases from plant and non-plant species are functional in plants and can provide high levels of tryptophan. Surprisingly, monomeric anthranilate synthases from non-plant species function very well in plants even though the sequences of these monomeric anthranilate synthases have low homology with most plant anthranilate synthases. For example, monomeric anthranilate synthases from species as diverse as bacteria, protists, and microbes can be used successfully. In particular, monomeric anthranilate synthases from bacterial species such as *Agrobacterium tumefaciens, Rhizobium meliloti, Mesorhizobium loti, Brucella melitensis, Nostoc sp.* PCC7120, *Azospirillum brasilense* and *Anabaena* M22983 are functional in plants and can provide high levels of tryptophan, despite the rather low sequence identity of these monomeric anthranilate synthases with most plant anthranilate synthases.

Transgenic plants containing, for example, the wild type monomeric *Agrobacterium tumefaciens* anthranilate synthase can produce up to about 10,000 to about 12,000 ppm tryptophan in seeds, with average trp levels ranging up to about 7,000 to about 8,000 ppm. Non-transgenic soybean plants normally have up to only about 100 to about 200 ppm tryptophan in seeds. By comparison transgenic plants containing an added mutant *Zea mays* α domain produce somewhat lower levels of tryptophan (e.g., averages up to about 3000 to about 4000 ppm).

Monomeric enzymes may have certain advantages over multimeric enzymes. For example, while the invention is not to be limited to a specific mechanism, a monomeric enzyme may provide greater stability, coordinated expression, and the like. When domains or subunits of a heterotetrameric anthranilate synthase are synthesized in vivo, those domains/subunits must properly assemble into a heterotetrameric form before the enzyme becomes active. Addition of a single domain of anthranilate synthase by transgenic means to a plant may not provide overproduction of the entire heterotetrameric enzyme because there may not be sufficient endogenous amounts of the non-transgenic domains to substantially increase levels of the functional tetramer. Hence, nucleic acids, vectors and enzymes encoding a monomeric anthranilate synthase can advantageously be used to overproduce all of the enzymatic functions of anthranilate synthase.

According to the invention, anthranilate synthase domains from species that naturally produce heterotetrameric anthranilate synthases can be fused or linked to provide monomeric anthranilate synthases that can generate high tryptophan levels when expressed within a plant cell, plant tissue or seed. For example, a monomeric anthranilate synthase can be made by fusing or linking the α and β domains of anthranilate synthase so that the sequence of the α-β fusion generally aligns with an anthranilate synthase that is naturally monomeric. Examples of sequence alignments of monomeric and heterotetrameric anthranilate synthases are shown in FIGS. 21 and 35. Using such sequence alignments, the spacing and orientation of anthranilate synthase domains can be adjusted or modified to generate a monomeric anthranilate construct from heterotetrameric domains that optimally aligns with naturally monomeric anthranilate synthases. Such a fusion protein can be used to increase tryptophan levels in the tissues of a plant.

Heterotetrameric anthranilate synthases, such as the *Sulfolobus solfataricus* anthranilate synthase (e.g., Genbank Accession No. GI1004323), share between about 30% to about 87% sequence homology with heterotetrameric anthranilate synthases from other plant and microbial species. Monomeric anthranilate synthases, such as the *A. tumefaciens* anthranilate synthase, have between about 83% and about 52% identity to the other monomeric enzymes such as *Rhizobium meliloti* (Genbank Accession No. GI 15966140) and *Azospirillum brasilense* (Genbank Accession No. 1717765), respectively. Bae et al., *Rhizobium meliloti* anthranilate synthase gene: cloning, sequence, and expression in *Escherichia coli. J Bacteriol.* 171, 3471–3478 (1989); De Troch et al., Isolation and characterization of the *Azospirillum brasilense* trpE(G) gene, encoding anthranilate synthase. *Curr. Microbiol.* 34, 27–32 (1997).

However, the overall sequence identity shared between naturally monomeric and naturally heterotetrameric anthranilate synthases can be less than 30%. Hence, visual alignment rather than computer-generated alignment, may be needed to optimally align monomeric and heterotetrameric anthranilate synthases. Landmark structures and sequences within the anthranilate synthases can facilitate sequences alignments. For example, the motif "LLES" (SEQ ID NO:

104) is part of a β-sheet of the β-sandwich that forms the tryptophan-binding pocket of anthranilate synthases. Such landmark sequences can be used to more confidently align divergent anthranilate synthase sequences, and are especially useful for determination of key residues involved in tryptophan binding.

To accomplish the fusion or linkage of anthranilate synthase domains, the C-terminus of the selected TrpE or α-domain is linked to the N-terminus of the TrpG domain or β-domain. In some cases, a linker peptide may be utilized between the domains to provide the appropriate spacing and/or flexibility. Appropriate linker sequences can be identified by sequence alignment of monomeric and heterotetrameric anthranilate synthases.

The selected β-domains can be cloned, for example, by hybridization, PCR amplification or as described in Anderson et al., U.S. Pat. No. 6,118,047. A plastid transit peptide sequence can also be linked to the anthranilate synthase coding region using standard methods. For example, an *Arabidopsis* small subunit (SSU) chloroplast targeting peptide (CTP, SEQ ID NO:71–74) may be used for this purpose. See also, Stark et al., (1992) Science 258: 287. The fused gene can then be inserted into a suitable vector for plant transformation as described herein.

Anthranilate Synthase Mutants

Mutant anthranilate synthases contemplated by the invention can have any type of mutation including, for example, amino acid substitutions, deletions, insertions and/or rearrangements. Such mutants can be derivatives or variants of anthranilate synthase nucleic acids and polypeptides specifically identified herein. Alternatively, mutant anthranilate synthases can be obtained from any available species, including those not explicitly identified herein. The mutants, derivatives and variants can have identity with at least about 30% of the amino acid positions of any one of SEQ ID NO:4–8, 43–45, 57–66, 69–70, 77–82, 99–103 and have anthranilate synthase activity. In a preferred embodiment, polypeptide derivatives and variants have identity with at least about 50% of the amino acid positions of any one of SEQ ID NO:4–8, 43–45, 57–66, 69–70, 77–82, 99–103 and have anthranilate synthase activity. In a more preferred embodiment, polypeptide derivatives and variants have identity with at least about 60% of the amino acid positions of any one of SEQ ID NO:4–8, 43–45, 57–66, 69–70, 77–82, 99–103 and have anthranilate synthase activity. In a more preferred embodiment, polypeptide derivatives and variants have identity with at least about 70% of the amino acid positions of any one of SEQ ID NO:4–8, 43–45, 57–66, 69–70, 77–82, 99–103 and have anthranilate synthase activity. In an even more preferred embodiment, polypeptide derivatives and variants have identity with at least about 80% of the amino acid positions of any one of SEQ ID NO:4–8, 43–45, 57–66, 69–70, 77–82, 99–103 and have anthranilate synthase activity. In an even more preferred embodiment, polypeptide derivatives and variants have identity with at least about 90% of the amino acid positions of any one of SEQ ID NO:4–8, 43–45, 57–66, 69–70, 77–82, 99–103 and have anthranilate synthase activity. In an even more preferred embodiment, polypeptide derivatives and variants have identity with at least about 95% of the amino acid positions of any one of SEQ ID NO:4–8, 43–45, 57–66, 69–70, 77–82, 99–103 and have anthranilate synthase activity.

In one embodiment, anthranilate synthase mutants, variants and derivatives can be identified by hybridization of any one of SEQ ID NO:1–3,9–42, 46, 47–56, 67–68, 75–76, 83–98, or a fragment or primer thereof under moderate or, preferably, high stringency conditions to a selected source of nucleic acids. Moderate and stringent hybridization conditions are well known to the art, see, for example sections 0.47–9.51 of Sambrook et al., Molecular Cloning: A Laboratory Manual, 2$^{nd}$ Edition (1989); see also, Sambrook and Russell, Molecular Cloning: A Laboratory Manual, 3$^{rd}$ Edition (Jan. 15, 2001). For example, stringent conditions are those that (1) employ low ionic strength and high temperature for washing, for example, 0.015 M NaCl/0.0015 M sodium citrate (SSC); 0.1% sodium lauryl sulfate (SDS) at 50° C., or (2) employ a denaturing agent such as formamide during hybridization, e.g., 50% formamide with 0.1% bovine serum albumin/0.1% Ficoll/0.1% polyvinylpyrrolidone/50 mM sodium phosphate buffer at pH 6.5 with 750 mM NaCl, 75 mM sodium citrate at 42° C. Another example is use of 50% formamide, 5× SSC (0.75 M NaCl, 0.075 M sodium citrate), 50 mM sodium phosphate (pH 6.8), 0.1% sodium pyrophosphate, 5× Denhardt's solution, sonicated salmon sperm DNA (50 μg/ml), 0.1% sodium dodecylsulfate (SDS), and 10% dextran sulfate at 42° C., with washes at 42° C. in 0.2×SSC and 0.1% SDS.

The invention further provides hybridization probes and primers comprising a novel isolated and purified DNA segment of at least seven nucleotide bases, which can be detectably labeled or bind to a detectable label. Such a hybridization probe or primer can hybridize under moderate or high stringency conditions to either strand of a DNA molecule that encodes an anthranilate synthase. Examples of such hybridization probes and primers include any one of SEQ ID NO:9–42, 47–56.

The anthranilate synthase can be any anthranilate synthase, or a mutant or domain thereof, such as the α-domain. The anthranilate synthase can be a monomeric anthranilate synthase. Functional mutants are preferred, particularly those that can generate high levels of tryptophan in a plant, for example, those mutants that are substantially resistant to inhibition by an amino acid analog of tryptophan.

Nucleic acids encoding mutant anthranilate synthases can also be generated from any convenient species, for example, from nucleic acids encoding any domain of *Agrobacterium tumefaciens, Anabaena* M22983 (e.g. Genbank Accession No. GI 152445), *Arabidopsis thaliana, Azospirillum brasilense* (e.g., Genbank Accession No. GI 1174156), *Brucella melitensis* (e.g., Genbank Accession No. GI 17982357), *Escherichia coli, Euglena gracilis, Mesorhizobium loti* (e.g., Genbank Accession No. GI 13472468), *Nostoc* sp. PCC7120 (e.g., Genbank Accession No. GI 17227910 or GI 17230725), *Rhizobium meliloti* (e.g., Genbank Accession No. GI 95177), *Ruta graveolens, Rhodopseudomonas palustris, Salmonella typhimurium, Serratia marcescens, Sulfolobus solfataricus,* soybean, rice, cotton, wheat, tobacco *Zea mays* (maize) or any gene encoding a subunit or domain of anthranilate synthase.

Mutants having increased anthranilate synthase activity, reduced sensitivity to feedback inhibition by tryptophan or analogs thereof, and/or the ability to generate increased amounts of tryptophan in a plant are desirable. Such mutants do have a functional change in the level or type of activity they exhibit and are sometimes referred to as "derivatives" of the anthranilate synthase nucleic acids and polypeptides provided herein.

However, the invention also contemplates anthranilate synthase variants as well as anthranilate synthase nucleic acids with "silent" mutations. As used herein, a silent mutation is a mutation that changes the nucleotide sequence of the anthranilate synthase but that does not change the amino acid sequence of the encoded anthranilate synthase. A variant anthranilate synthase is encoded by a mutant nucleic acid and the variant has one or more amino acid changes that do not substantially change its activity when compared to the corresponding wild type anthranilate synthase. The invention is directed to all such derivatives, variants and anthranilate synthases nucleic acids with silent mutations.

DNA encoding a mutated anthranilate synthase that is resistant and/or tolerant to L-tryptophan or amino acid analogs of tryptophan can be obtained by several methods. The methods include, but are not limited to:

1. spontaneous variation and direct mutant selection in cultures;
2. direct or indirect mutagenesis procedures on tissue cultures of any cell types or tissue, seeds or plants;
3. mutation of the cloned anthranilate synthase gene by methods such as by chemical mutagenesis; site specific or site directed mutagenesis Sambrook et al., cited supra), transposon mediated mutagenesis (Berg et al., *Biotechnology*, 1, 417 (1983)), and deletion mutagenesis (Mitra et al., *Molec. Gen. Genetic.*, 215, 294 (1989));
4. rational design of mutations in key residues; and
5. DNA shuffling to incorporate mutations of interest into various anthranilate synthase nucleic acids.

For example, protein structural information from available anthranilate synthase proteins can be used to rationally design anthranilate synthase mutants that have a high probability of having increased activity or reduced sensitivity to tryptophan or tryptophan analogs. Such protein structural information is available, for example, on the *Sulfolobus solfataricus* anthranilate synthase (Knochel et. al., *Proc. Natl. Acad. Sci. USA*, 96, 9479–9484 (1999)). Rational design of mutations can be accomplished by alignment of the selected anthranilate synthase amino acid sequence with the anthranilate synthase amino acid sequence from an anthranilate synthase of known structure, for example, *Sulfolobus solfataricus*. See FIGS. 6, 21 and 35. The predicted tryptophan binding and catalysis regions of the anthranilate synthase protein can be assigned by combining the knowledge of the structural information with the sequence homology. For example, residues in the tryptophan binding pocket can be identified as potential candidates for mutation to alter the resistance of the enzyme to feedback inhibition by tryptophan. Using such structural information, several *Agrobacterium tumefaciens* anthranilate synthase mutants were rationally designed in the site or domain involved in tryptophan binding.

Using such sequence and structural analysis, regions analogous to the monomeric *Agrobacterium tumefaciens* anthranilate synthase at approximately positions 25–60 or 200–225 or 290–300 or 370–375 were identified in the monomeric *Agrobacterium tumefaciens* anthranilate synthase as being potentially useful residues for mutation to produce active anthranilate synthases that may have less sensitivity to tryptophan feedback inhibition. More specifically, amino acids analogous to P29, E30, S31, I32, S42, V43, V48, S50, S51, N52, N2O4, P205, M209, F210, G221, N292, P293, F298 and A373 in the monomeric *Agrobacterium tumefaciens* anthranilate synthase are being potentially useful residues for mutation to produce active anthranilate synthases that may have less sensitivity to tryptophan feedback inhibition. The invention contemplates any amino acid substitution or insertion at any of these positions. Alternatively, the amino acid at any of these positions can be deleted.

Site directed mutagenesis can be used to generate amino acid substitutions, deletions and insertions at a variety of sites. Examples of specific mutations made within the *Agrobacterium tumefaciens* anthranilate synthase coding region include the following:

at about position 48 replace Val with Phe (see e.g., SEQ ID NO:58);

at about position 48 replace Val with Tyr (see e.g., SEQ ID NO:59);

at about position 51 replace Ser with Phe (see e.g., SEQ ID NO:60);

at about position 51 replace Ser with Cys (see e.g., SEQ ID NO:61);

at about position 52 replace Asn with Phe (see e.g., SEQ ID NO:62);

at about position 293 replace Pro with Ala (see e.g., SEQ ID NO:63);

at about position 293 replace Pro with Gly (see e.g., SEQ ID NO:64); or at about position 298 replace Phe with Trp (see e.g., SEQ ID NO:65).

Similar mutations can be made in analogous positions of any anthranilate synthase by alignment of the amino acid sequence of the anthranilate synthase to be mutated with an *Agrobacterium tumefaciens* anthranilate synthase amino acid sequence. One example of an *Agrobacterium tumefaciens* anthranilate synthase amino acid sequence that can be used for alignment is SEQ ID NO:4.

Useful mutants can also be identified by classical mutagenesis and genetic selection. A functional change can be detected in the activity of the enzyme encoded by the gene by exposing the enzyme to free L-tryptophan or amino acid analogs of tryptophan, or by detecting a change in the DNA molecule using restriction enzyme mapping or DNA sequence analysis.

For example, a gene encoding an anthranilate synthase substantially tolerant to 5-methyltryptophan can be isolated from a 5-methyltryptophan tolerant cell line. See U.S. Pat. No. 4,581,847, issued Apr. 15, 1986, the disclosure of which is incorporated by reference herein. Briefly, partially differentiated plant cell cultures are grown and subcultured with continuous exposures to low levels of 5-methyltryptophan. 5-methyltryptophan concentrations are then gradually increased over several subculture intervals. Cells or tissues growing in the presence of normally toxic 5-methyltryptophan levels are repeatedly subcultured in the presence of 5-methyltryptophan and characterized. Stability of the 5-methyltryptophan tolerance trait of the cultured cells may be evaluated by growing the selected cell lines in the absence of 5-methyltryptophan for various periods of time and then analyzing growth after exposing the tissue to 5-methyltryptophan. Cell lines that are tolerant by virtue of having an altered anthranilate synthase enzyme can be selected by identifying cell lines having enzyme activity in the presence of normally toxic, i.e., growth inhibitor, levels of 5-methyltryptophan.

The anthranilate synthase gene cloned from a 5-MT- or 6-MA-resistant cell line can be assessed for tolerance to 5-MT, 6-MA, or other amino acid analogs of tryptophan by standard methods, as described in U.S. Pat. No. 4,581,847, issued Apr. 15, 1986, the disclosure of which is incorporated by reference herein.

Cell lines with an anthranilate synthase of reduced sensitivity to 5-methyltryptophan inhibition can be used to isolate a 5-methyltryptophan-resistant anthranilate synthase. A DNA library from a cell line tolerant to 5-methyltryptophan can be generated and DNA fragments encoding all or a portion of an anthranilate synthase gene can be identified by hybridization to a cDNA probe encoding a portion of an anthranilate synthase gene. A complete copy of the altered gene can be obtained either by cloning and ligation or by PCR synthesis using appropriate primers. The isolation of the altered gene coding for anthranilate synthase can be confirmed in transformed plant cells by determining whether the anthranilate synthase being expressed retains enzyme activity when exposed to normally toxic levels of 5-methyltryptophan. See, Anderson et al., U.S. Pat. No. 6,118,047.

Coding regions of any DNA molecule provided herein can also be optimized for expression in a selected organism, for example, a selected plant or other host cell type. An example of a DNA molecule having optimized codon usage for a selected plant is an *Agrobacterium tumefaciens* anthranilate synthase DNA molecule having SEQ ID NO:75. This optimized *Agrobacterium tumefaciens* anthranilate synthase DNA (SEQ ID NO:75) has 94% identity with SEQ ID NO:1.

Transgenes and Vectors

Once a nucleic acid encoding anthranilate synthase or a domain thereof is obtained and amplified, it is operably combined with a promoter and, optionally, with other elements to form a transgene.

Most genes have regions of DNA sequence that are known as promoters and which regulate gene expression. Promoter regions are typically found in the flanking DNA sequence upstream from the coding sequence in both prokaryotic and eukaryotic cells. A promoter sequence provides for regulation of transcription of the downstream gene sequence and typically includes from about 50 to about 2,000 nucleotide base pairs. Promoter sequences also contain regulatory sequences such as enhancer sequences that can influence the level of gene expression. Some isolated promoter sequences can provide for gene expression of heterologous genes, that is, a gene different from the native or homologous gene. Promoter sequences are also known to be strong or weak or inducible. A strong promoter provides for a high level of gene expression, whereas a weak promoter provides for a very low level of gene expression. An inducible promoter is a promoter that provides for turning on and off of gene expression in response to an exogenously added agent or to an environmental or developmental stimulus. Promoters can also provide for tissue specific or developmental regulation. An isolated promoter sequence that is a strong promoter for heterologous genes is advantageous because it provides for a sufficient level of gene expression to allow for easy detection and selection of transformed cells and provides for a high level of gene expression when desired.

The promoter in a transgene of the invention can provide for expression of anthranilate synthase from a DNA sequence encoding anthranilate synthase. Preferably, the coding sequence is expressed so as to result in an increase in tryptophan levels within plant tissues, for example, within the seeds of the plant. In another embodiment, the coding sequence is expressed so as to result in increased tolerance of the plant cells to feedback inhibition or to growth inhibition by an amino acid analog of tryptophan or so as to result in an increase in the total tryptophan content of the cells. The promoter can also be inducible so that gene expression can be turned on or off by an exogenously added agent. For example, a bacterial promoter such as the $P_{tac}$ promoter can be induced to varying levels of gene expression depending on the level of isothiopropylgalactoside added to the transformed bacterial cells. It may also be preferable to combine the gene with a promoter that provides tissue specific expression or developmentally regulated gene expression in plants. Many promoters useful in the practice of the invention are available to those of skill in the art.

Preferred promoters will generally include, but are not limited to, promoters that function in bacteria, bacteriophage, plastids or plant cells. Useful promoters include the CaMV 35S promoter (Odell et al., *Nature*, 313, 810 (1985)), the CaMV 19S (Lawton et al., *Plant Mol. Biol.*, 9, 31F (1987)), nos (Ebert et al., *PNAS USA*, 84, 5745 (1987)), Adh (Walker et al., *PNAS USA*, 84, 6624 (1987)), sucrose synthase (Yang et al., *PNAS USA* 87, 4144 (1990)), α-tubulin, napin, actin (Wang et al., *Mol. Cell. Biol.*, 12, 3399 (1992)), cab (Sullivan et al., *Mol. Gen. Genet.*, 215, 431 (1989)), PEPCase promoter (Hudspeth et al., *Plant Mol. Biol.*, 12, 579 (1989)), the 7S-alpha'-conglycinin promoter (Beachy et al., *EMBO J*, 4, 3047 (1985)) or those associated with the R gene complex (Chandler et al., *The Plant Cell*, 1, 1175 (1989)). Other useful promoters include the bacteriophage SP6, T3, and T7 promoters.

Plastid promoters can be also be used. Most plastid genes contain a promoter for the multi-subunit plastid-encoded RNA polymerase (PEP) as well as the single-subunit nuclear-encoded RNA polymerase. A consensus sequence for the nuclear-encoded polymerase (NEP) promoters and listing of specific promoter sequences for several native plastid genes can be found in Hajdukiewicz et al., 1997, EMBO J. Vol. 16 pp. 4041–4048, which is hereby in its entirety incorporated by reference.

Examples of plastid promoters that can be used include the *Zea mays* plastid RRN (ZMRRN) promoter. The ZMRRN promoter can drive expression of a gene when the *Arabidopsis thaliana* plastid RNA polymerase is present. Similar promoters that can be used in the present invention are the *Glycine max* plastid RRN (SOYRRN) and the *Nicotiana tabacum* plastid RRN (NTRRN) promoters. All three promoters can be recognized by the *Arabidopsis* plastid RNA polymerase. The general features of RRN promoters are described by Hajdukiewicz et al. and U.S. Pat. No. 6,218,145.

Moreover, transcription enhancers or duplications of enhancers can be used to increase expression from a particular promoter. Examples of such enhancers include, but are not limited to, elements from the CaMV 35S promoter and octopine synthase genes (Last et al., U.S. Pat. No. 5,290,924, issued Mar. 1, 1994). For example, it is contemplated that vectors for use in accordance with the present invention may be constructed to include the ocs enhancer element. This element was first identified as a 16 bp palindromic enhancer from the octopine synthase (ocs) gene of *Agrobacterium* (Ellis et al., *EMBO J.*, 6, 3203 (1987)), and is present in at least 10 other promoters (Bouchez et al., *EMBO J.* 8, 4197 (1989)). It is proposed that the use of an enhancer element, such as the ocs element and particularly multiple copies of the element, will act to increase the level of transcription from adjacent promoters when applied in the context of monocot transformation. Tissue-specific promoters, including but not limited to, root-cell promoters (Conkling et al., *Plant Physiol.*, 93, 1203 (1990)), and tissue-specific enhancers (Fromm et al., *The Plant Cell*, 1, 977 (1989)) are also contemplated to be particularly useful, as are inducible promoters such as ABA- and turgor-inducible promoters, and the like.

As the DNA sequence between the transcription initiation site and the start of the coding sequence, i.e., the untranslated leader sequence, can influence gene expression, one may also wish to employ a particular leader sequence. Any leader sequence available to one of skill in the art may be employed. Preferred leader sequences direct optimum levels of expression of the attached gene, for example, by increasing or maintaining mRNA stability and/or by preventing inappropriate initiation of translation (Joshi, *Nucl. Acid Res.*, 15, 6643 (1987)). The choice of such sequences is at the discretion of those of skill in the art. Sequences that are derived from genes that are highly expressed in dicots, and in soybean in particular, are contemplated.

In some cases, extremely high expression of anthranilate synthase or a domain thereof, is not necessary. For example, using the methods of the invention such high levels of anthranilate synthase may be generated that the availability of substrate, rather than enzyme, may limit the levels of tryptophan generated. In such cases, more moderate or regulated levels of expression can be selected by one of skill in the art. Such a skilled artisan can readily modulate or regulate the levels of expression, for example, by use of a weaker promoter or by use of a developmentally regulated or tissue specific promoter.

Nucleic acids encoding the anthranilate synthase of interest can also include a plastid transit peptide (e.g. SEQ ID NO:72 or 74) to facilitate transport of the anthranilate synthase polypeptide into plastids, for example, into chloroplasts. A nucleic acid encoding the selected plastid transit peptide (e.g. SEQ ID NO:71 or 73) is generally linked in-frame with the coding sequence of the anthranilate synthase. However, the plastid transit peptide can be placed at either the N-terminal or C-terminal end of the anthranilate synthase.

Constructs also include the nucleic acid of interest (e.g. DNA encoding an anthranilate synthase) along with a nucleic acid sequence that acts as a transcription termination signal and that allows for the polyadenylation of the resultant mRNA. Such transcription termination signals are placed 3' or downstream of the coding region of interest. Preferred transcription termination signals contemplated include the transcription termination signal from the nopaline synthase gene of *Agrobacterium tumefaciens* (Bevan et al., *Nucl. Acid Res.*, 11, 369 (1983)), the terminator from the octopine synthase gene of *Agrobacterium tumefaciens*, and the 3' end of genes encoding protease inhibitor I or II from potato or tomato, although other transcription termination signals known to those of skill in the art are also contemplated. Regulatory elements such as Adh intron 1 (Callis et al., *Genes Develop.*, 1, 1183 (1987)), sucrose synthase intron (Vasil et al., *Plant Physiol.*, 91, 5175 (1989)) or TMV omega element (Gallie et al., *The Plant Cell*, 1, 301 (1989)) may further be included where desired. These 3' nontranslated regulatory sequences can be obtained as described in An, *Methods in Enzymology*, 153, 292 (1987) or are already present in plasmids available from commercial sources such as Clontech, Palo Alto, Calif. The 3' nontranslated regulatory sequences can be operably linked to the 3 terminus of an anthranilate synthase gene by standard methods. Other such regulatory elements useful in the practice of the invention are known to those of skill in the art.

Selectable marker genes or reporter genes are also useful in the present invention. Such genes can impart a distinct phenotype to cells expressing the marker gene and thus allow such transformed cells to be distinguished from cells that do not have the marker. Selectable marker genes confer a trait that one can 'select' for by chemical means, i.e., through the use of a selective agent (e.g., a herbicide, antibiotic, or the like). Reporter genes, or screenable genes, confer a trait that one can identify through observation or testing, i.e., by 'screening' (e.g., the R-locus trait). Of course, many examples of suitable marker genes are known to the art and can be employed in the practice of the invention.

Possible selectable markers for use in connection with the present invention include, but are not limited to, a neo gene (Potrykus et al., *Mol. Gen. Genet.*, 199, 183 (1985)) which codes for neomycin resistance and can be selected for using kanamycin, G418, and the like; a bar gene which codes for bialaphos resistance; a gene which encodes an altered EPSP synthase protein (Hinchee et al., *Biotech.*, 6, 915 (1988)) thus conferring glyphosate resistance; a nitrilase gene such as bxn from *Klebsiella ozaenae* which confers resistance to bromoxynil (Stalker et al., *Science*, 242, 419 (1988)); a mutant acetolactate synthase gene (ALS) that confers resistance to imidazolinone, sulfonylurea or other ALS-inhibiting chemicals (European Patent Application 154,204, 1985); a methotrexate-resistant DHFR gene (Thillet et al., *J. Biol. Chem.*, 263, 12500 (1988)); a dalapon dehalogenase gene that confers resistance to the herbicide dalapon; or a mutated anthranilate synthase gene that confers resistance to 5-methyl tryptophan. Where a mutant EPSP synthase gene is employed, additional benefit may be realized through the incorporation of a suitable plastid transit peptide (CTP).

An illustrative embodiment of a selectable marker gene capable of being used in systems to select transformants is the genes that encode the enzyme phosphinothricin acetyltransferase, such as the bar gene from *Streptomyces hygroscopicus* or the pat gene from *Streptomyces viridochromogenes* (U.S. Pat. No. 5,550,318, which is incorporated by reference herein). The enzyme phosphinothricin acetyl transferase (PAT) inactivates the active ingredient in the herbicide bialaphos, phosphinothricin (PPT). PPT inhibits glutamine synthetase, (Murakami et al., *Mol. Gen. Genet.*, 205, 42 (1986); Twell et al., *Plant Physiol.*, 91, 1270 (1989)) causing rapid accumulation of ammonia and cell death.

Screenable markers that may be employed include, but are not limited to, a β-glucuronidase or uidA gene (GUS) which encodes an enzyme for which various chromogenic substrates are known; an R-locus gene, which encodes a product that regulates the production of anthocyanin pigments (red color) in plant tissues (Dellaporta et al., in *Chromosome Structure and Function*, pp. 263–282 (1988)); a β-lactamase gene (Sutcliffe, *PNAS USA*, 75, 3737 (1978)), which encodes an enzyme for which various chromogenic substrates are known (e.g., PADAC, a chromogenic cephalosporin); a xylE gene (Zukowsky et al., *PNAS USA*, 80, 1101 (1983)) that encodes a catechol dioxygenase that can convert chromogenic catechols; an α-amylase gene (Ikuta et al., *Biotech.*, 8, 241 (1990)); a tyrosinase gene (Katz et al., *J. Gen. Microbiol.*, 129, 2703 (1983)) that encodes an enzyme capable of oxidizing tyrosine to DOPA and dopaquinone which in turn condenses to form the easily detectable compound melanin; a β-galactosidase gene, which encodes an enzyme for which there are chromogenic substrates; a luciferase (lux) gene (Ow et al., *Science*, 234, 856 (1986)), which allows for bioluminescence detection; or even an aequorin gene (Prasher et al., *Biochem. Biophys. Res. Comm.*, 126, 1259 (1985)), which may be employed in calcium-sensitive bioluminescence detection, or a green fluorescent protein gene (Niedz et al., *Plant Cell Reports*, 14, 403 (1995)). The presence of the lux gene in transformed cells may be detected using, for example, X-ray film, scintillation counting, fluorescent spectrophotometry, low-light video cameras, photon-counting cameras, or multiwell luminometry. It is also envisioned that this system may be developed for populational screening for bioluminescence, such as on tissue culture plates, or even for whole plant screening.

Additionally, transgenes may be constructed and employed to provide targeting of the gene product to an intracellular compartment within plant cells or in directing a protein to the extracellular environment. This will generally be achieved by joining a DNA sequence encoding a transit or signal peptide sequence to the coding sequence of a particular gene. The resultant transit, or signal, peptide will transport the protein to a particular intracellular, or extracellular destination, respectively, and may then be post-translationally removed. Transit or signal peptides act by facilitating the transport of proteins through intracellular membranes, e.g., vacuole, vesicle, plastid and mitochondrial membranes, whereas signal peptides direct proteins through the extracellular membrane. By facilitating transport of the protein into compartments inside or outside the cell, these sequences may increase the accumulation of gene product.

A particular example of such a use concerns the direction of an anthranilate synthase to a particular organelle, such as the plastid, rather than to the cytoplasm. This is exemplified by the use of the *Arabidopsis* SSU1A transit peptide that confers plastid-specific targeting of proteins. Alternatively, the transgene can comprise a plastid transit peptide-encoding DNA sequence or a DNA sequence encoding the the rbcS (RuBISCO) transit peptide operably linked between a promoter and the DNA sequence encoding an anthranilate synthase (for a review of plastid targeting peptides, see Heijne et al., *Eur. J. Biochem.,* 180, 535 (1989); Keegstra et al., *Ann. Rev. Plant Physiol. Plant Mol. Biol.,* 40, 471 (1989)). If the transgene is to be introduced into a plant cell, the transgene can also contain plant transcriptional termination and polyadenylation signals and translational signals linked to the 3' terminus of a plant anthranilate synthase gene.

An exogenous plastid transit peptide can be used which is not encoded within a native plant anthranilate synthase gene. A plastid transit peptide is typically 40 to 70 amino acids in length and functions post-translationally to direct a protein to the plastid. The transit peptide is cleaved either during or just after import into the plastid to yield the mature protein. The complete copy of a gene encoding a plant anthranilate synthase may contain a plastid transit peptide sequence. In that case, it may not be necessary to combine an exogenously obtained plastid transit peptide sequence into the transgene.

Exogenous plastid transit peptide encoding sequences can be obtained from a variety of plant nuclear genes, so long as the products of the genes are expressed as preproteins comprising an amino terminal transit peptide and transported into plastid. Examples of plant gene products known to include such transit peptide sequences include, but are not limited to, the small subunit of ribulose biphosphate carboxylase, chlorophyll a/b binding protein, plastid ribosomal proteins encoded by nuclear genes, certain heatshock proteins, amino acid biosynthetic enzymes such as acetolactate acid synthase, 3-enolpyruvylphosphoshikimate synthase, dihydrodipicolinate synthase, anthranilate synthase and the like. In some instances a plastid transport protein already may be encoded in the anthranilate synthase gene of interest, in which case there may be no need to add such plastid transit sequences. Alternatively, the DNA fragment coding for the transit peptide may be chemically synthesized either wholly or in part from the known sequences of transit peptides such as those listed above.

Regardless of the source of the DNA fragment coding for the transit peptide, it should include a translation initiation codon, for example, an ATG codon, and be expressed as an amino acid sequence that is recognized by and will function properly in plastids of the host plant. Attention should also be given to the amino acid sequence at the junction between the transit peptide and the anthranilate synthase enzyme where it is cleaved to yield the mature enzyme. Certain conserved amino acid sequences have been identified and may serve as a guideline. Precise fusion of the transit peptide coding sequence with the anthranilate synthase coding sequence may require manipulation of one or both DNA sequences to introduce, for example, a convenient restriction site. This may be accomplished by methods including site-directed mutagenesis, insertion of chemically synthesized oligonucleotide linkers, and the like.

Precise fusion of the nucleic acids encoding the plastid transport protein may not be necessary so long as the coding sequence of the plastid transport protein is in-frame with that of the anthranilate synthase. For example, additional peptidyl or amino acids can often be included without adversely affecting the expression or localization of the protein of interest.

Once obtained, the plastid transit peptide sequence can be appropriately linked to the promoter and an anthranilate synthase coding region in a transgene using standard methods. A plasmid containing a promoter functional in plant cells and having multiple cloning sites downstream can be constructed or obtained from commercial sources. The plastid transit peptide sequence can be inserted downstream from the promoter using restriction enzymes. An anthranilate synthase coding region can then be translationally fused or inserted immediately downstream from and in frame with the 3' terminus of the plastid transit peptide sequence. Hence, the plastid transit peptide is preferably linked to the amino terminus of the anthranilate synthase. Once formed, the transgene can be subcloned into other plasmids or vectors.

In addition to nuclear plant transformation, the present invention also extends to direct transformation of the plastid genome of plants. Hence, targeting of the gene product to an intracellular compartment within plant cells may also be achieved by direct delivery of a gene to the intracellular compartment. Direct transformation of plastid genome may provide additional benefits over nuclear transformation. For example, direct plastid transformation of anthranilate synthase eliminates the requirement for a plastid targeting peptide and post-translational transport and processing of the pre-protein derived from the corresponding nuclear transformants. Plastid transformation of plants has been described by P. Maliga. Current Opinion in Plant Biology 5, 164–172 (2002), P. B. Heifetz. Biochimie vol. 82, 655–666 (2000), R. Bock. J. Mol. Biol. 312, 425–438 (2001), and H. Daniell et al., Trends in Plant Science 7, 84–91 (2002) and references within.

After constructing a transgene containing an anthranilate synthase gene, the cassette can then be introduced into a plant cell. Depending on the type of plant cell, the level of gene expression, and the activity of the enzyme encoded by the gene, introduction of DNA encoding an anthranilate synthase into the plant cell can lead to the overproduction of tryptophan, confer tolerance to an amino acid analog of tryptophan, such as 5-methyltryptophan or 6-methylanthranilate, and/or otherwise alter the tryptophan content of the plant cell.

Transformation of Host Cells

A transgene comprising an anthranilate synthase gene can be subcloned into a known expression vector, and AS expression can be detected and/or quantitated. This method of screening is useful to identify transgenes providing for an expression of an anthranilate synthase gene, and expression of an anthranilate synthase in the plastid of a transformed plant cell.

Plasmid vectors include additional DNA sequences that provide for easy selection, amplification, and transformation of the transgene in prokaryotic and eukaryotic cells, e.g., pUC-derived vectors, pSK-derived vectors, pGEM-derived vectors, pSP-derived vectors, or pBS-derived vectors. The additional DNA sequences include origins of replication to provide for autonomous replication of the vector, selectable marker genes, preferably encoding antibiotic or herbicide resistance, unique multiple cloning sites providing for multiple sites to insert DNA sequences or genes encoded in the transgene, and sequences that enhance transformation of prokaryotic and eukaryotic cells.

Another vector that is useful for expression in both plant and prokaryotic cells is the binary Ti plasmid (as disclosed in Schilperoort et al., U.S. Pat. No. 4,940,838, issued Jul. 10, 1990) as exemplified by vector pGA582. This binary Ti plasmid vector has been previously characterized by An, cited supra. This binary Ti vector can be replicated in prokaryotic bacteria such as *E. coli* and *Agrobacterium*. The *Agrobacterium* plasmid vectors can also be used to transfer the transgene to plant cells. The binary Ti vectors preferably include the nopaline T DNA right and left borders to provide for efficient plant cell transformation, a selectable marker gene, unique multiple cloning sites in the T border regions, the colE1 replication of origin and a wide host range replicon. The binary Ti vectors carrying a transgene of the invention can be used to transform both prokaryotic and eukaryotic cells, but is preferably used to transform plant cells. See, for example, Glassman et al., U.S. Pat. No. 5,258,300.

The expression vector can then be introduced into prokaryotic or eukaryotic cells by available methods. Methods of transformation especially effective for monocots and dicots, include, but are not limited to, microprojectile bombardment of immature embryos (U.S. Pat. No. 5,990,390) or Type II embryogenic callus cells as described by W. J. Gordon-Kamm et al. (*Plant Cell*, 2, 603 (1990)), M. E. Fromm et al. (*Bio/Technology*, 8, 833 (1990)) and D. A. Walters et al. (*Plant Molecular Biology*, 18, 189 (1992)), or by electroporation of type I embryogenic calluses described by D'Halluin et al. (*The Plant Cell*, 4, 1495 (1992)), or by Krzyzek (U.S. Pat. No. 5,384,253, issued Jan. 24, 1995). Transformation of plant cells by vortexing with DNA-coated tungsten whiskers (Coffee et al., U.S. Pat. No. 5,302,523, issued Apr. 12, 1994) and transformation by exposure of cells to DNA-containing liposomes can also be used.

After transformation of the selected anthranilate synthase construct into a host cell, the host cell may be used for production of useful products generated by the transgenic anthranilate synthase in combination with the host cell's enzymatic machinery. Culturing the transformed cells can lead to enhanced production of tryptophan and other useful compounds, which can be recovered from the cells or from the culture media. Examples of useful compounds that may be generated upon expression in a variety of host cells and/or organisms include tryptophan, indole acetic acid and other auxins, isoflavonoid compounds important to cardiovascular health found in soy, volatile indole compounds which act as signals to natural enemies of herbivorous insects in maize, anticarcinogens such as indole glucosinolates (indole-3-carbinol) found in the Cruciferae plant family, as well as indole alkaloids such as ergot compounds produced by certain species of fungi. (Barnes et al., *Adv Exp Med Biol*, 401, 87 (1996); Frey et al., *Proc Natl Acad Sci*, 97, 14801 (2000); Muller et al., *Biol Chem*, 381, 679 (2000); Mantegani et al., *Farmaco*, 54, 288 (1999); Zeligs, *J Med Food*, 1, 67 (1998); Mash et al., *Ann NY Acad Sci*, 844, 274 (1998); Melanson et al., *Proc Natl Acad Sci*, 94, 13345 (1997); Broadbent et al., *Curr Med Chem*, 5, 469 (1998)).

Accumulation of tryptophan may also lead to the increased production of secondary metabolites in microbes and plants, for example, indole containing metabolites such as simple indoles, indole conjugates, indole alkaloids, indole phytoalexins and indole glucosinalates in plants.

Anthranilate synthases insensitive to tryptophan have the potential to increase a variety of chorismate-derived metabolites, including those derived from phenylalanine due to the stimulation of phenylalanine synthesis by tryptophan via chorismate mutase. See Siehl, D. The biosynthesis of tryptophan, tyrosine, and phenylalanine from chorismate in Plant Amino Acids: Biochemistry and Biotechnology, ed. B K Singh, pp 171–204. Other chorismate-derived metabolites that may increase when feedback insensitive anthranilate synthases are present include phenylpropanoids, flavonoids, and isoflavonoids, as well as those derived from anthranilate, such as indole, indole alkaloids, and indole glucosinolates. Many of these compounds are important plant hormones, plant defense compounds, chemopreventive agents of various health conditions, and/or pharmacologically active compounds.

The range of these compounds whose synthesis might be increased by expression of anthranilate synthase depends on the organism in which the anthranilate synthase is expressed. One of skill in the art can readily assess which organisms and host cells to use and/or test in order to generate the desired compounds. The invention contemplates synthesis of tryptophan and other useful compounds in a variety of organisms, including plants, microbes, fungi, yeast, bacteria, insect cells, and mammalian cells.

Strategy for Selection of Tryptophan Overproducer Cell Lines

Efficient selection of a desired tryptophan analog resistant, tryptophan overproducer variant using tissue culture techniques requires careful determination of selection conditions. These conditions are optimized to allow growth and accumulation of tryptophan analog resistant, tryptophan overproducer cells in the culture while inhibiting the growth of the bulk of the cell population. The situation is complicated by the fact that the vitality of individual cells in a population can be highly dependent on the vitality of neighboring cells.

Conditions under which cell cultures are exposed to tryptophan analog are determined by the characteristics of the interaction of the compound with the tissue. Such factors as the degree of toxicity and the rate of inhibition should be considered. The accumulation of the compounds by cells in culture, and the persistence and stability of the compounds, both in the media and in the cells, also need to be considered along with the extent of uptake and transmission to the desired cellular compartment. Additionally, it is important to determine whether the effects of the compounds can be readily reversed by the addition of tryptophan.

The effects of the analog on culture viability and morphology is carefully evaluated. It is especially important to choose analog exposure conditions that have no impact on plant regeneration capability of cultures. Choice of analog exposure conditions is also influenced by whether the analog kills cells or simply inhibits cell divisions.

The choice of a selection protocol is dependent upon the considerations described above. The protocols briefly described below can be utilized in the selection procedure. For example, to select for cells that are resistant to growth inhibition by a tryptophan analog, finely divided cells in liquid suspension culture can be exposed to high tryptophan analog levels for brief periods of time. Surviving cells are then allowed to recover and accumulate and are then reexposed for subsequently longer periods of time. Alternatively, organized partially differentiated cell cultures are grown and subcultured with continuous exposure to initially low levels of a tryptophan analog. Concentrations are then gradually increased over several subculture intervals. While these protocols can be utilized in a selection procedure, the present invention is not limited to these procedures.

Genes for Plant Modification

As described hereinabove, genes that function as selectable marker genes and reporter genes can be operably combined with the DNA sequence encoding the anthranilate synthase, or domain thereof, in transgenes, vectors and plants of the present invention. Additionally, other agronomical traits can be added to the transgenes, vectors and plants of the present invention. Such traits include, but are not limited to, insect resistance or tolerance; disease resistance or tolerance (viral, bacterial, fungal, nematode); stress resistance or tolerance, as exemplified by resistance or tolerance to drought, heat, chilling, freezing, excessive moisture, salt stress, oxidative stress; increased yields; food content and makeup; physical appearance; male sterility; drydown; standability; prolificacy; starch properties; oil quantity and quality; and the like. One may incorporate one or more genes conferring such traits into the plants of the invention.

Insect Resistance or Tolerance

*Bacillus thuringiensis* (or "Bt") bacteria include nearly 20 known subspecies of bacteria which produce endotoxin polypeptides that are toxic when ingested by a wide variety of insect species. The biology and molecular biology of the endotoxin proteins (Bt proteins) and corresponding genes (Bt genes) has been reviewed by H. R. Whitely et al., *Ann. Rev. Microbiol.*, 40, 549 (1986) and by H. Hofte et al., *Microbiol. Rev.*, 53, 242 (1989). Genes coding for a variety of Bt proteins have been cloned and sequenced. A segment of the Bt polypeptide is essential for toxicity to a variety of *Lepidoptera* pests and is contained within approximately the first 50% of the Bt polypeptide molecule. Consequently, a truncated Bt polypeptide coded by a truncated Bt gene will in many cases retain its toxicity towards a number of *Lepidoptera* insect pests. For example, the HD73 and HD1 Bt polypeptides have been shown to be toxic to the larvae of the important *Lepidoptera* insect pests of plants in the USA such as the European corn borer, cutworms and earworms. The genes coding for the HD1 and HD73 Bt polypeptides have been cloned and sequenced by M. Geiser et al., *Gene*, 48, 109 (1986) and M. J. Adang et al., *Gene*, 36, 289 (1985), respectively, and can be cloned from HD1 and HD73 strains obtained from culture collections (e.g. Bacillus Genetic Stock Center, Columbus, Ohio or USDA Bt stock collection Peoria, Ill.) using standard protocols. Examples of Bt genes and polypeptides are described, for example, in U.S. Pat. Nos. 6,329,574, 6,303,364, 6,320,100 and 6,331,655.

DNA coding for new, previously uncharacterized Bt toxins, may be cloned from the host *Bacillus* organism using protocols that have previously been used to clone Bt genes, and new synthetic forms of Bt toxins may also be produced.

A Bt gene useful in the present invention may include a 5' DNA sequence including a sequence of DNA which will allow for the initiation of transcription and translation of a downstream located Bt sequence in a plant. The Bt gene may also comprise a 3' DNA sequence that includes a sequence derived from the 3' non-coding region of a gene that can be expressed in the plant of interest. The Bt gene would also include a DNA sequence coding for a toxic Bt polypeptide produced by *Bacillus thuringiensis* or toxic portions thereof or having substantial amino sequence homology thereto. The Bt coding sequence may include: (i) DNA sequences which code for insecticidal proteins that have substantial homology to Bt endotoxins that are active against insect pests of the plant of interest, e.g., the HD73 or HD1 Bt sequences; (ii) sequences coding for insecticidally-active segments of the Bt endotoxin polypeptide, e.g., insecticidally active HD73 or HD1 polypeptides truncated from the carboxy and/or amino termini; and/or (iii) a truncated Bt sequence fused in frame with a sequence(s) that codes for a polypeptide that provides some additional advantage such as: (a) genes that are selectable, e.g., genes that confer resistance to antibiotics or herbicides, (b) reporter genes whose products are easy to detect or assay, e.g., luciferase or beta-glucuronidase; (c) DNA sequences that code for polypeptide sequences that have some additional use in stabilizing the Bt protein against degradation or enhance the efficacy of the Bt protein against insects, e.g., protease inhibitors and (d) sequences that help direct the Bt protein to a specific compartment inside or outside the plant cell, e.g., a signal sequence.

To obtain optimum synthesis of the Bt protein in the plant, it may also be appropriate to adjust the DNA sequence of the Bt gene to more resemble the genes that are efficiently expressed in the plant of interest. Since the codon usage of Bt genes may be dissimilar to that used by genes that are expressed in the plant of interest, the expression of the Bt gene in plant cells may be improved by the replacement of these codons with those that are more efficiently expressed in plants, e.g., are used more frequently in the plants of interest (See E. Murray et al., *Nucl. Acids Res.*, 17, 477 (1989)). Such replacement of codons may require the substitution of bases without changing the amino acid sequence of the resulting Bt polypeptide. The Bt polypeptide may be identical in sequence to the bacterial gene or segments thereof. The complete Bt coding sequence, or sections thereof, containing a higher proportion of preferred codons than the original bacterial gene could be synthesized using standard chemical synthesis protocols, and introduced or assembled into the Bt gene using standard protocols, such as site-directed mutagenesis or DNA polymerization and ligation and the like.

Protease inhibitors may also provide insect resistance. For example, use of a protease inhibitor II gene, pinII, from tomato or potato may be useful. Also advantageous is the use of a pinII gene in combination with a Bt toxin gene. Other genes which encode inhibitors of the insects' digestive system, or those that encode enzymes or co-factors that facilitate the production of inhibitors, may also be useful. This group includes oryzacystatin and amylase inhibitors such as those from wheat and barley.

Genes encoding lectins may confer additional or alternative insecticide properties. (Murdock et al., *Phytochemistr*, 29 85 (1990); Czapla & Lang, *J. Econ. Entomol.*, 83, 2480 (1990) Lectin genes contemplated to be useful include, for example, barley and wheat germ agglutinin (WGA) and rice lectins. (Gatehouse et al., *J Sci Food Agric*, 35, 373 (1984))

Genes controlling the production of large or small polypeptides active against insects when introduced into the insect pests such as lytic peptides, peptide hormones and toxins and venoms, may also be useful. For example, the expression of juvenile hormone esterase, directed towards specific insect pests, may also result in insecticidal activity, or perhaps cause cessation of metamorphosis. (Hammock et al., *Nature*, 344, 458 (1990))

Transgenic plants expressing genes encoding enzymes that affect the integrity of the insect cuticle may also be useful. Such genes include those encoding, for example, chitinase, proteases, lipases and also genes for the production of nikkomycin. Genes that code for activities that affect insect molting, such those affecting the production of ecdysteroid UDP-glucosyl transferase, may also be useful.

Genes that code for enzymes that facilitate the production of compounds that reduce the nutritional quality of the plant to insect pests a may also be useful. It may be possible, for instance, to confer insecticidal activity to a plant by altering its sterol composition. Further embodiments of the invention concern transgenic plants with enhanced lipoxygenase activity.

The present invention also provides methods and compositions useful in altering plant secondary metabolites. One example concerns altering plants to produce DIMBOA which, it is contemplated, will confer resistance to European corn borer, rootworm and several other insect pests. See, e.g., U.S. Pat. No. 6,331,880. DIMBOA is derived from indole-related compounds. The present invention provides methods for increasing the content of indole-related compounds like tryptophan within plant cells and tissues. Hence, according to the invention the methods provided herein may also increase the levels of DIMBOA, and thereby increase the resistance of plants to insects.

The introduction of genes that can regulate the production of maysin, and genes involved in the production of dhurrin in sorghum, is also contemplated to be of use in facilitating resistance to earworm and rootworm, respectively.

Further genes encoding proteins characterized as having potential insecticidal activity may also be used. Such genes include, for example, the cowpea trypsin inhibitor (CpTI; Hilder et al., *Nature*, 330, 160 (1987)) which may be used as a rootworm deterrent; genes encoding avermectin (Avermectin and Abamectin., Campbell, W. C., Ed., 1989; Ikeda et al., *J Bacteriol* 169, 5615 1987) which may prove useful as a corn rootworm deterrent; ribosome inactivating protein genes; and genes that regulate plant structures. Transgenic plants including anti-insect antibody genes and genes that code for enzymes that can convert a non-toxic insecticide (pro-insecticide) applied to the outside of the plant into an insecticide inside the plant are also contemplated.

Environmental or Stress Resistance or Tolerance

Improvement of a plant's ability to tolerate various environmental stresses can be effected through expression of genes. For example, increased resistance to freezing temperatures may be conferred through the introduction of an "antifreeze" protein such as that of the Winter Flounder (Cutler et al., *J Plant Physiol*, 135, 351 1989) or synthetic gene derivatives thereof. Improved chilling tolerance may also be conferred through increased expression of glycerol-3-phosphate acetyltransferase in plastids (Wolter et al., *The EMBO J.*, 11 4685 (1992)). Resistance to oxidative stress can be conferred by expression of superoxide dismutase (Gupta et al., *Proc. Natl. Acad. Sci USA*, 90, 1629 (1993)), and can be improved by glutathione reductase (Bowler et al., *Ann Rev. Plant Physiol.*, 43, 83 (1992)).

It is contemplated that the expression of genes that favorably affect plant water content, total water potential, osmotic potential, and turgor will enhance the ability of the plant to tolerate drought and will therefore be useful. It is proposed, for example, that the expression of genes encoding for the biosynthesis of osmotically-active solutes may impart protection against drought. Within this class are genes encoding for mannitol dehydrogenase (Lee and Saier, *J. Bacteriol.*, 258, 10761 (1982)) and trehalose-6-phosphate synthase (Kaasen et al., *J. Bacteriology*, 174, 889 (1992)).

Similarly, other metabolites may protect either enzyme function or membrane integrity (Loomis et al., *J. Expt. Zoology*, 252, 9 (1989)), and therefore expression of genes encoding for the biosynthesis of these compounds might confer drought resistance in a manner similar to or complimentary to mannitol. Other examples of naturally occurring metabolites that are osmotically active and/or provide some direct protective effect during drought and/or desiccation include fructose, erythritol, sorbitol, dulcitol, glucosylglycerol, sucrose, stachyose, raffinose, proline, glycine, betaine, ononitol and pinitol. See, e.g., U.S. Pat. No. 6,281,411.

Three classes of Late Embryogenic Proteins have been assigned based on structural similarities (see Dure et al., *Plant Molecular Biology*, 12, 475 (1989)). Expression of structural genes from all three LEA groups may confer drought tolerance. Other types of proteins induced during water stress, which may be useful, include thiol proteases, aldolases and transmembrane transporters, which may confer various protective and/or repair-type functions during drought stress. See, e.g., PCT/CA99/00219 (Na+/H+ exchanger polypeptide genes). Genes that effect lipid biosynthesis might also be useful in conferring drought resistance.

The expression of genes involved with specific morphological traits that allow for increased water extractions from drying soil may also be useful. The expression of genes that enhance reproductive fitness during times of stress may also be useful. It is also proposed that expression of genes that minimize kernel abortion during times of stress would increase the amount of grain to be harvested and hence be of value.

Enabling plants to utilize water more efficiently, through the introduction and expression of genes, may improve the overall performance even when soil water availability is not limiting. By introducing genes that improve the ability of plants to maximize water usage across a full range of stresses relating to water availability, yield stability or consistency of yield performance may be realized.

Disease Resistance or Tolerance

Resistance to viruses may be produced through expression of genes. For example, expression of antisense genes targeted at essential viral functions or expression of genes encoding viral coat proteins may impart resistance to the virus.

Resistance to diseases caused by bacteria and fungi may be conferred through introduction of genes. For example, genes encoding so-called "peptide antibiotics," pathogenesis related (PR) proteins, toxin resistance, and proteins affecting host-pathogen interactions such as morphological characteristics may be useful.

Mycotoxin Reduction/Elimination

Production of mycotoxins, including aflatoxin and fumonisin, by fungi associated with plants is a significant factor in rendering grain not useful. Inhibition of the growth of these fungi may reduce the synthesis of these toxic substances and therefore reduce grain losses due to mycotoxin contamination. It may be possible to introduce genes into plants such that would inhibit synthesis of the mycotoxin without interfering with fungal growth. Further, expression of a novel gene which encodes an enzyme capable of rendering the mycotoxin nontoxic would be useful in order to achieve reduced mycotoxin contamination of grain.

Plant Composition or Quality

The composition of the plant may be altered, for example, to improve the balance of amino acids in a variety of ways including elevating expression of native proteins, decreasing expression of those with poor composition, changing the composition of native proteins, or introducing genes encoding entirely new proteins possessing superior composition. See, e.g., U.S. Pat. No. 6,160,208 (alteration of seed storage protein expression). The introduction of genes that alter the oil content of the plant may be of value. See, e.g., U.S. Pat. Nos. 6,069,289 and 6,268,550 (ACCase gene). Genes may be introduced that enhance the nutritive value of the starch component of the plant, for example by increasing the degree of branching, resulting in improved utilization of the starch in cows by delaying its metabolism.

Plant Agronomic Characteristics

Two of the factors determining where plants can be grown are the average daily temperature during the growing season and the length of time between frosts. Expression of genes that are involved in regulation of plant development may be useful, e.g., the liguleless and rough sheath genes that have been identified in corn.

Genes may be introduced into corn that would improve standability and other plant growth characteristics. Expression of genes which confer stronger stalks, improved root systems, or prevent or reduce ear droppage would be of value to the farmer Nutrient Utilization The ability to utilize available nutrients may be a limiting factor in growth of plants. It may be possible to alter nutrient uptake, tolerate pH extremes, mobilization through the plant, storage pools, and availability for metabolic activities by the introduction of genes. These modifications would allow a plant to more efficiently utilize available nutrients. For example, an increase in the activity of an enzyme that is normally present in the plant and involved in nutrient utilization may increase the availability of a nutrient. An example of such an enzyme would be phytase.

Male Sterility

Male sterility is useful in the production of hybrid seed, and male sterility may be produced through expression of genes. It may be possible through the introduction of TURF-13 via transformation to separate male sterility from disease sensitivity. See Levings, Science, 250:942–947, 1990. As it may be necessary to restore male fertility for breeding purposes and for grain production, genes encoding restoration of male fertility may also be introduced.

Selection and Characterization of Resistant Cell Lines

Selections are carried out until cells or tissue are recovered which are observed to be growing well in the presence of normally inhibitory levels of a tryptophan analog thereof. These cell "lines" are subcultured several additional times in the presence of a tryptophan analog to remove non-resistant cells and then characterized. The amount of resistance that has been obtained is determined by comparing the growth of these cell lines with the growth of unselected cells or tissue in the presence of various tryptophan analogs at various concentrations. Stability of the resistance trait of the cultured cells may be evaluated by simply growing the selected cell lines in the absence of the tryptophan analog for various periods of time and then analyzing growth after re-exposing the tissue to the analog. The resistant cell lines may also be evaluated using in vitro chemical studies to verify that the site of action of the analog is altered to a form that is less sensitive to inhibition by tryptophan analogs.

Transient expression of an anthranilate synthase gene can be detected and quantitated in the transformed cells. Gene expression can be quantitated by RT-PCR analysis, a quantitative Western blot using antibodies specific for the cloned anthranilate synthase or by detecting enzyme activity in the presence of tryptophan or an amino acid analog of tryptophan. The tissue and subcellular location of the cloned anthranilate synthase can be determined by immunochemical staining methods using antibodies specific for the cloned anthranilate synthase or subcellular fractionation and subsequent biochemical and/or immunological analyses. Sensitivity of the cloned anthranilate synthase to agents can also be assessed. Transgenes providing for expression of an anthranilate synthase or anthranilate synthase tolerant to inhibition by an amino acid analog of tryptophan or free L-tryptophan can then be used to transform monocot and/or dicot plant tissue cells and to regenerate transformed plants and seeds. Transformed cells can be selected by detecting the presence of a selectable marker gene or a reporter gene, for example, by detecting a selectable herbicide resistance marker. Transient expression of an anthranilate synthase gene can be detected in the transgenic embryogenic calli using antibodies specific for the cloned anthranilate synthase, or by RT-PCR analyses.

Plant Regeneration and Production of Seed

Transformed embryogenic calli, meristemate tissue, embryos, leaf discs and the like can then be used to generate transgenic plants that exhibit stable inheritance of the transformed anthranilate synthase gene. Plant cell lines exhibiting satisfactory levels of tolerance to an amino acid analog of tryptophan are put through a plant regeneration protocol to obtain mature plants and seeds expressing the tolerance traits by methods well known in the art (for example, see U.S. Pat. Nos. 5,990,390, 5,489,520; and Laursen et al., *Plant Mol. Biol.*, 24, 51 (1994)). The plant regeneration protocol allows the development of somatic embryos and the subsequent growth of roots and shoots. To determine that the tolerance trait is expressed in differentiated organs of the plant, and not solely in undifferentiated cell culture, regenerated plants can be assayed for the levels of tryptophan present in various portions of the plant relative to regenerated, non-transformed plants. Transgenic plants and seeds can be generated from transformed cells and tissues showing a change in tryptophan content or in resistance to a tryptophan analog using standard methods. It is especially preferred that the tryptophan content of the leaves or seeds is increased. A change in specific activity of the enzyme in the presence of inhibitory amounts of tryptophan or an analog thereof can be detected by measuring enzyme activity in the transformed cells as described by Widholm, *Biochimica et Biophysica Acta*, 279, 48 (1972). A change in total tryptophan content can also be examined by standard methods as described by Jones et al., *Analyst*, 106, 968 (1981).

Mature plants are then obtained from cell lines that are known to express the trait. If possible, the regenerated plants are self pollinated. In addition, pollen obtained from the regenerated plants is crossed to seed grown plants of agronomically important inbred lines. In some cases, pollen from plants of these inbred lines is used to pollinate regenerated plants. The trait is genetically characterized by evaluating the segregation of the trait in first and later generation progeny. The heritability and expression in plants of traits selected in tissue culture are of particular importance if the traits are to be commercially useful.

The commercial value of tryptophan overproducer soybeans, cereals and other plants is greatest if many different hybrid combinations are available for sale. The farmer typically grows more than one kind of hybrid based on such differences as maturity, standability or other agronomic traits. Additionally, hybrids adapted to one part of the country are not adapted to another part because of differences in such traits as maturity, disease, and insect resistance. Because of this, it is necessary to breed tryptophan overproduction into a large number of parental inbred lines so that many hybrid combinations can be produced.

A conversion process (backcrossing) is carried out by crossing the original overproducer line to normal elite lines and crossing the progeny back to the normal parent. The progeny from this cross will segregate such that some plants carry the gene responsible for overproduction whereas some do not. Plants carrying such genes will be crossed again to the normal parent resulting in progeny which segregate for overproduction and normal production once more. This is repeated until the original normal parent has been converted to an overproducing line, yet possesses all other important attributes as originally found in the normal parent. A separate backcrossing program is implemented for every elite line that is to be converted to tryptophan overproducer line.

Subsequent to the backcrossing, the new overproducer lines and the appropriate combinations of lines which make good commercial hybrids are evaluated for overproduction as well as a battery of important agronomic traits. Overproducer lines and hybrids are produced which are true to type of the original normal lines and hybrids. This requires evaluation under a range of environmental conditions where the lines or hybrids will generally be grown commercially. For production of high tryptophan soybeans, it may be necessary that both parents of the hybrid seed be homozygous for the high tryptophan character. Parental lines of hybrids that perform satisfactorily are increased and used for hybrid production using standard hybrid seed production practices.

The transgenic plants produced herein are expected to be useful for a variety of commercial and research purposes. Transgenic plants can be created for use in traditional agriculture to possess traits beneficial to the consumer of the grain harvested from the plant (e.g., improved nutritive content in human food or animal feed). In such uses, the plants are generally grown for the use of their grain in human or animal foods. However, other parts of the plants, including stalks, husks, vegetative parts, and the like, may also have utility, including use as part of animal silage, fermentation feed, biocatalysis, or for ornamental purposes.

Transgenic plants may also find use in the commercial manufacture of proteins or other molecules, where the molecule of interest is extracted or purified from plant parts, seeds, and the like. Cells or tissue from the plants may also be cultured, grown in vitro, or fermented to manufacture such molecules.

The transgenic plants may also be used in commercial breeding programs, or may be crossed or bred to plants of related crop species. Improvements encoded by the recombinant DNA may be transferred, e.g., from soybean cells to cells of other species, e.g., by protoplast fusion.

In one embodiment, a transgene comprised of a maize anthranilate α-domain isolated from a maize cell line tolerant to 5-MT and linked to the 35S CaMV promoter is introduced into a 5-MT sensitive monocot or dicot tissue using microprojectile bombardment. Transformed embryos or meristems are selected and used to generate transgenic plants. Transformed calli and transgenic plants can be evaluated for tolerance to 5-MT or 6-MA and for stable inheritance of the tolerance trait.

The following examples further illustrate the invention and are not intended to be limiting thereof.

EXAMPLE 1

Isolation and *E. coli* Expression of Anthranilate Synthase from *Agrobacterium tumefaciens*.

This example describes the isolation of anthranilate synthase from *Agrobacterium tumefaciens* and its expression in *E. coli*.

Cloning of *Agrobacterium tumefaciens* AS

The nucleotide and amino acid sequences of the anthranilate synthase coding region from *Rhizobium meliloti* (GenBank accession number: P15395) was used to search an *Agrobacterium tumefaciens* C58 genomic sequence database (Goodner et al. *Science* 294, 2323–2328 (2001)). The search consisted of tblastn using blosum62 matrix, (Altschul et. al., *Nucleic Acid Res.*, 25, 3389–3402 (1997)).

The identified AS homolog in the *Agrobacterium tumefaciens* C58 genomic sequence database was cloned by PCR using genomic DNA from *Agrobacterium tumefaciens* strain C58 (ATCC No. 33970) as the template. The primary PCR reaction was carried out using the following primers:

```
5'-TTATGCCGCCTGTCATCG-3' and      (SEQ ID NO:47)

5'-ATAGGCTTAATGGTAACCG-3'.         (SEQ ID NO:48)
```

Gene amplification parameters were as follows: (a) denature at 95° C. for 30 seconds, (b) anneal at 50° C. for 30 seconds and (c) extend at 72° C. for 2 minutes, using Expand high fidelity PCR (Roche Biochemicals), according to manufacturer directions.

An additional round of PCR amplification, yielding a product of approximately 2.3 Kb in length, was carried out using the amplified template from above and the following nested primers:

```
5'-CTGAACAACAGAAGTACG-3'           (SEQ ID NO:49)

5'-TAACCGTGTCATCGAGCG-3'.          (SEQ ID NO:50)
```

The purified PCR product was ligated into pGEM-T easy (Promega Biotech) resulting in the plasmid pMON61600 (FIG. 1). pMON61600 was sequenced using standard sequencing methodology. Confirmation of the correct sequence was obtained by comparison of the sequence the *Rhizobium meliloti* anthranilate synthase sequence (FIG. 2). The translated amino acid sequence from the isolated clone (SEQ ID NO:4) shared 88% identity with the *Rhizobium meliloti* enzyme (SEQ ID NO:7) (FIG. 2).

The abbreviation "AgroAS" or *A. tumefaciens* AS is sometimes used herein to refer to *Agrobacterium tumefaciens* anthranilate synthase.

*E. coli* Expression of *Agrobacterium tumefaciens* AS

The following vectors were constructed to facilitate subcloning of the *Agrobacterium tumefaciens* AS gene into a suitable expression vector.

A 2215 base pair PCR fragment was generated using pMON61600 as the template and the following primers:

(SEQ ID NO:51)
5'-AAAAAGATCTCCATGG TAACGATCATTCAGG-3'

(SEQ ID NO:52)
5'-AAAAGAA TTCTTATCACGCGGCCTTGGTCTTCGCC-3'.

Figure 3:
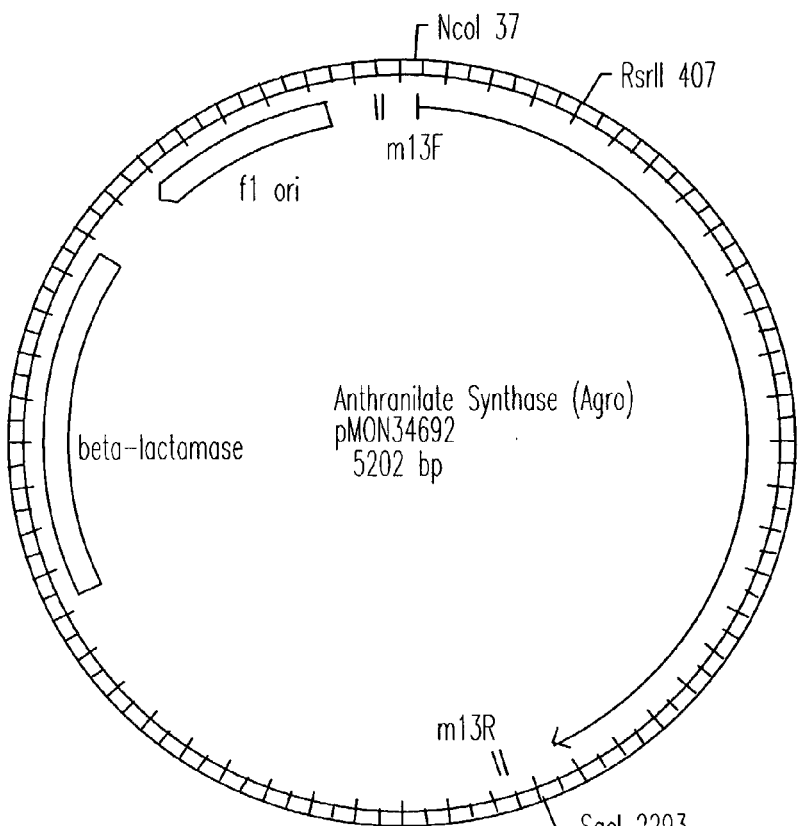
FIG. 3 is a restriction map of pMON34692.

The plasmid pMON61600 was digested with restriction enzymes NcoI and RsrII. In addition, a 409 bp fragment (derived by digesting the 2215 base pair PCR product with NcoI and RsrII) was then ligated into the digested pMON61600 plasmid, thereby replacing the NcoI/RsrII fragment, and resulting in a NcoI site in frame with the translation initiation codon (ATG) of *Agrobacterium tumefaciens* AS to yield plasmid pMON34692 (FIG. 3).

Figure 4:
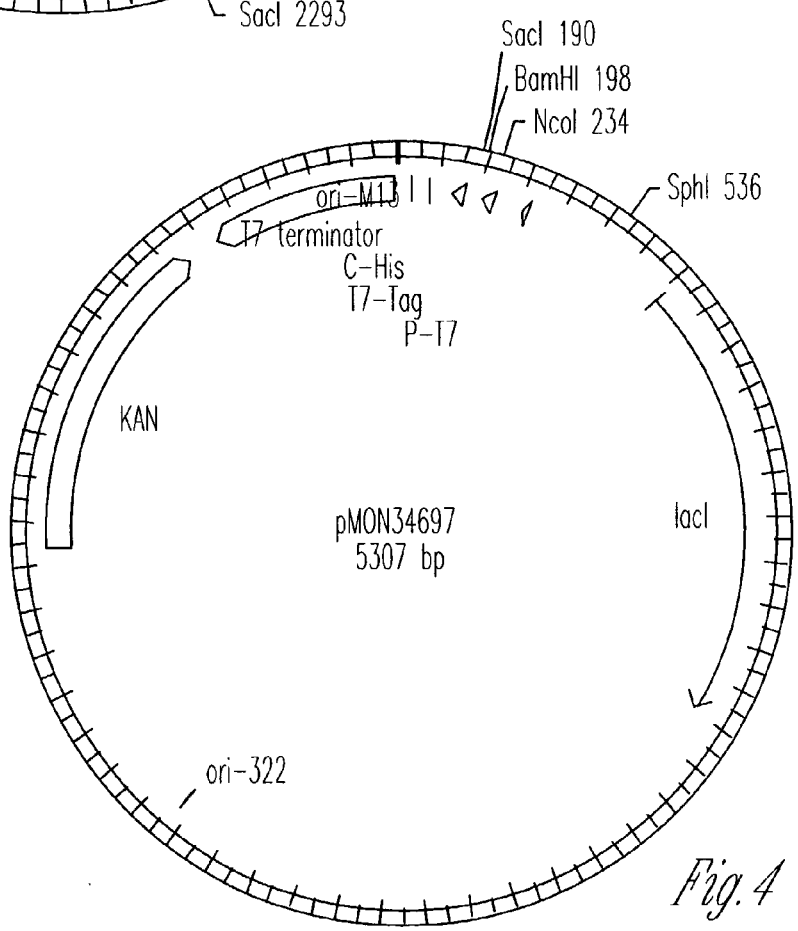
FIG. 4 is a restriction map of pMON34697.

The base T7 *E. coli* expression plasmid, pMON34697 (FIG. 4), was generated by restriction digestion of pET30a (Novogen, Inc) with SphI and BamHI. The resulting 4,969 bp fragment was purified and subcloned with a 338 bp SphI and BamHI fragment from pET11d (Novogen, Inc).

Figure 5:
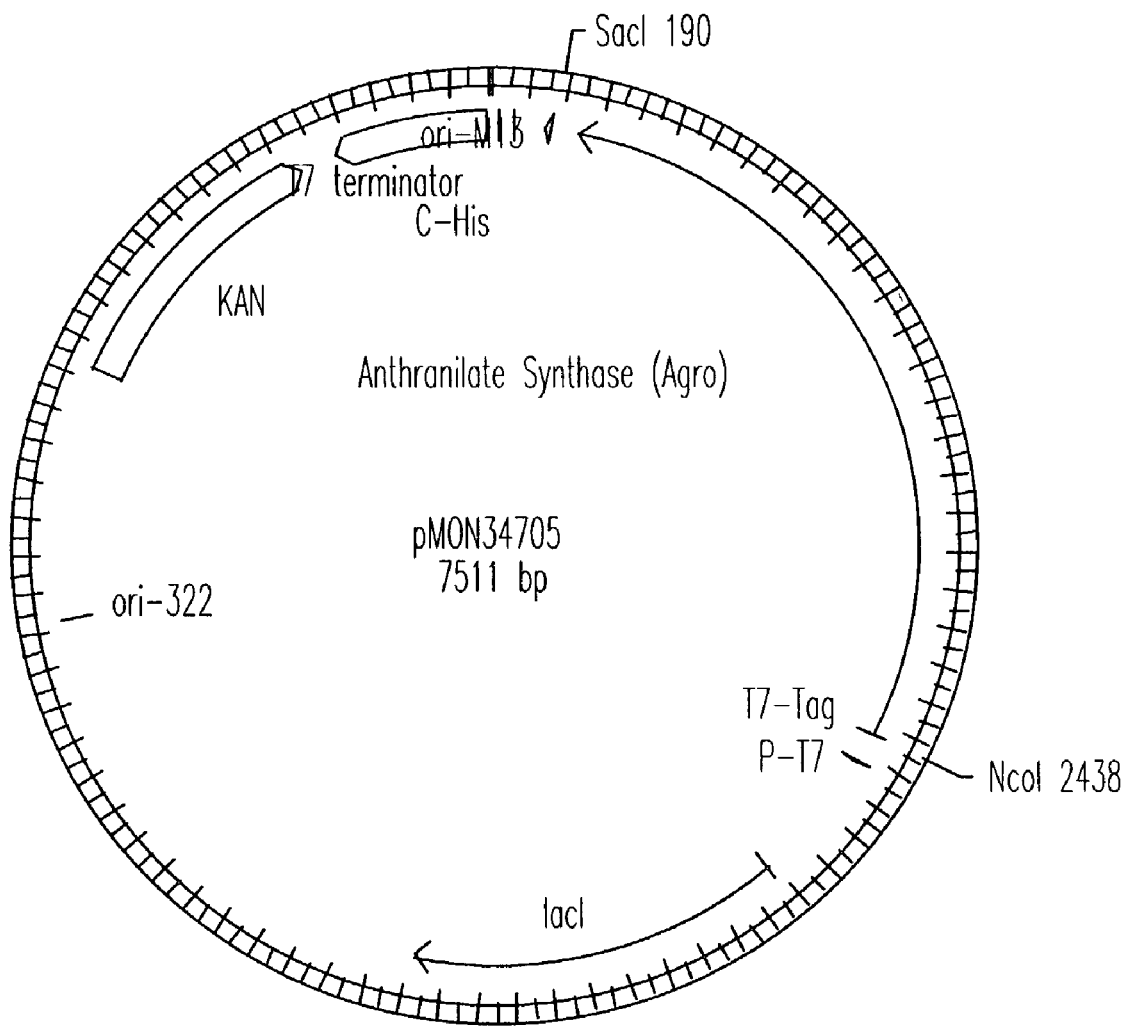
FIG. 5 is a restriction map of pMON34705.

The plasmid pMON34705 (FIG. 5) was generated by restriction digestion of pMON34697 with NcoI and SacI. The resulting 5,263 bp fragment was then purified and ligated with a 2,256 bp NcoI and SacI fragment from pMON34692 containing *Agrobacterium tumefaciens* AS.

The plasmid pMON34705 was transformed into *E. coli* BL21(DE3) (F-ompT $HsdS_b(r_B^- m_B^-)$gal dcm (DE3)) according to manufacturer's instructions (Novogen, Inc). DE3 is a host lysogen of λDE3 containing chromosomal copy of T7 RNA polymerase under control of an isopropyl-1-thio-D-galactopyranoside (IPTG) inducible lacUV5.

Transformed cells were selected on kanamyacin plates that had been incubated at 37° C. overnight (10 hours). Single colonies were transferred to 2 ml of LB (Luria Broth; per liter, 10 g tryptone, 5 g yeast extract, 10 g NaCl, and 1 g glucose (optional)) or 2×-YT broth (per liter, 16 g tryptone, 10 g yeast extract, 5 g NaCl) and then placed in a 37° C. incubator and shaken at 225 rpm for 3 hours. The cells were removed and 4 μL of 100 mM IPTG was added to the culture and returned to the 37° C. incubator for an additional 2 to 3 hours. A 1 mL aliquot of the cells was removed and sonicated in sonication buffer, (50 mM potassium phosphate (pH 7.3), 10% glycerol, 10 mM 2-mercaptoethanol and 1 mM $MgCl_2$). The resulting lysed cell extract was the source material for the standard AS assay described below. The results established that the expression system based on plamid pMON34705 was able to produce soluble and enzymatically active *Agrobacterium tumefaciens* AS protein that accounts for approximately 50% of total soluble extracted protein.

EXAMPLE 2

High Trp Seed Levels are Achieved by Transformation of Plants with Wild Type Agrobacterium Anthranilate Synthase Expression Vector pMON58120

Figure 34:
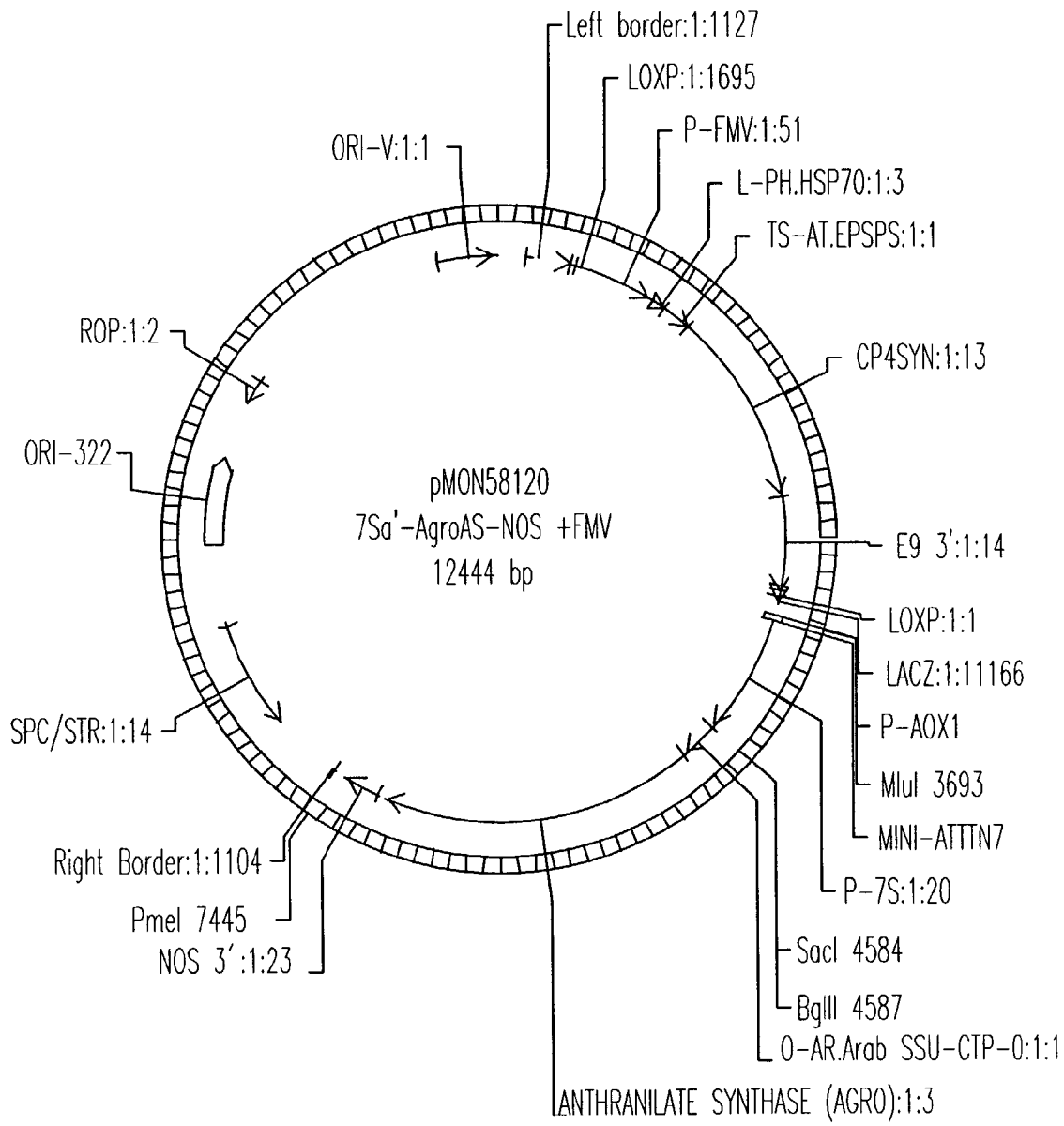
FIG. 34 is a restriction map of plasmid pMON58120.

The vector pMON58120 (FIG. 34) encodes a fusion between a 264 base pair *Arabidopsis* small subunit (SSU) chloroplast targeting peptide (CTP, SEQ ID NO:71) and a 2187 base pair wild type *Agrobacterium* anthranilate synthase (AgroAS) open reading frame (SEQ ID NO:1). See, Stark et al., (1992) Science 258: 287. Expression of this open reading frame is driven by the soy 7S alpha prime (7Sα') promoter.

Upon translation on cytoplasmic ribosomes, the fusion (immature protein) is imported into chloroplast where the chloroplast targeting sequence is removed. There are two cleavage sites in the CTP1. The first site is 30 base pairs upstream of the CDS start (C/M), and the other is at the initial methionine (C/M). The second cleavage site does not seem to be processed efficiently. The cleavage is predicted to yield a mature protein of about 70 Kd that has AS activity as shown by enzyme activity data and trp efficacy data.

The AS gene was transformed with the synthetic CP4 gene that confers glyphosate resistance, however the CP4 gene is processed separately from the AS gene. Expression of the CP4 gene was driven by the FMV promoter, which is a 35S promoter from Figwort Mosaic Virus. Glyphosate resistance allows for selection of the transformed plants.

Western Analysis of AS Protein

Thirty-five transformation events of pMON58120 were analyzed for AgroAS protein presence. AgroAS protein was detected with a polyclonal antibody raised in rabbits against purified His-tagged AgroAS. The His-tagged, full-length Agro-AS polypeptide was used as an antigen to generate a population of polyclonal antibodies in rabbits by CoCalico Biological, INC. The recombinant His-tagged Agro-AS DNA was placed into a pMON 34701 (pet-30a-agroAS) expression vector. The His-AgroAS fusion protein was expressed in *E.coli* BL21(DE3) and purified by Ni-NTA resin system (Qiagen protocol). For western analysis, primary rabbit anti-AgroAS antibodies were used at 1:5,000 dilution. Secondary, goat anti-rabbit alkaline phosphatase-conjugated antibodies were used at 1:5,000 dilution. In transgenic lines carrying 7Salpha'-Agro AS genes, western blot analysis consistently revealed the presence of a single band that specifically cross-reacted with anti-AgroAS antibodies. This band was not detected in the nontransgenic control line.

Free Amino Acid Analysis of Soy and *Arabidopsis* Seed

Amino Acid Extraction: About 50 mg of crushed soy seed (5 mg of *Arabidopsis*) material was placed in each centrifuge vial. One milliliter of 5% trichloroacetic acid was added to each sample (100 μl for *Arabidopsis*). The samples were vortexed, and allowed to sit, with agitation, at room temperature for 15 min. They were then microcentrifuged for 15 min at 14000 rpm. Some of the supernate was then removed, placed in a HPLC vial and sealed. Samples were kept at 4° C. in the analysis queue.

Amino Acid Analysis: The reagents utilized for amino acid analysis included the OPA reagent (o-phthalaldehyde and 3-mercaptopropionic acid in borate buffer (Hewlett-Packard, PN 5061–3335)) where the borate buffer (0.4 N in water, pH 10.2). The analysis was performed using the Agilent 1100 series HPLC system as described in the Agilent Technical Publication, "Amino Acid Analysis Using Zorbax Eclipse-AAA Columns and the Agilent 1100 HPLC."Mar. 17, 2000. First, 0.5 μl of the sample was derivatized with 2.5 μl of OPA reagent in 10 μl of borate buffer. Second, the derivative is injected onto a Eclipse XDB-C18 5 μm, 4.6× 150 mm column using a flow rate of 1.2 ml/min. Amino acid concentrations were measured using fluorescence: excitation at 340 nm, emission at 450 nm. Elution was with a gradient of HPLC Buffers A and B according to Table A, where HPLC Buffer A was 40 mM $Na_2HPO_4$, pH=7.8 and HPLC Buffer B was 9:9:2::Methanol:Acetonitrile:Water.

TABLE A

| Amino Acid Elution | | | | | |
| --- | --- | --- | --- | --- | --- |
| Time | 0 | 20 | 21 | 26 | 27 |
| % Buffer B | 5 | 65 | 100 | 100 | 100 |

Amino acid standards were prepared from the dry chemicals, using all amino acids of interest. Proline analysis required an additional derivatization step with 9-fluorenylmethyl-chloroformate (FMOC). Amino acid standards were also sometimes purchased in concentrations ranging from 0 to 100 µg/ml. Samples were reported in µg/g of seed powder. Calculations were performed using an MS Excel spreadsheet found on Mynabird TMBROW>Public>Calculators>External Standard.xls.

Expression of Wild Type Agrobacterium Anthranilate Synthase in *Arabidopsis*.

The vector pMON 58120 was transformed into Arabidopsis plants by vacuum infiltration of the secondary influorescences, and plants were allowed to set transgenic seed. The seed was collected and screened for the presence of a selectable marker (glyphosate resistance). Glyphosate resistant plants were grown to maturity and seed from each plant, which was designated a transformation event, and analyzed for tryptophan content (Table B). Selected transformation events were also analyzed for the presence of the expressed *Agrobacterium* anthranilate synthase protein in the mature seed by Western blot analysis as shown in Table B.

TABLE B

Analysis of Transformants

| Transformation Event | Trp (ppm) | Protein present |
|---|---|---|
| 7317 | 2547 | + |
| 7315 | 2960 | + |
| 7319 | 3628 | + |
| 7313 | 3979 | + |

Expression of Wild Type *Agrobacterium* Anthranilate Synthase in Soy (Glycine Max)

Thirty-three out of thirty-five soy transformation events analyzed had an increase in seed trp levels, for example, from above 500 ppm and up to 12,000 ppm. In nontransgenic soy seeds, the trp level is less than 200 ppm. All seeds that contained high amounts of trp demonstrated anthranilate synthase protein expression by western blotting. Table C presents data for nineteen soy events that contain high trp levels and also are positive for anthranilate synthase anthranilate synthase protein by western blot analysis.

TABLE C

Correlation between the Presence of the Agro AS Protein and Tryptophan Levels in Nineteen Soy Transgenic Events bearing pMON58120

| Pedigree | Trp max (ppm) | Trp average (ppm) | Protein present? |
|---|---|---|---|
| A3244 (ctr) | 306 | 96 | NO |
| GM_A20380:@. | 6444 | 2246.4 | YES |
| GM_A20532:@. | 6055 | 2556.6 | YES |
| GM_A22043:@. | 10422 | 2557.2 | YES |
| GM_A20598:@. | 8861 | 2859.9 | YES |
| GM_A20744:@. | 7121 | 3373.3 | YES |
| GM_A20381:@. | 6392 | 3572.9 | YES |
| GM_A20536:@. | 9951 | 3581.5 | YES |
| GM_A20510:@. | 8916 | 3592.7 | YES |
| GM_A20459:@. | 8043 | 3900.4 | YES |
| GM_A20337:@. | 7674 | 4088.6 | YES |
| GM_A20533:@. | 9666 | 4183.2 | YES |
| GM_A20577:@. | 6276 | 4434.1 | YES |
| GM_A20339:@. | 9028 | 4687.8 | YES |
| GM_A20386:@. | 8487 | 5285.3 | YES |

TABLE C-continued

Correlation between the Presence of the Agro AS Protein and Tryptophan Levels in Nineteen Soy Transgenic Events bearing pMON58120

| Pedigree | Trp max (ppm) | Trp average (ppm) | Protein present? |
|---|---|---|---|
| GM_A20457:@. | 11007 | 5888.9 | YES |
| GM_A20379:@. | 7672 | 6416.1 | YES |
| GM_A20537:@. | 9163 | 6695.8 | YES |
| GM_A20534:@. | 12676 | 7618.2 | YES |
| GM_A20576:@. | 10814 | 7870.1 | YES |

The Agro AS Enzyme Assay

The specific activity of anthranylate synthase was measured in eleven transformation events carrying the pMON58120 construct. Individual soybean immature seeds were analyzed using an HPLC-based end-point assay based on the method described by C. Paulsen (J. Chromatogr. 547, 1991, 155–160). Briefly, desalted extracts were generated from individual seeds in grinding buffer (100 mM Tris pH 7.5, 10% glycerol, 1 mM EDTA, 1 mM DTT) and incubated for 30 min with reaction buffer (100 mM tris pH 7.5, 1 mM chorismate, 20 mM glutamine, and 10 mM $MgCl_2$). Agro AS activity was measured in the presence or absence of 25 mM trp. The reaction was stopped with phosphoric acid and the amount of anthranilate formed was quantified by HPLC using a fluorescence detector set at 340 nm/excitation and 410 nm/emission.

The specific activity of AS in immature segregating transgenic seeds ranged from 1.5-fold up to 70-fold increase compared to a nontransgenic control, reaching as high as 6,000 pmoles/mg/min. As shown in the last column of Table D, the anthranilate synthase activity in transgenic plants is resistant to tryptophan inhibition (see Table D).

TABLE D

Agro AS Enzyme Activity in Transgenic Event 20576

| Event | Seed No. | Specific Activity (pmoles/mg/min) | Specific Activity (pmoles/mg/min) (+25 micromolar Trp) |
|---|---|---|---|
| Control | 3244-1 | 95.4 | 42.4 |
| Control | 3244-2 | 85.5 | 40.6 |
| 20576 | 20576-1 | 6060.2 | 4407.1 |
| 20576 | 20576-2 | 3783.8 | 1709.4 |
| 20576 | 20576-3 | 2768.3 | 2431.7 |
| 20576 | 20576-4 | 4244.08 | 2125.2 |

EXAMPLE 3

Soybean Transformation with a Vector Containing a Maize Anthranilate Synthase α-Subunit Gene.

Figure 22:
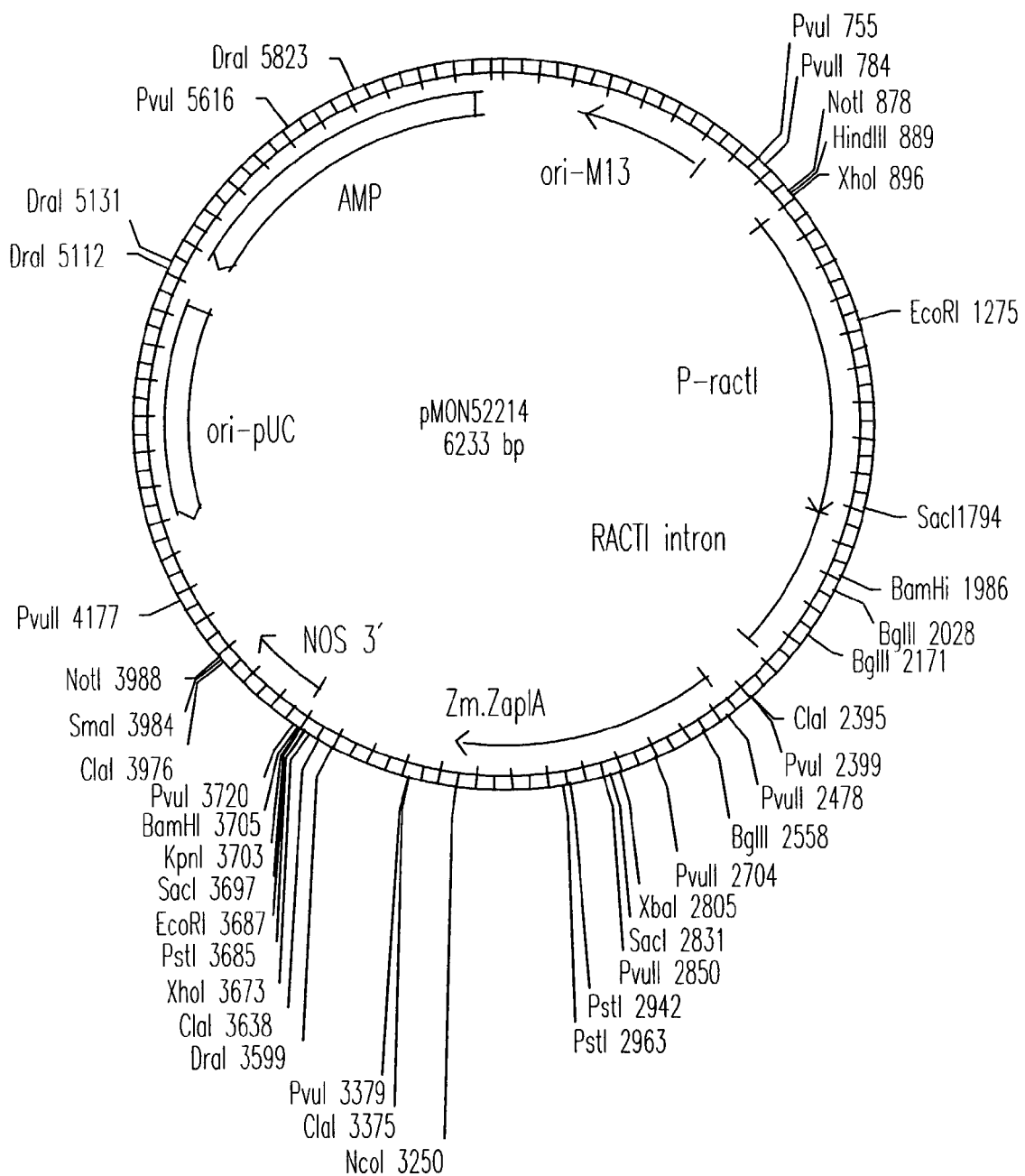
FIG. 22 is a restriction map of plasmid pMON52214.
Figure 23:
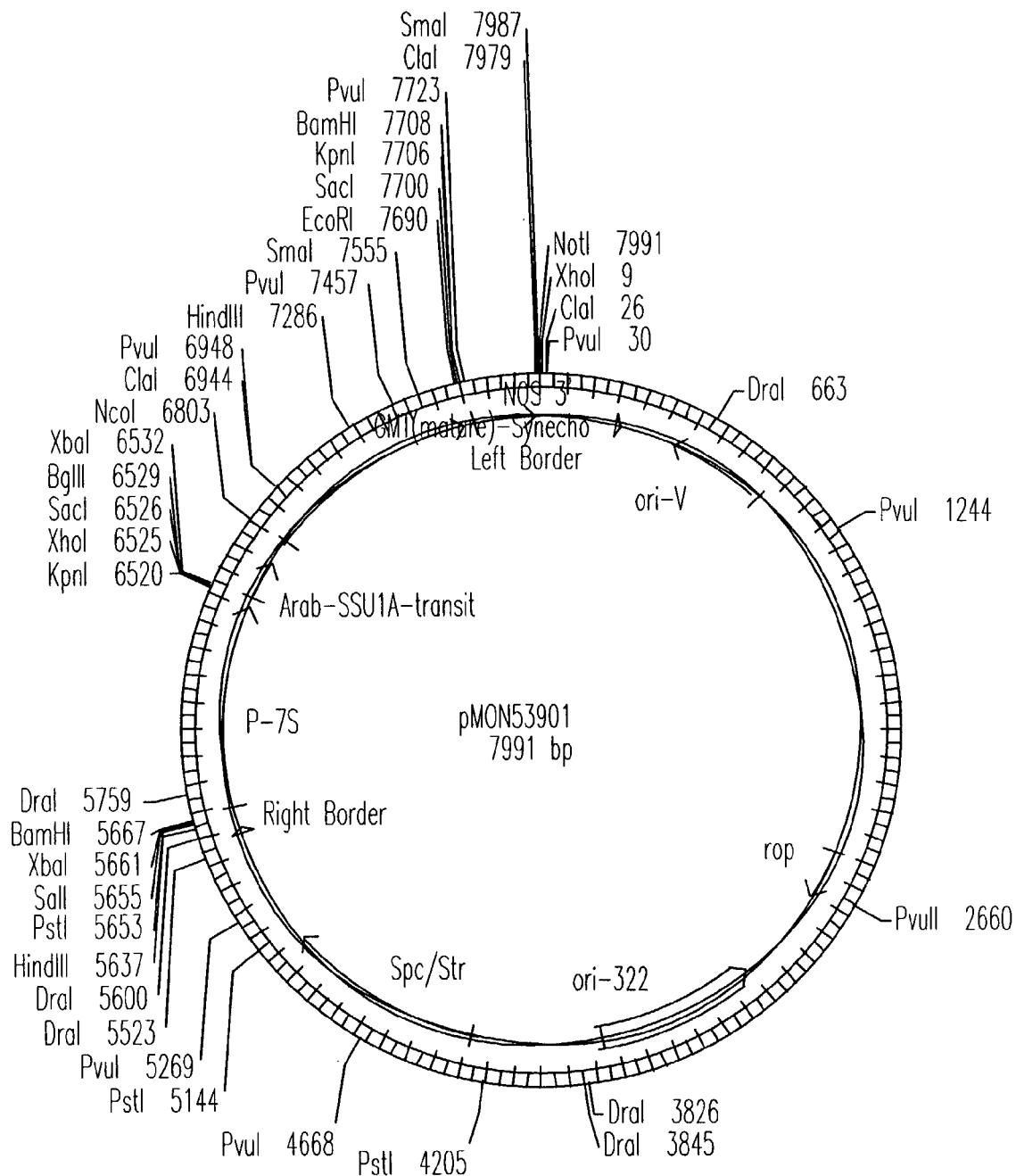
FIG. 23 is a restriction map of plasmid pMON53901.
Figure 24:
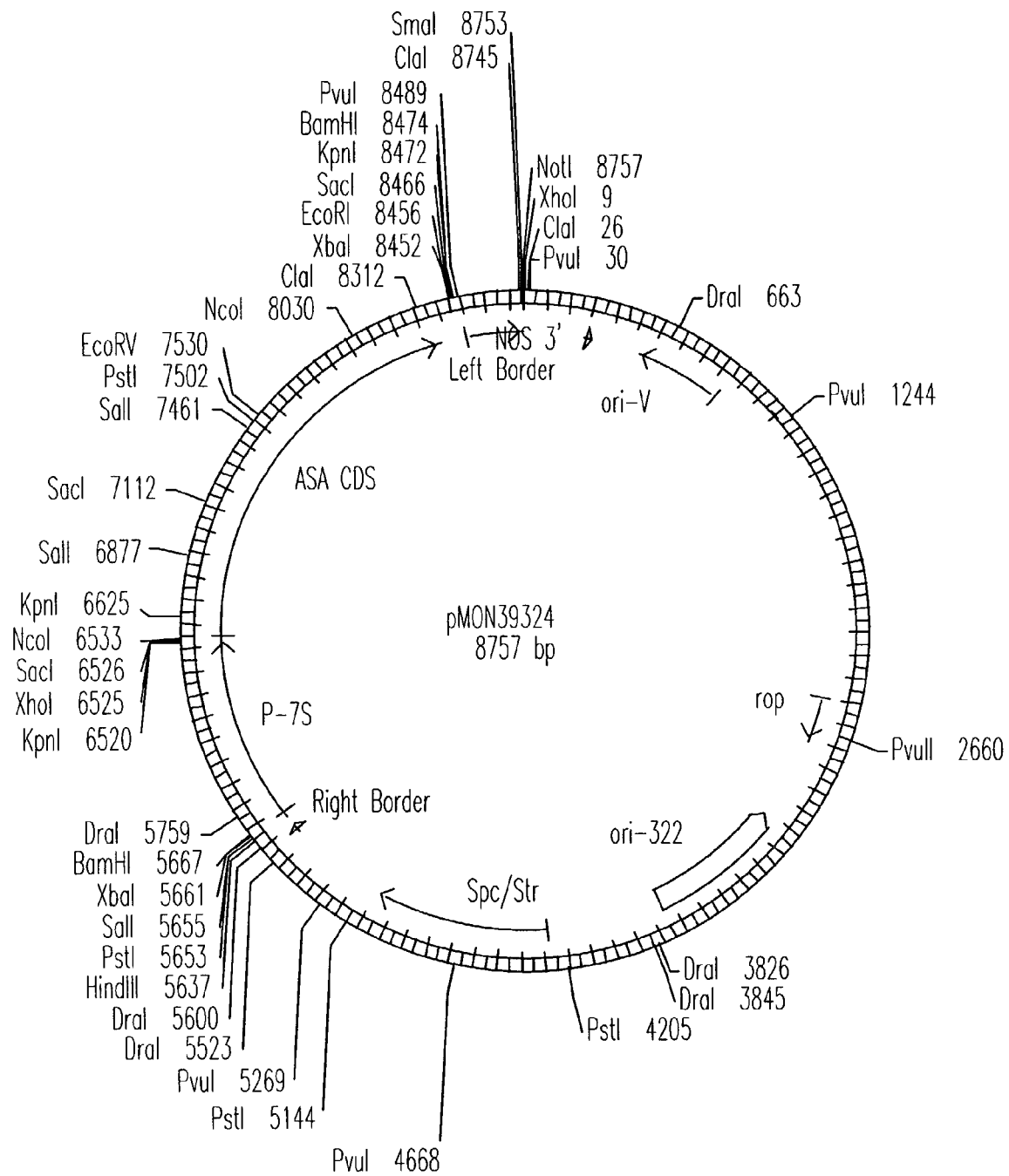
FIG. 24 is a restriction map of plasmid pMON39324.

The coding sequence for a maize anthranilate synthase α-subunit was isolated from pMON52214 (FIG. 22) by digesting with XbaI in combination with a partial NcoI digest (see Anderson et. al. U.S. Pat. No. 6,118,047). The resulting 1952 bp DNA fragment representing the anthranilate synthase α coding region was gel purified, and the ends were made blunt. The plasmid pMON53901 (FIG. 23) was digested with BglII and EcoRI, to generate a 6.8 Kb fragment. After isolation, the ends of the 6.8 Kb fragment were made blunt and dephosphorylated. The 1952 Kb fragment containing the ASα gene was then ligated into the blunt-ended 6.8 kb pMON53901 fragment to generate pMON39324, a maize 7Sα'-ASα-NOS expression vector (FIG. 24).

Figure 25:
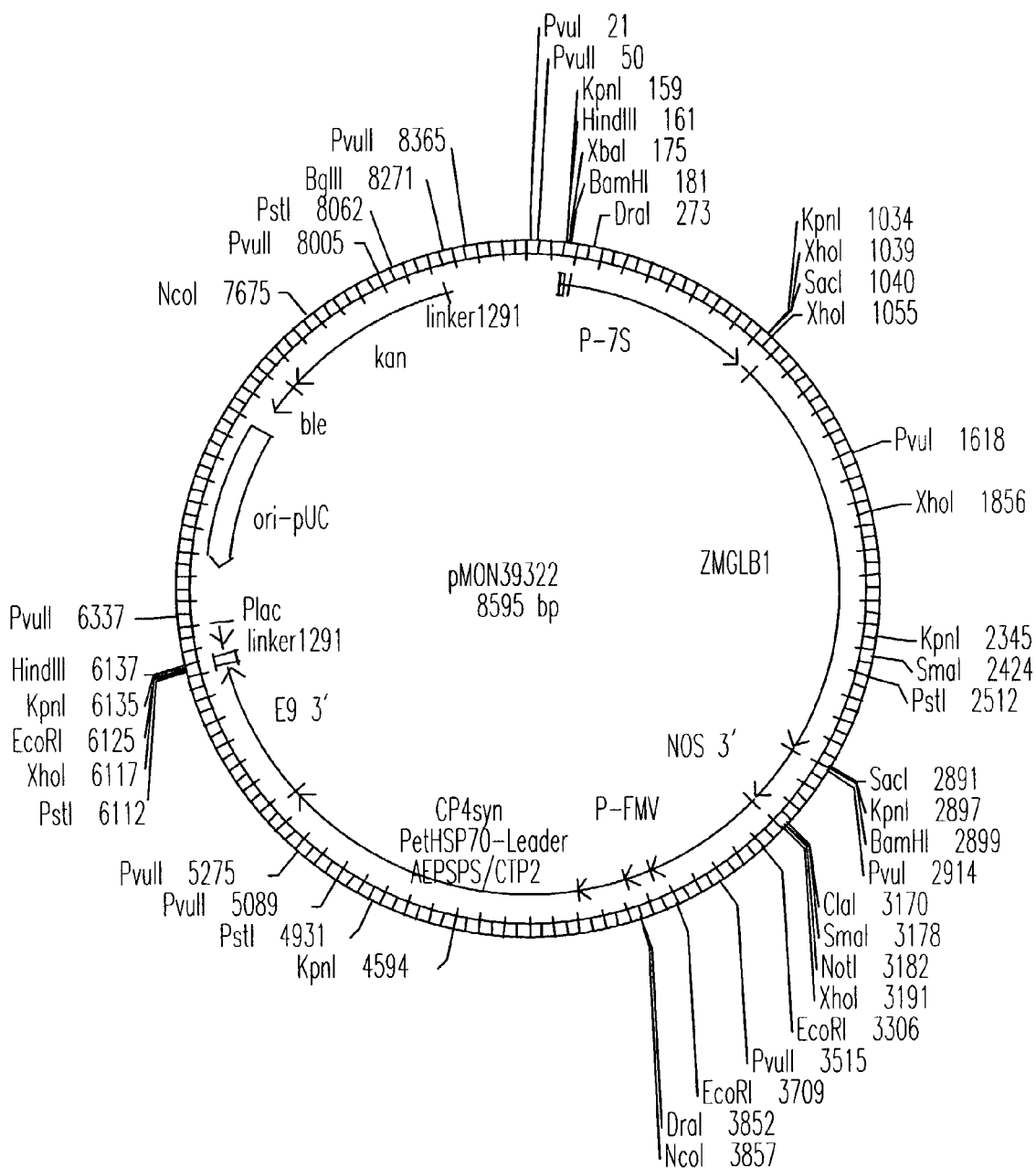
FIG. 25 is a restriction map of plasmid pMON39322.
Figure 26:
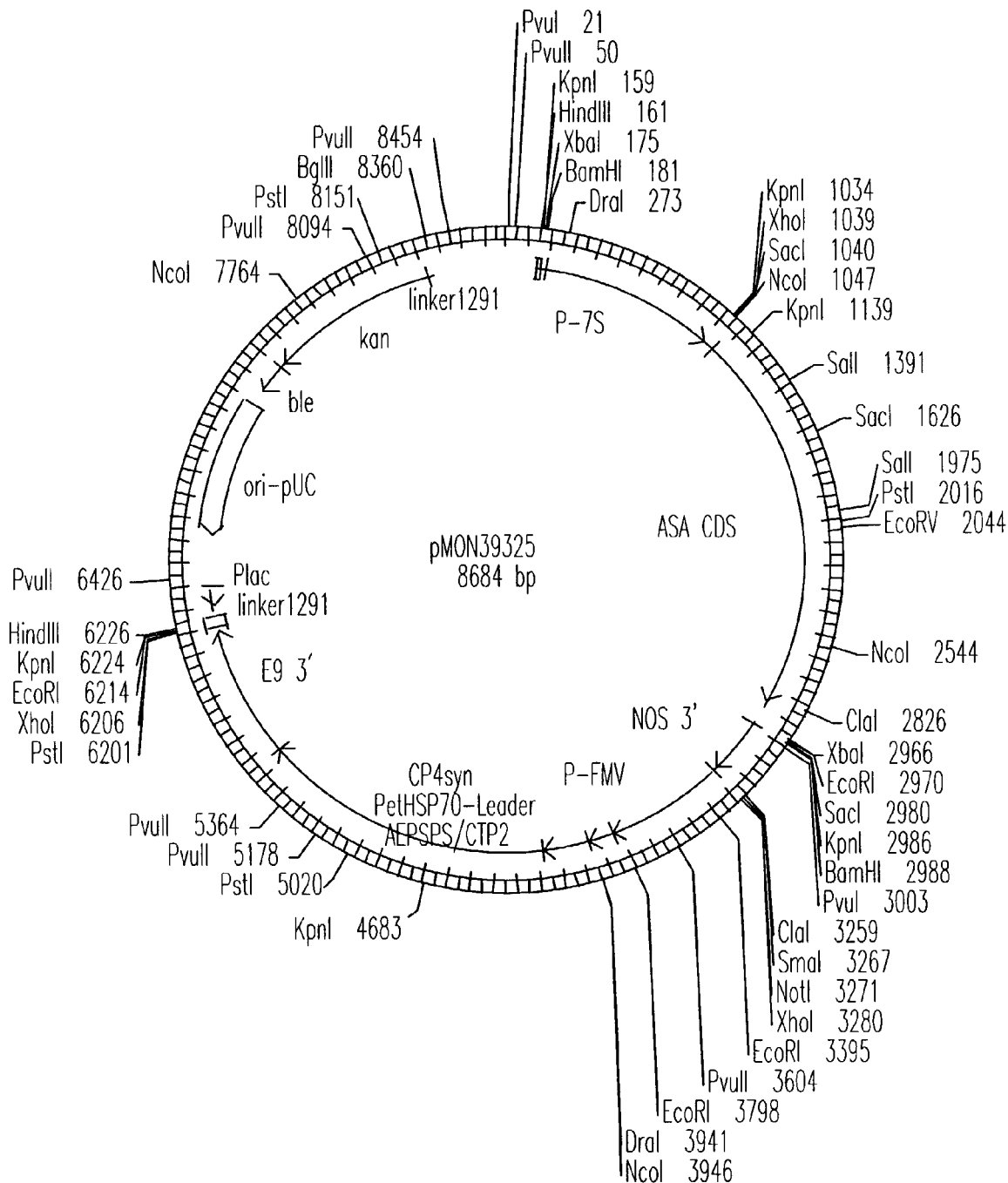
FIG. 26 is a restriction map of plasmid pMON39325.

This pMON39324, a maize 7Sα'-ASα-NOS cassette was subsequently digested with BamHI resulting in a 2.84 Kb DNA fragment, containing the 7S promoter and maize ASα coding sequence. The plasmid pMON39322 (FIG. 25) was digested with BamHI resulting in a 5.88 kb DNA fragment. These two fragments were then ligated together to create pMON39325 (FIG. 26), a transformation vector containing 7Sα' promoter-maize ASα-NOS terminator cassette subcloned into pMON39322.

Using similar procedures, the coding sequence for a maize anthranilate synthase α-subunit was cloned downstream from the USP promoter to generate a pMON58130 expression vector, downstream from the Arc5 promoter to generate a pMON69662 expression vector, downstream from the Lea9 promoter to generate a pMON69650 expression vector, and downstream from the Per1 promoter to generate a pMON69651 expression vector. A list with these expression vectors is presented in Table E.

TABLE E

C28-Maize Anthranilate Synthase Constructs

| Seed Generation | Expression Cassette | Vector Name |
| --- | --- | --- |
| R4 | 7Sa'-maize-ASα | PMON39325 |
| R2 | Napin-maize-ASα | PMON58023 |
| R1 | USP-maize-ASα | PMON58130 |
| R1 | Arc5-maize-ASα | PMON69662 |
| R1 | Lea9-maize-ASα | PMON69650 |
| R1 | Per1-maize-ASα | PMON69651 |

These vectors were used for plant transformation and propagation experiments. Soybean plants were transformed with the maize AS-containing vectors using the microprojectile bombardment technology as described herein. Several transgenic soybean lines were established for each type of vector and propagated through the number of generations indicated in Table E.

For example, three homozygous lines were established that carried the 7Salpha'-maize-AS transgene from pMON39325. These three lines were grown in a randomized block design in two different locations. Mature seed was produced and analyzed for free amino acid content. Controls were included to establish baseline trp levels, i.e. the three corresponding negative isolines and the nontransgenic controls.

Figure 27:
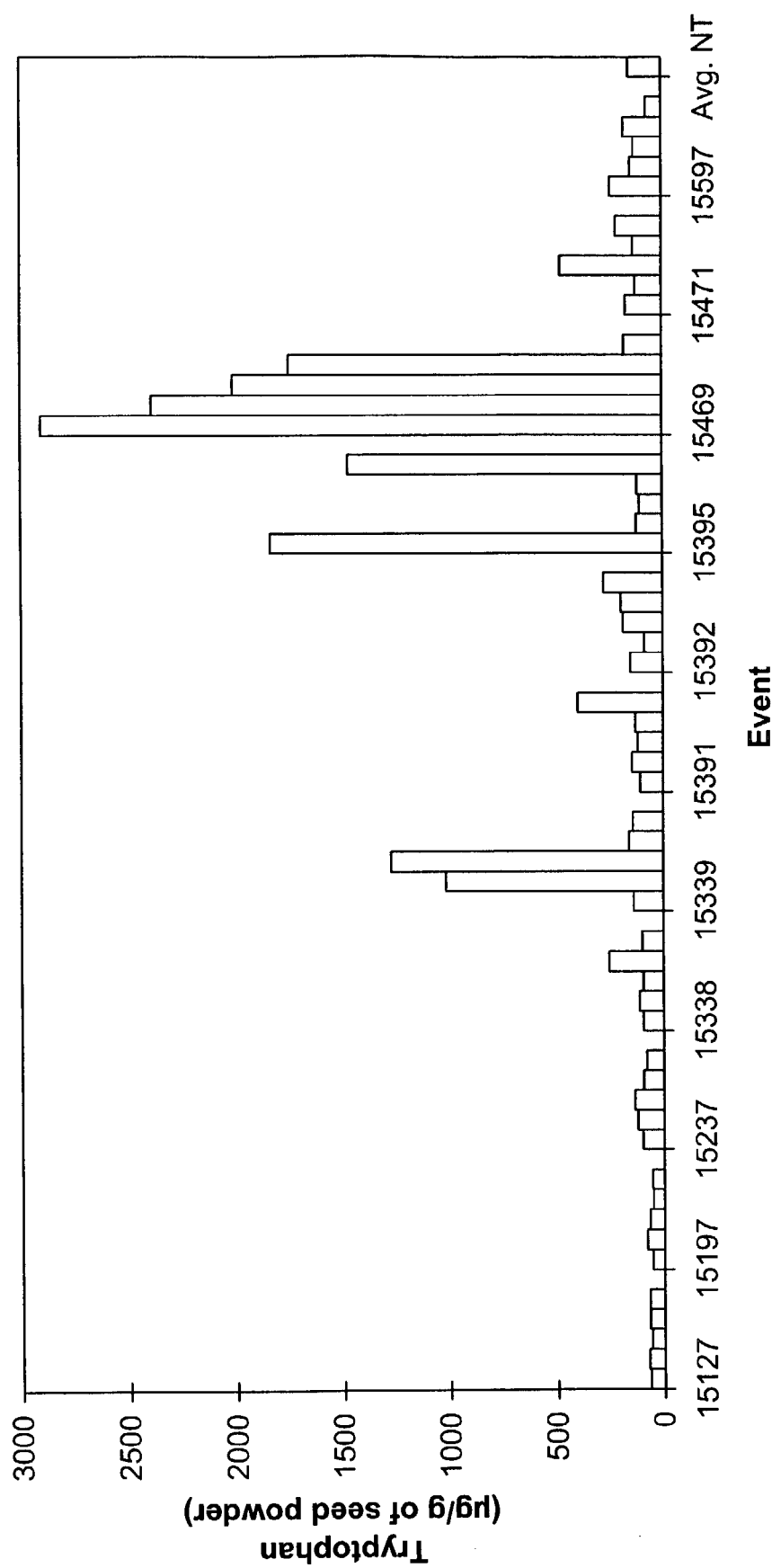
FIG. 27 is a graph depicting free tryptophan levels in soybean seeds transformed with pMON39325. There were five observations from each event. NT represents non-transgenic soybean seed.

Table F provides R4 seed tryptophan in ppm for pMON39325 transformant and control lines, showing that the average non-transgenic soybeans contain about 100–200 μg tryptophan/g seed powder whereas the pMON39325 transformants contain substantially more Trp. See also FIG. 27.

TABLE F

Trp Levels in seeds of Soybean Plants Transformed with the C28 Zea mays mutant (pMON39325)

| Positive isoline number | Average trp of Positive Isoline (ppm) | Standard deviation | Average trp of corresponding Negative isoline (ppm) | Standard deviation |
| --- | --- | --- | --- | --- |
| 39325-1 | 3467 | 377 | 226 | 55 |
| 35325-2 | 2623 | 307 | 164 | 20 |

TABLE F-continued

Trp Levels in seeds of Soybean Plants Transformed with the C28 Zea mays mutant (pMON39325)

| Positive isoline number | Average trp of Positive Isoline (ppm) | Standard deviation | Average trp of corresponding Negative isoline (ppm) | Standard deviation |
| --- | --- | --- | --- | --- |
| 35325-3 | 3715 | 152 | 184 | 64 |
| 35325-4 | 2833 | 165 | 202 | 146 |
| 35325-5 | 3315 | 161 | 173 | 34 |
| 35325-6 | 2394 | 318 | 144 | 22 |
| non-transgenic control-7 | | | 191 | 24 |
| non-transgenic control-8 | | | 118 | 23 |

Five other constructs, expressing the C28 maize anthranilate synthase under the control of five different promoters (Table E) were transformed into soy and transgenic plants were obtained. Each construct generated events high in trp. An example illustrating events generated by Per1-C28 maize anthranilate synthase is shown in Tables G and H.

TABLE G

C28 maize AS Protein Expression Correlates with Increased Trp Levels in Three Transgenic Events bearing Per1-C28 maize AS (pMON69651)

| Pedigree | Trp average (ppm) | Protein present? |
| --- | --- | --- |
| Control | 96 | NO |
| 22689 | 2375 | Yes |
| 22787 | 1707 | Yes |
| 22631 | 1116 | Yes |

Table H illustrates the enzymatic activity of C28 maize AS in R1 seeds from soybean plants transformed with the pMON69651 expression vector.

TABLE H

Specific Activity of C28 maize AS in R1 Seeds of pMON69651 Transformants

| Event | Seed number | Specific activity (pmoles/mg/min) | Specific activity (pmoles/mg/min) (+25 micromolar tryptophan) |
| --- | --- | --- | --- |
| Control | | 51.6 | 2.6 |
| 22689 | 22689-1 | 130.9 | 64.7 |
| | 22689-2 | 115.3 | |
| | 22689-3 | 148.5 | 61.1 |
| | 22689-4 | 149.5 | |
| | 22698-5 | 133.8 | 60.3 |

These results indicate that there is a substantial increase in tryptophan when soybean plant tissues are transformed with the C28 maize AS gene. The high trp levels shown in Table G correlate with the presence of the AS protein and with increased specific activity (2.5 fold higher than in nontransgenic controls) for the transgenic enzyme (Table H). As shown in Table H—and as predicted by the biochemical properties of the C28 maize AS enzyme—the specific activity of transgenic events is tryptophan-resistant.

EXAMPLE 4

Rational Design of *Agrobacterium tumefacians* Anthranilate Synthase Tryptophan Feedback Insensitive Mutants.

This example describes vectors containing mutant *Agrobacterium tumefaciens* anthranilate synthase enzymes that have various degrees of sensitivity or insensitivity to feedback inhibition by tryptophan or tryptophan analogs.

Generation of *Agrobacterium tumefaciens* Mutant Anthranilate Synthase Genes.

Using protein structural information from *Sulfolobus solfataricus* anthranilate synthase as a guide (Knochel et. al., Proc. Natl. Acad. Sci. USA, 96, 9479–9484 (1999)) several *Agrobacterium tumefaciens* anthranilate synthase mutants were rationally designed utilizing protein informatics to confidently assign several residues involved in tryptophan binding. This was accomplished by alignment of the *Agrobacterium tumefaciens* anthranilate synthase gene with the anthranilate synthase amino acid sequence from *Sulfolobus solfataricus* (FIG. 6). The putative tryptophan binding and catalysis regions of the *Agrobacterium tumefaciens* were assigned by combining the knowledge of the structural information with the sequence homology. Residues in the binding pocket were identified as potential candidates for altering to provide resistance to feedback inhibition by tryptophan.

Based on the structural analysis of the *Sulfolobus solfataricus* anthranilate synthase enzyme, it suggested that amino acids E30, S31, I32, S42, V43, N2O4, P205, M209, F210, G221, and A373 were involved in tryptophan binding. Based on the pairwise alignment, N204, P205, and F210 of *Sulfolobus solfataricus* were also conserved in the monomeric *Agrobacterium tumefaciens* anthranilate synthase as residues N292, P293, and F298 respectively.

However, due to multiple insertions and deletions, the N-terminal regions of the *Sulfolobus solfataricus* and *Agrobacterium tumefaciens* enzymes were highly divergent. For this reason, it was necessary to manually assign residues at the N-terminal region of the *Agrobacterium tumefaciens* anthranilate synthase involved in tryptophan regulation (FIG. 6). Structural analysis indicated that the motif "LLES" formed a β sheet in the tryptophan-binding pocket. This structure appeared to be highly conserved among the heterotetrameric enzymes. The known monomeric enzymes were then manually aligned to the *Sulfolobus solfataricus* sequence using the "LLES" motif as a landmark (FIG. 21). Based on this protein informatics analysis, amino acid residues V48, S50, S51, and N52 in *Agrobacterium tumefaciens* AS were also likely to be involved in tryptophan binding.

With the putative tryptophan binding residues assigned in the *Agrobacterium tumefaciens* monomeric enzyme, several distinct strategies were rationalized for reducing the sensitivity of the enzyme to tryptophan inhibition. These substitutions included for example, enlarging the tryptophan-binding pocket (F298A), narrowing the binding pocket (V48F, V48Y, S51F, S51C, N52F, F298W), increasing the polarity of the binding pocket (S50K), or distorting the shape of the binding pocket by changing the protein main chain conformation (P293A, P29G).

*A. tumefaciens* AS Site-directed Mutagenesis

Site directed mutagenesis was used to generate ten single amino acid substitutions six sites. The mutations were introduced into the *Agrobacterium tumefaciens* AS in pMON34705 using the QuikChange™ Site-Directed Mutagenesis Kit (Stratagene). The primers used for site directed mutagenesis were SEQ ID NO:9–42 (FIG. 7; F=forward, R=reverse). Each primer sequence is specific for alteration of the nucleic acid at a specific location in the sequence and thus changing the encoded codon to code for a new amino acid. For example, S51C designates a change from serine to cysteine at amino acid position 51 in the *Agrobacterium tumefaciens* AS peptide sequence.

Following mutagenesis the sequence of the entire gene was reconfirmed and the variants expressed and purified from *E. coli* as described below for the wild type enzyme. The resultant plasmids comprising mutant *Agrobacterium tumefaciens* AS are suitably cloned into a plasmid for overproduction of protein using the T7 expression system as described in Example 1.

*Agrobacterium tumefaciens* AS Protein Expression and Purification

*Agrobacterium tumefaciens* AS wild type and mutant enzymes were expressed in *E. coli* as described in Example 1. The purification of all the *Agrobacterium tumefaciens* AS enzymes, including wild type and mutants therof, was performed at 4° C. The cells (approximate wet weight of 1 g) were suspended in 20 ml of purification buffer (50 mM potassium phosphate, pH 7.3, mM $MgCl_2$, 10 mM 2-mercaptoethanol, 10% glycerol) and lysed by ultrasonication (Branson sonifier Cell Disruptor, W185). Supernatant was collected after centrifugation of the homogenate at 20,000× g for 15 min. The supernatant was subjected to ammonium sulfate fractionation (30 to 65% saturation). The precipitate was collected after centrifugation at 20,000× g for min and dissolved in 3 ml of the purification buffer and then loaded as a whole on an Econo-Pac 10DG desalting column, pre-equilibrated with the same buffer. Fractions containing the enzyme were detected by the developed assay and pooled. The pooled enzyme (4.3 mls) was loaded on a 10 ml DEAE Sephacel (Pharmacia Biotech) column (1.5×7.5 cm) equilibrated with the same buffer. The column was washed with 30 ml of the purification buffer and the enzyme was eluted with 30 ml of 50 mM NaCl in the same buffer. Fractions containing high AS activity were pooled and precipitated by 65% ammonium sulfate saturation and isolated and desalted as above. Fractions containing the enzyme were pooled and stored at −80° C.

Anthranilate Synthase Enzyme Assay and Kinetic Analysis.

The standard assay for *Agrobacterium tumefaciens* AS was performed at 25° C. in an assay buffer containing 100 mM potassium phosphate, pH 7.0, 1 0 mM $MgCl_2$, 1 mM dithiothreitol, 200 μM chorismate and 10 mM L-glutamine. The reaction was started by adding 30 μl of enzyme to the reaction mixture and mixing. The formation of anthranilate was directly monitored by the absorbance increase at 320 m for 3 min. Initial rate of reaction was calculated as unit absorbance increase per second based on the slope of the absorbance change over the reaction time. $K_m$ for chorismate ($K_m^{Cho}$) was determined in the total volume of 1 ml assay buffer containing 100 mM potassium phosphate, pH 7.0, 10 mM $MgCl_2$, 1 mM dithiothreitol with 10 mM L-glutamine and varying the concentration of chorismate between 2.5–100 μM chorismate. The $K_m$ for glutamine ($K_m^{Gln}$) was determined in the total volume of 1 ml assay buffer containing 100 mM potassium phosphate, pH 7.0, 10 mM $MgCl_2$, 1 mM dithiothreitol with 200 μM chorismate and varying the concentration of L-glutamine between 0.1–2 mM L-glutamine. $IC_{50}$ for tryptophan ($IC_{50}TrP$) was determined with in the total volume of 1 ml assay buffer containing 100 mM potassium phosphate, pH 7.0, 10 mM MgCl$_2$, 1 mM dithiothreitol, 10 mM L-glutamine, 200 μM chorismate and varying the concentration of L-tryptophan between 0.1–10 mM L-tryptophan. Kinetic parameters and IC$_{50}$ of AS were calculated after fitting the data to a non-linear regression program (GraFit).

Several mutants demonstrated reduced sensitivity to tryptophan inhibition while still maintaining enzymatic activity comparable to the wild type enzyme (Table I). These results demonstrate that the extent of sensitivity to tryptophan inhibition can be decreased, for example, by mutating amino acids in the tryptophan-binding pocket of anthranilate synthase and by optimizing of the mutations demonstrating feedback insensitivity.

TABLE I

Anthranilate Synthase Activity and Effect of Tryptophan on *Agrobacterium tumefaciens* AS Mutants

| Mutation | Codon | $K_m^{Cho}$ (μM) | $K_m^{Gln}$ (mM) | $k_{cat}$ (s$^{-1}$) | $k_{cat}/K_m^{Cho}$ (μM$^{-1}$s$^{-1}$) | $IC_{50}^{Trp}$ (μM) |
|---|---|---|---|---|---|---|
| WT |  | 8.0 | 0.11 | 0.43 | 5.37 × 10$^{-2}$ | 5 |
| V48F | TTT | 4.5 | 0.08 | 0.24 | 5.33 × 10$^{-2}$ | 150 |
| V48Y | TAT | 4.2 | 0.10 | 0.18 | 4.28 × 10$^{-2}$ | 650 |
| S50K | AAG | 13 | 0.01 | 0.13 | 1.00 × 10$^{-2}$ | 0.1 |
| S51F | TTC | 10 | 0.06 | 0.08 | 0.80 × 10$^{-2}$ | >32,000 |
| S51C | TGC | 2.8 | 0.08 | 0.15 | 5.36 × 10$^{-2}$ | 1,500 |
| N52F | TTC | 5.5 | 0.04 | 0.21 | 3.82 × 10$^{-2}$ | 41 |
| P293A | GCG | 24 | 0.16 | 0.35 | 1.46 × 10$^{-2}$ | 14 |
| P293G | GGG | 33 | 0.07 | 0.48 | 1.45 × 10$^{-2}$ | 17 |
| F298A | GCC | 9.2 | 0.10 | 0.46 | 5.00 × 10$^{-2}$ | 5.5 |
| F298W | TGG | 18 | 0.14 | 0.44 | 2.44 × 10$^{-2}$ | 450 |

EXAMPLE 5

Random Mutagenesis of *Agrobacterium tumefaciens* AS to Generate Tryptophan Feedback Insensitive Mutants.

In addition to the rational design approaches described in Example 4, other strategies to generate feedback insensitive mutants of anthranilate synthase include, but are not limited to, random mutageneseis. Random mutagenesis of the *Agrobacterium tumefaciens* AS, can be accomplished, for example, by chemical mutagenesis (isolated DNA or whole organism), error prone PCR, and DNA shuffling. This example describes the use of chemical mutagenesis followed by genetic selection. The genetic selection approach is also useful for selection of desirable mutants derived from other mutagenesis techniques.

Generation of *E. coli* Expression Plasmid Containing *A. tumefaciens* AS

Figure 28:
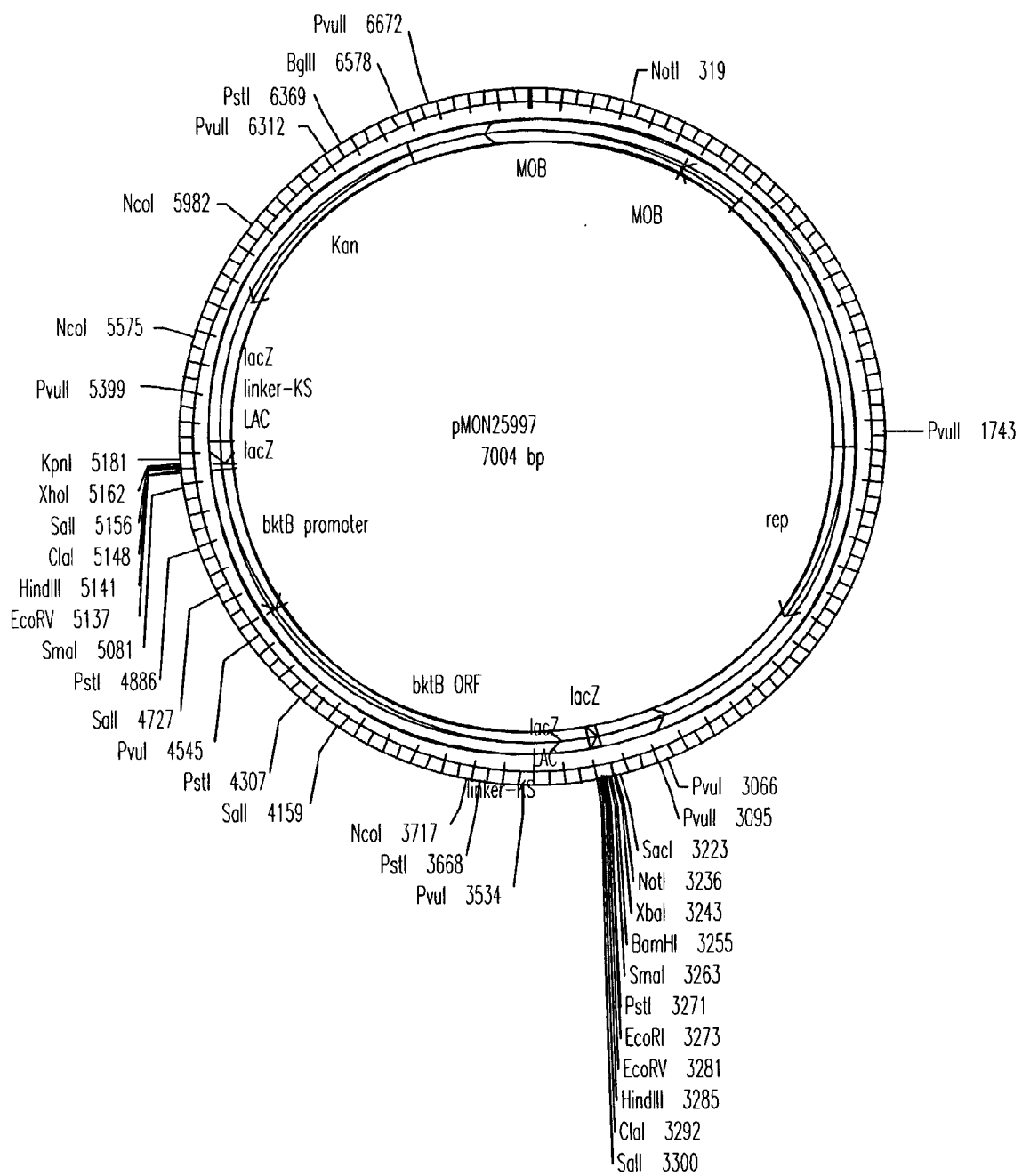
FIG. 28 is a restriction map of plasmid pMON25997.
Figure 29:
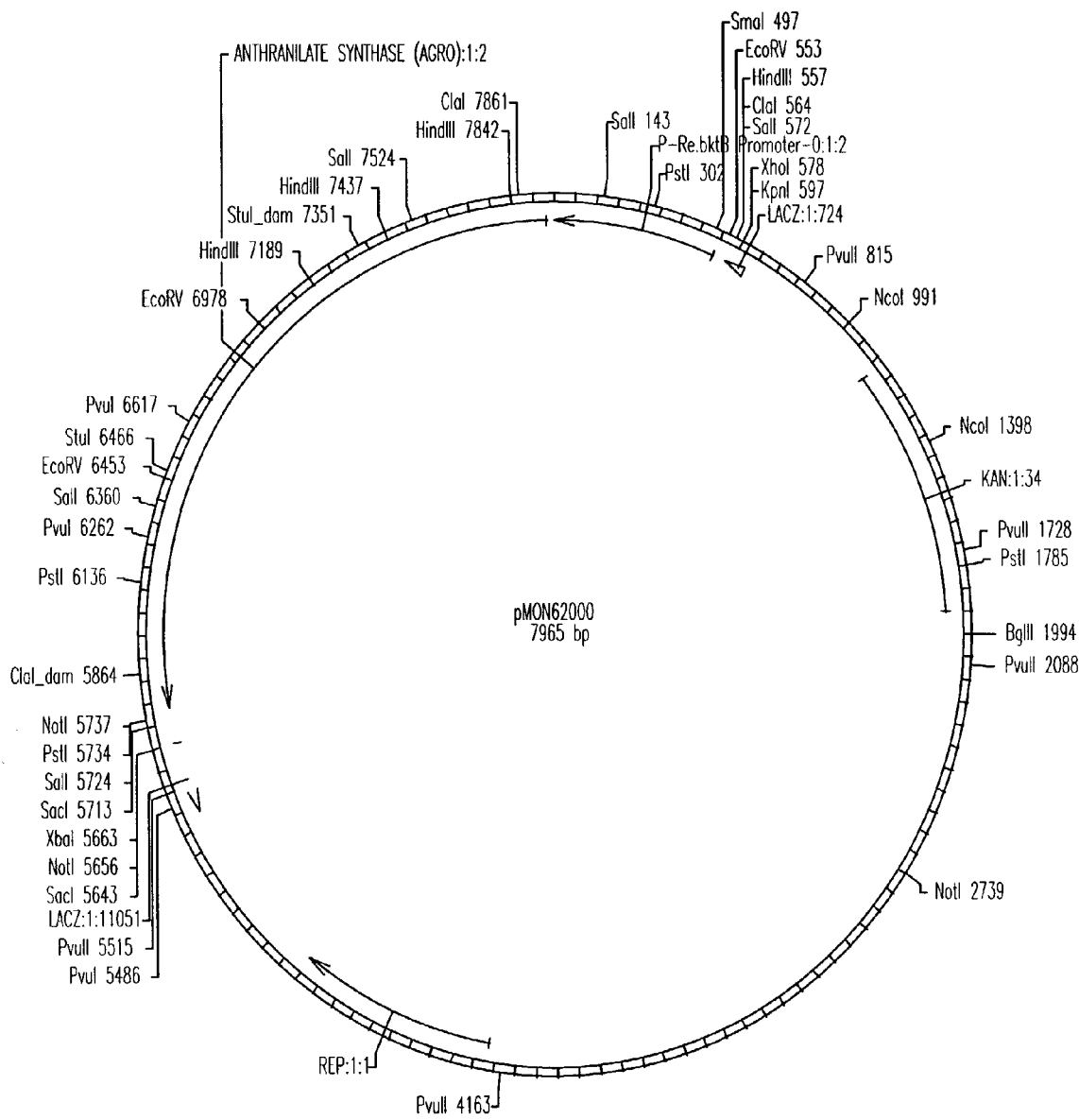
FIG. 29 is a restriction map of plasmid pMON62000.
Figure 31:
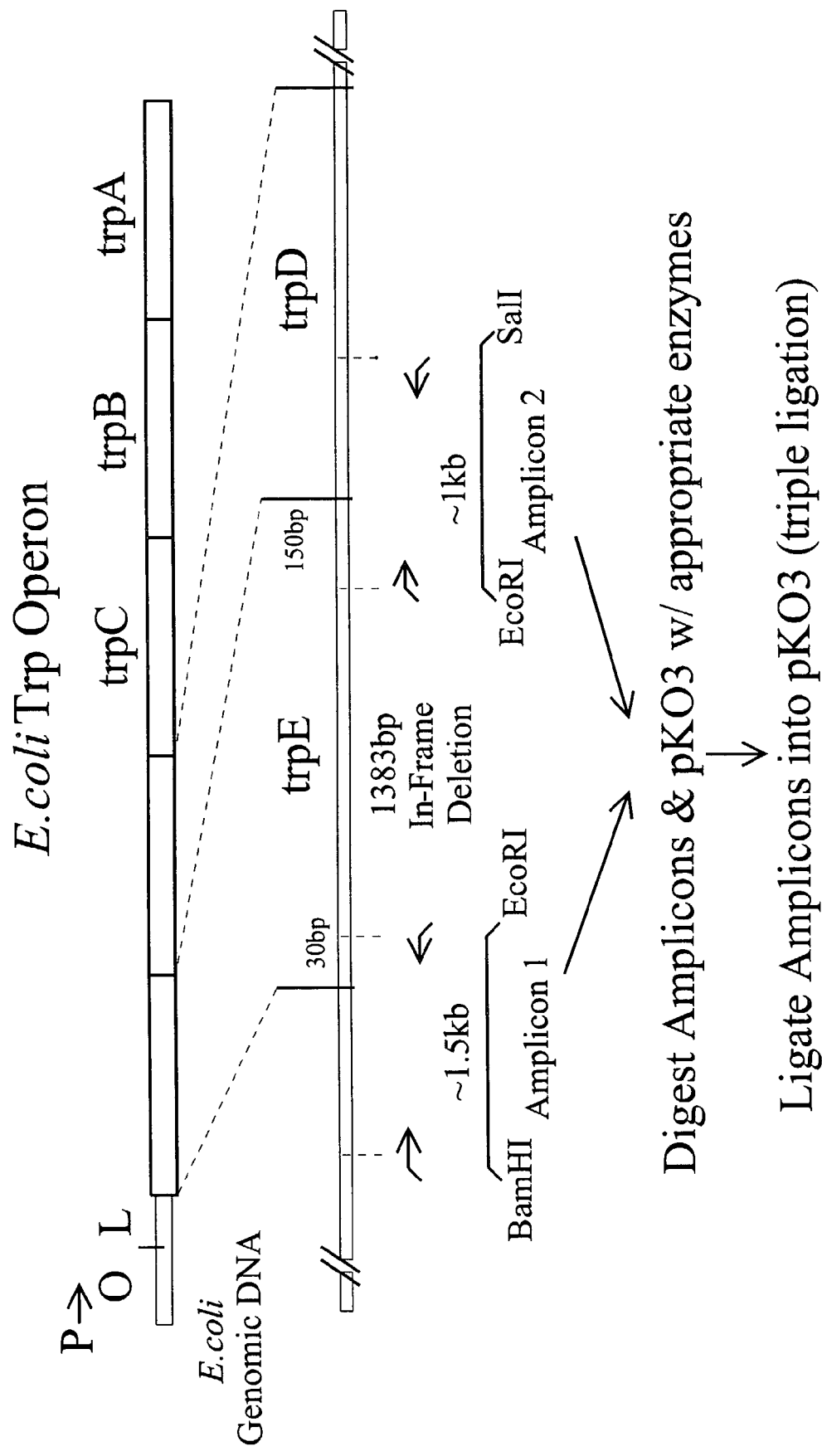
FIG. 31 schematically depicts construction of the in-frame deletion in the *E. coli* trpE gene.

The open reading frame from the *Agrobacterium tumefaciens* AS clone pMON61600 (SEQ ID NO:1, described in Example 1) was amplified by PCR using primers that contain an Nco 1 site on the 5' end of the forward primer and an XbaI site on the 3' end of the reverse primer:

(SEQ ID NO:55)
5'-CATCCCATGGATGGTAACGATCATT CAGGAT-3'; and (SEQ ID NO:56)
5'-GATGTCTAGAGACAC TATAGAATACTCAAGC-3', The resulting PCR product was ligated into pMON25997 (FIG. 28), which had the bktB open reading frame (Slater et al., *J. Bact.* 180, p1979–1987 (1998)) removed by digestion with BspH1 and Xba1 resulting in plasmid pMON62000 (FIG. 29). pMON62000 is the base plasmid used for mutagenesis and complementation of the tryptophan auxotroph (EMG2ΔtrpE).

Generation of an *E. coli* Tryptophan Auxotroph EMG2ΔtrpE.

*E. coli* strain Ec-8 (EMG2ΔtrpE) was constructed using the suicide vector pKO3 to delete 1,383 base pairs from the chromosomal trpE gene of *E. coli* strain EMG2(K-12 wt F+) (*E. coli* Genetic Stock Center). Two amplicons from *E. coli* genomic DNA were PCR amplified. The first amplicon was approximately 1.5 kb and contained the first 30 bp of the trpE ORF at the 3' end. This amplicon contains a BamHI site at the 5' end and an EcoR1 site at the 3' end. The second amplicon was approximately 1 kb and contained the last 150 bp of the trpE ORF at the 5' end. This amplicon contains an EcoR1 site at the 5' end and a Sal1 site at the 3' end. The two amplicons were digested with the appropriate enzymes and ligated together at the EcoR1 site to create an in-frame deletion of trpE. FIG. 30 shows the resulting sequence of the truncated gene (SEQ ID NO:46). The trpE deletion amplicon was ligated into pKO3 at the BamH1 and Sal1 sites. Gene disruption was performed as described in A. J. Link et al. *J. Bacteriol.*, 179, 6228 (1997).

Complementation of *E. coli* Tryptophan Auxotroph EMG2ΔtrpE with pMON62000

*E. coli* strain Ec-8 (EMG2ΔtrpE) was transformed with pMON62000 and plated on M9 minimal medium to determine if the deletion was complemented by the addition of pMON62000. A plasmid control (minus the *Agrobacterium tumefaciens* AS insert) and a strain control Ec-8 were also plated onto M9 minimal medium and onto M9 minimal medium with 40 μg/ml tryptophan. Growth of strain Ec-8 transformed with pMON62000 was observed on M9 without tryptophan, no growth of either of the controls was observed, indicating complementation of the trpE deletion in strain Ec-8 by pMON62000.

Hydroxylamine Mutagenesis of pMON62000 and Genetic Selection of Mutants

To generate mutants of anthranilate synthase, pMON62000 was mutated with the chemical mutagen hydroxylamine. The following ingredients were combined in an eppendorf tube: 20 μg pMON62000 plasmid DNA and 40 μl 2.5 M hydroxylamine, pH 6.0. The volume was brought to a volume of 200 μl with 0.1M NaH$_2$PO$_4$,pH 6.0+5 mM EDTA, pH 6.0. The tube was incubated at 70° C. After 1.5 hours, 100 μl of reaction mixture was dialyzed on a nitrocellulose filter that was floating on approximately 500 ml H$_2$O. After 15 minutes, the DNA was concentrated using Qiagen PCR Purification Kit. After 3 hours, the remaining 100 μl of the reaction mixture was removed and purified in the same manner.

*E. coli* strain Ec-8 was then transformed by electroporation with 100 ng of pMON62000 that had been mutagenized for either 1.5 or 3 hours with hydroxylamine. Two transformation procedures were performed for each time point. Transformed cells were allowed to recover for 4 or 6 hours in SOC medium (20 g/L Bacto-Tryptone, 5 g/L Bacto Yeast Extract, 10 ml/L 1M NaCl, 2.5 ml/L 1M KCl, 18 g glucose).

Two 245 mm square bioassay plates were prepared containing M9 minimal medium, plus 2% agar, and 50 μg/ml 5-methyl-DL-tryptophan (5-MT). An aliquot of 900 μl of the 1.5 hour mutagenized transformation mixture was plated onto one 50 μg/ml 5-MT plate. The remaining 100 μl was plated onto the M9 control plate. The same procedure was performed for the transformation mixture containing the 3.0 hour mutagenized plasmid.

The plates were then incubated at 37° C. for approx. 2.5 days. Resistant colonies were isolated from the 5-MT plates and were streaked onto LB-kanamycin (50 μg/ml) plates to confirm the presence of the plasmid. All of the selected colonies grew on these plates. Individual colonies from each of the resistant clones were prepped in duplicate to isolate the plasmid. Restriction digests and PCR were performed and confirmed that all the clones contained the desired *Agrobacterium tumefaciens* AS insert.

The rescued plasmids were then transformed back into strain Ec-8. One colony from each tranformation was purified by streaking onto new LB-Kanamycin plates. To confirm resistance to 5-MT, individual purified colonies were streaked onto plates containing M9 plus 50 μg/ml 5-MT and 2% agar, and then grown at 37° C. for 3 days. Resistance was confirmed for most of the clones. To determine if resistant mutants would remain resistant at an even higher concentration of 5-MT, they were plated onto M9 plus 300 μg/ml 5-MT and 2% Agar. Most clones demonstrated resistance at this high concentration also.

The plasmids from all of the resistant clones were isolated and sequenced on both strands. Some of the mutations from this experiment are diagrammed in Table J.

TABLE J

*A. tumefaciens* trpEG Sequence Variations in 5-MT Resistant Clones.

| Database Clone # | Original Clone # | Determined Sequence Variations | $K_m^{cho}$ (μM) | $IC_{50}^{trp}$ (μM) |
|---|---|---|---|---|
| Wt |  |  | 8.0 | 5.0 |
| Ec-12 | 1 | G4A Val2Ile |  |  |
| Ec-18 | 8 | C35T Thr12Ile | 15 | 2.5 |
| Ec-19 | 9 | C2068T Pro690Ser | 5.0 | 3.4 |
| Ec-20 | 11 | G1066A Glu356Lys & C1779T Ile593Ile |  |  |

As indicated by the data in Table J, several mutants had little effect on the $K_m$ and $IC_{50}$ of the mutant enzyme, indicating that these mutations are likely not the source of resistance to tryptophan feedback inhibition. For example, the mutation of C to T at nucleotide 35, which changes a threonine residue to isoleucine at amino acid position 12 (Thr12Ile), gives rise to a minor change in $K_m^{cho}$ and $IC_{50}^{trp}$ values. Similarly, a change of C to T at nucleotide position 2068, which changes a proline to a serine also gives rise to a minor change in $K_m^{cho}$ and $IC_{50}^{trp}$ values. These mutations may therefore, may be "silent" mutations that give rise to variant gene products having enzymatic properties like those of wild type.

EXAMPLE 6

High Tryptophan Transgenic Soybean Plants.

This example sets forth preparation of transgenic soybean plants having elevated tryptophan levels resulting from transformation with tryptophan feedback insensitive mutants of anthranilate synthase from *Agrobacterium tumefaciens*.

Vector Construction

Figure 8:
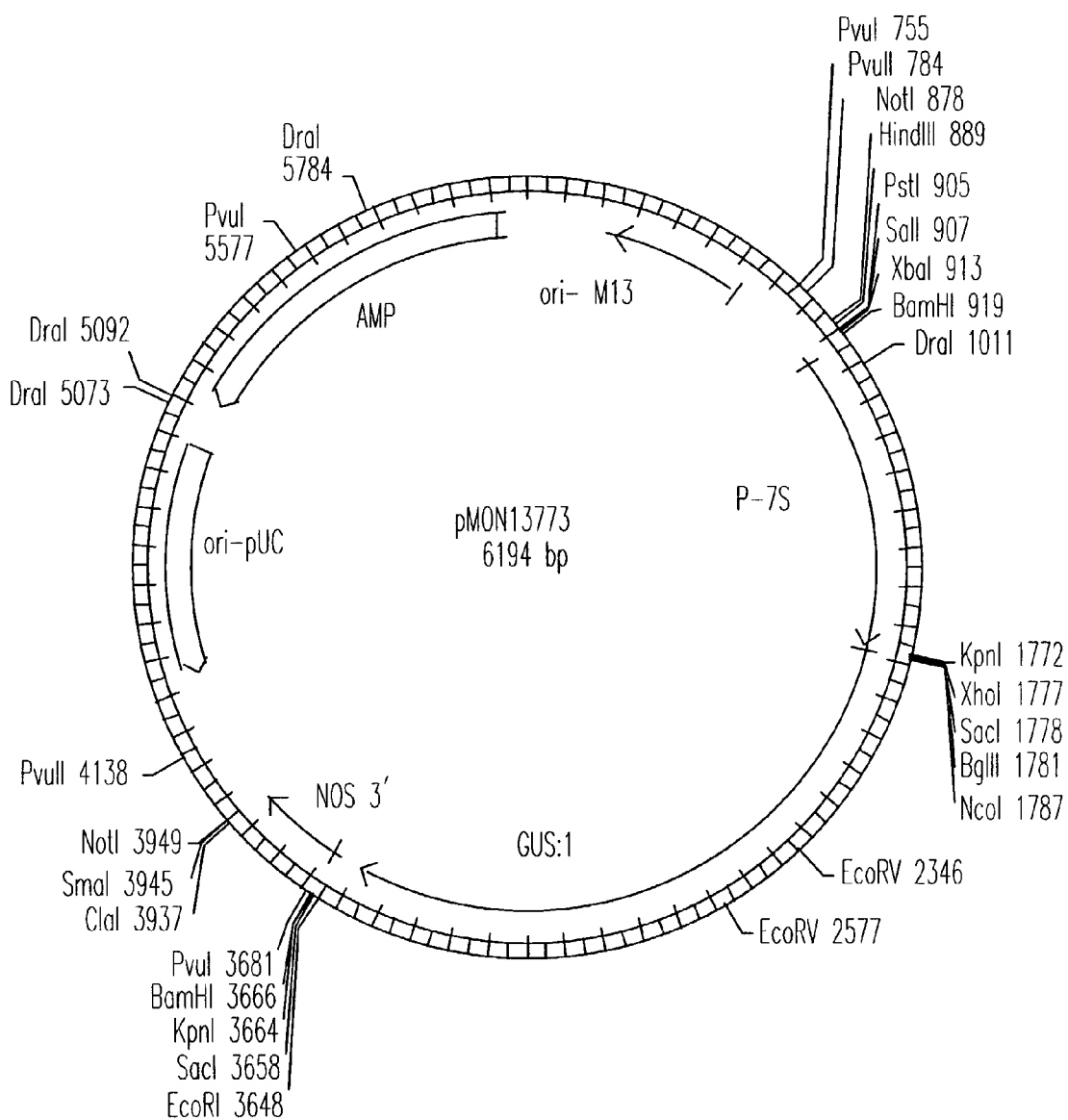
FIG. 8 depicts a restriction map of plasmid pMON13773.
Figure 9:
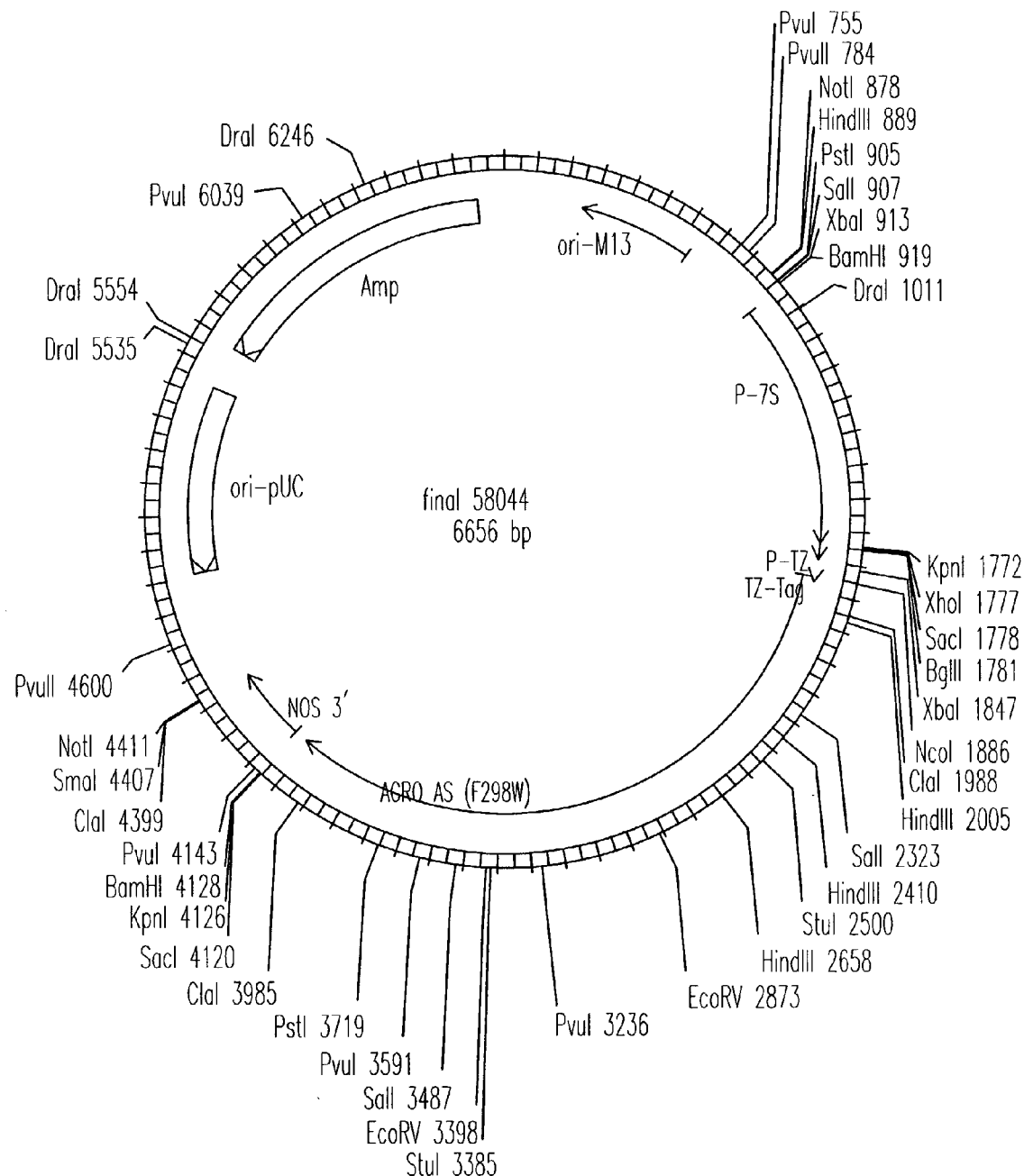
FIG. 9 depicts a restriction map of plasmid pMON58044.

Plasmid pMON347 11, which harbors the anthranilate synthase clone from *Agrobacterium tumefaciens* containing the F298W mutation described in Example 4, was digested with restriction enzyme NotI. The ends of the resulting fragment were blunted and then digested with NcoI. The plasmid pMON13773 (FIG. 8) was then digested with restriction enzyme EcoRI, the ends blunted and then digested with NcoI. The resulting fragments were ligated resulting in plasmid pMON58044, which contained the AS gene under the control of the 7S promoter and NOS3' terminator (FIG. 9).

Figure 10:
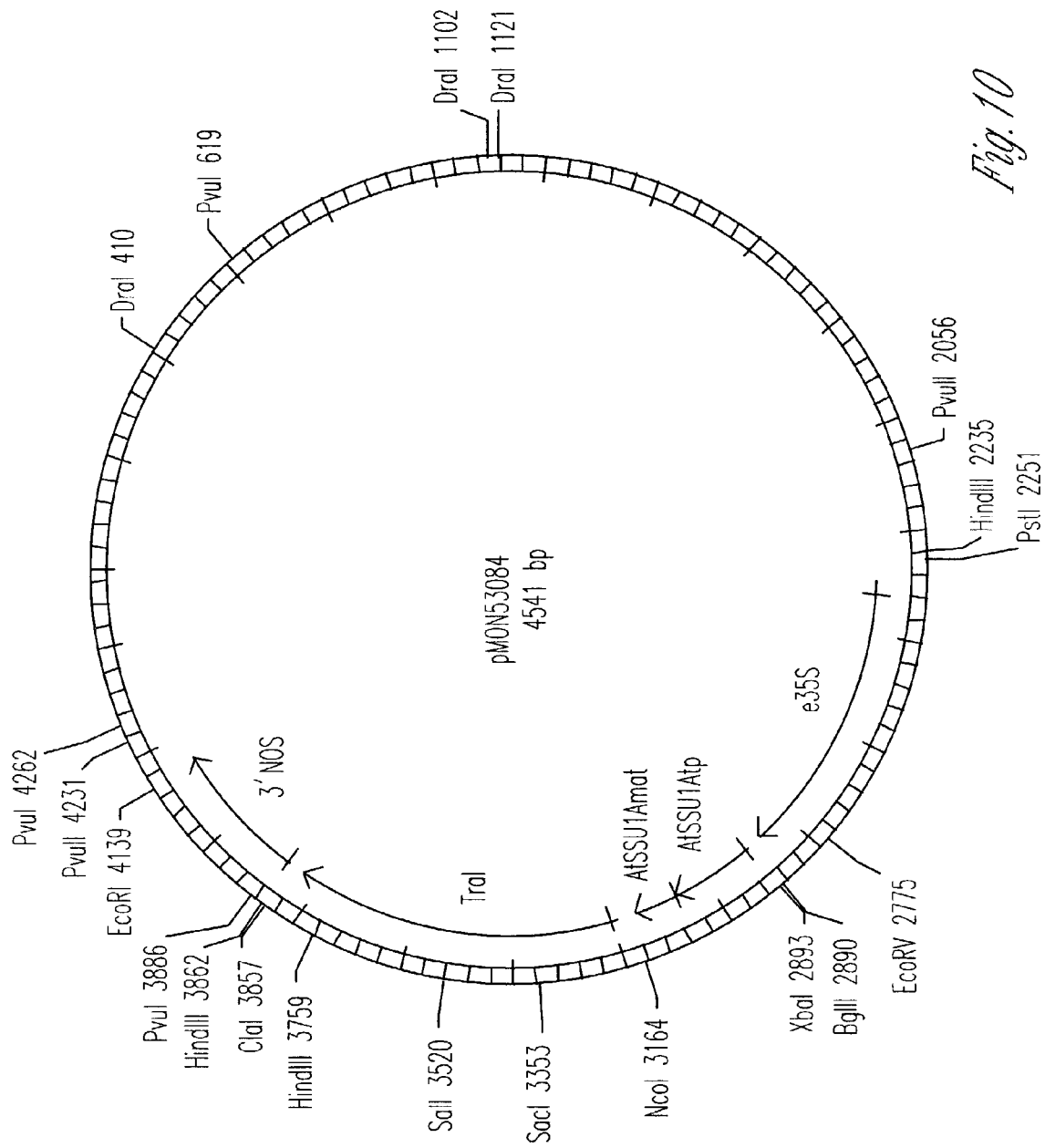
FIG. 10 depicts a restriction map of plasmid pMON53084.
Figure 11:
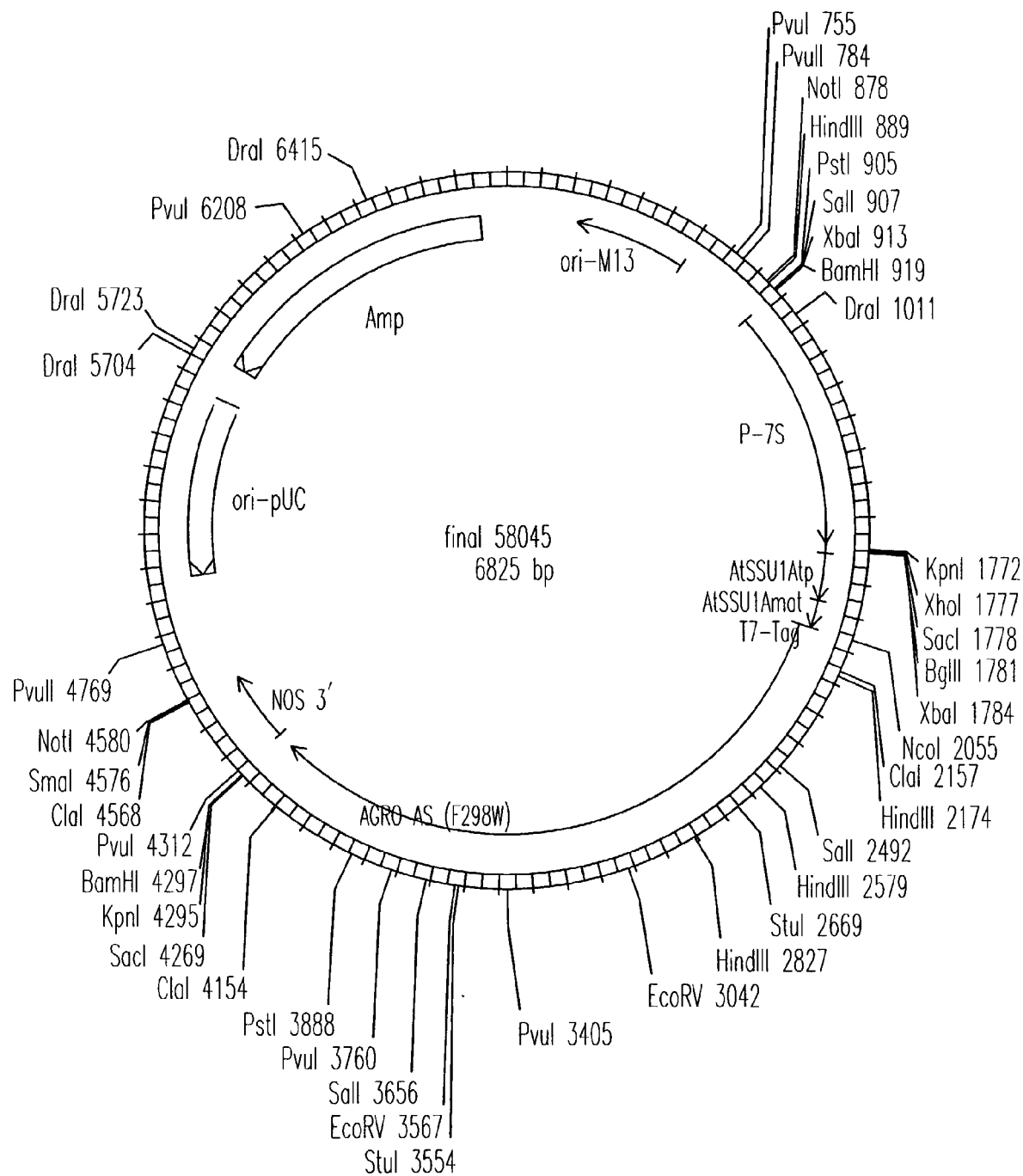
FIG. 11 depicts a restriction map of plasmid pMON58045.

Plasmid pMON58044 was then cut with restriction enzymes BglII and NcoI and ligated with a fragment that was generated by digesting pMON53084 (FIG. 10) with BglII and NcoI. The resulting fragment was named pMON58045 (FIG. 11) and contained the sequence for the *Arabidopsis* SSU1A transit peptide.

Figure 12:
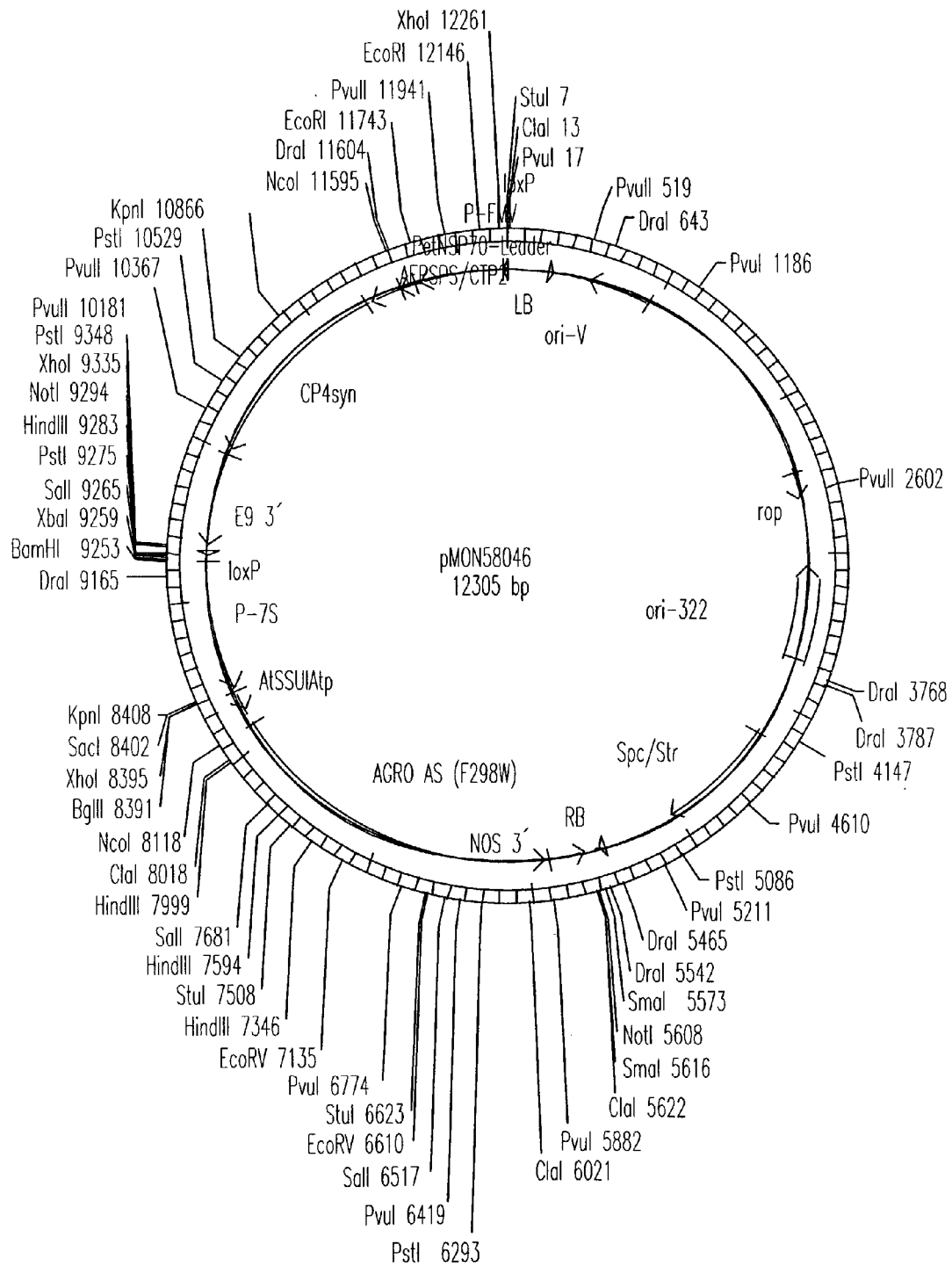
FIG. 12 depicts a restriction map of plasmid pMON58046.
Figure 13:
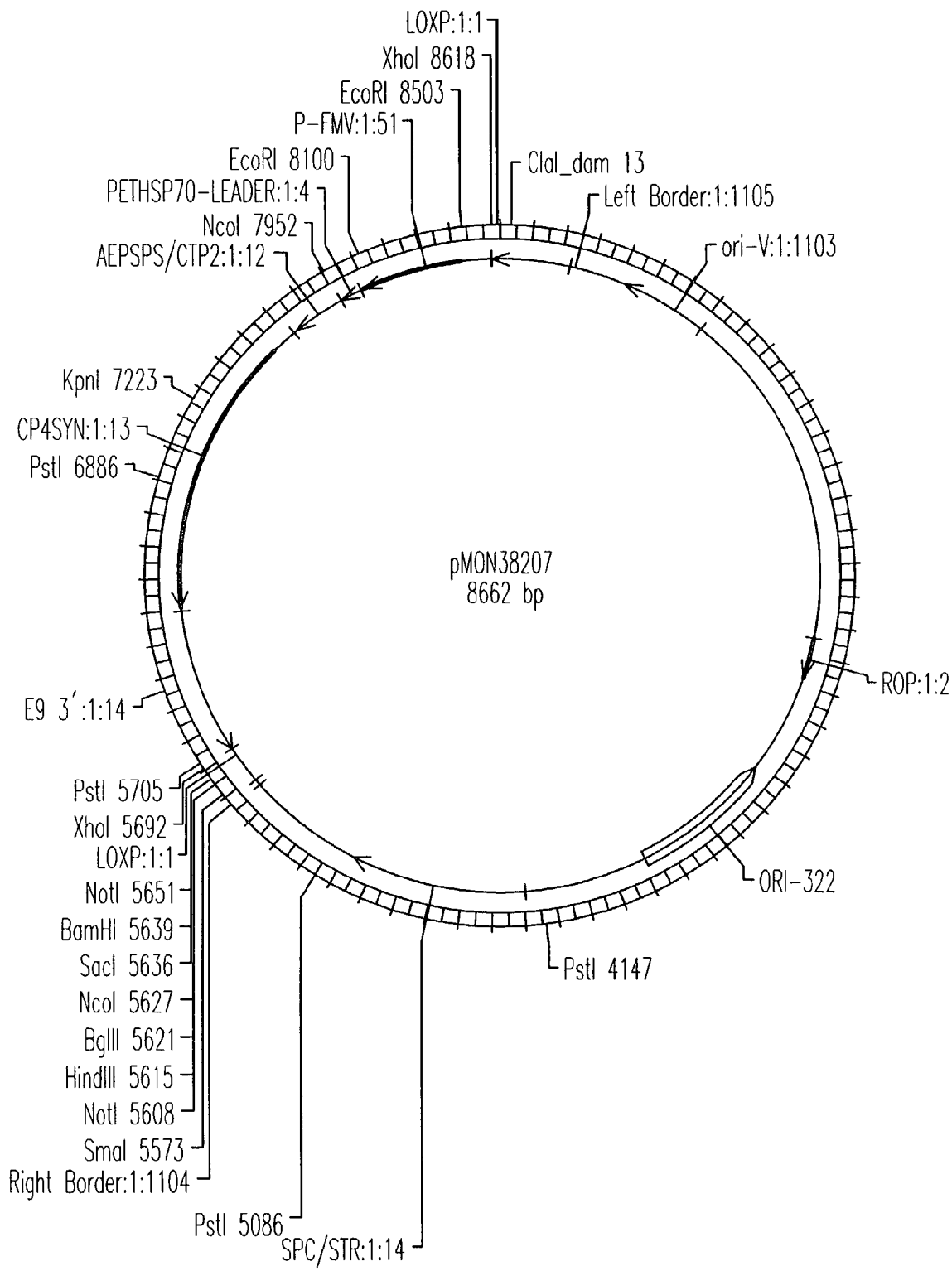
FIG. 13 depicts a restriction map of plasmid pMON38207.

Finally, plasmid pMON58046 (FIG. 12) was constructed by ligating the fragments generated by digesting pMON58045 (FIG. 11) and pMON38207 (FIG. 13) with restriction enzyme NotI. This resulted in the pMON58046 vector (FIG. 12) that was used for soybean transformation.

Soybean Transformation By Microprojectile Bombardment

For the particle bombardment transformation method, commercially available soybean seeds (i.e., Asgrow A3244, A4922) were germinated overnight for approximately 18–24 hours and the meristem explants were excised. The primary leaves were removed to expose the meristems and the explants were placed in targeting media with the meristems positioned perpendicular to the direction of the particle delivery.

The pMON58046 transformation vector described above was precipitated onto microscopic gold particles with $CaCl_2$ and spermidine and subsequently resuspended in ethanol. The suspension was coated onto a Mylar sheet that was then placed onto the electric discharge device. The particles were accelerated into the plant tissue by electric discharge at approximately 60% capacitance.

Following bombardment, the explants were placed in selection media (WPM+0.075 mM glyphosate) (WPM=Woody Plant Medium (McCown & Lloyd, Proc. International Plant Propagation Soc., 30:421, 1981) minus BAP)) for 5–7 weeks to allow for selection and growth of transgenic shoots. Phenotype positive shoots were harvested approximately 5–7 weeks post-bombardment and placed into selective rooting media (BRM+0.025 mM glyphosate) (see below for BRM recipe) for 2–3 weeks. Shoots producing roots were transferred to the greenhouse and potted in soil. Shoots that remained healthy on selection, but did not produce roots were transferred to non-selective rooting media (BRM without glyphosate) for an additional two weeks. The roots from any shoots that produced roots off the selection were tested for expression of the plant selectable marker before transferring to the greenhouse and potting in soil. Plants were maintained under standard greenhouse conditions until R1 seed harvest.

The recipe used for Bean Rooting Medium (BRM) is provided below.

| Compound | Quantity for 4L |
|---|---|
| MS Salts*** | 8.6 g |
| Myo-inositol(cell culture grade) | 0.40 g |

-continued

| Compound | Quantity for 4L |
|---|---|
| SBRM Vitamin Stock** | 8.0 ml |
| L-Cysteine (10 mg/ml) | 40.0 ml |
| Sucrose (ultra pure) | 120 g |
| Adjust pH to 5.8 | |
| Washed Agar | 32 g |
| Additions after autoclaving: | |
| SBRM/TSG Hormone Stock* | 20.0 ml |

*SBRM/TSG Hormone Stock (per 1 L of BRM): 3.0 ml IAA (0.033 mg/ml), 2.0 ml sterile distilled water. Store stock in dark at 4° C.
**SBRM Vitamin Stock (per 1 L of stock): Glycine (1.0 g), Nicotinic Acid (0.25 g), Pyridoxine HCl (0.25 g), Thiamine HCl (0.25 g).
***3X Minor MS Salts (per 1 L stock): $H_2BO_3$ (1.86 g), $MnSO_4$ (5.07 g), $ZnSO_4$-$H_2O$ (2.58 g), KI (0.249 g), 7.5 ul NaMoO-$2H_2O$ (1.0 mg/ml), 7.5 ul $CoSO_4$-$5H_2O$ (1.0 mg/ml), 7.5 ul $CoCl_2$-$6H_2O$ (1.0 mg/ml).
One ingredient at a time was added and dissolved, the volume was brought to one liter with sterile distilled water, and the solution was stored in a foil-covered bottle in the refrigerator for no longer than one month.

Soybean Transformation Using *Agrobacterium tumefaciens*

For the *Agrobacterium* transformation method, commercially available soybean seeds (Asgrow A3244, A4922) were germinated overnight (approximately 10–12 hours) and the meristem explants were excised. The primary leaves may or may not have been removed to expose the meristems and the explants were placed in a wounding vessel.

*Agrobacterium* strain ABI containing the plasmid of interest was grown to log phase. Cells were harvested by centrifugation and resuspended in inoculation media containing inducers. Soybean explants and the induced *Agrobacterium* culture were mixed no later than 14 hours from the time of initiation of seed germination and wounded using sonication.

Following wounding, explants were incubated in *Agrobacterium* for a period of approximately one hour. Following this inoculation step, the *Agrobacterium* was removed by pipetting and the explants were placed in co-culture for 2–4 days. At this point, they were transferred to selection media (WPM+0.075 mM glyphosate+antibiotics to control *Agrobacterium* overgrowth) for 5–7 weeks to allow selection and growth of transgenic shoots.

Phenotype positive shoots were harvested approximately 5–7 weeks post-bombardment and placed into selective rooting media (BRM+0.025 mM glyphosate) for 2–3 weeks. Shoots producing roots were transferred to the greenhouse and potted in soil. Shoots that remained healthy on selection, but did not produce roots were transferred to non-selective rooting media (BRM without glyphosate) for an additional two weeks. The roots from any shoots that produced roots off the selection were tested for expression of the plant selectable marker glyphosate resistance before transferring to the greenhouse and potting in soil. Plants were maintained under standard greenhouse conditions until R1 seed harvest.

Analysis of Amino Acid Content of R1 Seed

Mature R1 seed is produced and analyzed for free amino acid content using fluorescence detection as described in Agilent Technologies Technical Bulletin REV14. Five seeds are chosen for single seed analysis from each event. Soy seeds expressing the AgroAS F298W or the AgroAS S51F mutant proteins generate very high amounts of tryptophan. Results are shown in Tables K and L.

TABLE K

Protein expression in Seeds Transformed with pMON58046

| Pedigree | Trp average (ppm) | Protein present? |
|---|---|---|
| Control | 96 | no |
| 22817 | 9922 | yes |
| 22891 | 12955 | yes |
| 23026 | 7968 | yes |

TABLE L

AS Protein expression Correlated with pMON58123 Transformation

| Pedigree | Trp average (ppm) | Protein present? |
|---|---|---|
| Control | 96 | no |
| 23562 | 88 | no |
| 23590 | 8795 | yes |
| 23911 | 388 | no |

AS Enzyme Activity in R1 Seed Transformed with Agro AS

Mature R1 seed is produced and analyzed for anthranilate synthase activity. Anthranilate synthase enzymatic activity was determined in R1 soy seeds carrying the Argo AS F298W (SEQ ID NO:65 or 91) or the Agro AS S51F (SEQ ID NO:60 or 86) mutant alleles. Very high levels of tryptophan-resistant anthranilate synthase activity was observed, consistent with the high amounts of tryptophan generated by these seeds. Results are shown in Tables M and N.

TABLE M

Specific activity of AS in R1 Seeds Transformed with pMON58046

| Event | Seed number | Specific activity (pmoles/mg/min) | Specific activity (pmoles/mg/min) (+25 micromolar Trp) |
|---|---|---|---|
| Control | | 77.6 | |
| 23076 | 23076-1 | 100.5 | 1.04 |
| | 23076-2 | 4512.8 | |
| | 23076-3 | 9737.4 | 9290.4 |
| | 23076-4 | 136.12 | |
| | 23076-5 | 8992.5 | 9749.9 |

TABLE N

Specific activity of AS in R1 Seeds Transformed with pMON58123

| Event | Seed number | Specific activity (pmoles/mg/min) | Specific activity (pmoles/mg/min) (+25 micromolar Trp) |
|---|---|---|---|
| Control | | 83.7 | 32.7 |
| 23590 | 23590-1 | 891 | 692.3 |
| | 23590-2 | 466.2 | 186.5 |
| | 23590-3 | 71.7 | 38.3 |
| | 23590-4 | 320.5 | 316.2 |

EXAMPLE 7

Figure 14:
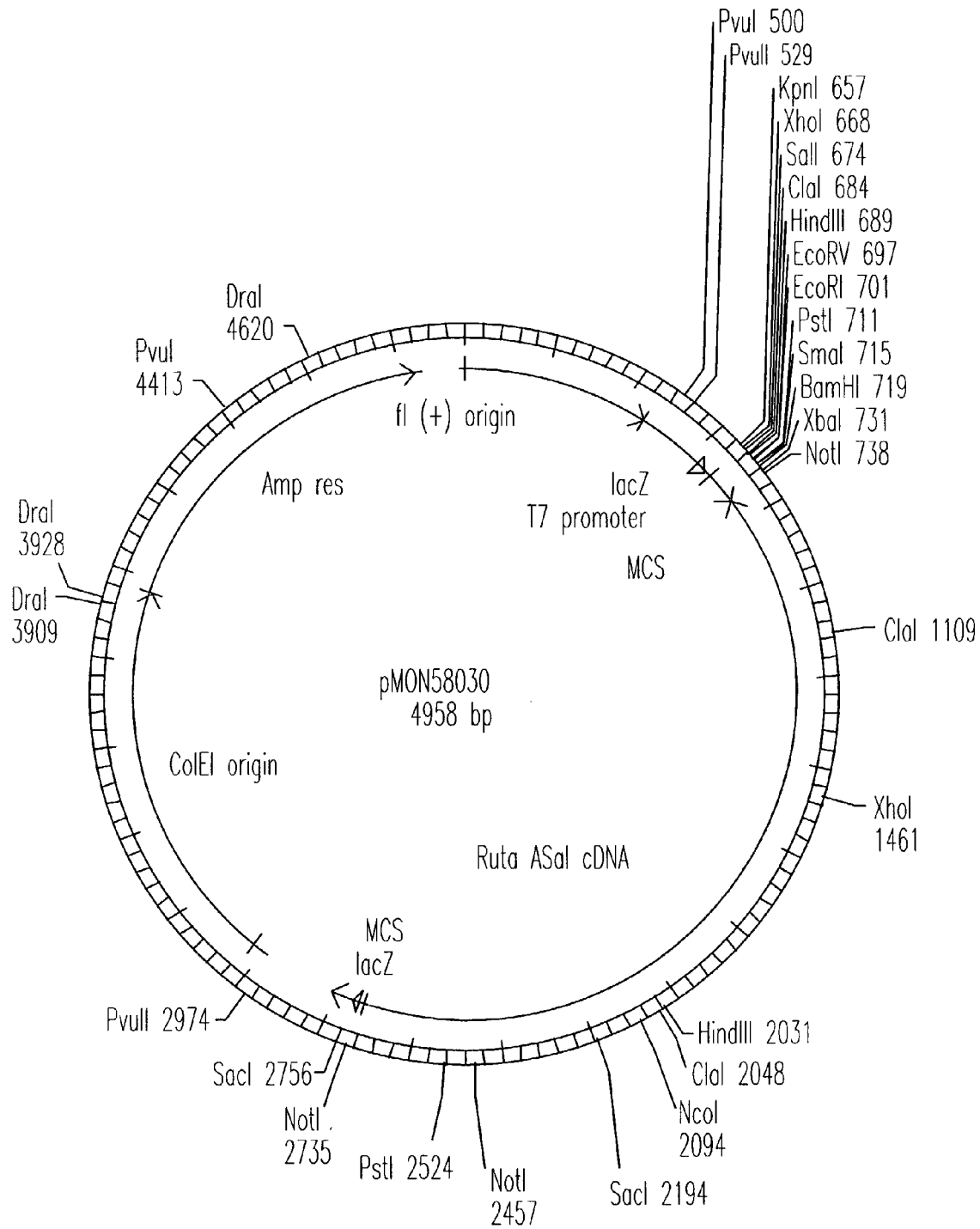
FIG. 14 depicts a restriction map of plasmid pMON58030.
Figure 15:
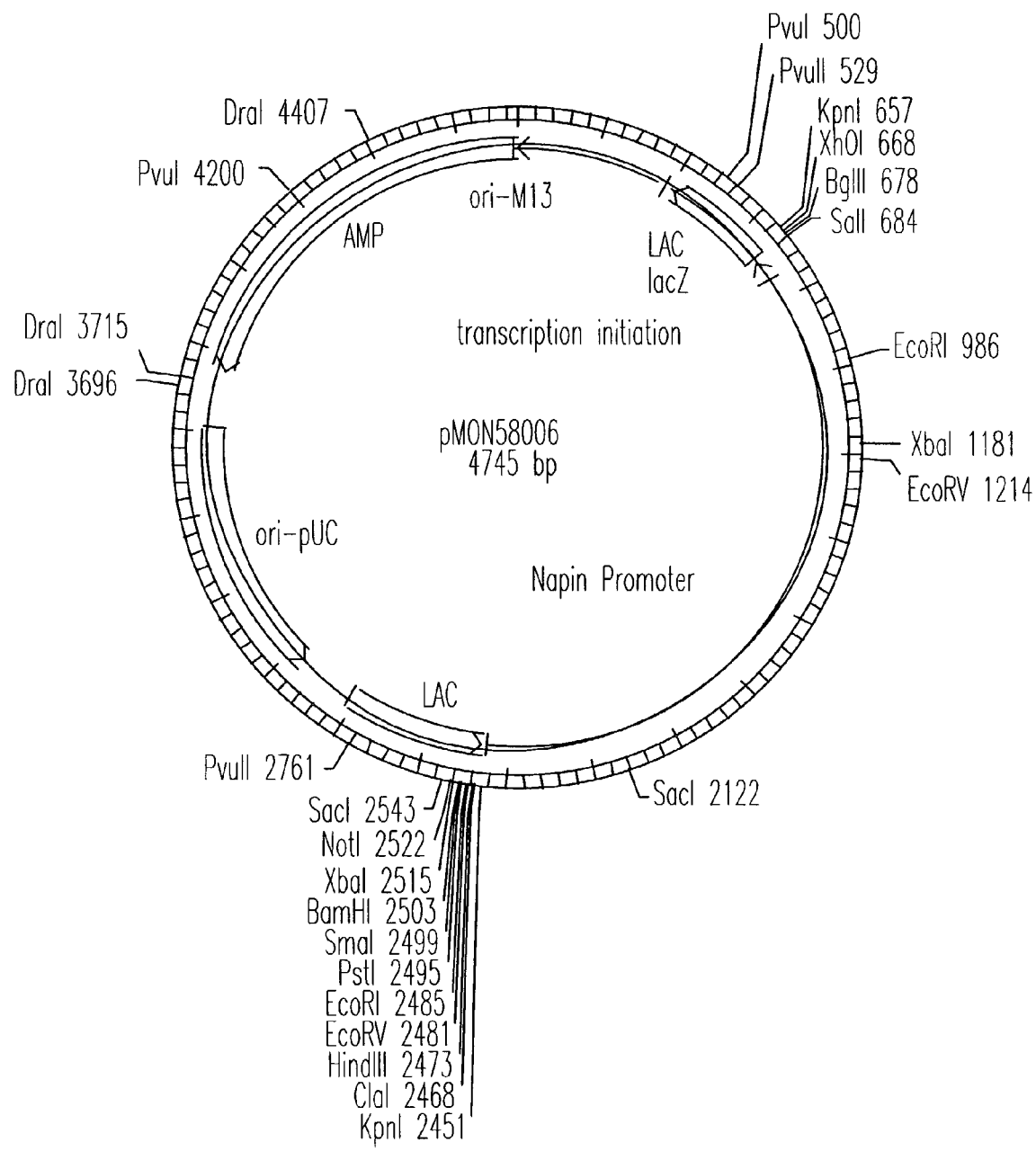
FIG. 15 depicts a restriction map of plasmid pMON58006.
Figure 16:
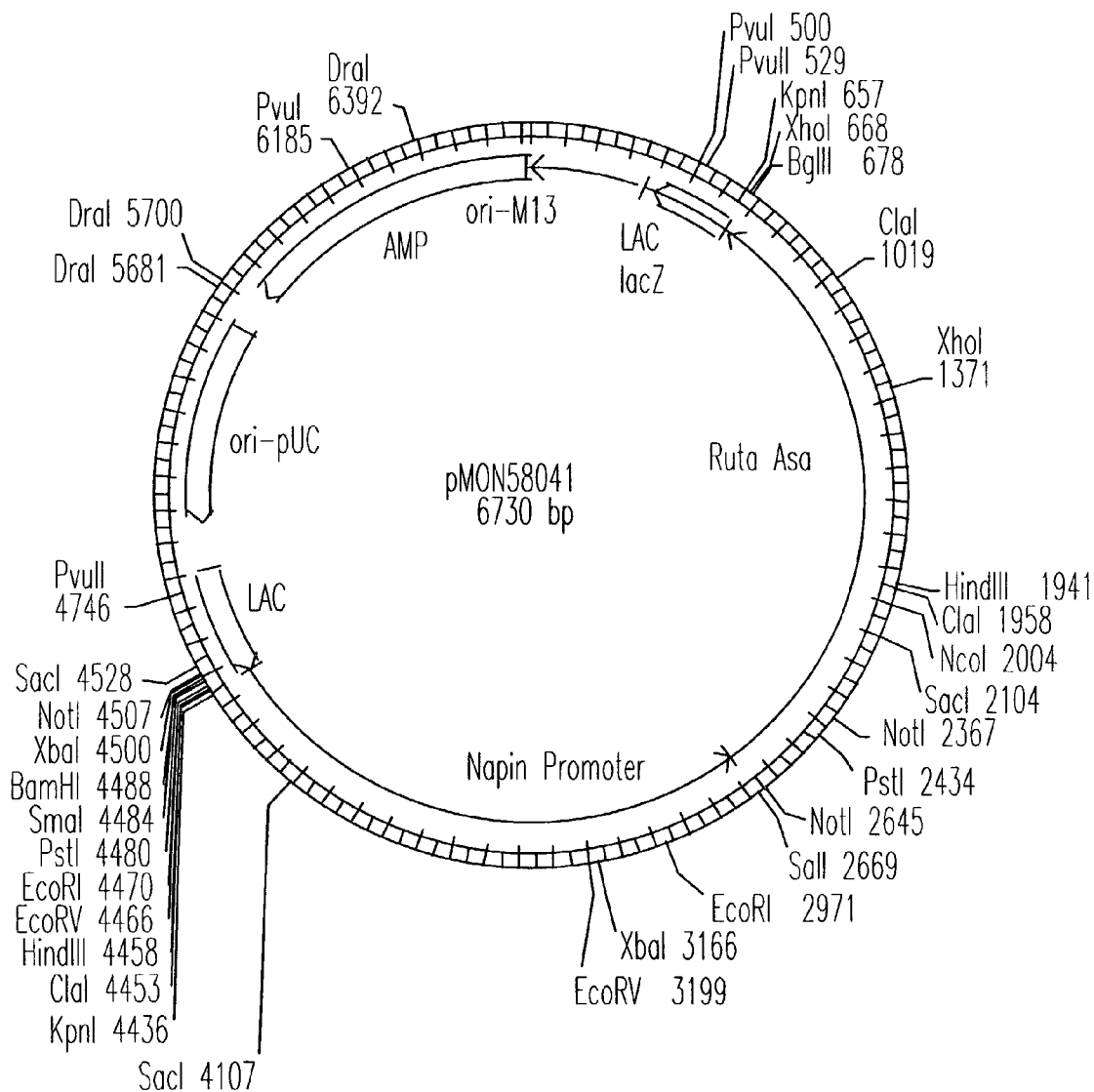
FIG. 16 depicts a restriction map of plasmid pMON58041.
Figure 17:
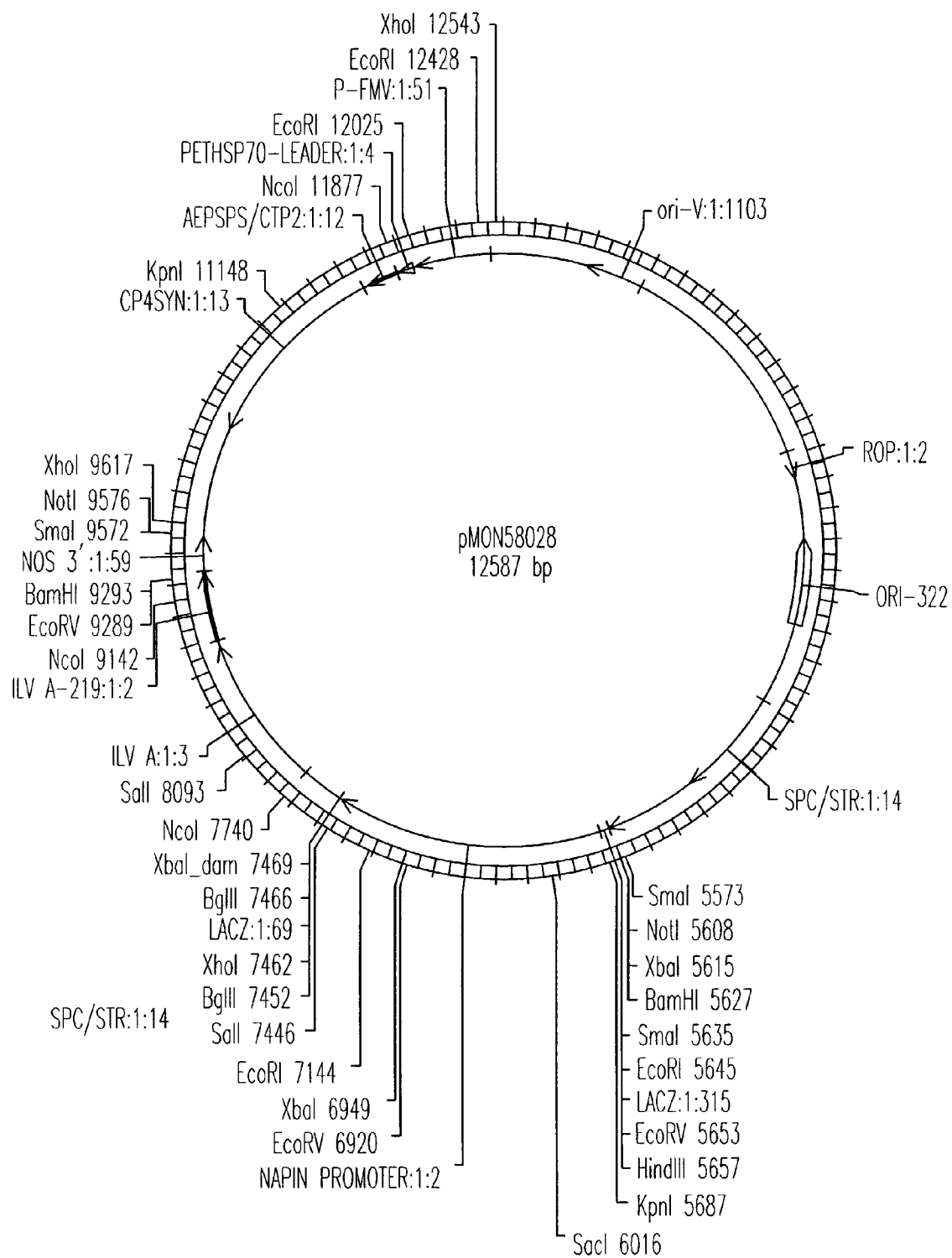
FIG. 17 depicts a restriction map of plasmid pMON58028.
Figure 18:
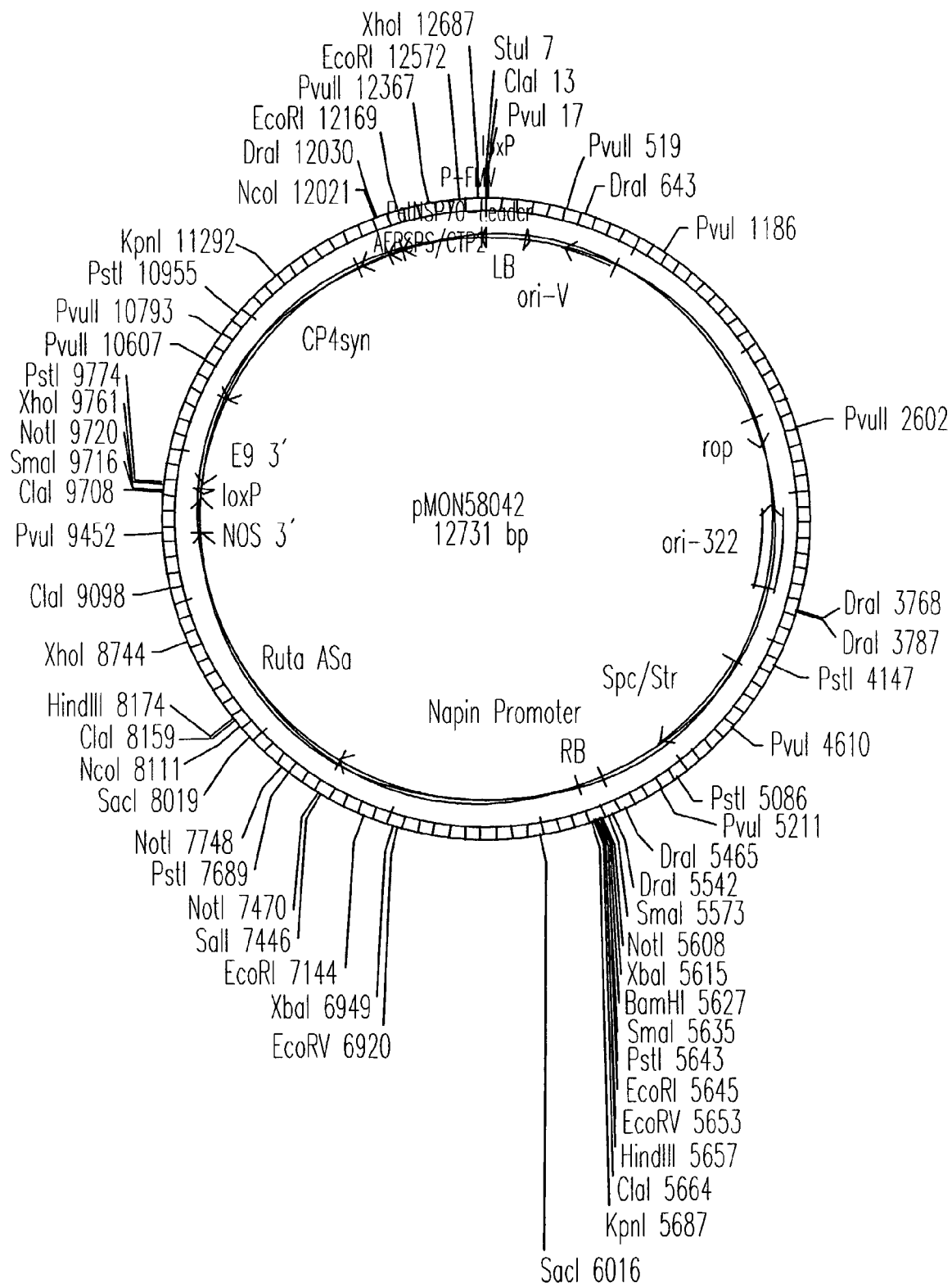
FIG. 18 depicts a restriction map of plasmid pMON58042.
Figure 19:
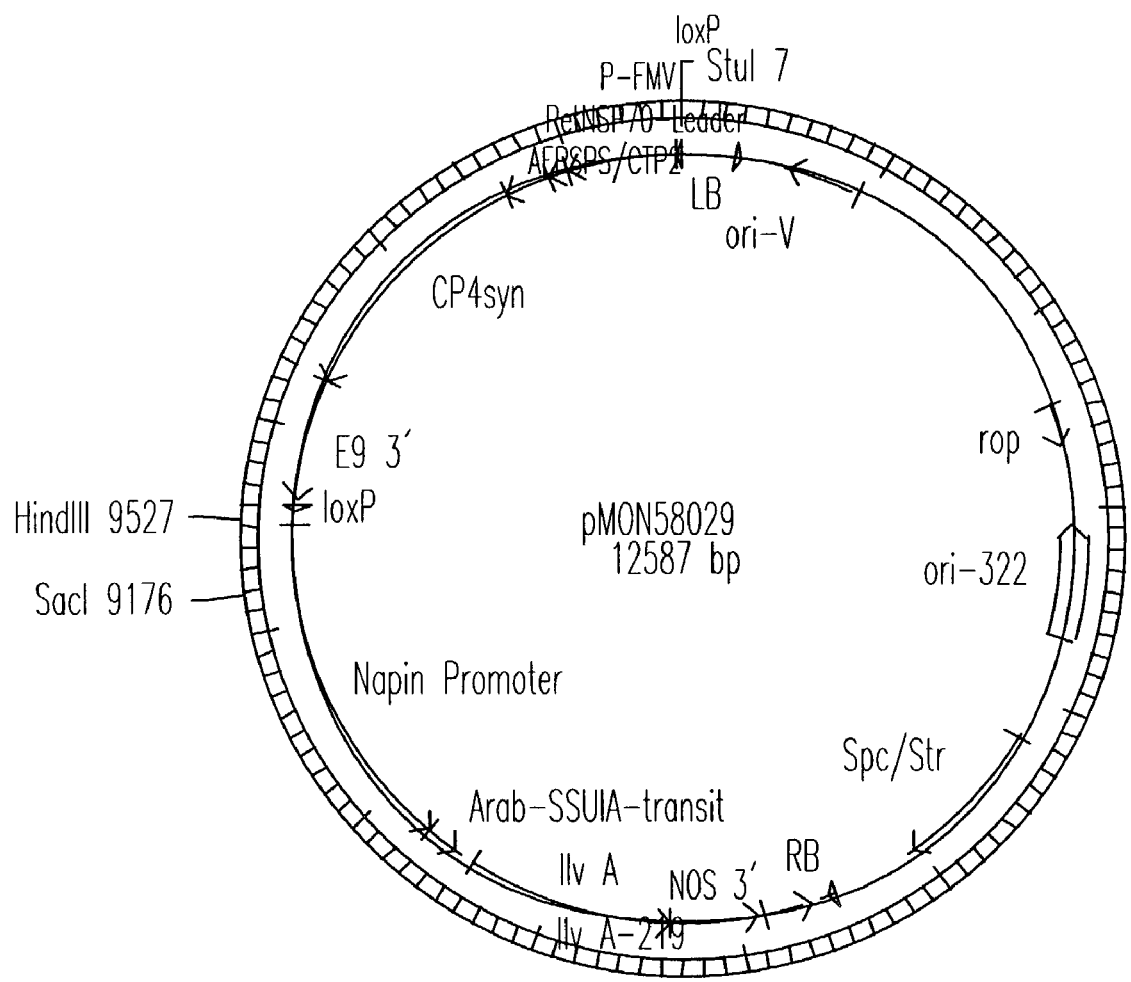
FIG. 19 depicts a restriction map of plasmid pMON58029.
Figure 20:
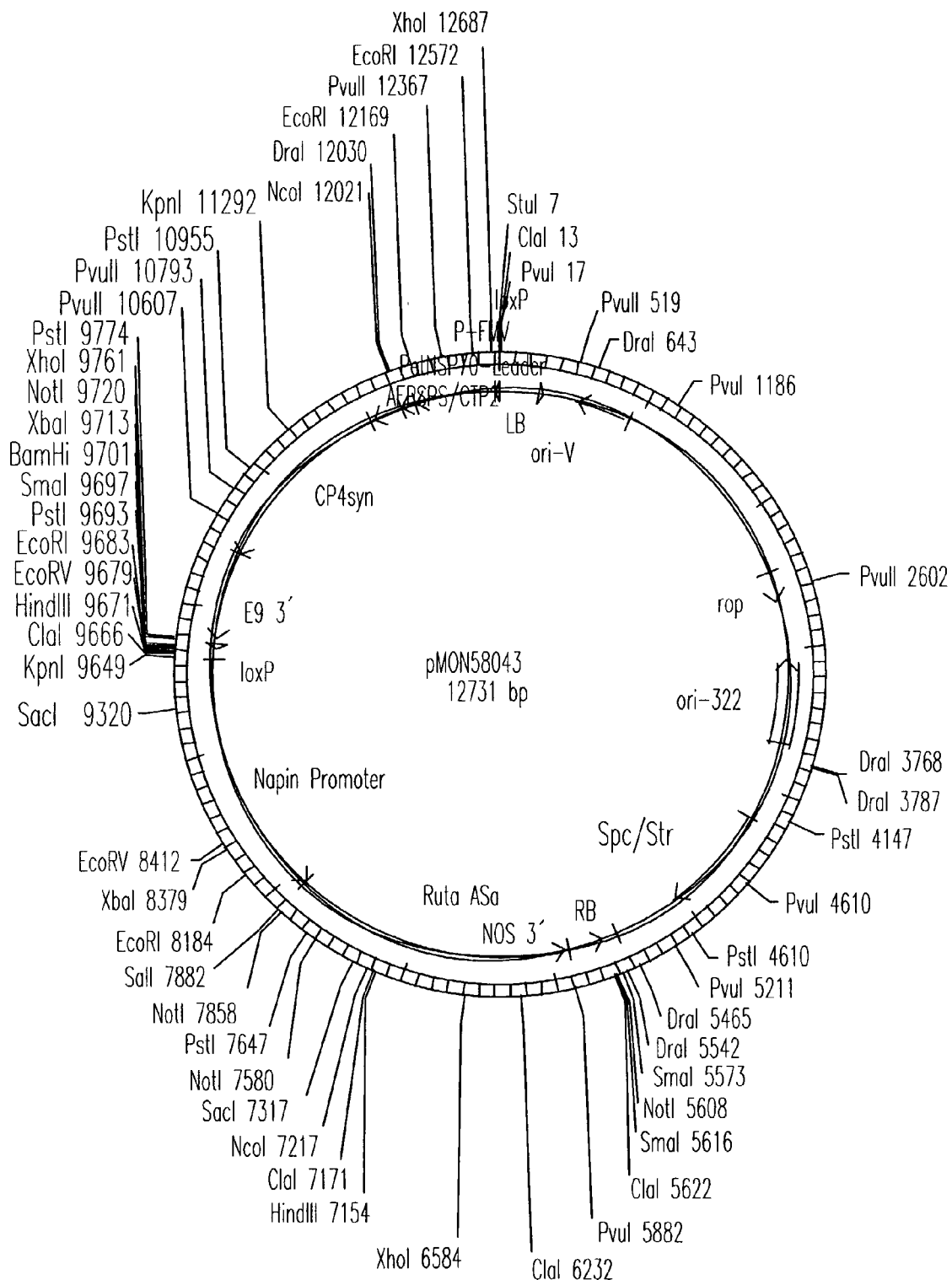
FIG. 20 depicts a restriction map of plasmid pMON58043.

Preparation of Transformation Vector Comprising *Ruta graveolens* Anthranilate Synthase α-Subunit The anthranilate synthase a gene from *Ruta graveolens* (Genbank Accession No. GI 960291) provides another anthranilate synthase domain useful in the present invention (Bohlmann, J et al., *Plant Phys* 111 507–514 (1996)). One isoenzyme of anthranilate synthase present in the genome of *Ruta graveolens* demonstrates less susceptibility to feedback inhibition by L-tryptophan. This allele may also be useful in the present invention to elevate the levels of free L-tryptophan in transgenic plants. The vector pMON58030 (FIG. 14) contains the *Ruta graveolens* anthranilate synthase α-subunit that is less sensitive to tryptophan inhibition. The *Ruta graveolens* anthranilate synthase α gene was PCR amplified from pMON58030 to provide a BamHI site at the 5' end and a BglII site at the 3' end of the *Ruta graveolens* anthranilate synthase α gene fragment by utilizing PCR primers that contained these two restriction enzyme sites:

```
5'-CAAAAGCTGGATCCCCACC-3'       (SEQ ID NO:53)
and
5'-CCTATCCGAGATCTCTCAACTCC-3'.  (SEQ ID NO:54)
```

The PCR fragment was purified, digested with the respective restriction enzymes, to form pMON58041, which contains the transcriptional fusion of the *Ruta graveolens* ASα to the napin promoter. The *Agrobacterium* mediated plant transformation plasmid, pMON58043, was created comprising the napin promoter, *Ruta graveolens* AS, NOS terminator, glyphosate resistance (CP4) selectable marker and borders suitable for proper chromosomal integration of the cassette as described. The resulting plant transformation vector was used to transform plants using standard plant transformation techniques as described in Examples 2, 3 and 6.

EXAMPLE 8

Transforming Multi-Polypeptide Anthranilate Synthases into Monomeric Single Polypeptide Anthranilate Synthases Generation of a monomeric anthranilate synthase by fusion of selected multi-subunit enzymes is desirable, for example, to maximize the catalytic efficiency, to stabilize the enzyme, to achieve coordinated expression, for example, of subunits comprising activities of TrpE and TrpG and for effective communication between the two subunits. In some instances, it may be useful to employ TrpE or α-subunits from either plant or microbial source that are deregulated with respect to feedback inhibition by standard mutagenesis techniques or by rational design as described in the foregoing Examples, e.g. in Example 4. In other instances, wild type TrpE or α-subunits from either plant or microbial source are employed.

The C-terminus of the selected TrpE or α-subunit is linked to the N-terminus of the TrpG subunit or β-subunit, preferably with a peptide linker. A linker can be rationally designed to provide suitable spacing and flexibility for both subunits to properly align. Alternatively a linker can be identified by sequence alignment of monomeric and heterotetrameric anthranilate synthases. Examples of sequence alignments of monomeric and heterotetrameric anthranilate synthase forms are shown in FIGS. 21 and 35. It is also envisioned that it may be necessary to generate monometic anthranilate synthases comprising heterologous subunit in order to maximize the benefits. For example, an α-subunit may be obtained from a bacterial source, for example, *E. coli* and fused to a β-subunit from a plant source, for example, *Arabidopsis*.

The novel protein produced can be introduced into plants, for example, as described in Examples 2, 3 or 6. The invention is not limited to the exact details shown and described, for it should be understood that many variations and modifications may be made while remaining within the spirit and scope of the invention defined by the claims.

EXAMPLE 9

Identification of Anthranilate Synthases from Genomic Sequence Databases.

Monomeric anthranilate synthases as well as α and β domains useful in the invention can be identified by bioinformatics analysis by searching for example, genbank and/or swissprot databases using BLAST (Altschul et al., (1990) *J. Mol. Biol.*, 215:403–410).

Useful query sequences to identify monomeric anthranilate synthase include, for example, domains of anthranilate synthase such as the α-domain (GI 1004323) or β-domain (GI 1004324) from *Sulfolobus solfataricus*, or monomeric anthranilate synthase such as *Agrobacterium tumefaciens* AS (GI 15889565). Putative monomeric anthranilate synthase will have between 50% and 100% homology with the query sequence and should minimally contain 700 amino acids. If the AS-α-domain is used to query the genomic database, in addition to identifying putative anthranilate synthase genes it is also likely to identify genes involved in PABA synthesis for example 4-amino-4-deoxychorismate (ADC) synthase. The monomeric ADC synthase genes can be easily identified away from putative monomeric AS genes based on the observation that the amidotransferase domain (β-domain) of ADC synthase resides at the N-terminus of the protein whereas the amidotransferase domain (p-domain) of AS resides at the C-terminus. Monomeric anthranilate synthases useful in the present invention identified by bioinformatics analysis include, but are not limited to, for example, *Rhizobium meliloti* (GI 95177), *Mesorhizobium loti* (GI 13472468), *Brucella melitensis* (GI 17982357), *Nostoc* sp. PCC7120 (GI 17227910, GI 17230725), *Azospirillum brasilense* (GI 1174156), *Rhodopseudomonas palustris, Anabaena* M22983 (GI 152445). FIG. 21 is an example of a sequence alignment of two monomeric anthranilate synthases (*Agrobacterium tumefaciens* and *Rhizobium meliloti*) with two heterotetrameric anthranilate synthases (*Sulfolobus solfataricus* and *Arabidopsis thaliana*) useful in the present invention. FIG. 35 is an example of a sequence alignment of several monomeric anthranilate synthases with the *Rhodopseudomonas palustris* heterotetrameric anthranilate synthase.

EXAMPLE 10

Optimized Codon Usage

This example sets forth a method of improving the expression of an anthranilate synthase gene in the seed of a plant by optimization of the codon usage.

The nucleotide sequence of the anthranilate synthase (AS) gene from wild type *Agrobacterium tumefaciens* (SEQ ID NO:1) was inspected for the presence of underexpressed codons. To identify underexpressed codons sequences of highly expressed seed proteins from corn and soybeans were examined for relative codon frequency. The relative codon usage frequencies are 110 shown in Table O represented in an expected value format. Expected value format can be exemplified as follows: Assume there are four codons that encode a given amino acid, and assume that they are used equally well, then each codon would be expected to account for 25% (0.25) of the frequency for that amino acid. However, due to redundancy, 0.25 was normalized to 1.0 to give a relative score for each codon as compared to other codons that encode that amino acid. For this analysis, if a codon was more prevalent that the other choices for a given amino acid, it received a number that was greater than 1.0. Correspondingly, if a codon was less prevalent, it received a number less than 1.0. For this study, a particular codon was considered underrepresented if it's relative codon usage frequency was lower than 0.5.

Using the results from Table O, a close examination of the wild type *Agrobacterium* AS sequence revealed that 125 codons were considered underrepresented (below the threshold of 0.5) in corn and soybeans (Table P).

Figure 37A:
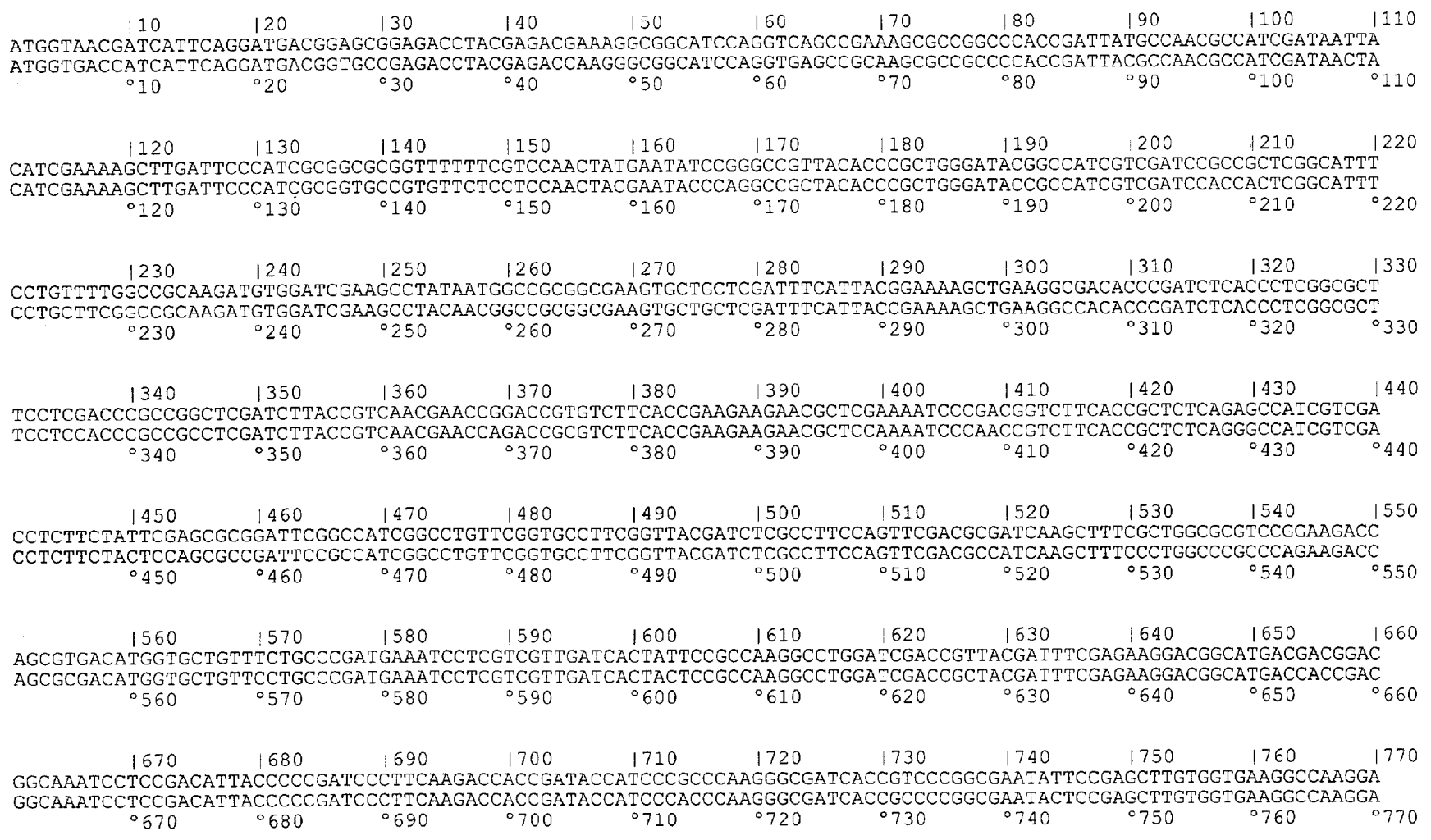
Figure 37B:
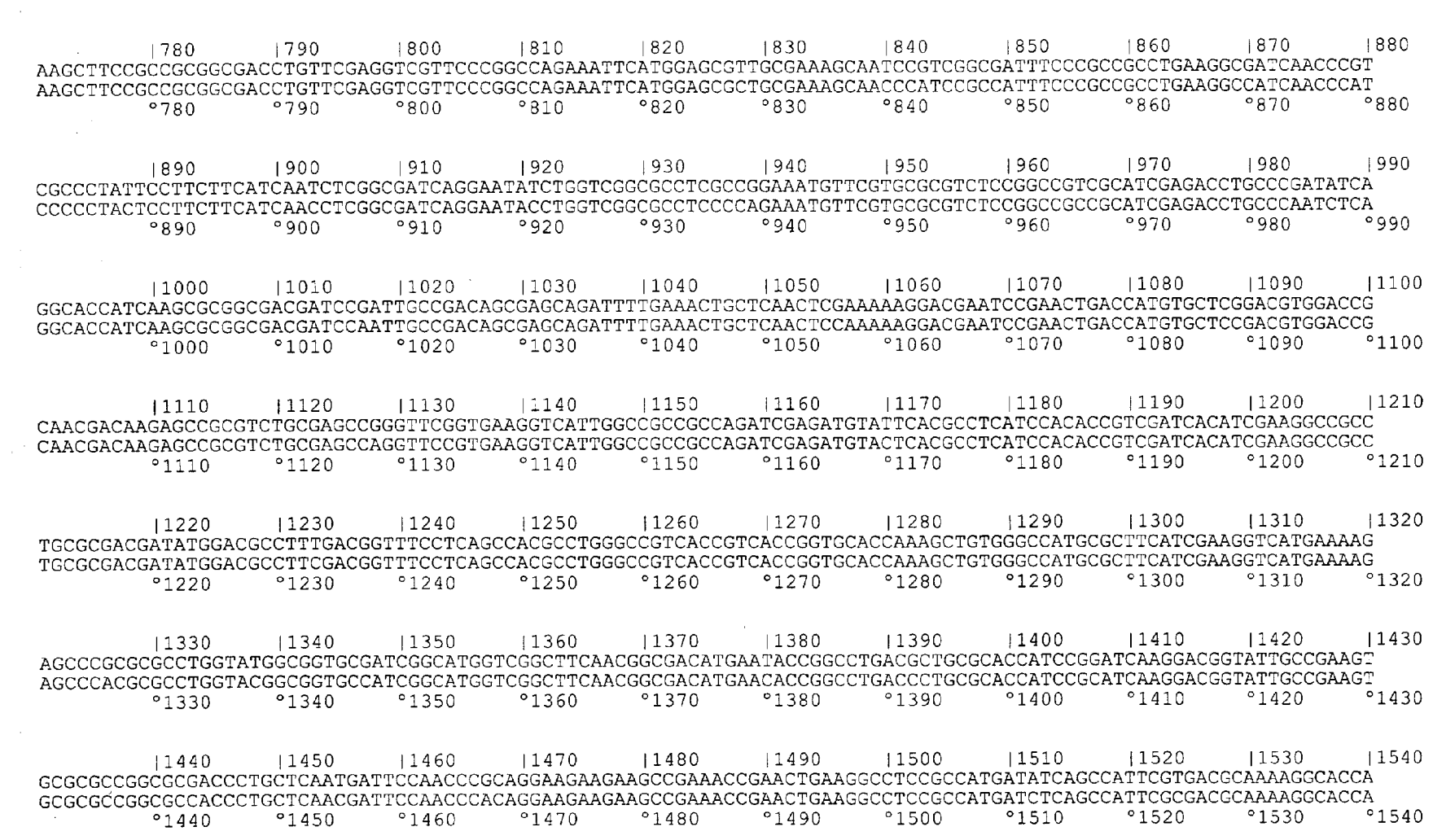

These underrepresented codons were replaced by more prevalent codons as defined above. The modified nucleotide sequence is shown in FIG. 36. Using bioinformatics tools, the resulting sequence was assembled and analyzed for integrity by translation and alignment of the nucleotide and protein sequences with the corresponding wild type AS sequences. While, the protein sequence was unchanged the nucleotide sequence of the optimized sequence had 94% identity with the wild type *Agrobacterium* AS sequence (FIG. 37). The optimized nucleotide sequence was analyzed for the absence of cryptic polyadenylation signals (AATAAA, AATAAT) and cryptic introns using Lasergene EditSeq (DNASTAR, Inc., Madison, Wis.) and Grail2 (Oak Ridge National Laboratory, Oak Ridge, Tenn.), respectively. No cryptic signals were found.

The modified nucleotide sequence is synthesized using techniques well known in the art or by commercial providers such as Egea Biosciencesces, Inc. (San Diego, Calif.). The resulting nucleotide is cloned into an appropriate expression vector and tested for efficacy in corn, soybeans and *Arabidopsis* using procedures detailed in earlier examples of this specification.

TABLE O

Relative codon usage frequencies in maize and soybean seed-expressed genes[1].

| Codon | AA | Maize Seed | Soy Seed | Codon | AA | Maize Seed | Soy Seed |
|---|---|---|---|---|---|---|---|
| TTT | F | 0.4211 | 0.7348 | ATC | I | 1.7143 | 1.0563 |
| TTC | F | 1.5789 | 1.2652 | ATA | I | 0.3673 | 0.6654 |
| TTA | L | 0.4557 | 0.3875 | ATG | M | 1.0000 | 1.0000 |
| TTG | L | 0.9494 | 1.2060 | ACT | T | 0.6153 | 1.0008 |
| TCT | S | 0.9624 | 1.4851 | ACC | T | 1.2213 | 2.1020 |
| TCC | S | 1.3707 | 1.1249 | ACA | T | 0.8372 | 0.7146 |
| TCA | S | 0.9107 | 1.0044 | ACG | T | 1.3262 | 0.1826 |
| TCG | S | 0.7851 | 0.3266 | AAT | N | 0.2885 | 0.5409 |
| TAT | Y | 0.2455 | 0.6861 | AAC | N | 1.7115 | 1.4591 |
| TAC | Y | 1.7545 | 1.3139 | AAA | K | 0.5333 | 0.9030 |
| TGT | C | 0.2778 | 0.7572 | AAG | K | 1.4667 | 1.0970 |
| TGC | C | 1.7222 | 1.2428 | AGT | S | 0.2679 | 0.9714 |
| TGG | W | 1.0000 | 1.0000 | AGC | S | 1.7032 | 1.0876 |
| CTT | L | 0.7975 | 1.6298 | AGA | R | 0.3913 | 1.9459 |
| CTC | L | 1.0610 | 1.6301 | AGG | R | 2.9185 | 1.3087 |
| CTA | L | 0.8544 | 0.5905 | GTT | V | 0.5714 | 1.2381 |
| CTG | L | 1.8820 | 0.5562 | GTC | V | 1.0119 | 0.6864 |
| CCT | P | 0.6500 | 1.5822 | GTA | V | 0.3810 | 0.3472 |
| CCC | P | 0.8520 | 0.7694 | GTG | V | 2.0357 | 1.7284 |
| CCA | P | 1.2240 | 1.5838 | GCT | A | 0.9876 | 1.3583 |
| CCG | P | 1.2740 | 0.0645 | GCC | A | 1.1618 | 1.1283 |
| CAT | H | 0.8438 | 0.6066 | GCA | A | 0.8011 | 1.2898 |
| CAC | H | 1.1563 | 1.3934 | GCG | A | 1.0495 | 0.2235 |
| CAA | Q | 0.8639 | 1.2162 | GAT | D | 0.8500 | 0.9523 |
| CAG | Q | 1.1361 | 0.7838 | GAC | D | 1.1500 | 1.0477 |
| CGT | R | 0.2582 | 0.5903 | GAA | E | 0.6818 | 1.0463 |
| CGC | R | 1.0082 | 1.1159 | GAG | E | 1.3182 | 0.9537 |
| CGA | R | 0.1957 | 0.6700 | GGT | G | 1.1268 | 1.1431 |
| CGG | R | 1.2283 | 0.3692 | GGC | G | 1.8758 | 0.6577 |
| ATT | I | 0.9184 | 1.2783 | GGA | G | 0.3085 | 1.2759 |
| ATC | I | 1.7143 | 1.0563 | GGG | G | 0.6889 | 0.9233 |

[1]The relative codon frequencies are represented in the expected value format. This means that if there are four codons that encode a given amino acid, and they are used equally well, each codon is expected to account for 25% (0.25). Due to the redundancy, 0.25 was normalized to 1 to give a relative score for each codon as compared to all codons that encode that amino acid. In real life if a codon is more prevalent than the other choices for a given amino acid, it would get a number >1. And if it is less preferred than the other codons for the amino acid, it would get a number <1.

TABLE P

Underrepresented Agro AS codons and modifications for improved seed expression[2].

| Codon | Codon (wt) | Amino Acid | Modified Codon | Under-rep in Crop[2] | Codon | Codon (wt) | Amino Acid | Modified Codon | Under-rep in Crop | Codon | Codon (wt) | Amino Acid | Modified Codon | Under-rep in Crop |
|---|---|---|---|---|---|---|---|---|---|---|---|---|---|---|
| 2 | GTA | V | GTG | corn, soy | 177 | TCG | S | TCC | soy | 481 | GCG | A | GCC | soy |
| 3 | ACG | T | ACC | soy | 179 | GCG | A | GCC | soy | 485 | AAT | N | AAC | corn, soy |
| 9 | GGA | G | GGT | corn | 180 | CGT | R | CGC | corn | 489 | CCG | P | CCA | soy |
| 10 | GCG | A | GCC | soy | 181 | CCG | P | CCA | soy | 504 | ATA | I | ATC | corn |
| 15 | ACG | T | ACC | soy | 185 | CGT | R | CGC | corn | 508 | CGT | R | CGC | corn |
| 16 | AAA | K | AAG | corn | 190 | TTT | F | TTC | corn | 520 | CGT | R | CGC | corn |
| 21 | GTC | V | GTG | soy | 201 | TAT | Y | TAC | corn | 543 | ACG | T | ACC | soy |
| 23 | CGA | R | CGC | corn | 209 | CGT | R | CGC | corn | 545 | GCG | A | GCC | soy |
| 26 | CGG | R | CGC | soy | 218 | ACG | T | ACC | soy | 546 | AAT | N | AAC | corn, soy |
| 30 | TAT | Y | TAC | corn | 219 | ACG | T | ACC | soy | 547 | TAT | Y | TAC | corn |
| 36 | AAT | N | AAC | corn, soy | 238 | CCG | P | CCA | soy | 551 | ACG | T | ACC | soy |
| 46 | GGC | G | GGT | soy | 244 | CGT | R | CGC | corn | 553 | GCG | A | GCC | soy |
| 47 | GCG | A | GCC | soy | 248 | TAT | Y | TAC | corn | 554 | ACG | T | ACC | soy |

TABLE P-continued

Underrepresented Agro AS codons and modifications for improved seed expression[2].

| Codon | Codon (wt) | Amino Acid | Modified Codon | Underrep in Crop[2] | Codon | Codon (wt) | Amino Acid | Modified Codon | Underrep in Crop | Codon | Codon (wt) | Amino Acid | Modified Codon | Underrep in Crop |
|---|---|---|---|---|---|---|---|---|---|---|---|---|---|---|
| 48 | GTT | V | GTG | corn | 276 | CGT | R | CGC | corn | 556 | TCG | S | TCC | soy |
| 49 | TTT | F | TTC | corn | 280 | AAT | N | AAC | corn, soy | 559 | AGA | R | AGG | corn |
| 50 | TCG | S | TCC | soy | 281 | CCG | P | CCA | soy | 561 | CCG | P | CCA | soy |
| 53 | TAT | Y | TAC | corn | 282 | TCG | S | TCC | soy | 572 | CCG | P | CCA | soy |
| 55 | TAT | Y | TAC | corn | 283 | GCG | A | GCC | soy | 578 | TCG | S | TCC | soy |
| 56 | CCG | P | CCA | soy | 290 | GCG | A | GCC | soy | 580 | GGA | G | GGT | corn |
| 58 | CGT | R | CGC | corn | 293 | CCG | P | CCA | soy | 584 | CCG | P | CCA | Soy |
| 64 | ACG | T | ACC | soy | 294 | TCG | S | TCC | soy | 585 | ACG | T | ACC | Soy |
| 69 | CCG | P | CCA | soy | 296 | TAT | Y | TAC | corn | 592 | ACG | T | ACC | Soy |
| 70 | CCG | P | CCA | soy | 301 | AAT | N | AAC | corn, soy | 602 | CCG | P | CCA | Soy |
| 75 | TGT | C | TGC | corn | 307 | TAT | Y | TAC | corn | 617 | TAT | Y | TAC | Corn |
| 76 | TTT | F | TTC | corn | 312 | TCG | S | TCC | soy | 633 | TCG | S | TCC | Soy |
| 85 | TAT | Y | TAC | corn | 313 | CCG | P | CCA | soy | 652 | ACG | T | ACC | Soy |
| 86 | AAT | N | AAC | corn, soy | 322 | CGT | R | CGC | corn | 655 | CGT | R | CGC | Corn |
| 97 | ACG | T | ACC | soy | 328 | CCG | P | CCA | soy | 658 | TCG | S | TCC | Soy |
| 102 | GCG | A | GCC | soy | 329 | ATA | I | ATC | corn | 667 | CCG | P | CCA | Soy |
| 112 | TCG | S | TCC | soy | 339 | CCG | P | CCA | soy | 668 | CGT | R | CGC | Corn |
| 115 | CGG | R | CGC | soy | 352 | TCG | S | TCC | soy | 680 | ACG | T | ACC | Soy |
| 123 | CCG | P | CCA | soy | 363 | TCG | S | TCC | soy | 690 | CCG | P | CCA | Soy |
| 125 | CGT | R | CGC | corn | 376 | CCG | P | CCA | soy | 698 | CCG | P | CCA | Soy |
| 133 | TCG | S | TCC | soy | 378 | TCG | S | TCC | soy | 700 | TCG | S | TCC | Soy |
| 136 | CCG | P | CCA | soy | 390 | TAT | Y | TAC | corn | 703 | ACG | T | ACC | Soy |
| 137 | ACG | T | ACC | soy | 411 | TTT | F | TTC | corn | 705 | GGA | G | GGT | Corn |
| 143 | AGA | R | AGG | corn | 442 | CCG | P | CCA | soy | 708 | GCG | A | GCC | Soy |
| 150 | TAT | Y | TAC | corn | 446 | TAT | Y | TAC | corn | 711 | CGG | R | CGC | Soy |
| 151 | TCG | S | TCC | soy | 449 | GCG | A | GCC | soy | 715 | AAT | N | AAC | corn, soy |
| 153 | GCG | A | GCC | soy | 460 | AAT | N | AAC | corn, soy | 724 | GCG | A | GCC | Soy |
| 155 | TCG | S | TCC | soy | 464 | ACG | T | ACC | soy | 729 | GCG | A | GCC | Soy |
| 173 | GCG | A | GCC | soy | 469 | CGG | R | CGC | soy | | | | | |

[2]The columns titled "Underrep in Crop" indicate in which crop (maize or soybean) a particular codon is underrepresented.

All publications and patents are incorporated by reference herein, as though individually incorporated by reference. The invention is not limited to the exact details shown and described, for it should be understood that many variations and modifications may be made while remaining within the spirit and scope of the invention defined by the claims.

---

What is claimed:

1. An isolated DNA encoding a monomeric anthranilate synthase, wherein the isolated DNA is selected from the group consisting of (a) a DNA sequence encoding a monomeric anthranilate synthase comprising at least 95% identity to SEQ ID NO:4; (b) a DNA sequence that hybridizes to SEQ ID NO:1 under stringent conditions; and (c) a DNA sequence that hybridizes to SEQ ID NO:75 under stringent conditions; wherein the stringent conditions include a wash at 50° C. in 0.015 M NaCl/0.0015 M sodium citrate (SSC) and 0.1% sodium lauryl sulfate (SLS).

2. The isolated DNA of claim 1, wherein the isolated DNA comprises SEQ ID NO:1.

3. The isolated DNA of claim 1, wherein the isolated DNA further encodes a plastid transit peptide.

4. The isolated DNA of claim 3, wherein the plastid transit peptide comprises SEQ ID NO:72 or 74.

5. The isolated DNA of claim 1, wherein the isolated DNA further encodes a selectable marker gene or a reporter gene.

6. The isolated DNA of claim 5, wherein the selectable marker gene, when expressed in a plant, imparts herbicide resistance to cells of said plant.

7. The isolated DNA of claim 6, wherein the herbicide resistance comprises resistance to glyphosate, glufosinate or dalapon.

8. The isolated DNA of claim 1, wherein the isolated DNA further encodes a *Bacillus thuringiensis* protein that, when expressed in a plant, imparts insect resistance to the plant.

9. The isolated DNA of claim 1, wherein the isolated DNA encoding the anthranilate synthase comprises a promoter operably linked thereto.

10. A vector comprising the isolated DNA of claim 1.

11. A seed comprising the isolated DNA of claim 1.

12. A transgenic plant comprising the isolated DNA of claim 1 encoding a monomeric anthranilate synthase operably linked to a promoter.

13. The transgenic plant of claim 12, wherein expression of the monomeric anthranilate synthase elevates the level of L-tryptophan in the plant relative to a second plant of the same or similar genetic background that does not include the transgene.

14. The transgenic plant of claim 12, wherein the isolated DNA encodes SEQ ID NO:4.

15. The transgenic plant of claim 12, wherein the isolated DNA further comprises a DNA encoding a plastid transit peptide.

16. The transgenic plant of claim 15, wherein the plastid transit peptide comprises SEQ ID NO:72 or 74.

17. The transgenic plant of claim 12, wherein the isolated DNA further encodes a selectable marker gene or a reporter gene.

18. The transgenic plant of claim 17, wherein the selectable marker gene, when expressed in a plant, imparts herbicide resistance to cells of said plant.

19. The transgenic plant of claim 18, wherein the herbicide resistance comprises resistance to glyphosate, glufosinate or dalapon.

20. The transgenic plant of claim 12, wherein the isolated DNA further encodes a *Bacillus thuringiensis* protein that, when expressed in a plant, imparts insect resistance to the plant.

21. The transgenic plant of claim 12, wherein the plant is a dicot.

22. The transgenic plant of claim 21, wherein the plant is soybean or canola.

23. The transgenic plant of claim 12, wherein the plant is a monocot.

24. The tranagenic plant of claim 23, wherein the plant is maize, rice, wheat, barley or sorghum.

25. A seed of the transgenic plant of claim 12, wherein the seed contains the isolated DNA encoding the monomeric anthranilate synthase.

26. The transgenic plant of claim 12, wherein the monomeric anthranilate synthase comprises at least 95% identity to SEQ ID NO:4.

27. The transgenic plant of claim 12, wherein the isolated DNA comprises SEQ ID NO:1.

28. The transgenic plant of claim 26, wherein the isolated DNA further comprises a DNA encoding a plastid transit peptide.

29. The transgenic plant of claim 28, wherein the plastid transit peptide comprises SEQ ID NO:72 or 74.

30. The transgenic plant of claim 26, wherein the isolated DNA further encodes a selectable marker gene or a reporter gene.

31. The transgenic plant of claim 30, wherein the selectable marker gene, when expressed in a plant, imparts herbicide resistance to cells of said plant.

32. The transgenic plant of claim 31, wherein the herbicide resistance comprises resistance to glyphosate, glufosinate or dalapon.

33. The transgenic plant of claim 26, wherein the isolated DNA further encodes a *Bacillus thuringiensis* protein that, when expressed in a plant, imparts insect resistance to the plant.

34. The transgene plant of claim 26, wherein the plant is a dicot.

35. The transgenic plant of claim 34, wherein the plant is soybean or canola.

36. The transgenic plant of claim 26, wherein the plant is a monocot.

37. The transgenic plant of claim 34, wherein the plant is maize, rice, wheat, barley or sorghum.

38. A seed of the transgenic plant of claim 26 wherein the seed contains the isolated DNA.

39. The isolated DNA of claim 1, wherein the isolated DNA encodes a monomeric anthranilate synthase comprising at least 95% identity to SEQ ID NO:4.

40. The isolated DNA of claim 1, wherein the isolated DNA comprises a DNA sequence that hybridizes to SEQ ID NO:1 under stringent conditions, wherein the stringent conditions include a wash at 50° C. in 0.015 M NaCl/0.0015 M sodium citrate (SSC) and 0.1% sodium lauryl sulfate (SLS).

41. The isolated DNA of claim 1, wherein the isolated DNA comprises a DNA sequence that hybridizes to SEQ ID NO:75 under stringent conditions, wherein the stringent conditions include a wash at 50° C. in 0.015 M NaCl/0.0015 M sodium citrate (SSC) and 0.1% sodium lauryl sulfate (SLS).

42. The transgenic plant of claim 12, wherein the isolated DNA comprises a DNA sequence that hybridizes to SEQ ID NO:1 under stringent conditions, wherein the stringent conditions include a wash at 50° C. in 0.015 M NaCl/0.0015 M sodium citrate (SSC) and 0.1% sodium lauryl sulfate (SLS).

43. The transgenic plant of claim 12, wherein the isolated DNA comprises a DNA sequence that hybridizes to SEQ ID NO:75 under stringent conditions, wherein the stringent conditions include a wash at 50° C. in 0.015 M NaCl/0.0015 M sodium citrate (SSC) and 0.1% sodium lauryl sulfate (SLS).

* * * * *

SEQUENCE LISTING

```
<160> NUMBER OF SEQ ID NOS: 103

<210> SEQ ID NO 1
<211> LENGTH: 2190
<212> TYPE: DNA
<213> ORGANISM: Agrobacterium tumefaciens

<400> SEQUENCE: 1
atggtaacga tcattcagga tgacggagcg gagacctacg agacgaaagg cggcatccag      60
gtcagccgaa agcgccggcc caccgattat gccaacgcca tcgataatta catcgaaaag     120
cttgattccc atcgcggcgc ggttttttcg tccaactatg aatatccggg ccgttacacc     180
cgctgggata cggccatcgt cgatccgccg ctcggcattt cctgttttgg ccgcaagatg     240
tggatcgaag cctataatgg ccgcggcgaa gtgctgctcg atttcattac ggaaaagctg     300
aaggcgacac ccgatctcac cctcggcgct tcctcgaccc gccggctcga tcttaccgtc     360
aacgaaccgg accgtgtctt caccgaagaa gaacgctcga aaatcccgac ggtcttcacc     420
```

```
gctctcagag ccatcgtcga cctcttctat tcgagcgcgg attcggccat cggcctgttc      480
ggtgccttcg gttacgatct cgccttccag ttcgacgcga tcaagctttc gctggcgcgt      540
ccggaagacc agcgtgacat ggtgctgttt ctgcccgatg aaatcctcgt cgttgatcac      600
tattccgcca aggcctggat cgaccgttac gatttcgaga aggacggcat gacgacggac      660
ggcaaatcct ccgacattac ccccgatccc ttcaagacca ccgataccat cccgcccaag      720
ggcgatcacc gtcccggcga atattccgag cttgtggtga aggccaagga aagcttccgc      780
cgcggcgacc tgttcgaggt cgttcccggc cagaaattca tggagcgttg cgaaagcaat      840
ccgtcggcga tttcccgccg cctgaaggcg atcaacccgt cgccctattc cttcttcatc      900
aatctcggcg atcaggaata tctggtcggc gcctcgccgg aaatgttcgt gcgcgtctcc      960
ggccgtcgca tcgagacctg cccgatatca ggcaccatca agcgcggcga cgatccgatt     1020
gccgacagcg agcagatttt gaaactgctc aactcgaaaa aggacgaatc cgaactgacc     1080
atgtgctcgg acgtggaccg caacgacaag agccgcgtct gcgagccggg ttcggtgaag     1140
gtcattggcc gccgccagat cgagatgtat tcacgcctca tccacaccgt cgatcacatc     1200
gaaggccgcc tgcgcgacga tatggacgcc tttgacggtt tcctcagcca cgcctgggcc     1260
gtcaccgtca ccggtgcacc aaagctgtgg gccatgcgct tcatcgaagg tcatgaaaag     1320
agcccgcgcg cctggtatgg cggtgcgatc ggcatggtcg gcttcaacgg cgacatgaat     1380
accggcctga cgctgcgcac catccggatc aaggacggta ttgccgaagt gcgcgccggc     1440
gcgaccctgc tcaatgattc caacccgcag gaagaagaag ccgaaaccga actgaaggcc     1500
tccgccatga tatcagccat cgtgacgca aaaggcacca actctgccgc caccaagcgt     1560
gatgccgcca agtcggcac cggcgtcaag atcctgctcg tcgaccacga agacagcttc     1620
gtgcacacgc tggcgaatta tttccgccag acgggcgcga cggtctcgac cgtcagatca     1680
ccggtcgcag ccgacgtgtt cgatcgcttc cagccggacc tcgttgtcct gtcgcccgga     1740
cccggcagcc cgacggattt cgactgcaag gcaacgatca aggccgcccg cgcccgcgat     1800
ctgccgatct cggcgtttg cctcggtctg caggcattgg cagaagccta tggcggcgag     1860
ctgcgccagc ttgctgtgcc catgcacggc aagccttcgc gcatccgcgt gctggaaccc     1920
ggcctcgtct tctccggtct cggcaaggaa gtcacggtcg gtcgttacca ttcgatcttc     1980
gccgatcccg ccaccctgcc gcgtgatttc atcatcaccg cagaaagcga ggacggcacg     2040
atcatgggca tcgaacacgc caaggaaccg gtggccgccg ttcagttcca cccggaatcg     2100
atcatgacgc tcggacagga cgcgggcatg cggatgatcg agaatgtcgt ggtgcatctg     2160
acccgcaagg cgaagaccaa ggccgcgtga                                     2190
```

<210> SEQ ID NO 2
<211> LENGTH: 1815
<212> TYPE: DNA
<213> ORGANISM: Zea mays

<400> SEQUENCE: 2

```
atggaatccc tagccgccac ctccgtgttc gcgccctccc gcgtcgccgt ccggcggcg       60 cgggccctgg ttagggcggg gacggtggta ccaaccaggc ggacgagcag ccggagcgga      120
accagcgggg tgaaatgctc tgctgccgtg acgccgcagg cgagcccagt gattagcagg      180
agcgctgcgg cggcgaaggc ggcggaggag acaagaggc ggttcttcga ggcggcggcg       240
cgggggagcg ggaaggggaa cctggtgccc atgtgggagt gcatcgtgtc ggaccatctc      300 accccgtgc tcgcctaccg ctgcctcgtc cccgaggaca acgtcgacgc cccagccttc      360
```

-continued

```
ctcttcgagt ccgtcgagca ggggccccag ggcaccacca acgtcggccg ctatagcatg      420
gtgggagccc acccagtgat ggagattgtg gccaaagacc acaaggttac gatcatggac      480
cacgagaaga gccaagtgac agagcaggta gtggacgacc cgatgcagat cccgaggacc      540
atgatggagg gatggcaccc acagcagatc gacgagctcc ctgaatcctt ctccggtgga      600
tgggttgggt tcttttccta tgatacggtt aggtatgttg agaagaagaa gctaccgttc      660
tccagtgctc ctcaggacga taggaacctt cctgatgtgc acttgggact ctatgatgat      720
gttctagtct tcgataatgt tgagaagaaa gtatatgtta tccattgggt caatgtggac      780
cggcatgcat ctgttgagga agcataccaa gatggcaggt cccgactaaa catgttgcta      840
tctaaagtgc acaattccaa tgtccccaca ctctctcctg gatttgtgaa gctgcacaca      900
cgcaagtttg gtacaccttt gaacaagtcg accatgacaa gtgatgagta taagaatgct      960
gttctgcagg ctaaggaaca tattatggct ggggatatct tccagattgt tttaagccag     1020
aggttcgaga gacgaacata tgccaaccca tttgaggttt atcgagcatt acggattgtg     1080
aatcctagcc catacatggc gtatgtacag gcaagaggct gtgtattggt tgcgtctagt     1140
cctgaaattc ttacacgagt cagtaagggg aagattatta atcgaccact tgctggaact     1200
gttcgaaggg gcaagacaga gaaggaagat caaatgcaag agcagcaact gttaagtgat     1260
gaaaaacagt gtgccgagca cataatgctt gtggacttgg aaggaatga tgttggcaag      1320
gtatccaaac caggatcagt gaaggtggag aagttgatga acattgagag atactcccat     1380
gttatgcaca tcagctcaac ggttagtgga cagttggatg atcatctcca gagttgggat     1440
gccttgagag ctgccttgcc cgttggaaca gtcagtggtg caccaaaggt gaaggccatg     1500
gagttgattg ataagttgga agttacgagg cgaggaccat atagtggtgg tctaggagga     1560
atatcgtttg atggtgacat gcaaattgca ctttctctcc gcaccatcgt attctcaaca     1620
gcgccgagcc acaacacgat gtactcatac aaagacgcag ataggcgtcg ggagtgggtc     1680
gctcatcttc aggctggtgc aggcattgtt gccgacagta gcccagatga cgaacaacgt     1740
gaatgcgaga ataaggctgc tgcactagct cgggccatcg atcttgcaga gtcagctttt     1800
gtagacaaag aatag                                                       1815

<210> SEQ ID NO 3
<211> LENGTH: 1993
<212> TYPE: DNA
<213> ORGANISM: Ruta graveolens

<400> SEQUENCE: 3
aaaaaatctg tctgttttc gtgtttggac atttcagcgg cactgggtgc catcagttga       60
ttcgactcat ttgatttatt tgtttgttg gccatgagtg cagcggcaac gtcgatgcaa      120
tcccttaaat tctccaaccg tctggtccca cccagtcgcc gtctgtctcc ggttccgaac      180
aatgtcacct gcaataacct ccccaagtct gcagctcccg tccggacagt caaatgctgc      240
gcttcttcct ggaacagtac catcaacggc gcggccgcca cgaccaacgg tgcgtccgcc      300
gccagtaacg gcgcatccac gaccaccact acatatgtta gtgatgcaac cagatttatc      360
gactcttcta aagggcaaa tctagtgcca ttataccgtt gcatattcgc ggatcatctc      420
acgccggtgc ttgcctatag atgtttggtt caagaagacg ataaagagac tccaagtttt      480
ttattcgaat cagtagagcc gggtcggatt tctactgttg ggaggtatag tgtggttgga      540
gctcatcccg tgatggaagt tatagctaaa gataatatgg ttacggtgat ggatcatgag      600
```

-continued

```
aaagggagct tagttgagga ggtggtcgat gatcccatgg agattcctag aagaatttcc    660
gaggattgga agcctcaaat aatcgatgat cttcctgaag cttttttgcgg tggttgggtt   720
ggtttcttct catacgatac agttcgatat gtggagaaga aaaagttacc attctcaaag    780
gcacctcagg atgataggaa tcttgcagat atgcatctag gtctctataa cgatgttatt    840
gtgtttgatc atgtgaaaa gaaagtatat gttattcatt gggtgaggct aaatcaacag     900
tcttctgaag aaaaagcata tgccgagggt ctggaacact ggagagact agtatccaga     960
gtacaggatg agaacacgcc aaggctcgcc ccaggttcca tagacttaca cactggtcat    1020
tttggacctc cattaaaaaa gtcaaacatg acatgtgaag aatacaaaat ggctgtacta    1080
gcggcaaaag aacatattca ggctggggat attttttcaaa tcgtactaag ccaacgtttt   1140
gaacgtcgaa catttgctga tccatttgaa gtttataggg cactgagagt tgttaatccg    1200
agtccctata tgacgtatat gcaggcaaga gggtgtgttc tggtagcttc aagtccagaa    1260
attcttactc gagtaaagaa gaataagatt gtgaatcgac cttttggctgg aacagcccga   1320
agagggagga ctactgaaga agatgagatg ttggaaacac agttgctaaa agacgcaaag    1380
caatgtgctg agcatgttat gctggtcgat ttgggacgga atgatgttgg caaggtttca   1440
aaatctggtt ctgtgaaagt ggaaaagctg atgaatgttg aacgatattc acatgttatg    1500
cacataagct ctacggtcac aggtgagttg caagataatc tcagttgctg ggatgccctg    1560
cgtgctgcac tgcctgtcgg gactgttagt ggagcaccaa aggtgaaggc aatggagtta    1620
atcgatgaat tggaggtaaa tagacgtggc ccctacagtg gtgggtttgg cggtatctcc   1680
ttcaccggag atatggacat tgccctggct ctaaggacca ttgttttcca aaccggtaca    1740
cgctatgaca caatgtactc gtacaagaat gctaccaaac gccggcagtg ggtggcatac    1800
cttcaagccg gggctggcat tgttgctgat agtgatccag acgacgagca tcgtgagtgc    1860
cagaacaaag ccgccggact ggcccgtgcc atcgacctag ctgagtctgc ttttgtgaac    1920
aaatcaagta gctaaagttt tggatttgga agtggagttg agtctcggat aggatttaga    1980
gtaaaaaaag agg                                                       1993
```

<210> SEQ ID NO 4
<211> LENGTH: 729
<212> TYPE: PRT
<213> ORGANISM: Agrobacterium tumefaciens

<400> SEQUENCE: 4

```
Met Val Thr Ile Ile Gln Asp Asp Gly Ala Glu Thr Tyr Glu Thr Lys
  1               5                  10                  15

Gly Gly Ile Gln Val Ser Arg Lys Arg Arg Pro Thr Asp Tyr Ala Asn
             20                  25                  30

Ala Ile Asp Asn Tyr Ile Glu Lys Leu Asp Ser His Arg Gly Ala Val
         35                  40                  45

Phe Ser Ser Asn Tyr Glu Tyr Pro Gly Arg Tyr Thr Arg Trp Asp Thr
     50                  55                  60

Ala Ile Val Asp Pro Pro Leu Gly Ile Ser Cys Phe Gly Arg Lys Met
 65                  70                  75                  80

Trp Ile Glu Ala Tyr Asn Gly Arg Gly Glu Val Leu Leu Asp Phe Ile
                 85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125
```

-continued

```
Glu Glu Glu Arg Ser Lys Ile Pro Thr Val Phe Thr Ala Leu Arg Ala
    130                 135                 140
Ile Val Asp Leu Phe Tyr Ser Ser Ala Asp Ser Ala Ile Gly Leu Phe
145                 150                 155                 160
Gly Ala Phe Gly Tyr Asp Leu Ala Phe Gln Phe Asp Ala Ile Lys Leu
                165                 170                 175
Ser Leu Ala Arg Pro Glu Asp Gln Arg Asp Met Val Leu Phe Leu Pro
            180                 185                 190
Asp Glu Ile Leu Val Asp His Tyr Ser Ala Lys Ala Trp Ile Asp
        195                 200                 205
Arg Tyr Asp Phe Glu Lys Asp Gly Met Thr Thr Asp Gly Lys Ser Ser
    210                 215                 220
Asp Ile Thr Pro Asp Pro Phe Lys Thr Thr Asp Thr Ile Pro Pro Lys
225                 230                 235                 240
Gly Asp His Arg Pro Gly Glu Tyr Ser Glu Leu Val Val Lys Ala Lys
                245                 250                 255
Glu Ser Phe Arg Arg Gly Asp Leu Phe Glu Val Val Pro Gly Gln Lys
            260                 265                 270
Phe Met Glu Arg Cys Glu Ser Asn Pro Ser Ala Ile Ser Arg Arg Leu
        275                 280                 285
Lys Ala Ile Asn Pro Ser Pro Tyr Ser Phe Phe Ile Asn Leu Gly Asp
290                 295                 300
Gln Glu Tyr Leu Val Gly Ala Ser Pro Glu Met Phe Val Arg Val Ser
305                 310                 315                 320
Gly Arg Arg Ile Glu Thr Cys Pro Ile Ser Gly Thr Ile Lys Arg Gly
                325                 330                 335
Asp Asp Pro Ile Ala Asp Ser Glu Gln Ile Leu Lys Leu Leu Asn Ser
            340                 345                 350
Lys Lys Asp Glu Ser Glu Leu Thr Met Cys Ser Asp Val Asp Arg Asn
        355                 360                 365
Asp Lys Ser Arg Val Cys Glu Pro Gly Ser Val Lys Val Ile Gly Arg
    370                 375                 380
Arg Gln Ile Glu Met Tyr Ser Arg Leu Ile His Thr Val Asp His Ile
385                 390                 395                 400
Glu Gly Arg Leu Arg Asp Asp Met Asp Ala Phe Asp Gly Phe Leu Ser
                405                 410                 415
His Ala Trp Ala Val Thr Val Thr Gly Ala Pro Lys Leu Trp Ala Met
            420                 425                 430
Arg Phe Ile Glu Gly His Glu Lys Ser Pro Arg Ala Trp Tyr Gly Gly
        435                 440                 445
Ala Ile Gly Met Val Gly Phe Asn Gly Asp Met Asn Thr Gly Leu Thr
    450                 455                 460
Leu Arg Thr Ile Arg Ile Lys Asp Gly Ile Ala Glu Val Arg Ala Gly
465                 470                 475                 480
Ala Thr Leu Leu Asn Asp Ser Asn Pro Gln Glu Glu Glu Ala Glu Thr
                485                 490                 495
Glu Leu Lys Ala Ser Ala Met Ile Ser Ala Ile Arg Asp Ala Lys Gly
            500                 505                 510
Thr Asn Ser Ala Ala Thr Lys Arg Asp Ala Ala Lys Val Gly Thr Gly
        515                 520                 525
Val Lys Ile Leu Leu Val Asp His Glu Asp Ser Phe Val His Thr Leu
    530                 535                 540
```

```
Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
            565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
            595                 600                 605

Gly Leu Gln Ala Leu Ala Glu Ala Tyr Gly Gly Glu Leu Arg Gln Leu
            610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
            645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
            675                 680                 685

Glu Pro Val Ala Ala Val Gln Phe His Pro Glu Ser Ile Met Thr Leu
            690                 695                 700

Gly Gln Asp Ala Gly Met Arg Met Ile Glu Asn Val Val His Leu
705                 710                 715                 720

Thr Arg Lys Ala Lys Thr Lys Ala Ala
                725

<210> SEQ ID NO 5
<211> LENGTH: 604
<212> TYPE: PRT
<213> ORGANISM: Zea mays

<400> SEQUENCE: 5

Met Glu Ser Leu Ala Ala Thr Ser Val Phe Ala Pro Ser Arg Val Ala
1               5                   10                  15

Val Pro Ala Ala Arg Ala Leu Val Arg Ala Gly Thr Val Val Pro Thr
            20                  25                  30

Arg Arg Thr Ser Ser Arg Ser Gly Thr Ser Gly Val Lys Cys Ser Ala
        35                  40                  45

Ala Val Thr Pro Gln Ala Ser Pro Val Ile Ser Arg Ser Ala Ala Ala
    50                  55                  60

Ala Lys Ala Ala Glu Glu Asp Lys Arg Arg Phe Phe Glu Ala Ala Ala
65                  70                  75                  80

Arg Gly Ser Gly Lys Gly Asn Leu Val Pro Met Trp Glu Cys Ile Val
                85                  90                  95

Ser Asp His Leu Thr Pro Val Leu Ala Tyr Arg Cys Leu Val Pro Glu
            100                 105                 110

Asp Asn Val Asp Ala Pro Ser Phe Leu Phe Glu Ser Val Glu Gln Gly
            115                 120                 125

Pro Gln Gly Thr Thr Asn Val Gly Arg Tyr Ser Met Val Gly Ala His
        130                 135                 140

Pro Val Met Glu Ile Val Ala Lys Asp His Lys Val Thr Ile Met Asp
145                 150                 155                 160

His Glu Lys Ser Gln Val Thr Glu Gln Val Val Asp Pro Met Gln
            165                 170                 175

Ile Pro Arg Thr Met Met Glu Gly Trp His Pro Gln Gln Ile Asp Glu
            180                 185                 190
```

```
Leu Pro Glu Ser Phe Ser Gly Gly Trp Val Gly Phe Ser Tyr Asp
        195                 200                 205

Thr Val Arg Tyr Val Glu Lys Lys Leu Pro Phe Ser Ser Ala Pro
        210                 215                 220

Gln Asp Asp Arg Asn Leu Pro Asp Val His Leu Gly Leu Tyr Asp Asp
225                     230                 235                 240

Val Leu Val Phe Asp Asn Val Glu Lys Val Tyr Val Ile His Trp
                245                 250                 255

Val Asn Val Asp Arg His Ala Ser Val Glu Glu Ala Tyr Gln Asp Gly
                260                 265                 270

Arg Ser Arg Leu Asn Met Leu Leu Ser Lys Val His Asn Ser Asn Val
        275                 280                 285

Pro Thr Leu Ser Pro Gly Phe Val Lys Leu His Thr Arg Lys Phe Gly
        290                 295                 300

Thr Pro Leu Asn Lys Ser Thr Met Thr Ser Asp Glu Tyr Lys Asn Ala
305                     310                 315                 320

Val Leu Gln Ala Lys Glu His Ile Met Ala Gly Asp Ile Phe Gln Ile
                325                 330                 335

Val Leu Ser Gln Arg Phe Glu Arg Arg Thr Tyr Ala Asn Pro Phe Glu
                340                 345                 350

Val Tyr Arg Ala Leu Arg Ile Val Asn Pro Ser Pro Tyr Met Ala Tyr
                355                 360                 365

Val Gln Ala Arg Gly Cys Val Leu Val Ala Ser Ser Pro Glu Ile Leu
        370                 375                 380

Thr Arg Val Ser Lys Gly Lys Ile Ile Asn Arg Pro Leu Ala Gly Thr
385                     390                 395                 400

Val Arg Arg Gly Lys Thr Glu Lys Glu Asp Gln Met Gln Glu Gln Gln
                405                 410                 415

Leu Leu Ser Asp Glu Lys Gln Cys Ala Glu His Ile Met Leu Val Asp
                420                 425                 430

Leu Gly Arg Asn Asp Val Gly Lys Val Ser Lys Pro Gly Ser Val Lys
        435                 440                 445

Val Glu Lys Leu Met Asn Ile Glu Arg Tyr Ser His Val Met His Ile
        450                 455                 460

Ser Ser Thr Val Ser Gly Gln Leu Asp Asp His Leu Gln Ser Trp Asp
465                     470                 475                 480

Ala Leu Arg Ala Ala Leu Pro Val Gly Thr Val Ser Gly Ala Pro Lys
                485                 490                 495

Val Lys Ala Met Glu Leu Ile Asp Lys Leu Glu Val Thr Arg Arg Gly
                500                 505                 510

Pro Tyr Ser Gly Gly Leu Gly Gly Ile Ser Phe Asp Gly Asp Met Gln
        515                 520                 525

Ile Ala Leu Ser Leu Arg Thr Ile Val Phe Ser Thr Ala Pro Ser His
        530                 535                 540

Asn Thr Met Tyr Ser Tyr Lys Asp Ala Asp Arg Arg Glu Trp Val
545                     550                 555                 560

Ala His Leu Gln Ala Gly Ala Gly Ile Val Ala Asp Ser Ser Pro Asp
                565                 570                 575

Asp Glu Gln Arg Glu Cys Glu Asn Lys Ala Ala Ala Leu Ala Arg Ala
                580                 585                 590

Ile Asp Leu Ala Glu Ser Ala Phe Val Asp Lys Glu
        595                 600
```

<210> SEQ ID NO 6
<211> LENGTH: 613
<212> TYPE: PRT
<213> ORGANISM: Ruta graveolens

<400> SEQUENCE: 6

```
Met Ser Ala Ala Thr Ser Met Gln Ser Leu Lys Phe Ser Asn Arg
 1               5                  10                  15

Leu Val Pro Pro Ser Arg Arg Leu Ser Pro Val Pro Asn Asn Val Thr
                 20                  25                  30

Cys Asn Asn Leu Pro Lys Ser Ala Ala Pro Val Arg Thr Val Lys Cys
             35                  40                  45

Cys Ala Ser Ser Trp Asn Ser Thr Ile Asn Gly Ala Ala Thr Thr
 50                  55                  60

Asn Gly Ala Ser Ala Ala Ser Asn Gly Ala Ser Thr Thr Thr Thr Thr
 65                  70                  75                  80

Tyr Val Ser Asp Ala Thr Arg Phe Ile Asp Ser Ser Lys Arg Ala Asn
                 85                  90                  95

Leu Val Pro Leu Tyr Arg Cys Ile Phe Ala Asp His Leu Thr Pro Val
             100                 105                 110

Leu Ala Tyr Arg Cys Leu Val Gln Glu Asp Asp Lys Glu Thr Pro Ser
             115                 120                 125

Phe Leu Phe Glu Ser Val Glu Pro Gly Arg Ile Ser Thr Val Gly Arg
130                 135                 140

Tyr Ser Val Val Gly Ala His Pro Val Met Glu Val Ile Ala Lys Asp
145                 150                 155                 160

Asn Met Val Thr Val Met Asp His Glu Lys Gly Ser Leu Val Glu Glu
                 165                 170                 175

Val Val Asp Asp Pro Met Glu Ile Pro Arg Arg Ile Ser Glu Asp Trp
             180                 185                 190

Lys Pro Gln Ile Ile Asp Asp Leu Pro Glu Ala Phe Cys Gly Gly Trp
             195                 200                 205

Val Gly Phe Phe Ser Tyr Asp Thr Val Arg Tyr Val Glu Lys Lys Lys
210                 215                 220

Leu Pro Phe Ser Lys Ala Pro Gln Asp Asp Arg Asn Leu Ala Asp Met
225                 230                 235                 240

His Leu Gly Leu Tyr Asn Asp Val Ile Val Phe Asp His Val Glu Lys
                 245                 250                 255

Lys Val Tyr Val Ile His Trp Val Arg Leu Asn Gln Gln Ser Ser Glu
             260                 265                 270

Glu Lys Ala Tyr Ala Glu Gly Leu Glu His Leu Glu Arg Leu Val Ser
             275                 280                 285

Arg Val Gln Asp Glu Asn Thr Pro Arg Leu Ala Pro Gly Ser Ile Asp
290                 295                 300

Leu His Thr Gly His Phe Gly Pro Pro Leu Lys Lys Ser Asn Met Thr
305                 310                 315                 320

Cys Glu Glu Tyr Lys Met Ala Val Leu Ala Lys Glu His Ile Gln
                 325                 330                 335

Ala Gly Asp Ile Phe Gln Ile Val Leu Ser Gln Arg Phe Glu Arg Arg
             340                 345                 350

Thr Phe Ala Asp Pro Phe Glu Val Tyr Arg Ala Leu Arg Val Val Asn
             355                 360                 365

Pro Ser Pro Tyr Met Thr Tyr Met Gln Ala Arg Gly Cys Val Leu Val
370                 375                 380
```

```
Ala Ser Ser Pro Glu Ile Leu Thr Arg Val Lys Lys Asn Lys Ile Val
385                 390                 395                 400

Asn Arg Pro Leu Ala Gly Thr Ala Arg Arg Gly Arg Thr Thr Glu Glu
            405                 410                 415

Asp Glu Met Leu Glu Thr Gln Leu Leu Lys Asp Ala Lys Gln Cys Ala
        420                 425                 430

Glu His Val Met Leu Val Asp Leu Gly Arg Asn Asp Val Gly Lys Val
                435                 440                 445

Ser Lys Ser Gly Ser Val Lys Val Glu Lys Leu Met Asn Val Glu Arg
    450                 455                 460

Tyr Ser His Val Met His Ile Ser Ser Thr Val Thr Gly Glu Leu Gln
465                 470                 475                 480

Asp Asn Leu Ser Cys Trp Asp Ala Leu Ala Ala Leu Pro Val Gly
                485                 490                 495

Thr Val Ser Gly Ala Pro Lys Val Lys Ala Met Glu Leu Ile Asp Glu
            500                 505                 510

Leu Glu Val Asn Arg Arg Gly Pro Tyr Ser Gly Gly Phe Gly Gly Ile
        515                 520                 525

Ser Phe Thr Gly Asp Met Asp Ile Ala Leu Ala Leu Arg Thr Ile Val
    530                 535                 540

Phe Gln Thr Gly Thr Arg Tyr Asp Thr Met Tyr Ser Tyr Lys Asn Ala
545                 550                 555                 560

Thr Lys Arg Arg Gln Trp Val Ala Tyr Leu Gln Ala Gly Ala Gly Ile
                565                 570                 575

Val Ala Asp Ser Asp Pro Asp Asp Glu His Arg Glu Cys Gln Asn Lys
            580                 585                 590

Ala Ala Gly Leu Ala Arg Ala Ile Asp Leu Ala Glu Ser Ala Phe Val
        595                 600                 605

Asn Lys Ser Ser Ser
        610

<210> SEQ ID NO 7
<211> LENGTH: 729
<212> TYPE: PRT
<213> ORGANISM: Rhizobium meliloti

<400> SEQUENCE: 7

Met Ala Ala Val Ile Leu Glu Asp Gly Ala Glu Ser Tyr Thr Thr Lys
1               5                   10                  15

Gly Gly Ile Val Val Thr Arg Arg Arg Glu Ala Ser Tyr Ser Asp
            20                  25                  30

Ala Ile Ala Gly Tyr Val Asp Arg Leu Asp Glu Arg Arg Gly Ala Val
            35                  40                  45

Phe Ser Ser Asn Tyr Glu Tyr Pro Gly Arg Tyr Thr Arg Trp Asp Thr
50                  55                  60

Ala Val Val Asp Pro Pro Leu Ala Ile Ser Ser Phe Gly Arg Ser Leu
65                  70                  75                  80

Trp Ile Glu Ala Tyr Asn Glu Arg Gly Glu Val Leu Leu Ala Leu Ile
                85                  90                  95

Ala Glu Asp Leu Lys Ser Val Ala Asp Ile Thr Leu Gly Ser Leu Ala
            100                 105                 110

Ala Arg Arg Leu Asp Leu Thr Ile Asn Glu Pro Asp Arg Val Phe Thr
        115                 120                 125

Glu Glu Glu Arg Ser Lys Met Pro Thr Val Phe Thr Val Leu Arg Ala
```

-continued

```
            130                 135                 140
Val Thr Asn Leu Phe His Ser Glu Glu Asp Ser Asn Leu Gly Leu Tyr
145                 150                 155                 160

Gly Ala Phe Gly Tyr Asp Leu Ala Phe Gln Phe Asp Ala Ile Glu Leu
                165                 170                 175

Lys Leu Ser Arg Pro Asp Asp Gln Arg Asp Met Val Leu Phe Leu Pro
                180                 185                 190

Asp Glu Ile Leu Val Val Asp His Tyr Ala Ala Lys Ala Trp Ile Asp
            195                 200                 205

Arg Tyr Asp Phe Ala Arg Glu Asn Leu Ser Thr Glu Gly Lys Ala Ala
210                 215                 220

Asp Ile Ala Pro Glu Pro Phe Arg Ser Val Asp Ser Ile Pro Pro His
225                 230                 235                 240

Gly Asp His Arg Pro Gly Glu Tyr Ala Glu Leu Val Lys Ala Lys
                245                 250                 255

Glu Ser Phe Arg Arg Gly Asp Leu Phe Glu Val Val Pro Gly Gln Lys
                260                 265                 270

Phe Tyr Glu Arg Cys Glu Ser Arg Pro Ser Glu Ile Ser Asn Arg Leu
            275                 280                 285

Lys Ala Ile Asn Pro Ser Pro Tyr Ser Phe Phe Ile Asn Leu Gly Asn
290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
                355                 360                 365

Asp Lys Ser Arg Val Cys Val Pro Gly Ser Val Lys Val Ile Gly Arg
            370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
                420                 425                 430

Arg Phe Ile Glu Ser His Glu Lys Ser Pro Arg Ala Trp Tyr Gly Gly
            435                 440                 445

Ala Ile Gly Met Val Gly Phe Asn Gly Asp Met Asn Thr Gly Leu Thr
450                 455                 460

Leu Arg Thr Ile Arg Ile Lys Asp Gly Ile Ala Glu Val Arg Ala Gly
465                 470                 475                 480

Ala Thr Leu Leu Tyr Asp Ser Asn Pro Glu Glu Glu Ala Glu Thr
                485                 490                 495

Glu Leu Lys Ala Ser Ala Met Ile Ala Ala Ile Arg Asp Ala Lys Ser
            500                 505                 510

Ala Asn Ser Ala Lys Ser Ala Arg Asp Val Ala Val Gly Ala Gly
                515                 520                 525

Val Ser Ile Leu Leu Val Asp His Glu Asp Ser Phe Val His Thr Leu
530                 535                 540

Ala Asn Tyr Phe Arg Gln Thr Gly Ala Ser Val Thr Thr Val Arg Thr
545                 550                 555                 560
```

```
Pro Val Ala Glu Glu Ile Phe Asp Arg Val Lys Pro Asp Leu Val Val
                565                 570                 575

Leu Ser Pro Gly Pro Gly Thr Pro Lys Asp Phe Asp Cys Lys Ala Thr
            580                 585                 590

Ile Lys Lys Ala Arg Ala Arg Asp Leu Pro Ile Phe Gly Val Cys Leu
        595                 600                 605

Gly Leu Gln Ala Leu Ala Glu Ala Tyr Gly Gly Asp Leu Arg Gln Leu
    610                 615                 620

Ala Ile Pro Met His Gly Lys Pro Ser Arg Ile Arg Val Leu Glu Pro
625                 630                 635                 640

Gly Ile Val Phe Ser Gly Leu Gly Lys Glu Val Thr Val Gly Arg Tyr
                645                 650                 655

His Ser Ile Phe Ala Asp Pro Ser Asn Leu Pro Arg Glu Phe Val Ile
            660                 665                 670

Thr Ala Glu Ser Glu Asp Gly Thr Ile Met Gly Ile Glu His Ser Lys
        675                 680                 685

Glu Pro Val Ala Ala Val Gln Phe His Pro Glu Ser Ile Met Thr Leu
    690                 695                 700

Gly Gly Asp Ala Gly Met Arg Met Ile Glu Asn Val Val Ala His Leu
705                 710                 715                 720

Ala Lys Arg Ala Lys Thr Lys Ala Ala
                725

<210> SEQ ID NO 8
<211> LENGTH: 421
<212> TYPE: PRT
<213> ORGANISM: Sulfolobus solfataricus

<400> SEQUENCE: 8

Met Glu Val His Pro Ile Ser Glu Phe Ala Ser Pro Phe Glu Val Phe
1               5                   10                  15

Lys Cys Ile Glu Arg Asp Phe Lys Val Ala Gly Leu Leu Glu Ser Ile
            20                  25                  30

Gly Gly Pro Gln Tyr Lys Ala Arg Tyr Ser Val Ile Ala Trp Ser Thr
        35                  40                  45

Asn Gly Tyr Leu Lys Ile His Asp Asp Pro Val Asn Ile Leu Asn Gly
    50                  55                  60

Tyr Leu Lys Asp Leu Lys Leu Ala Asp Ile Pro Gly Leu Phe Lys Gly
65                  70                  75                  80

Gly Met Ile Gly Tyr Ile Ser Tyr Asp Ala Val Arg Phe Trp Glu Lys
                85                  90                  95

Ile Arg Asp Leu Lys Pro Ala Ala Glu Asp Trp Pro Tyr Ala Glu Phe
            100                 105                 110

Phe Thr Pro Asp Asn Ile Ile Ile Tyr Asp His Asn Glu Gly Lys Val
        115                 120                 125

Tyr Val Asn Ala Asp Leu Ser Ser Val Gly Gly Cys Gly Asp Ile Gly
    130                 135                 140

Glu Phe Lys Val Ser Phe Tyr Asp Glu Ser Leu Asn Lys Asn Ser Tyr
145                 150                 155                 160

Glu Arg Ile Val Ser Glu Ser Leu Glu Tyr Ile Arg Ser Gly Tyr Ile
                165                 170                 175

Phe Gln Val Val Leu Ser Arg Phe Tyr Arg Tyr Ile Phe Ser Gly Asp
            180                 185                 190

Pro Leu Arg Ile Tyr Tyr Asn Leu Arg Arg Ile Asn Pro Ser Pro Tyr
```

-continued

```
                195                 200                 205
Met Phe Tyr Leu Lys Phe Asp Glu Lys Tyr Leu Ile Gly Ser Ser Pro
    210                 215                 220

Glu Leu Leu Phe Arg Val Gln Asp Asn Ile Val Glu Thr Tyr Pro Ile
225                 230                 235                 240

Ala Gly Thr Arg Pro Arg Gly Ala Asp Gln Glu Asp Leu Lys Leu
                245                 250                 255

Glu Leu Glu Leu Met Asn Ser Glu Lys Asp Lys Ala Glu His Leu Met
            260                 265                 270

Leu Val Asp Leu Ala Arg Asn Asp Leu Gly Lys Val Cys Val Pro Gly
        275                 280                 285

Thr Val Lys Val Pro Glu Leu Met Tyr Val Glu Lys Tyr Ser His Val
    290                 295                 300

Gln His Ile Val Ser Lys Val Ile Gly Thr Leu Lys Lys Tyr Asn
305                 310                 315                 320

Ala Leu Asn Val Leu Ser Ala Thr Phe Pro Ala Gly Thr Val Ser Gly
                325                 330                 335

Arg Pro Lys Pro Met Ala Met Asn Ile Ile Glu Thr Leu Glu Glu Tyr
            340                 345                 350

Lys Arg Gly Pro Tyr Ala Gly Ala Val Gly Phe Ile Ser Ala Asp Gly
        355                 360                 365

Asn Ala Glu Phe Ala Ile Ala Ile Arg Thr Ala Phe Leu Asn Lys Glu
    370                 375                 380

Leu Leu Arg Ile His Ala Gly Ala Gly Ile Val Tyr Asp Ser Asn Pro
385                 390                 395                 400

Glu Ser Glu Tyr Phe Glu Thr Glu His Lys Leu Lys Ala Leu Lys Thr
                405                 410                 415

Ala Ile Gly Val Arg
            420

<210> SEQ ID NO 9
<211> LENGTH: 32
<212> TYPE: DNA
<213> ORGANISM: Artificial Sequence
<220> FEATURE:
<223> OTHER INFORMATION: A primer.

<400> SEQUENCE: 9
ccatcgcggc gcgttttttt cgtccaacta tg                              32

<210> SEQ ID NO 10
<211> LENGTH: 32
<212> TYPE: DNA
<213> ORGANISM: Artificial Sequence
<220> FEATURE:
<223> OTHER INFORMATION: A primer.

<400> SEQUENCE: 10
catagttgga cgaaaaaaac gcgccgcgat gg                              32

<210> SEQ ID NO 11
<211> LENGTH: 39
<212> TYPE: DNA
<213> ORGANISM: Artificial Sequence
<220> FEATURE:
<223> OTHER INFORMATION: A primer.

<400> SEQUENCE: 11
ccatcgcggc gcgtattttt cgtccaacta tgaatatcc                       39
```

<210> SEQ ID NO 12
<211> LENGTH: 39
<212> TYPE: DNA
<213> ORGANISM: Artificial Sequence
<220> FEATURE:
<223> OTHER INFORMATION: A primer.

<400> SEQUENCE: 12
ggatattcat agttggacga aaaatacgcg ccgcgatgg                    39

<210> SEQ ID NO 13
<211> LENGTH: 39
<212> TYPE: DNA
<213> ORGANISM: Artificial Sequence
<220> FEATURE:
<223> OTHER INFORMATION: A primer.

<400> SEQUENCE: 13
ccatcgcggc gcgtggtttt cgtccaacta tgaatatcc                    39

<210> SEQ ID NO 14
<211> LENGTH: 39
<212> TYPE: DNA
<213> ORGANISM: Artificial Sequence
<220> FEATURE:
<223> OTHER INFORMATION: A primer.

<400> SEQUENCE: 14
ggatattcat agttggacga aaaccacgcg ccgcgatgg                    39

<210> SEQ ID NO 15
<211> LENGTH: 39
<212> TYPE: DNA
<213> ORGANISM: Artificial Sequence
<220> FEATURE:
<223> OTHER INFORMATION: A primer.

<400> SEQUENCE: 15
ccatcgcggc gcggttttta agtccaacta tgaatatcc                    39

<210> SEQ ID NO 16
<211> LENGTH: 39
<212> TYPE: DNA
<213> ORGANISM: Artificial Sequence
<220> FEATURE:
<223> OTHER INFORMATION: A primer.

<400> SEQUENCE: 16
ggatattcat agttggactt aaaaccgcg ccgcgatgg                     39

<210> SEQ ID NO 17
<211> LENGTH: 34
<212> TYPE: DNA
<213> ORGANISM: Artificial Sequence
<220> FEATURE:
<223> OTHER INFORMATION: A primer.

<400> SEQUENCE: 17
gcgcggtttt ttcgtgcaac tatgaatatc cggg                         34

<210> SEQ ID NO 18
<211> LENGTH: 34
<212> TYPE: DNA
<213> ORGANISM: Artificial Sequence
<220> FEATURE:

<223> OTHER INFORMATION: A primer.

<400> SEQUENCE: 18
cccggatatt catagttgca cgaaaaaacc gcgc        34

<210> SEQ ID NO 19
<211> LENGTH: 34
<212> TYPE: DNA
<213> ORGANISM: Artificial Sequence
<220> FEATURE:
<223> OTHER INFORMATION: A primer.

<400> SEQUENCE: 19
cgcggttttt tcgttcaact atgaatatcc gggc        34

<210> SEQ ID NO 20
<211> LENGTH: 34
<212> TYPE: DNA
<213> ORGANISM: Artificial Sequence
<220> FEATURE:
<223> OTHER INFORMATION: A primer.

<400> SEQUENCE: 20
gcccggatat tcatagttga acgaaaaaac cgcg        34

<210> SEQ ID NO 21
<211> LENGTH: 37
<212> TYPE: DNA
<213> ORGANISM: Artificial Sequence
<220> FEATURE:
<223> OTHER INFORMATION: A primer.

<400> SEQUENCE: 21
cggcgcggtt ttttcgatca actatgaata tccgggc        37

<210> SEQ ID NO 22
<211> LENGTH: 37
<212> TYPE: DNA
<213> ORGANISM: Artificial Sequence
<220> FEATURE:
<223> OTHER INFORMATION: A primer.

<400> SEQUENCE: 22
gcccggatat tcatagttga tcgaaaaaac cgcgccg        37

<210> SEQ ID NO 23
<211> LENGTH: 36
<212> TYPE: DNA
<213> ORGANISM: Artificial Sequence
<220> FEATURE:
<223> OTHER INFORMATION: A primer.

<400> SEQUENCE: 23
ggcgcggttt ttcgctcaa ctatgaatat ccgggc        36

<210> SEQ ID NO 24
<211> LENGTH: 36
<212> TYPE: DNA
<213> ORGANISM: Artificial Sequence
<220> FEATURE:
<223> OTHER INFORMATION: A primer.

<400> SEQUENCE: 24
gcccggatat tcatagttga gcgaaaaaac cgcgcc        36

```
<210> SEQ ID NO 25
<211> LENGTH: 39
<212> TYPE: DNA
<213> ORGANISM: Artificial Sequence
<220> FEATURE:
<223> OTHER INFORMATION: A primer.

<400> SEQUENCE: 25
cggcgcggtt ttttcgatga actatgaata tccgggccg                              39

<210> SEQ ID NO 26
<211> LENGTH: 39
<212> TYPE: DNA
<213> ORGANISM: Artificial Sequence
<220> FEATURE:
<223> OTHER INFORMATION: A primer.

<400> SEQUENCE: 26
cggcccggat attcatagtt catcgaaaaa accgcgccg                              39

<210> SEQ ID NO 27
<211> LENGTH: 34
<212> TYPE: DNA
<213> ORGANISM: Artificial Sequence
<220> FEATURE:
<223> OTHER INFORMATION: A primer.

<400> SEQUENCE: 27
cgcggttttt tcgaccaact atgaatatcc gggc                                   34

<210> SEQ ID NO 28
<211> LENGTH: 34
<212> TYPE: DNA
<213> ORGANISM: Artificial Sequence
<220> FEATURE:
<223> OTHER INFORMATION: A primer.

<400> SEQUENCE: 28
gcccggatat tcatagttgg tcgaaaaaac cgcg                                   34

<210> SEQ ID NO 29
<211> LENGTH: 36
<212> TYPE: DNA
<213> ORGANISM: Artificial Sequence
<220> FEATURE:
<223> OTHER INFORMATION: A primer.

<400> SEQUENCE: 29
ggcgcggttt tttcggtcaa ctatgaatat ccgggc                                 36

<210> SEQ ID NO 30
<211> LENGTH: 36
<212> TYPE: DNA
<213> ORGANISM: Artificial Sequence
<220> FEATURE:
<223> OTHER INFORMATION: A primer.

<400> SEQUENCE: 30
gcccggatat tcatagttga ccgaaaaaac cgcgcc                                 36

<210> SEQ ID NO 31
<211> LENGTH: 35
<212> TYPE: DNA
<213> ORGANISM: Artificial Sequence
<220> FEATURE:
<223> OTHER INFORMATION: A primer.
```

```
<400> SEQUENCE: 31
gcgcggtttt ttcgtacaac tatgaatatc cgggc                          35

<210> SEQ ID NO 32
<211> LENGTH: 35
<212> TYPE: DNA
<213> ORGANISM: Artificial Sequence
<220> FEATURE:
<223> OTHER INFORMATION: A primer.

<400> SEQUENCE: 32
gcccggatat tcatagttgt acgaaaaaac cgcgc                          35

<210> SEQ ID NO 33
<211> LENGTH: 36
<212> TYPE: DNA
<213> ORGANISM: Artificial Sequence
<220> FEATURE:
<223> OTHER INFORMATION: A primer.

<400> SEQUENCE: 33
cggcgcggtt tttcgtcct tctatgaata tccggg                          36

<210> SEQ ID NO 34
<211> LENGTH: 36
<212> TYPE: DNA
<213> ORGANISM: Artificial Sequence
<220> FEATURE:
<223> OTHER INFORMATION: A primer.

<400> SEQUENCE: 34
cccggatatt catagaagga cgaaaaaacc gcgccg                         36

<210> SEQ ID NO 35
<211> LENGTH: 29
<212> TYPE: DNA
<213> ORGANISM: Artificial Sequence
<220> FEATURE:
<223> OTHER INFORMATION: A primer.

<400> SEQUENCE: 35
ctgaaggcga tcaacgcgtc gccctattc                                 29

<210> SEQ ID NO 36
<211> LENGTH: 29
<212> TYPE: DNA
<213> ORGANISM: Artificial Sequence
<220> FEATURE:
<223> OTHER INFORMATION: A primer.

<400> SEQUENCE: 36
gaatagggcg acgcgttgat cgccttcag                                 29

<210> SEQ ID NO 37
<211> LENGTH: 31
<212> TYPE: DNA
<213> ORGANISM: Artificial Sequence
<220> FEATURE:
<223> OTHER INFORMATION: A primer.

<400> SEQUENCE: 37
cctgaaggcg atcaacgggt cgccctattc c                              31

<210> SEQ ID NO 38
<211> LENGTH: 31
```

-continued

```
<212> TYPE: DNA
<213> ORGANISM: Artificial Sequence
<220> FEATURE:
<223> OTHER INFORMATION: A primer.

<400> SEQUENCE: 38
ggaatagggc gacccgttga tcgccttcag g                          31

<210> SEQ ID NO 39
<211> LENGTH: 33
<212> TYPE: DNA
<213> ORGANISM: Artificial Sequence
<220> FEATURE:
<223> OTHER INFORMATION: A primer.

<400> SEQUENCE: 39
cgtcgcccta ttccgccttc atcaatctcg gcg                        33

<210> SEQ ID NO 40
<211> LENGTH: 33
<212> TYPE: DNA
<213> ORGANISM: Artificial Sequence
<220> FEATURE:
<223> OTHER INFORMATION: A primer.

<400> SEQUENCE: 40
cgccgagatt gatgaaggcg gaatagggcg acg                        33

<210> SEQ ID NO 41
<211> LENGTH: 33
<212> TYPE: DNA
<213> ORGANISM: Artificial Sequence
<220> FEATURE:
<223> OTHER INFORMATION: A primer.

<400> SEQUENCE: 41
cgtcgcccta ttcctggttc atcaatctcg gcg                        33

<210> SEQ ID NO 42
<211> LENGTH: 33
<212> TYPE: DNA
<213> ORGANISM: Artificial Sequence
<220> FEATURE:
<223> OTHER INFORMATION: A primer.

<400> SEQUENCE: 42
cgccgagatt gatgaaccag gaatagggcg acg                        33

<210> SEQ ID NO 43
<211> LENGTH: 729
<212> TYPE: PRT
<213> ORGANISM: Rhizobium meliloti

<400> SEQUENCE: 43

Met Ala Ala Val Ile Leu Glu Asp Gly Ala Glu Ser Tyr Thr Thr Lys
 1               5                  10                  15

Gly Gly Ile Val Val Thr Arg Arg Arg Glu Ala Ser Tyr Ser Asp
            20                  25                  30

Ala Ile Ala Gly Tyr Val Asp Arg Leu Asp Glu Arg Gly Ala Val
        35                  40                  45

Phe Ser Ser Asn Tyr Glu Tyr Pro Gly Arg Tyr Thr Arg Trp Asp Thr
    50                  55                  60

Ala Val Val Asp Pro Pro Leu Ala Ile Ser Ser Phe Gly Arg Ser Leu
65                  70                  75                  80
```

-continued

```
Trp Ile Glu Ala Tyr Asn Glu Arg Gly Glu Val Leu Ala Leu Ile
                 85                  90                  95

Ala Glu Asp Leu Lys Ser Val Ala Asp Ile Thr Leu Gly Ser Leu Ala
            100                 105                 110

Ala Arg Arg Leu Asp Leu Thr Ile Asn Glu Pro Asp Arg Val Phe Thr
            115                 120                 125

Glu Glu Glu Arg Ser Lys Met Pro Thr Val Phe Thr Val Leu Arg Ala
    130                 135                 140

Val Thr Asn Leu Phe His Ser Glu Glu Asp Ser Asn Leu Gly Leu Tyr
145                 150                 155                 160

Gly Ala Phe Gly Tyr Asp Leu Ala Phe Gln Phe Asp Ala Ile Glu Leu
                165                 170                 175

Lys Leu Ser Arg Pro Asp Asp Gln Arg Asp Met Val Leu Phe Leu Pro
            180                 185                 190

Asp Glu Ile Leu Val Val Asp His Tyr Ala Ala Lys Ala Trp Ile Asp
            195                 200                 205

Arg Tyr Asp Phe Ala Arg Glu Asn Leu Ser Thr Glu Gly Lys Ala Ala
    210                 215                 220

Asp Ile Ala Pro Glu Pro Phe Arg Ser Val Asp Ser Ile Pro Pro His
225                 230                 235                 240

Gly Asp His Arg Pro Gly Glu Tyr Ala Glu Leu Val Val Lys Ala Lys
                245                 250                 255

Glu Ser Phe Arg Arg Gly Asp Leu Phe Glu Val Val Pro Gly Gln Lys
            260                 265                 270

Phe Tyr Glu Arg Cys Glu Ser Arg Pro Ser Glu Ile Ser Asn Arg Leu
            275                 280                 285

Lys Ala Ile Asn Pro Ser Pro Tyr Ser Phe Phe Ile Asn Leu Gly Asn
    290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
            355                 360                 365

Asp Lys Ser Arg Val Cys Val Pro Gly Ser Val Lys Val Ile Gly Arg
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Ser His Glu Lys Ser Pro Arg Ala Trp Tyr Gly Gly
            435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Tyr Asp Ser Asn Pro Glu Glu Glu Ala Glu Thr
                485                 490                 495
```

```
Glu Leu Lys Ala Ser Ala Met Ile Ala Ala Ile Arg Asp Ala Lys Ser
                500                 505                 510

Ala Asn Ser Ala Lys Ser Ala Arg Asp Val Ala Ala Val Gly Ala Gly
            515                 520                 525

Val Ser Ile Leu Leu Val Asp His Glu Asp Ser Phe Val His Thr Leu
        530                 535                 540

Ala Asn Tyr Phe Arg Gln Thr Gly Ala Ser Val Thr Thr Val Arg Thr
545                 550                 555                 560

Pro Val Ala Glu Glu Ile Phe Asp Arg Val Lys Pro Asp Leu Val Val
                565                 570                 575

Leu Ser Pro Gly Pro Gly Thr Pro Lys Asp Phe Asp Cys Lys Ala Thr
            580                 585                 590

Ile Lys Lys Ala Arg Ala Arg Asp Leu Pro Ile Phe Gly Val Cys Leu
        595                 600                 605

Gly Leu Gln Ala Leu Ala Glu Ala Tyr Gly Gly Asp Leu Arg Gln Leu
    610                 615                 620

Ala Ile Pro Met His Gly Lys Pro Ser Arg Ile Arg Val Leu Glu Pro
625                 630                 635                 640

Gly Ile Val Phe Ser Gly Leu Gly Lys Glu Val Thr Val Gly Arg Tyr
                645                 650                 655

His Ser Ile Phe Ala Asp Pro Ser Asn Leu Pro Arg Glu Phe Val Ile
            660                 665                 670

Thr Ala Glu Ser Glu Asp Gly Thr Ile Met Gly Ile Glu His Ser Lys
        675                 680                 685

Glu Pro Val Ala Ala Val Gln Phe His Pro Glu Ser Ile Met Thr Leu
    690                 695                 700

Gly Gly Asp Ala Gly Met Arg Met Ile Glu Asn Val Val Ala His Leu
705                 710                 715                 720

Ala Lys Arg Ala Lys Thr Lys Ala Ala
                725

<210> SEQ ID NO 44
<211> LENGTH: 616
<212> TYPE: PRT
<213> ORGANISM: Sulfolobus solfataricus

<400> SEQUENCE: 44

Met Glu Val His Pro Ile Ser Glu Phe Ala Ser Pro Phe Glu Val Phe
1               5                   10                  15

Lys Cys Ile Glu Arg Asp Phe Lys Val Ala Gly Leu Leu Glu Ser Ile
                20                  25                  30

Gly Gly Pro Gln Tyr Lys Ala Arg Tyr Ser Val Ile Ala Trp Ser Thr
            35                  40                  45

Asn Gly Tyr Leu Lys Ile His Asp Asp Pro Val Asn Ile Leu Asn Gly
        50                  55                  60

Tyr Leu Lys Asp Leu Lys Leu Ala Asp Ile Pro Gly Leu Phe Lys Gly
65                  70                  75                  80

Gly Met Ile Gly Tyr Ile Ser Tyr Asp Ala Val Arg Phe Trp Glu Lys
                85                  90                  95

Ile Arg Asp Leu Lys Pro Ala Ala Glu Asp Trp Pro Tyr Ala Glu Phe
            100                 105                 110

Phe Thr Pro Asp Asn Ile Ile Ile Tyr Asp His Asn Glu Gly Lys Val
        115                 120                 125

Tyr Val Asn Ala Asp Leu Ser Ser Val Gly Gly Cys Gly Asp Ile Gly
    130                 135                 140
```

```
Glu Phe Lys Val Ser Phe Tyr Asp Glu Ser Leu Asn Lys Asn Ser Tyr
145                 150                 155                 160

Glu Arg Ile Val Ser Glu Ser Leu Glu Tyr Ile Arg Ser Gly Tyr Ile
                165                 170                 175

Phe Gln Val Val Leu Ser Arg Phe Tyr Arg Tyr Ile Phe Ser Gly Asp
            180                 185                 190

Pro Leu Arg Ile Tyr Tyr Asn Leu Arg Arg Ile Asn Pro Ser Pro Tyr
        195                 200                 205

Met Phe Tyr Leu Lys Phe Asp Glu Lys Tyr Leu Ile Gly Ser Ser Pro
    210                 215                 220

Glu Leu Leu Phe Arg Val Gln Asp Asn Ile Val Glu Thr Tyr Pro Ile
225                 230                 235                 240

Ala Gly Thr Arg Pro Arg Gly Ala Asp Gln Glu Glu Asp Leu Lys Leu
                245                 250                 255

Glu Leu Glu Leu Met Asn Ser Glu Lys Asp Lys Ala Glu His Leu Met
            260                 265                 270

Leu Val Asp Leu Ala Arg Asn Asp Leu Gly Lys Val Cys Val Pro Gly
        275                 280                 285

Thr Val Lys Val Pro Glu Leu Met Tyr Val Glu Lys Tyr Ser His Val
    290                 295                 300

Gln His Ile Val Ser Lys Val Ile Gly Thr Leu Lys Lys Lys Tyr Asn
305                 310                 315                 320

Ala Leu Asn Val Leu Ser Ala Thr Phe Pro Ala Gly Thr Val Ser Gly
                325                 330                 335

Arg Pro Lys Pro Met Ala Met Asn Ile Ile Glu Thr Leu Glu Glu Tyr
            340                 345                 350

Lys Arg Gly Pro Tyr Ala Gly Ala Val Gly Phe Ile Ser Ala Asp Gly
        355                 360                 365

Asn Ala Glu Phe Ala Ile Ala Ile Arg Thr Ala Phe Leu Asn Lys Glu
    370                 375                 380

Leu Leu Arg Ile His Ala Gly Ala Gly Ile Val Tyr Asp Ser Asn Pro
385                 390                 395                 400

Glu Ser Glu Tyr Phe Glu Thr Glu His Lys Leu Lys Ala Leu Lys Thr
                405                 410                 415

Ala Ile Gly Val Arg Met Asp Leu Thr Leu Ile Ile Asp Asn Tyr Asp
            420                 425                 430

Ser Phe Val Tyr Asn Ile Ala Gln Ile Val Gly Glu Leu Gly Ser Tyr
        435                 440                 445

Pro Ile Val Ile Arg Asn Asp Glu Ile Ser Ile Lys Gly Ile Glu Arg
    450                 455                 460

Ile Asp Pro Asp Arg Leu Ile Ile Ser Pro Gly Pro Gly Thr Pro Glu
465                 470                 475                 480

Lys Arg Glu Asp Ile Gly Val Ser Leu Asp Val Ile Lys Tyr Leu Gly
                485                 490                 495

Lys Arg Thr Pro Ile Leu Gly Val Cys Leu Gly His Gln Ala Ile Gly
            500                 505                 510

Tyr Ala Phe Gly Ala Lys Ile Arg Arg Ala Arg Lys Val Phe His Gly
        515                 520                 525

Lys Ile Ser Asn Ile Ile Leu Val Asn Asn Ser Pro Leu Ser Leu Tyr
    530                 535                 540

Tyr Gly Ile Ala Lys Glu Phe Lys Ala Thr Arg Tyr His Ser Leu Val
545                 550                 555                 560
```

-continued

```
Val Asp Glu Val His Arg Pro Leu Ile Val Asp Ala Ile Ser Ala Glu
            565                 570                 575

Asp Asn Glu Ile Met Ala Ile His His Glu Glu Tyr Pro Ile Tyr Gly
            580                 585                 590

Val Gln Phe His Pro Glu Ser Val Gly Thr Ser Leu Gly Tyr Lys Ile
        595                 600                 605

Leu Tyr Asn Phe Leu Asn Arg Val
    610                 615

<210> SEQ ID NO 45
<211> LENGTH: 897
<212> TYPE: PRT
<213> ORGANISM: Arabidopsis thaliana

<400> SEQUENCE: 45

Met Ser Ala Val Ser Ile Ser Ala Val Lys Ser Asp Phe Phe Thr Val
1               5                   10                  15

Glu Ala Ile Ala Val Thr His His Arg Thr Pro His Pro Pro His Phe
            20                  25                  30

Pro Ser Leu Arg Phe Pro Leu Ser Leu Lys Ser Pro Pro Ala Thr Ser
        35                  40                  45

Leu Asn Leu Val Ala Gly Ser Lys Leu Leu His Phe Ser Arg Arg Leu
    50                  55                  60

Pro Ser Ile Lys Cys Ser Tyr Thr Pro Ser Leu Asp Leu Ser Glu Glu
65                  70                  75                  80

Gln Phe Thr Lys Phe Lys Lys Ala Ser Glu Lys Gly Asn Leu Val Pro
                85                  90                  95

Leu Phe Arg Cys Val Phe Ser Asp His Leu Thr Pro Ile Leu Ala Tyr
            100                 105                 110

Arg Cys Leu Val Lys Glu Asp Arg Asp Ala Pro Ser Phe Leu Phe
            115                 120                 125

Glu Ser Val Glu Pro Gly Ser Gln Ser Ser Asn Ile Gly Arg Tyr Ser
    130                 135                 140

Val Val Gly Ala Gln Pro Thr Ile Glu Ile Val Ala Lys Gly Asn Val
145                 150                 155                 160

Val Thr Val Met Asp His Gly Ala Ser Leu Arg Thr Glu Glu Val
                165                 170                 175

Asp Asp Pro Met Met Val Pro Gln Lys Ile Met Glu Glu Trp Asn Pro
            180                 185                 190

Gln Gly Ile Asp Glu Leu Pro Glu Ala Phe Cys Gly Gly Trp Val Gly
        195                 200                 205

Tyr Phe Ser Tyr Asp Thr Val Arg Tyr Val Glu Lys Lys Leu Pro
    210                 215                 220

Phe Ser Asn Ala Pro Glu Asp Arg Ser Leu Pro Asp Val Asn Leu
225                 230                 235                 240

Gly Leu Tyr Asp Asp Val Ile Val Phe Asp His Val Glu Lys Lys Ala
                245                 250                 255

Tyr Val Ile His Trp Val Arg Ile Asp Lys Asp Arg Ser Val Glu Glu
            260                 265                 270

Asn Phe Arg Glu Gly Met Asn Arg Leu Glu Ser Leu Thr Ser Arg Ile
        275                 280                 285

Gln Asp Gln Lys Pro Pro Lys Met Pro Thr Gly Phe Ile Lys Leu Arg
    290                 295                 300

Thr Gln Leu Phe Gly Pro Lys Leu Glu Lys Ser Thr Met Thr Ser Glu
305                 310                 315                 320
```

-continued

```
Ala Tyr Lys Glu Ala Val Val Glu Ala Lys Glu His Ile Leu Ala Gly
            325                 330                 335

Asp Ile Phe Gln Ile Val Leu Ser Gln Arg Phe Glu Arg Arg Thr Phe
            340                 345                 350

Ala Asp Pro Phe Glu Ile Tyr Arg Ala Leu Arg Ile Val Asn Pro Ser
            355                 360                 365

Pro Tyr Met Ala Tyr Leu Gln Val Arg Gly Cys Ile Leu Val Ala Ser
            370                 375                 380

Ser Pro Glu Ile Leu Leu Arg Ser Lys Asn Arg Lys Ile Thr Asn Arg
385                 390                 395                 400

Pro Leu Ala Gly Thr Val Arg Arg Gly Lys Thr Pro Lys Glu Asp Leu
            405                 410                 415

Met Leu Glu Lys Glu Leu Leu Ser Asp Glu Lys Gln Cys Ala Glu His
            420                 425                 430

Ile Met Leu Val Asp Leu Gly Arg Asn Asp Val Gly Lys Val Ser Lys
            435                 440                 445

Pro Gly Ser Val Glu Val Lys Lys Leu Lys Asp Ile Glu Trp Phe Ser
            450                 455                 460

His Val Met His Ile Ser Ser Thr Val Val Gly Glu Leu Leu Asp His
465                 470                 475                 480

Leu Thr Ser Trp Asp Ala Leu Arg Ala Val Leu Pro Val Gly Thr Val
            485                 490                 495

Ser Gly Ala Pro Lys Val Lys Ala Met Glu Leu Ile Asp Glu Leu Glu
            500                 505                 510

Val Thr Arg Arg Gly Pro Tyr Ser Gly Gly Phe Gly Gly Ile Ser Phe
            515                 520                 525

Asn Gly Asp Met Asp Ile Ala Leu Ala Leu Arg Thr Met Val Phe Pro
            530                 535                 540

Thr Asn Thr Arg Tyr Asp Thr Leu Tyr Ser Tyr Lys His Pro Gln Arg
545                 550                 555                 560

Arg Arg Glu Trp Ile Ala His Ile Gln Ala Gly Ala Gly Ile Val Ala
            565                 570                 575

Asp Ser Asn Pro Asp Asp Glu His Arg Glu Cys Glu Asn Lys Ala Ala
            580                 585                 590

Ala Leu Ala Arg Ala Ile Asp Leu Ala Glu Ser Ser Phe Leu Glu Ala
            595                 600                 605

Pro Glu Phe Thr Thr Ile Thr Pro His Ile Asn Asn Ile Met Ala Ala
            610                 615                 620

Ser Thr Leu Tyr Lys Ser Cys Leu Leu Gln Pro Lys Ser Gly Ser Thr
625                 630                 635                 640

Thr Arg Arg Leu Asn Pro Ser Leu Val Asn Pro Leu Thr Asn Pro Thr
            645                 650                 655

Arg Val Ser Val Leu Gly Lys Ser Arg Arg Asp Val Phe Ala Lys Ala
            660                 665                 670

Ser Ile Glu Met Ala Glu Ser Asn Ser Ile Pro Ser Val Val Val Asn
            675                 680                 685

Ser Ser Lys Gln His Gly Pro Ile Ile Val Ile Asp Asn Tyr Asp Ser
            690                 695                 700

Phe Thr Tyr Asn Leu Cys Gln Tyr Met Gly Leu Gly Cys His Phe
705                 710                 715                 720

Glu Val Tyr Arg Asn Asp Glu Leu Thr Val Glu Glu Leu Lys Lys Lys
            725                 730                 735
```

```
Asn Pro Arg Gly Val Leu Ile Ser Pro Gly Pro Gly Thr Pro Gln Asp
                740                 745                 750

Ser Gly Ile Ser Leu Gln Thr Val Leu Glu Leu Gly Pro Leu Val Pro
            755                 760                 765

Leu Phe Gly Val Cys Met Gly Leu Gln Cys Ile Gly Glu Ala Phe Gly
770                 775                 780

Gly Lys Ile Val Arg Ser Pro Phe Gly Val Met His Gly Lys Ser Ser
785                 790                 795                 800

Met Val His Tyr Asp Glu Lys Gly Glu Glu Gly Leu Phe Ser Gly Leu
                805                 810                 815

Ser Asn Pro Phe Ile Val Gly Arg Tyr His Ser Leu Val Ile Glu Lys
            820                 825                 830

Asp Thr Phe Pro Ser Asp Glu Leu Glu Val Thr Ala Trp Thr Glu Asp
835                 840                 845

Gly Leu Val Met Ala Ala Arg His Arg Lys Tyr Lys His Ile Gln Gly
850                 855                 860

Val Gln Phe His Pro Glu Ser Ile Ile Thr Thr Gly Lys Thr Ile
865                 870                 875                 880

Val Arg Asn Phe Ile Lys Ile Val Glu Lys Lys Glu Ser Glu Lys Leu
                885                 890                 895

Thr
```

<210> SEQ ID NO 46
<211> LENGTH: 252
<212> TYPE: DNA
<213> ORGANISM: Artificial Sequence
<220> FEATURE:
<223> OTHER INFORMATION: A truncated gene

<400> SEQUENCE: 46

```
atgcaaacac aaaaaccgac tctcgaactg gaattcctgg tgaaaacgg tatcgccacc      60 gtgcaagcgg gtgctggtgt agtccttgat tctgttccgc agtcggaagc cgacgaaacc     120
cgtaacaaag cccgcgctgt actgcgcgct attgccaccg cgcatcatgc acaggagact     180
ttctgatggc tgacattctg ctgctcgata atatcgactc ttttacgtac aacctggcag     240
atcagttgcg ca                                                        252
```

<210> SEQ ID NO 47
<211> LENGTH: 18
<212> TYPE: DNA
<213> ORGANISM: Artificial Sequence
<220> FEATURE:
<223> OTHER INFORMATION: A primer.

<400> SEQUENCE: 47

```
ttatgccgcc tgtcatcg                                                    18
```

<210> SEQ ID NO 48
<211> LENGTH: 19
<212> TYPE: DNA
<213> ORGANISM: Artificial Sequence
<220> FEATURE:
<223> OTHER INFORMATION: A primer.

<400> SEQUENCE: 48

```
ataggcttaa tggtaaccg                                                   19
```

<210> SEQ ID NO 49
<211> LENGTH: 18

```
<212> TYPE: DNA
<213> ORGANISM: Artificial Sequence
<220> FEATURE:
<223> OTHER INFORMATION: A primer.

<400> SEQUENCE: 49
ctgaacaaca gaagtacg                                                 18

<210> SEQ ID NO 50
<211> LENGTH: 18
<212> TYPE: DNA
<213> ORGANISM: Artificial Sequence
<220> FEATURE:
<223> OTHER INFORMATION: A primer.

<400> SEQUENCE: 50
taaccgtgtc atcgagcg                                                 18

<210> SEQ ID NO 51
<211> LENGTH: 31
<212> TYPE: DNA
<213> ORGANISM: Artificial Sequence
<220> FEATURE:
<223> OTHER INFORMATION: A primer

<400> SEQUENCE: 51 aaaagatct ccatggtaac gatcattcag g                                   31

<210> SEQ ID NO 52
<211> LENGTH: 35
<212> TYPE: DNA
<213> ORGANISM: Artificial Sequence
<220> FEATURE:
<223> OTHER INFORMATION: A primer

<400> SEQUENCE: 52
aaaagaattc ttatcacgcg gccttggtct tcgcc                              35

<210> SEQ ID NO 53
<211> LENGTH: 19
<212> TYPE: DNA
<213> ORGANISM: Artificial Sequence
<220> FEATURE:
<223> OTHER INFORMATION: A primer

<400> SEQUENCE: 53
caaaagctgg atccccacc                                                19

<210> SEQ ID NO 54
<211> LENGTH: 23
<212> TYPE: DNA
<213> ORGANISM: Artificial Sequence
<220> FEATURE:
<223> OTHER INFORMATION: A primer

<400> SEQUENCE: 54
cctatccgag atctctcaac tcc                                           23

<210> SEQ ID NO 55
<211> LENGTH: 31
<212> TYPE: DNA
<213> ORGANISM: Artificial Sequence
<220> FEATURE:
<223> OTHER INFORMATION: A primer

<400> SEQUENCE: 55
```

-continued

```
catcccatgg atggtaacga tcattcagga t                              31
```

<210> SEQ ID NO 56
<211> LENGTH: 31
<212> TYPE: DNA
<213> ORGANISM: Artificial Sequence
<220> FEATURE:
<223> OTHER INFORMATION: A primer

<400> SEQUENCE: 56

```
gatgtctaga gacactatag aatactcaag c                              31
```

<210> SEQ ID NO 57
<211> LENGTH: 719
<212> TYPE: PRT
<213> ORGANISM: Rhodopseudomonas palustris

<400> SEQUENCE: 57

```
Met Asn Arg Thr Val Phe Ser Leu Pro Ala Thr Ser Asp Tyr Lys Thr
  1               5                  10                  15

Ala Ala Gly Leu Ala Val Thr Arg Ser Ala Gln Pro Phe Ala Gly Gly
             20                  25                  30

Gln Ala Leu Asp Glu Leu Ile Asp Leu Leu Asp His Arg Arg Gly Val
         35                  40                  45

Met Leu Ser Ser Gly Thr Thr Val Pro Gly Arg Tyr Glu Ser Phe Asp
     50                  55                  60

Leu Gly Phe Ala Asp Pro Pro Leu Ala Leu Thr Thr Arg Ala Glu Lys
 65                  70                  75                  80

Phe Thr Ile Glu Ala Leu Asn Pro Arg Gly Arg Val Leu Ile Ala Phe
                 85                  90                  95

Leu Ser Asp Lys Leu Glu Glu Pro Cys Val Val Glu Gln Ala Cys
            100                 105                 110

Ala Thr Lys Ile Arg Gly His Ile Val Arg Gly Glu Ala Pro Val Asp
        115                 120                 125

Glu Glu Gln Arg Thr Arg Arg Ala Ser Ala Ile Ser Leu Val Arg Ala
    130                 135                 140

Val Ile Ala Ala Phe Ala Ser Pro Ala Asp Pro Met Leu Gly Leu Tyr
145                 150                 155                 160

Gly Ala Phe Ala Tyr Asp Leu Val Phe Gln Phe Glu Asp Leu Lys Gln
                165                 170                 175

Lys Arg Ala Arg Glu Ala Asp Gln Arg Asp Ile Val Leu Tyr Val Pro
            180                 185                 190

Asp Arg Leu Leu Ala Tyr Asp Arg Ala Thr Gly Arg Gly Val Asp Ile
        195                 200                 205

Ser Tyr Glu Phe Ala Trp Lys Gly Gln Ser Thr Ala Gly Leu Pro Asn
    210                 215                 220

Glu Thr Ala Glu Ser Val Tyr Thr Gln Thr Gly Arg Gln Gly Phe Ala
225                 230                 235                 240

Asp His Ala Pro Gly Asp Tyr Pro Lys Val Val Glu Lys Ala Arg Ala
                245                 250                 255

Ala Phe Ala Arg Gly Asp Leu Phe Glu Ala Val Pro Gly Gln Leu Phe
            260                 265                 270

Gly Glu Pro Cys Glu Arg Ser Pro Ala Glu Val Phe Lys Arg Leu Cys
        275                 280                 285

Arg Ile Asn Pro Ser Pro Tyr Gly Gly Leu Leu Asn Leu Gly Asp Gly
    290                 295                 300
```

```
Glu Phe Leu Val Ser Ala Ser Pro Glu Met Phe Val Arg Ser Asp Gly
305                 310                 315                 320

Arg Arg Ile Glu Thr Cys Pro Ile Ser Gly Thr Ile Ala Arg Gly Val
                325                 330                 335

Asp Ala Ile Ser Asp Ala Glu Gln Ile Gln Lys Leu Leu Asn Ser Glu
            340                 345                 350

Lys Asp Glu Phe Glu Leu Asn Met Cys Thr Asp Val Asp Arg Asn Asp
        355                 360                 365

Lys Ala Arg Val Cys Val Pro Gly Thr Ile Lys Val Leu Ala Arg Arg
    370                 375                 380

Gln Ile Glu Thr Tyr Ser Lys Leu Phe His Thr Val Asp His Val Glu
385                 390                 395                 400

Gly Met Leu Arg Pro Gly Phe Asp Ala Leu Asp Ala Phe Leu Thr His
                405                 410                 415

Ala Trp Ala Val Thr Val Thr Gly Ala Pro Lys Leu Trp Ala Met Gln
            420                 425                 430

Phe Val Glu Asp His Glu Arg Ser Pro Arg Arg Trp Tyr Ala Gly Ala
        435                 440                 445

Phe Gly Val Val Gly Phe Asp Gly Ser Ile Asn Thr Gly Leu Thr Ile
    450                 455                 460

Arg Thr Ile Arg Met Lys Asp Gly Leu Ala Glu Val Arg Val Gly Ala
465                 470                 475                 480

Thr Cys Leu Phe Asp Ser Asn Pro Val Ala Glu Asp Lys Glu Cys Gln
                485                 490                 495

Val Lys Ala Ala Ala Leu Phe Gln Ala Leu Arg Gly Asp Pro Ala Lys
            500                 505                 510

Pro Leu Ser Ala Val Ala Pro Asp Ala Thr Gly Ser Gly Lys Lys Val
        515                 520                 525

Leu Leu Val Asp His Asp Asp Ser Phe Val His Met Leu Ala Asp Tyr
    530                 535                 540

Phe Arg Gln Val Gly Ala Gln Val Thr Val Val Arg Tyr Val His Gly
545                 550                 555                 560

Leu Lys Met Leu Ala Glu Asn Ser Tyr Asp Leu Leu Val Leu Ser Pro
                565                 570                 575

Gly Pro Gly Arg Pro Glu Asp Phe Lys Ile Lys Asp Thr Ile Asp Ala
            580                 585                 590

Ala Leu Ala Lys Lys Leu Pro Ile Phe Gly Val Cys Leu Gly Val Gln
        595                 600                 605

Ala Met Gly Glu Tyr Phe Gly Gly Thr Leu Gly Gln Leu Ala Gln Pro
    610                 615                 620

Ala His Gly Arg Pro Ser Arg Ile Gln Val Arg Gly Gly Ala Leu Met
625                 630                 635                 640

Arg Gly Leu Pro Asn Glu Val Thr Ile Gly Arg Tyr His Ser Leu Tyr
                645                 650                 655

Val Asp Met Arg Asp Met Pro Lys Glu Leu Thr Val Thr Ala Ser Thr
            660                 665                 670

Asp Asp Gly Ile Ala Met Ala Ile Glu His Lys Thr Leu Pro Val Gly
        675                 680                 685

Gly Val Gln Phe His Pro Glu Ser Leu Met Ser Leu Gly Gly Glu Val
    690                 695                 700

Gly Leu Arg Ile Val Glu Asn Ala Phe Arg Leu Gly Gln Ala Ala
705                 710                 715
```

-continued

```
<210> SEQ ID NO 58
<211> LENGTH: 729
<212> TYPE: PRT
<213> ORGANISM: Artificial Sequence
<220> FEATURE:
<223> OTHER INFORMATION: An A. tumefaciens mutant.

<400> SEQUENCE: 58

Met Val Thr Ile Ile Gln Asp Asp Gly Ala Glu Thr Tyr Glu Thr Lys
  1               5                  10                  15

Gly Gly Ile Gln Val Ser Arg Lys Arg Arg Pro Thr Asp Tyr Ala Asn
             20                  25                  30

Ala Ile Asp Asn Tyr Ile Glu Lys Leu Asp Ser His Arg Gly Ala Phe
         35                  40                  45

Phe Ser Ser Asn Tyr Glu Tyr Pro Gly Arg Tyr Thr Arg Trp Asp Thr
     50                  55                  60

Ala Ile Val Asp Pro Pro Leu Gly Ile Ser Cys Phe Gly Arg Lys Met
 65                  70                  75                  80

Trp Ile Glu Ala Tyr Asn Gly Arg Gly Glu Val Leu Leu Asp Phe Ile
                 85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
    130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
    210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Phe Phe Ile Asn Leu Gly Asp
    290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
```

-continued

```
            370                 375                 380
Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
                420                 425                 430

Arg Phe Ile Glu Gly His Glu Lys Ser Pro Arg Ala Trp Tyr Gly Gly
                435                 440                 445

Ala Ile Gly Met Val Gly Phe Asn Gly Asp Met Asn Thr Gly Leu Thr
450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
                500                 505                 510

Thr Asn Ser Ala Ala Thr Lys Arg Asp Ala Ala Lys Val Gly Thr Gly
                515                 520                 525

Val Lys Ile Leu Leu Val Asp His Glu Asp Ser Phe Val His Thr Leu
530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
                580                 585                 590

Ile Lys Ala Ala Arg Ala Arg Asp Leu Pro Ile Phe Gly Val Cys Leu
                595                 600                 605

Gly Leu Gln Ala Leu Ala Glu Ala Tyr Gly Gly Glu Leu Arg Gln Leu
                610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
                660                 665                 670

Thr Ala Glu Ser Glu Asp Gly Thr Ile Met Gly Ile Glu His Ala Lys
                675                 680                 685

Glu Pro Val Ala Ala Val Gln Phe His Pro Glu Ser Ile Met Thr Leu
690                 695                 700

Gly Gln Asp Ala Gly Met Arg Met Ile Glu Asn Val Val His Leu
705                 710                 715                 720

Thr Arg Lys Ala Lys Thr Lys Ala Ala
                725
```

<210> SEQ ID NO 59
<211> LENGTH: 729
<212> TYPE: PRT
<213> ORGANISM: Artificial Sequence
<220> FEATURE:
<223> OTHER INFORMATION: An A. tumefaciens mutant.

<400> SEQUENCE: 59

Met Val Thr Ile Ile Gln Asp Asp Gly Ala Glu Thr Tyr Glu Thr Lys

-continued

```
  1               5                  10                 15
Gly Gly Ile Gln Val Ser Arg Lys Arg Pro Thr Asp Tyr Ala Asn
             20                 25                 30
Ala Ile Asp Asn Tyr Ile Glu Lys Leu Asp Ser His Arg Gly Ala Tyr
             35                 40                 45
Phe Ser Ser Asn Tyr Glu Tyr Pro Gly Arg Tyr Thr Arg Trp Asp Thr
 50                 55                 60
Ala Ile Val Asp Pro Pro Leu Gly Ile Ser Cys Phe Gly Arg Lys Met
 65                 70                 75                 80
Trp Ile Glu Ala Tyr Asn Gly Arg Gly Glu Val Leu Leu Asp Phe Ile
             85                 90                 95
Thr Glu Lys Leu Lys Ala Thr Pro Asp Leu Thr Leu Gly Ala Ser Ser
             100                105                110
Thr Arg Arg Leu Asp Leu Thr Val Asn Glu Pro Asp Arg Val Phe Thr
             115                120                125
Glu Glu Glu Arg Ser Lys Ile Pro Thr Val Phe Thr Ala Leu Arg Ala
             130                135                140
Ile Val Asp Leu Phe Tyr Ser Ser Ala Asp Ser Ala Ile Gly Leu Phe
145                150                155                160
Gly Ala Phe Gly Tyr Asp Leu Ala Phe Gln Phe Asp Ala Ile Lys Leu
             165                170                175
Ser Leu Ala Arg Pro Glu Asp Gln Arg Asp Met Val Leu Phe Leu Pro
             180                185                190
Asp Glu Ile Leu Val Val Asp His Tyr Ser Ala Lys Ala Trp Ile Asp
             195                200                205
Arg Tyr Asp Phe Glu Lys Asp Gly Met Thr Thr Asp Gly Lys Ser Ser
210                215                220
Asp Ile Thr Pro Asp Pro Phe Lys Thr Thr Asp Thr Ile Pro Pro Lys
225                230                235                240
Gly Asp His Arg Pro Gly Glu Tyr Ser Glu Leu Val Val Lys Ala Lys
             245                250                255
Glu Ser Phe Arg Arg Gly Asp Leu Phe Glu Val Val Pro Gly Gln Lys
             260                265                270
Phe Met Glu Arg Cys Glu Ser Asn Pro Ser Ala Ile Ser Arg Arg Leu
             275                280                285
Lys Ala Ile Asn Pro Ser Pro Tyr Ser Phe Phe Ile Asn Leu Gly Asp
             290                295                300
Gln Glu Tyr Leu Val Gly Ala Ser Pro Glu Met Phe Val Arg Val Ser
305                310                315                320
Gly Arg Arg Ile Glu Thr Cys Pro Ile Ser Gly Thr Ile Lys Arg Gly
             325                330                335
Asp Asp Pro Ile Ala Asp Ser Glu Gln Ile Leu Lys Leu Leu Asn Ser
             340                345                350
Lys Lys Asp Glu Ser Glu Leu Thr Met Cys Ser Asp Val Asp Arg Asn
             355                360                365
Asp Lys Ser Arg Val Cys Glu Pro Gly Ser Val Lys Val Ile Gly Arg
             370                375                380
Arg Gln Ile Glu Met Tyr Ser Arg Leu Ile His Thr Val Asp His Ile
385                390                395                400
Glu Gly Arg Leu Arg Asp Asp Met Asp Ala Phe Asp Gly Phe Leu Ser
             405                410                415
His Ala Trp Ala Val Thr Val Thr Gly Ala Pro Lys Leu Trp Ala Met
             420                425                430
```

```
Arg Phe Ile Glu Gly His Glu Lys Ser Pro Arg Ala Trp Tyr Gly Gly
            435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
                500                 505                 510

Thr Asn Ser Ala Ala Thr Lys Arg Asp Ala Ala Lys Val Gly Thr Gly
                515                 520                 525

Val Lys Ile Leu Leu Val Asp His Glu Asp Ser Phe Val His Thr Leu
            530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
                580                 585                 590

Ile Lys Ala Ala Arg Ala Arg Asp Leu Pro Ile Phe Gly Val Cys Leu
            595                 600                 605

Gly Leu Gln Ala Leu Ala Glu Ala Tyr Gly Gly Glu Leu Arg Gln Leu
            610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
            675                 680                 685

Glu Pro Val Ala Ala Val Gln Phe His Pro Glu Ser Ile Met Thr Leu
            690                 695                 700

Gly Gln Asp Ala Gly Met Arg Met Ile Glu Asn Val Val Val His Leu
705                 710                 715                 720

Thr Arg Lys Ala Lys Thr Lys Ala Ala
                725

<210> SEQ ID NO 60
<211> LENGTH: 729
<212> TYPE: PRT
<213> ORGANISM: Artificial Sequence
<220> FEATURE:
<223> OTHER INFORMATION: An A. tumefaciens mutant.

<400> SEQUENCE: 60

Met Val Thr Ile Ile Gln Asp Asp Gly Ala Glu Thr Tyr Glu Thr Lys
  1               5                  10                  15

Gly Gly Ile Gln Val Ser Arg Lys Arg Pro Thr Asp Tyr Ala Asn
                20                  25                  30

Ala Ile Asp Asn Tyr Ile Glu Lys Leu Asp Ser His Arg Gly Ala Val
            35                  40                  45

Phe Ser Phe Asn Tyr Glu Tyr Pro Gly Arg Tyr Thr Arg Trp Asp Thr
    50                  55                  60
```

-continued

```
Ala Ile Val Asp Pro Pro Leu Gly Ile Ser Cys Phe Gly Arg Lys Met
 65                  70                  75                  80

Trp Ile Glu Ala Tyr Asn Gly Arg Gly Glu Val Leu Leu Asp Phe Ile
                 85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Phe Phe Ile Asn Leu Gly Asp
290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
450                 455                 460

Leu Arg Thr Ile Arg Ile Lys Asp Gly Ile Ala Glu Val Arg Ala Gly
465                 470                 475                 480
```

-continued

```
Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Ala Lys Val Gly Thr Gly
            515                 520                 525

Val Lys Ile Leu Leu Val Asp His Glu Asp Ser Phe Val His Thr Leu
530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
                580                 585                 590

Ile Lys Ala Ala Arg Ala Arg Asp Leu Pro Ile Phe Gly Val Cys Leu
            595                 600                 605

Gly Leu Gln Ala Leu Ala Glu Ala Tyr Gly Gly Glu Leu Arg Gln Leu
            610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
                660                 665                 670

Thr Ala Glu Ser Glu Asp Gly Thr Ile Met Gly Ile Glu His Ala Lys
            675                 680                 685

Glu Pro Val Ala Val Gln Phe His Pro Gly Ser Ile Met Thr Leu
            690                 695                 700

Gly Gln Asp Ala Gly Met Arg Met Ile Glu Asn Val Val Val His Leu
705                 710                 715                 720

Thr Arg Lys Ala Lys Thr Lys Ala Ala
                725
```

<210> SEQ ID NO 61
<211> LENGTH: 729
<212> TYPE: PRT
<213> ORGANISM: Artificial Sequence
<220> FEATURE:
<223> OTHER INFORMATION: An A. tumefaciens mutant.

<400> SEQUENCE: 61

```
Met Val Thr Ile Ile Gln Asp Asp Gly Ala Glu Thr Tyr Glu Thr Lys
1               5                   10                  15

Gly Gly Ile Gln Val Ser Arg Lys Arg Arg Pro Thr Asp Tyr Ala Asn
            20                  25                  30

Ala Ile Asp Asn Tyr Ile Glu Lys Leu Asp Ser His Arg Gly Ala Val
            35                  40                  45

Phe Ser Cys Asn Tyr Glu Tyr Pro Gly Arg Tyr Thr Arg Trp Asp Thr
        50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110
```

-continued

```
Thr Arg Arg Leu Asp Leu Thr Val Asn Glu Pro Asp Arg Val Phe Thr
        115                 120                 125
Glu Glu Glu Arg Ser Lys Ile Pro Thr Val Phe Thr Ala Leu Arg Ala
    130                 135                 140
Ile Val Asp Leu Phe Tyr Ser Ala Asp Ser Ala Ile Gly Leu Phe
145                 150                 155                 160
Gly Ala Phe Gly Tyr Asp Leu Ala Phe Gln Phe Asp Ala Ile Lys Leu
                165                 170                 175
Ser Leu Ala Arg Pro Glu Asp Gln Arg Asp Met Val Leu Phe Leu Pro
            180                 185                 190
Asp Glu Ile Leu Val Val Asp His Tyr Ser Ala Lys Ala Trp Ile Asp
        195                 200                 205
Arg Tyr Asp Phe Glu Lys Asp Gly Met Thr Thr Asp Gly Lys Ser Ser
    210                 215                 220
Asp Ile Thr Pro Asp Pro Phe Lys Thr Thr Asp Thr Ile Pro Pro Lys
225                 230                 235                 240
Gly Asp His Arg Pro Gly Glu Tyr Ser Glu Leu Val Val Lys Ala Lys
                245                 250                 255
Glu Ser Phe Arg Arg Gly Asp Leu Phe Glu Val Val Pro Gly Gln Lys
            260                 265                 270
Phe Met Glu Arg Cys Glu Ser Asn Pro Ser Ala Ile Ser Arg Arg Leu
        275                 280                 285
Lys Ala Ile Asn Pro Ser Pro Tyr Ser Phe Phe Ile Asn Leu Gly Asp
    290                 295                 300
Gln Glu Tyr Leu Val Gly Ala Ser Pro Glu Met Phe Val Arg Val Ser
305                 310                 315                 320
Gly Arg Arg Ile Glu Thr Cys Pro Ile Ser Gly Thr Ile Lys Arg Gly
                325                 330                 335
Asp Asp Pro Ile Ala Asp Ser Glu Gln Ile Leu Lys Leu Leu Asn Ser
            340                 345                 350
Lys Lys Asp Glu Ser Glu Leu Thr Met Cys Ser Asp Val Asp Arg Asn
        355                 360                 365
Asp Lys Ser Arg Val Cys Glu Pro Gly Ser Val Lys Val Ile Gly Arg
    370                 375                 380
Arg Gln Ile Glu Met Tyr Ser Arg Leu Ile His Thr Val Asp His Ile
385                 390                 395                 400
Glu Gly Arg Leu Arg Asp Asp Met Asp Ala Phe Asp Gly Phe Leu Ser
                405                 410                 415
His Ala Trp Ala Val Thr Val Thr Gly Ala Pro Lys Leu Trp Ala Met
            420                 425                 430
Arg Phe Ile Glu Gly His Glu Lys Ser Pro Arg Ala Trp Tyr Gly Gly
        435                 440                 445
Ala Ile Gly Met Val Gly Phe Asn Gly Asp Met Asn Thr Gly Leu Thr
    450                 455                 460
Leu Arg Thr Ile Arg Ile Lys Asp Gly Ile Ala Glu Val Arg Ala Gly
465                 470                 475                 480
Ala Thr Leu Leu Asn Asp Ser Asn Pro Gln Glu Glu Ala Glu Thr
                485                 490                 495
Glu Leu Lys Ala Ser Ala Met Ile Ser Ala Ile Arg Asp Ala Lys Gly
            500                 505                 510
Thr Asn Ser Ala Ala Thr Lys Arg Asp Ala Ala Lys Val Gly Thr Gly
        515                 520                 525
Val Lys Ile Leu Leu Val Asp His Glu Asp Ser Phe Val His Thr Leu
```

```
                530             535             540
Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
                580                 585                 590

Ile Lys Ala Ala Arg Ala Arg Asp Leu Pro Ile Phe Gly Val Cys Leu
                595                 600                 605

Gly Leu Gln Ala Leu Ala Glu Ala Tyr Gly Gly Glu Leu Arg Gln Leu
                610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
                660                 665                 670

Thr Ala Glu Ser Glu Asp Gly Thr Ile Met Gly Ile Glu His Ala Lys
                675                 680                 685

Glu Pro Val Ala Ala Val Gln Phe His Pro Glu Ser Ile Met Thr Leu
                690                 695                 700

Gly Gln Asp Ala Gly Met Arg Met Ile Glu Asn Val Val Val His Leu
705                 710                 715                 720

Thr Arg Lys Ala Lys Thr Lys Ala Ala
                725

<210> SEQ ID NO 62
<211> LENGTH: 729
<212> TYPE: PRT
<213> ORGANISM: Artificial Sequence
<220> FEATURE:
<223> OTHER INFORMATION: An A. tumefaciens mutant.

<400> SEQUENCE: 62

Met Val Thr Ile Ile Gln Asp Asp Gly Ala Glu Thr Tyr Glu Thr Lys
  1               5                  10                  15

Gly Gly Ile Gln Val Ser Arg Lys Arg Pro Thr Asp Tyr Ala Asn
                 20                  25                  30

Ala Ile Asp Asn Tyr Ile Glu Lys Leu Asp Ser His Arg Gly Ala Val
                 35                  40                  45

Phe Ser Ser Phe Tyr Glu Tyr Pro Gly Arg Tyr Thr Arg Trp Asp Thr
 50                  55                  60

Ala Ile Val Asp Pro Pro Leu Gly Ile Ser Cys Phe Gly Arg Lys Met
 65                  70                  75                  80

Trp Ile Glu Ala Tyr Asn Gly Arg Gly Glu Val Leu Leu Asp Phe Ile
                 85                  90                  95

Thr Glu Lys Leu Lys Ala Thr Pro Asp Leu Thr Leu Gly Ala Ser Ser
                100                 105                 110

Thr Arg Arg Leu Asp Leu Thr Val Asn Glu Pro Asp Arg Val Phe Thr
                115                 120                 125

Glu Glu Glu Arg Ser Lys Ile Pro Thr Val Phe Thr Ala Leu Arg Ala
                130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
```

-continued

```
                165                 170                 175
Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
            195                 200                 205

Arg Tyr Asp Phe Glu Lys Asp Gly Met Thr Thr Asp Gly Lys Ser Ser
            210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
            245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
            275                 280                 285

Lys Ala Ile Asn Pro Ser Pro Tyr Ser Phe Phe Ile Asn Leu Gly Asp
            290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
            325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
            355                 360                 365

Asp Lys Ser Arg Val Cys Glu Pro Gly Ser Val Lys Val Ile Gly Arg
            370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
            405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
            435                 440                 445

Ala Ile Gly Met Val Gly Phe Asn Gly Asp Met Asn Thr Gly Leu Thr
            450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
            485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Lys Val Gly Thr Gly
            515                 520                 525

Val Lys Ile Leu Leu Val Asp His Glu Asp Ser Phe Val His Thr Leu
530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
            565                 570                 575

Leu Ser Pro Gly Pro Gly Ser Pro Thr Asp Phe Asp Cys Lys Ala Thr
            580                 585                 590
```

Ile Lys Ala Ala Arg Ala Arg Asp Leu Pro Ile Phe Gly Val Cys Leu
            595                 600                 605

Gly Leu Gln Ala Leu Ala Glu Ala Tyr Gly Gly Glu Leu Arg Gln Leu
        610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Ala Val Gln Phe His Pro Glu Ser Ile Met Thr Leu
690                 695                 700

Gly Gln Asp Ala Gly Met Arg Met Ile Glu Asn Val Val His Leu
705                 710                 715                 720

Thr Arg Lys Ala Lys Thr Lys Ala Ala
            725

<210> SEQ ID NO 63
<211> LENGTH: 729
<212> TYPE: PRT
<213> ORGANISM: Artificial Sequence
<220> FEATURE:
<223> OTHER INFORMATION: An A. tumefaciens mutant.

<400> SEQUENCE: 63

Met Val Thr Ile Ile Gln Asp Asp Gly Ala Glu Thr Tyr Glu Thr Lys
1               5                   10                  15

Gly Gly Ile Gln Val Ser Arg Lys Arg Arg Pro Thr Asp Tyr Ala Asn
            20                  25                  30

Ala Ile Asp Asn Tyr Ile Glu Lys Leu Asp Ser His Arg Gly Ala Val
        35                  40                  45

Phe Ser Ser Asn Tyr Glu Tyr Pro Gly Arg Tyr Thr Arg Trp Asp Thr
    50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
    130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
    210                 215                 220

-continued

```
Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
                260                 265                 270

Phe Met Glu Arg Cys Glu Ser Asn Pro Ser Ala Ile Ser Arg Arg Leu
            275                 280                 285

Lys Ala Ile Asn Ala Ser Pro Tyr Ser Phe Phe Ile Asn Leu Gly Asp
290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
                340                 345                 350

Lys Lys Asp Glu Ser Glu Leu Thr Met Cys Ser Asp Val Asp Arg Asn
            355                 360                 365

Asp Lys Ser Arg Val Cys Glu Pro Gly Ser Val Lys Val Ile Gly Arg
370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
            435                 440                 445

Ala Ile Gly Met Val Gly Phe Asn Gly Asp Met Asn Thr Gly Leu Thr
450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Ala Lys Val Gly Thr Gly
            515                 520                 525

Val Lys Ile Leu Leu Val Asp His Glu Asp Ser Phe Val His Thr Leu
530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
            595                 600                 605

Gly Leu Gln Ala Leu Ala Glu Ala Tyr Gly Gly Glu Leu Arg Gln Leu
            610                 615                 620

Ala Val Pro Met His Gly Lys Pro Ser Arg Ile Arg Val Leu Glu Pro
625                 630                 635                 640
```

-continued

```
Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Ala Val Gln Phe His Pro Glu Ser Ile Met Thr Leu
    690                 695                 700

Gly Gln Asp Ala Gly Met Arg Met Ile Glu Asn Val Val His Leu
705                 710                 715                 720

Thr Arg Lys Ala Lys Thr Lys Ala Ala
                725
```

<210> SEQ ID NO 64
<211> LENGTH: 729
<212> TYPE: PRT
<213> ORGANISM: Artificial Sequence
<220> FEATURE:
<223> OTHER INFORMATION: An A. tumefaciens mutant.

<400> SEQUENCE: 64

```
Met Val Thr Ile Ile Gln Asp Asp Gly Ala Glu Thr Tyr Glu Thr Lys
 1               5                  10                  15

Gly Gly Ile Gln Val Ser Arg Lys Arg Pro Thr Asp Tyr Ala Asn
            20                  25                  30

Ala Ile Asp Asn Tyr Ile Glu Lys Leu Asp Ser His Arg Gly Ala Val
        35                  40                  45

Phe Ser Ser Asn Tyr Glu Tyr Pro Gly Arg Tyr Thr Arg Trp Asp Thr
    50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
    130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
    210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270
```

```
Phe Met Glu Arg Cys Glu Ser Asn Pro Ser Ala Ile Ser Arg Arg Leu
        275                 280                 285

Lys Ala Ile Asn Gly Ser Pro Tyr Ser Phe Ile Asn Leu Gly Asp
        290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
        370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
            450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Ala Lys Val Gly Thr Gly
        515                 520                 525

Val Lys Ile Leu Leu Val Asp His Glu Asp Ser Phe Val His Thr Leu
        530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
        595                 600                 605

Gly Leu Gln Ala Leu Ala Glu Ala Tyr Gly Gly Glu Leu Arg Gln Leu
        610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Ala Val Gln Phe His Pro Glu Ser Ile Met Thr Leu
```

```
                          690             695             700
Gly Gln Asp Ala Gly Met Arg Met Ile Glu Asn Val Val His Leu
705                     710             715                 720

Thr Arg Lys Ala Lys Thr Lys Ala Ala
                    725

<210> SEQ ID NO 65
<211> LENGTH: 729
<212> TYPE: PRT
<213> ORGANISM: Artificial Sequence
<220> FEATURE:
<223> OTHER INFORMATION: An A. tumefaciens mutant.

<400> SEQUENCE: 65

Met Val Thr Ile Ile Gln Asp Asp Gly Ala Glu Thr Tyr Glu Thr Lys
 1               5                  10                  15

Gly Gly Ile Gln Val Ser Arg Lys Arg Arg Pro Thr Asp Tyr Ala Asn
            20                  25                  30

Ala Ile Asp Asn Tyr Ile Glu Lys Leu Asp Ser His Arg Gly Ala Val
        35                  40                  45

Phe Ser Ser Asn Tyr Glu Tyr Pro Gly Arg Tyr Thr Arg Trp Asp Thr
 50                  55                  60

Ala Ile Val Asp Pro Pro Leu Gly Ile Ser Cys Phe Gly Arg Lys Met
65                   70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205

Arg Tyr Asp Phe Glu Lys Asp Gly Met Thr Thr Asp Gly Lys Ser Ser
210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Trp Phe Ile Asn Leu Gly Asp
290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
```

-continued

```
                325                 330                 335
Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
    370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
            405                 410                 415

His Ala Trp Ala Val Thr Val Thr Gly Ala Pro Lys Leu Trp Ala Met
        420                 425                 430

Arg Phe Ile Glu Gly His Glu Lys Ser Pro Arg Ala Trp Tyr Gly Gly
    435                 440                 445

Ala Ile Gly Met Val Gly Phe Asn Gly Asp Met Asn Thr Gly Leu Thr
    450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
            485                 490                 495

Glu Leu Lys Ala Ser Ala Met Ile Ser Ala Ile Arg Asp Ala Lys Gly
        500                 505                 510

Thr Asn Ser Ala Ala Thr Lys Arg Asp Ala Ala Lys Val Gly Thr Gly
    515                 520                 525

Val Lys Ile Leu Leu Val Asp His Glu Asp Ser Phe Val His Thr Leu
530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
            565                 570                 575

Leu Ser Pro Gly Pro Gly Ser Pro Thr Asp Phe Asp Cys Lys Ala Thr
        580                 585                 590

Ile Lys Ala Ala Arg Ala Arg Asp Leu Pro Ile Phe Gly Val Cys Leu
    595                 600                 605

Gly Leu Gln Ala Leu Ala Glu Ala Tyr Gly Gly Glu Leu Arg Gln Leu
    610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
            645                 650                 655

His Ser Ile Phe Ala Asp Pro Ala Thr Leu Pro Arg Asp Phe Ile Ile
        660                 665                 670

Thr Ala Glu Ser Glu Asp Gly Thr Ile Met Gly Ile Glu His Ala Lys
    675                 680                 685

Glu Pro Val Ala Ala Val Gln Phe His Pro Glu Ser Ile Met Thr Leu
    690                 695                 700

Gly Gln Asp Ala Gly Met Arg Met Ile Glu Asn Val Val His Leu
705                 710                 715                 720

Thr Arg Lys Ala Lys Thr Lys Ala Ala
            725
```

<210> SEQ ID NO 66

```
<211> LENGTH: 604
<212> TYPE: PRT
<213> ORGANISM: Artificial Sequence
<220> FEATURE:
<223> OTHER INFORMATION: A Zea mays mutant.

<400> SEQUENCE: 66
```

| | | | | | | | | | | | | | | | |
|---|---|---|---|---|---|---|---|---|---|---|---|---|---|---|---|
|Met|Glu|Ser|Leu|Ala|Ala|Thr|Ser|Val|Phe|Ala|Pro|Ser|Arg|Val|Ala|
|1| | | |5| | | | |10| | | | |15| |
|Val|Pro|Ala|Ala|Arg|Ala|Leu|Val|Arg|Ala|Gly|Thr|Val|Val|Pro|Thr|
| | | |20| | | | |25| | | | |30| | |
|Arg|Arg|Thr|Ser|Ser|Arg|Ser|Gly|Thr|Ser|Gly|Val|Lys|Cys|Ser|Ala|
| | |35| | | | |40| | | | |45| | | |
|Ala|Val|Thr|Pro|Gln|Ala|Ser|Pro|Val|Ile|Ser|Arg|Ser|Ala|Ala|Ala|
|50| | | | |55| | | | |60| | | | | |
|Ala|Lys|Ala|Ala|Glu|Glu|Asp|Lys|Arg|Arg|Phe|Glu|Ala|Ala|Ala| |
|65| | | | |70| | | | |75| | | | |80|
|Arg|Gly|Ser|Gly|Lys|Gly|Asn|Leu|Val|Pro|Met|Trp|Glu|Cys|Ile|Val|
| | | | |85| | | | |90| | | | |95| |
|Ser|Asp|His|Leu|Thr|Pro|Val|Leu|Ala|Tyr|Arg|Cys|Leu|Val|Pro|Glu|
| | | |100| | | | |105| | | | |110| | |
|Asp|Asn|Val|Asp|Ala|Pro|Ser|Phe|Leu|Phe|Glu|Ser|Val|Glu|Gln|Gly|
| | |115| | | | |120| | | | |125| | | |
|Pro|Gln|Gly|Thr|Thr|Asn|Val|Gly|Arg|Tyr|Ser|Met|Val|Gly|Ala|His|
| |130| | | | |135| | | | |140| | | | |
|Pro|Val|Met|Glu|Ile|Val|Ala|Lys|Asp|His|Lys|Val|Thr|Ile|Met|Asp|
|145| | | | |150| | | | |155| | | | |160|
|His|Glu|Lys|Ser|Gln|Val|Thr|Glu|Gln|Val|Val|Asp|Asp|Pro|Met|Gln|
| | | | |165| | | | |170| | | | |175| |
|Ile|Pro|Arg|Thr|Met|Met|Glu|Gly|Trp|His|Pro|Gln|Ile|Asp|Glu| |
| | | |180| | | | |185| | | | |190| | |
|Leu|Pro|Glu|Ser|Phe|Ser|Gly|Gly|Trp|Val|Gly|Phe|Phe|Ser|Tyr|Asp|
| | |195| | | | |200| | | | |205| | | |
|Thr|Val|Arg|Tyr|Val|Glu|Lys|Lys|Leu|Pro|Phe|Ser|Ser|Ala|Pro| |
| |210| | | | |215| | | | |220| | | | |
|Gln|Asp|Asp|Arg|Asn|Leu|Pro|Asp|Val|His|Leu|Gly|Leu|Tyr|Asp|Asp|
|225| | | | |230| | | | |235| | | | |240|
|Val|Leu|Val|Phe|Asp|Asn|Val|Glu|Lys|Lys|Val|Tyr|Val|Ile|His|Trp|
| | | | |245| | | | |250| | | | |255| |
|Val|Asn|Val|Asp|Arg|His|Ala|Ser|Val|Glu|Glu|Ala|Tyr|Gln|Asp|Gly|
| | | |260| | | | |265| | | | |270| | |
|Arg|Ser|Arg|Leu|Asn|Met|Leu|Leu|Ser|Lys|Val|His|Asn|Ser|Asn|Val|
| | |275| | | | |280| | | | |285| | | |
|Pro|Thr|Leu|Ser|Pro|Gly|Phe|Val|Lys|Leu|His|Thr|Arg|Lys|Phe|Gly|
| |290| | | | |295| | | | |300| | | | |
|Thr|Pro|Leu|Asn|Lys|Ser|Thr|Met|Thr|Ser|Asp|Glu|Tyr|Lys|Asn|Ala|
|305| | | | |310| | | | |315| | | | |320|
|Val|Leu|Gln|Ala|Lys|Glu|His|Ile|Met|Ala|Gly|Asp|Ile|Phe|Gln|Ile|
| | | | |325| | | | |330| | | | |335| |
|Val|Leu|Ser|Gln|Arg|Phe|Glu|Arg|Arg|Thr|Tyr|Ala|Asn|Pro|Phe|Glu|
| | | |340| | | | |345| | | | |350| | |
|Val|Tyr|Arg|Ala|Leu|Arg|Ile|Val|Asn|Pro|Ser|Pro|Tyr|Lys|Ala|Tyr|
| | |355| | | | |360| | | | |365| | | |
|Val|Gln|Ala|Arg|Gly|Cys|Val|Leu|Val|Ala|Ser|Ser|Pro|Glu|Ile|Leu|
| |370| | | | |375| | | | |380| | | | |

-continued

```
Thr Arg Val Ser Lys Gly Lys Ile Ile Asn Arg Pro Leu Ala Gly Thr
385                 390                 395                 400

Val Arg Arg Gly Lys Thr Glu Lys Glu Asp Gln Met Gln Glu Gln Gln
            405                 410                 415

Leu Leu Ser Asp Glu Lys Gln Cys Ala Glu His Ile Met Leu Val Asp
        420                 425                 430

Leu Gly Arg Asn Asp Val Gly Val Ser Lys Pro Gly Ser Val Lys
    435                 440                 445

Val Glu Lys Leu Met Asn Ile Glu Arg Tyr Ser His Val Met His Ile
450                 455                 460

Ser Ser Thr Val Ser Gly Gln Leu Asp Asp His Leu Gln Ser Trp Asp
465                 470                 475                 480

Ala Leu Arg Ala Ala Leu Pro Val Gly Thr Val Ser Gly Ala Pro Lys
            485                 490                 495

Val Lys Ala Met Glu Leu Ile Asp Lys Leu Glu Val Thr Arg Arg Gly
        500                 505                 510

Pro Tyr Ser Gly Gly Leu Gly Gly Ile Ser Phe Asp Gly Asp Met Gln
    515                 520                 525

Ile Ala Leu Ser Leu Arg Thr Ile Val Phe Ser Thr Ala Pro Ser His
530                 535                 540

Asn Thr Met Tyr Ser Tyr Lys Asp Ala Asp Arg Arg Glu Trp Val
545                 550                 555                 560

Ala His Leu Gln Ala Gly Ala Gly Ile Val Ala Asp Ser Ser Pro Asp
            565                 570                 575

Asp Glu Gln Arg Glu Cys Glu Asn Lys Ala Ala Ala Leu Ala Arg Ala
        580                 585                 590

Ile Asp Leu Ala Glu Ser Ala Phe Val Asp Lys Glu
    595                 600
```

<210> SEQ ID NO 67
<211> LENGTH: 1815
<212> TYPE: DNA
<213> ORGANISM: Artificial Sequence
<220> FEATURE:
<223> OTHER INFORMATION: A Zea mays mutant.

<400> SEQUENCE: 67

```
atggaatccc tagccgccac ctccgtgttc gcgccctccc gcgtcgccgt cccggcggcg      60
cgggccctgg ttagggcggg gacggtggta ccaaccaggc ggacgagcag ccggagcgga     120
accagcgggg tgaaatgctc tgctgccgtg acgccgcagg cgagcccagt gattagcagg     180
agcgctgcgg cggcgaaggc ggcggaggag gacaagaggg ggttcttcga ggcggcggcg     240
cggggagcg ggaagggga cctggtgccc atgtgggagt gcatcgtgtc ggaccatctc       300
accccgtgc tcgcctaccg ctgcctcgtc cccgaggaca cgtcgacgc cccagcttc        360
ctcttcgagt ccgtcgagca ggggccccag ggcaccacca acgtcggccg ctatagcatg     420
gtgggagccc acccagtgat ggagattgtg gccaaagacc acaaggttac gatcatggac     480
cacgagaaga gccaagtgac agagcaggta gtggacgacc cgatgcagat cccgaggacc     540
atgatggagg gatggcaccc acagcagatc gacgagctcc ctgaatcctt ctccggtgga     600
tgggttgggt tcttttccta tgatacggtt aggtatgttg agaagaagaa gctaccgttc     660
tccagtgctc ctcaggacga taggaaccct tcctgatgtgc acttgggact ctatgatgat     720
gttctagtct tcgataatgt tgagaagaaa gtatatgtta tccattgggt caatgtggac     780
```

-continued

```
cggcatgcat ctgttgagga agcataccaa gatggcaggt cccgactaaa catgttgcta      840
tctaaagtgc acaattccaa tgtccccaca ctctctcctg gatttgtgaa gctgcacaca      900
cgcaagtttg gtacaccttt gaacaagtcg accatgacaa gtgatgagta taagaatgct      960
gttctgcagg ctaaggaaca tattatggct ggggatatct tccagattgt tttaagccag     1020
aggttcgaga gacgaacata tgccaaccca tttgaggttt atcgagcatt acggattgtg     1080
aatcctagcc catacaaggc gtatgtacag gcaagaggct gtgtattggt tgcgtctagt     1140
cctgaaattc ttacacgagt cagtaagggg aagattatta atcgaccact tgctggaact     1200
gttcgaaggg gcaagacaga aaggaagat caaatgcaag agcagcaact gttaagtgat     1260
gaaaaacagt gtgccgagca cataatgctt gtggacttgg aaggaatga tgttggcaag     1320 gtatccaaac caggatcagt gaaggtggag aagttgatga acattgagag atactcccat     1380
gttatgcaca tcagctcaac ggttagtgga cagttggatg atcatctcca gagttgggat     1440
gccttgagag ctgccttgcc cgttggaaca gtcagtggtg caccaaaggt gaaggccatg     1500
gagttgattg ataagttgga agttacgagg cgaggaccat atagtggtgg tctaggagga     1560
atatcgtttg atggtgacat gcaaattgca ctttctctcc gcaccatcgt attctcaaca     1620
gcgccgagcc acaacacgat gtactcatac aaagacgcag ataggcgtcg ggagtgggtc     1680
gctcatcttc aggctggtgc aggcattgtt ccgacagta gcccagatga cgaacaacgt      1740
gaatgcgaga ataaggctgc tgcactagct cgggccatcg atcttgcaga gtcagctttt     1800
gtagacaaag aatag                                                      1815
```

<210> SEQ ID NO 68
<211> LENGTH: 2204
<212> TYPE: DNA
<213> ORGANISM: Artificial Sequence
<220> FEATURE:
<223> OTHER INFORMATION: A Zea mays mutant.

<400> SEQUENCE: 68

```
atggaatccc tagccgccac ctccgtgttc gcgccctccc gcgtcgccgt cccggcggcg       60
cgggccctgg ttagggcggg gacggtggta ccaaccaggc ggacgagcag ccggagcgga      120
accagcgggg tgaaatgctc tgctgccgtg acgccgcagg cgagcccagt gattagcagg      180
agcgctgcgg cggcgaaggc ggcggaggag gacaagaggc ggttcttcga ggcggcggcg      240
cgggggagcg ggaagggaa cctggtgccc atgtgggagt gcatcgtgtc ggaccatctc       300 accccgtgc tcgcctaccg ctgcctcgtc cccgaggaca cgtcgacgc ccccagcttc        360 ctcttcgagt ccgtcgagca ggggccccag ggcaccacca cgtcggccg ctatagcatg       420 gtgggagccc acccagtgat ggagattgtg gccaaagacc acaaggttac gatcatggac      480
cacgagaaga gccaagtgac agagcaggta gtggacgacc cgatgcagat cccgaggacc      540
atgatggagg atggcaccc acagcagatc gacgagctcc ctgaatcctt ctccggtgga      600
tgggttgggt tcttttccta tgatacggtt aggtatgttg agaagaagaa gctaccgttc     660
tccagtgctc tcaggacga taggaacctt cctgatgtgc acttgggact ctatgatgat      720
gttctagtct tcgataatgt tgagaagaaa gtatatgtta ccattgggt caatgtggac       780 cggcatgcat ctgttgagga agcataccaa gatggcaggt cccgactaaa catgttgcta      840
tctaaagtgc acaattccaa tgtccccaca ctctctcctg gatttgtgaa gctgcacaca      900
cgcaagtttg gtacaccttt gaacaagtcg accatgacaa gtgatgagta taagaatgct      960
gttctgcagg ctaaggaaca tattatggct ggggatatct tccagattgt tttaagccag     1020
```

-continued

```
aggttcgaga gacgaacata tgccaaccca tttgaggttt atcgagcatt acggattgtg    1080
aatcctagcc catacaaggc gtatgtacag gcaagaggct gtgtattggt tgcgtctagt    1140
cctgaaattc ttacacgagt cagtaagggg aagattatta atcgaccact tgctggaact    1200
gttcgaaggg gcaagacaga gaaggaagat caaatgcaag agcagcaact gttaagtgat    1260
gaaaaacagt gtgccgagca cataatgctt gtggacttgg gaaggaatga tgttggcaag    1320
gtatccaaac caggatcagt gaaggtggag aagttgatga acattgagag atactcccat    1380
gttatgcaca tcagctcaac ggttagtgga cagttggatg atcatctcca gagttgggat    1440
gccttgagag ctgccttgcc cgttggaaca gtcagtggtg caccaaaggt gaaggccatg    1500
gagttgattg ataagttgga agttacgagg cgaggaccat atagtggtgg tctaggagga    1560
atatcgtttg atggtgacat gcaaattgca ctttctctcc gcaccatcgt attctcaaca    1620
gcgccgagcc acaacacgat gtactcatac aaagacgcag ataggcgtcg ggagtgggtc    1680
gctcatcttc aggctggtgc aggcattgtt gccgacagta gcccagatga cgaacaacgt    1740
gaatgcgaga ataaggctgc tgcactagct cgggccatcg atcttgcaga gtcagctttt    1800
gtagacaaag aatagtgtgc tatggttatc gtttagttct tgttcatgtt tcttttaccc    1860
actttccgtt aaaaaaagat gtcattagtg ggtggagaaa agcaataaga ctgttctcta    1920
gaattcgagc tcggtaccgg atccaattcc cgatcgttca acatttggc aataaagttt     1980
cttaagattg aatcctgttg ccggtcttgc gatgattatc atataatttc tgttgaatta    2040
cgttaagcat gtaataatta acatgtaatg catgacgtta tttatgagat gggttttttat   2100
gattagagtc ccgcaattat acatttaata cgcgatagaa acaaaatat agcgcgcaaa     2160
ctaggataaa ttatcgcgcg cggtgtcatc tatgttacta gatc                     2204
```

<210> SEQ ID NO 69
<211> LENGTH: 729
<212> TYPE: PRT
<213> ORGANISM: Artificial Sequence
<220> FEATURE:
<223> OTHER INFORMATION: An A. tumefaciens mutant.

<400> SEQUENCE: 69

```
Met Val Thr Ile Ile Gln Asp Asp Gly Ala Glu Thr Tyr Glu Thr Lys
 1               5                  10                  15

Gly Gly Ile Gln Val Ser Arg Lys Arg Arg Pro Thr Asp Tyr Ala Asn
             20                  25                  30

Ala Ile Asp Asn Tyr Ile Glu Lys Leu Asp Ser His Arg Gly Ala Val
         35                  40                  45

Phe Lys Ser Asn Tyr Glu Tyr Pro Gly Arg Tyr Thr Arg Trp Asp Thr
     50                  55                  60

Ala Ile Val Asp Pro Pro Leu Gly Ile Ser Cys Phe Gly Arg Lys Met
 65                  70                  75                  80

Trp Ile Glu Ala Tyr Asn Gly Arg Gly Glu Val Leu Leu Asp Phe Ile
                 85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
    130                 135                 140

Ile Val Asp Leu Phe Tyr Ser Ser Ala Asp Ser Ala Ile Gly Leu Phe
```

-continued

```
            145                 150                 155                 160
        Gly Ala Phe Gly Tyr Asp Leu Ala Phe Gln Phe Asp Ala Ile Lys Leu
                        165                 170                 175
        Ser Leu Ala Arg Pro Glu Asp Gln Arg Asp Met Val Leu Phe Leu Pro
                        180                 185                 190
        Asp Glu Ile Leu Val Val Asp His Tyr Ser Ala Lys Ala Trp Ile Asp
                        195                 200                 205
        Arg Tyr Asp Phe Glu Lys Asp Gly Met Thr Thr Asp Gly Lys Ser Ser
                        210                 215                 220
        Asp Ile Thr Pro Asp Pro Phe Lys Thr Thr Asp Thr Ile Pro Pro Lys
        225                 230                 235                 240
        Gly Asp His Arg Pro Gly Glu Tyr Ser Glu Leu Val Val Lys Ala Lys
                        245                 250                 255
        Glu Ser Phe Arg Arg Gly Asp Leu Phe Glu Val Val Pro Gly Gln Lys
                        260                 265                 270
        Phe Met Glu Arg Cys Glu Ser Asn Pro Ser Ala Ile Ser Arg Arg Leu
                        275                 280                 285
        Lys Ala Ile Asn Pro Ser Pro Tyr Ser Phe Phe Ile Asn Leu Gly Asp
                        290                 295                 300
        Gln Glu Tyr Leu Val Gly Ala Ser Pro Glu Met Phe Val Arg Val Ser
        305                 310                 315                 320
        Gly Arg Arg Ile Glu Thr Cys Pro Ile Ser Gly Thr Ile Lys Arg Gly
                        325                 330                 335
        Asp Asp Pro Ile Ala Asp Ser Glu Gln Ile Leu Lys Leu Leu Asn Ser
                        340                 345                 350
        Lys Lys Asp Glu Ser Glu Leu Thr Met Cys Ser Asp Val Asp Arg Asn
                        355                 360                 365
        Asp Lys Ser Arg Val Cys Glu Pro Gly Ser Val Lys Val Ile Gly Arg
                        370                 375                 380
        Arg Gln Ile Glu Met Tyr Ser Arg Leu Ile His Thr Val Asp His Ile
        385                 390                 395                 400
        Glu Gly Arg Leu Arg Asp Asp Met Asp Ala Phe Asp Gly Phe Leu Ser
                        405                 410                 415
        His Ala Trp Ala Val Thr Val Thr Gly Ala Pro Lys Leu Trp Ala Met
                        420                 425                 430
        Arg Phe Ile Glu Gly His Glu Lys Ser Pro Arg Ala Trp Tyr Gly Gly
                        435                 440                 445
        Ala Ile Gly Met Val Gly Phe Asn Gly Asp Met Asn Thr Gly Leu Thr
                        450                 455                 460
        Leu Arg Thr Ile Arg Ile Lys Asp Gly Ile Ala Glu Val Arg Ala Gly
        465                 470                 475                 480
        Ala Thr Leu Leu Asn Asp Ser Asn Pro Gln Glu Glu Ala Glu Thr
                        485                 490                 495
        Glu Leu Lys Ala Ser Ala Met Ile Ser Ala Ile Arg Asp Ala Lys Gly
                        500                 505                 510
        Thr Asn Ser Ala Ala Thr Lys Arg Asp Ala Ala Lys Val Gly Thr Gly
                        515                 520                 525
        Val Lys Ile Leu Leu Val Asp His Glu Asp Ser Phe Val His Thr Leu
                        530                 535                 540
        Ala Asn Tyr Phe Arg Gln Thr Gly Ala Thr Val Ser Thr Val Arg Ser
        545                 550                 555                 560
        Pro Val Ala Ala Asp Val Phe Asp Arg Phe Gln Pro Asp Leu Val Val
                        565                 570                 575
```

-continued

```
Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
        595                 600                 605

Gly Leu Gln Ala Leu Ala Glu Ala Tyr Gly Gly Glu Leu Arg Gln Leu
        610                 615                 620

Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
                645                 650                 655

His Ser Ile Phe Ala Asp Pro Ala Thr Leu Pro Arg Asp Phe Ile Ile
                660                 665                 670

Thr Ala Glu Ser Glu Asp Gly Thr Ile Met Gly Ile Glu His Ala Lys
            675                 680                 685

Glu Pro Val Ala Val Gln Phe His Pro Glu Ser Ile Met Thr Leu
        690                 695                 700

Gly Gln Asp Ala Gly Met Arg Met Ile Glu Asn Val Val His Leu
705                 710                 715                 720

Thr Arg Lys Ala Lys Thr Lys Ala Ala
                725
```

```
<210> SEQ ID NO 70
<211> LENGTH: 729
<212> TYPE: PRT
<213> ORGANISM: Artificial Sequence
<220> FEATURE:
<223> OTHER INFORMATION: An A. tumefaciens mutant.

<400> SEQUENCE: 70
```

```
Met Val Thr Ile Ile Gln Asp Asp Gly Ala Glu Thr Tyr Glu Thr Lys
1               5                   10                  15

Gly Gly Ile Gln Val Ser Arg Lys Arg Arg Pro Thr Asp Tyr Ala Asn
            20                  25                  30

Ala Ile Asp Asn Tyr Ile Glu Lys Leu Asp Ser His Arg Gly Ala Val
        35                  40                  45

Phe Ser Ser Asn Tyr Glu Tyr Pro Gly Arg Tyr Thr Arg Trp Asp Thr
    50                  55                  60

Ala Ile Val Asp Pro Pro Leu Gly Ile Ser Cys Phe Gly Arg Lys Met
65                  70                  75                  80

Trp Ile Glu Ala Tyr Asn Gly Arg Gly Glu Val Leu Leu Asp Phe Ile
                85                  90                  95

Thr Glu Lys Leu Lys Ala Thr Pro Asp Leu Thr Leu Gly Ala Ser Ser
            100                 105                 110

Thr Arg Arg Leu Asp Leu Thr Val Asn Glu Pro Asp Arg Val Phe Thr
        115                 120                 125

Glu Glu Glu Arg Ser Lys Ile Pro Thr Val Phe Thr Ala Leu Arg Ala
    130                 135                 140

Ile Val Asp Leu Phe Tyr Ser Ser Ala Asp Ser Ala Ile Gly Leu Phe
145                 150                 155                 160

Gly Ala Phe Gly Tyr Asp Leu Ala Phe Gln Phe Asp Ala Ile Lys Leu
                165                 170                 175

Ser Leu Ala Arg Pro Glu Asp Gln Arg Asp Met Val Leu Phe Leu Pro
            180                 185                 190

Asp Glu Ile Leu Val Val Asp His Tyr Ser Ala Lys Ala Trp Ile Asp
        195                 200                 205
```

```
Arg Tyr Asp Phe Glu Lys Asp Gly Met Thr Thr Asp Gly Lys Ser Ser
    210                 215                 220

Asp Ile Thr Pro Asp Pro Phe Lys Thr Thr Asp Thr Ile Pro Pro Lys
225                 230                 235                 240

Gly Asp His Arg Pro Gly Glu Tyr Ser Glu Leu Val Val Lys Ala Lys
                245                 250                 255

Glu Ser Phe Arg Arg Gly Asp Leu Phe Glu Val Val Pro Gly Gln Lys
            260                 265                 270

Phe Met Glu Arg Cys Glu Ser Asn Pro Ser Ala Ile Ser Arg Arg Leu
        275                 280                 285

Lys Ala Ile Asn Pro Ser Pro Tyr Ser Ala Phe Ile Asn Leu Gly Asp
290                 295                 300

Gln Glu Tyr Leu Val Gly Ala Ser Pro Glu Met Phe Val Arg Val Ser
305                 310                 315                 320

Gly Arg Arg Ile Glu Thr Cys Pro Ile Ser Gly Thr Ile Lys Arg Gly
                325                 330                 335

Asp Asp Pro Ile Ala Asp Ser Glu Gln Ile Leu Lys Leu Leu Asn Ser
            340                 345                 350

Lys Lys Asp Glu Ser Glu Leu Thr Met Cys Ser Asp Val Asp Arg Asn
        355                 360                 365

Asp Lys Ser Arg Val Cys Glu Pro Gly Ser Val Lys Val Ile Gly Arg
370                 375                 380

Arg Gln Ile Glu Met Tyr Ser Arg Leu Ile His Thr Val Asp His Ile
385                 390                 395                 400

Glu Gly Arg Leu Arg Asp Asp Met Asp Ala Phe Asp Gly Phe Leu Ser
                405                 410                 415

His Ala Trp Ala Val Thr Val Thr Gly Ala Pro Lys Leu Trp Ala Met
            420                 425                 430

Arg Phe Ile Glu Gly His Glu Lys Ser Pro Arg Ala Trp Tyr Gly Gly
        435                 440                 445

Ala Ile Gly Met Val Gly Phe Asn Gly Asp Met Asn Thr Gly Leu Thr
450                 455                 460

Leu Arg Thr Ile Arg Ile Lys Asp Gly Ile Ala Glu Val Arg Ala Gly
465                 470                 475                 480

Ala Thr Leu Leu Asn Asp Ser Asn Pro Gln Glu Glu Ala Glu Thr
                485                 490                 495

Glu Leu Lys Ala Ser Ala Met Ile Ser Ala Ile Arg Asp Ala Lys Gly
            500                 505                 510

Thr Asn Ser Ala Ala Thr Lys Arg Asp Ala Ala Lys Val Gly Thr Gly
        515                 520                 525

Val Lys Ile Leu Leu Val Asp His Glu Asp Ser Phe Val His Thr Leu
530                 535                 540

Ala Asn Tyr Phe Arg Gln Thr Gly Ala Thr Val Ser Thr Val Arg Ser
545                 550                 555                 560

Pro Val Ala Ala Asp Val Phe Asp Arg Phe Gln Pro Asp Leu Val Val
                565                 570                 575

Leu Ser Pro Gly Pro Gly Ser Pro Thr Asp Phe Asp Cys Lys Ala Thr
            580                 585                 590

Ile Lys Ala Ala Arg Ala Arg Asp Leu Pro Ile Phe Gly Val Cys Leu
        595                 600                 605

Gly Leu Gln Ala Leu Ala Glu Ala Tyr Gly Gly Glu Leu Arg Gln Leu
610                 615                 620
```

```
Ala Val Pro Met His Gly Lys Pro Ser Arg Ile Arg Val Leu Glu Pro
625                 630                 635                 640

Gly Leu Val Phe Ser Gly Leu Gly Lys Glu Val Thr Val Gly Arg Tyr
            645                 650                 655

His Ser Ile Phe Ala Asp Pro Ala Thr Leu Pro Arg Asp Phe Ile Ile
            660                 665                 670

Thr Ala Glu Ser Glu Asp Gly Thr Ile Met Gly Ile Glu His Ala Lys
        675                 680                 685

Glu Pro Val Ala Ala Val Gln Phe His Pro Glu Ser Ile Met Thr Leu
    690                 695                 700

Gly Gln Asp Ala Gly Met Arg Met Ile Glu Asn Val Val Val His Leu
705                 710                 715                 720

Thr Arg Lys Ala Lys Thr Lys Ala Ala
                725
```

<210> SEQ ID NO 71
<211> LENGTH: 264
<212> TYPE: DNA
<213> ORGANISM: Artificial Sequence
<220> FEATURE:
<223> OTHER INFORMATION: The sequence of a CTP.

<400> SEQUENCE: 71

```
atggcttcct ctatgctctc ttccgctact atggttgcct ctccggctca ggccactatg      60
gtcgctcctt tcaacggact taagtcctcc gctgccttcc cagccacccg caaggctaac     120
aacgacatta cttccatcac aagcaacggc ggaagagtta actgcatgca ggtgtggcct     180
ccgattggaa agaagaagtt tgagactctc tcttaccttc ctgaccttac cgattccggt     240
ggtcgcgtca actgcatgca ggcc                                            264
```

<210> SEQ ID NO 72
<211> LENGTH: 88
<212> TYPE: PRT
<213> ORGANISM: Artificial Sequence
<220> FEATURE:
<223> OTHER INFORMATION: The sequence of a CTP.

<400> SEQUENCE: 72

```
Met Ala Ser Ser Met Leu Ser Ser Ala Thr Met Val Ala Ser Pro Ala
1               5                   10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Gly Lys
    50                  55                  60

Lys Lys Phe Glu Thr Leu Ser Tyr Leu Pro Asp Leu Thr Asp Ser Gly
65                  70                  75                  80

Gly Arg Val Asn Cys Met Gln Ala
                85
```

<210> SEQ ID NO 73
<211> LENGTH: 264
<212> TYPE: DNA
<213> ORGANISM: Artificial Sequence
<220> FEATURE:
<223> OTHER INFORMATION: The sequence of a CTP.

<400> SEQUENCE: 73

```
atggcttcct ctatgctctc ttccgctact atggttgcct ctccggctca ggccactatg    60
gtcgctcctt tcaacggact taagtcctcc gctgccttcc cagccacccg caaggctaac   120
aacgacatta cttccatcac aagcaacggc ggaagagtta actgcatgca ggtgtggcct   180
ccgattgaaa agaagaagtt tgagactctc tcttaccttc ctgaccttac cgattccggt   240
ggtcgcgtca actgcatgca ggcc                                          264
```

<210> SEQ ID NO 74
<211> LENGTH: 88
<212> TYPE: PRT
<213> ORGANISM: Artificial Sequence
<220> FEATURE:
<223> OTHER INFORMATION: The sequence of a CTP.

<400> SEQUENCE: 74

```
Met Ala Ser Ser Met Leu Ser Ser Ala Thr Met Val Ala Ser Pro Ala
 1               5                  10                  15

Gln Ala Thr Met Val Ala Pro Phe Asn Gly Leu Lys Ser Ser Ala Ala
            20                  25                  30

Phe Pro Ala Thr Arg Lys Ala Asn Asn Asp Ile Thr Ser Ile Thr Ser
        35                  40                  45

Asn Gly Gly Arg Val Asn Cys Met Gln Val Trp Pro Pro Ile Glu Lys
 50                  55                  60

Lys Lys Phe Glu Thr Leu Ser Tyr Leu Pro Asp Leu Thr Asp Ser Gly
65                   70                  75                  80

Gly Arg Val Asn Cys Met Gln Ala
                85
```

<210> SEQ ID NO 75
<211> LENGTH: 2190
<212> TYPE: DNA
<213> ORGANISM: Artificial Sequence
<220> FEATURE:
<223> OTHER INFORMATION: An optimized A. tumefaciens.

<400> SEQUENCE: 75

```
atggtgacca tcattcagga tgacggtgcc gagacctacg agaccaaggg cggcatccag    60
gtgagccgca agcgccgccc caccgattac gccaacgcca tcgataacta catcgaaaag   120
cttgattccc atcgcggtgc cgtgttctcc tccaactacg aatacccagg ccgctacacc   180
cgctgggata ccgccatcgt cgatccacca ctcggcattt cctgcttcgg ccgcaagatg   240
tggatcgaag cctacaacgg ccgcggcgaa gtgctgctcg atttcattac cgaaaagctg   300
aaggccacac ccgatctcac cctcggcgct cctccaccc gccgcctcga tcttaccgtc   360
aacgaaccag accgcgtctt caccgaagaa gaacgctcca aaatcccaac cgtcttcacc   420
gctctcaggg ccatcgtcga cctcttctac tccagcgccg attccgccat cggcctgttc   480
ggtgccttcg gttacgatct cgccttccag ttcgacgcca tcaagctttc cctggcccgc   540
ccagaagacc agcgcgacat ggtgctgttc ctgcccgatg aaatcctcgt cgttgatcac   600
tactccgcca aggcctggat cgaccgctac gatttcgaga aggacggcat gaccaccgac   660
ggcaaatcct ccgacattac ccccgatccc ttcaagacca ccgataccat cccacccaag   720
ggcgatcacc gccccggcga atactccgag cttgtggtga aggccaagga agcttccgc   780 cgcggcgacc tgttcgaggt cgttcccggc cagaaattca tggagcgctg cgaaagcaac   840
ccatccgcca tttcccgccg cctgaaggcc atcaacccat ccccctactc cttcttcatc   900
aacctcggcg atcaggaata cctggtcggc gcctcccag aaatgttcgt gcgcgtctcc   960
```

```
ggccgccgca tcgagacctg cccaatctca ggcaccatca agcgcggcga cgatccaatt    1020
gccgacagcg agcagatttt gaaactgctc aactccaaaa aggacgaatc cgaactgacc    1080
atgtgctccg acgtggaccg caacgacaag agccgcgtct gcgagccagg ttccgtgaag    1140
gtcattggcc gccgccagat cgagatgtac tcacgcctca tccacaccgt cgatcacatc    1200
gaaggccgct gcgcgacga tatggacgcc ttcgacggtt tcctcagcca cgcctgggcc    1260
gtcaccgtca ccggtgcacc aaagctgtgg gccatgcgct tcatcgaagg tcatgaaaag    1320
agcccacgcg cctggtacgg cggtgccatc ggcatggtcg gcttcaacgg cgacatgaac    1380
accggcctga ccctgcgcac catccgcatc aaggacggta ttgccgaagt gcgcgccggc    1440 gccacccctgc tcaacgattc caacccacag gaagaagaag ccgaaaccga actgaaggcc    1500
tccgccatga tctcagccat cgcgacgca aaaggcacca actctgccgc caccaagcgc    1560
gatgccgcca agtcggcac cggcgtcaag atcctgctcg tcgaccacga agacagcttc    1620
gtgcacaccc tggccaacta cttccgccag accggcgcca ccgtctccac cgtcaggtca    1680
ccagtcgcag ccgacgtgtt cgatcgcttc cagccagacc tcgttgtcct gtcccccggt    1740
cccggcagcc caaccgattt cgactgcaag gcaaccatca aggccgcccg cgcccgcgat    1800
ctgccaatct tcggcgtttg cctcggtctg caggcattgg cagaagccta cggcggcgag    1860
ctgcgccagc ttgctgtgcc catgcacggc aagccttccc gcatccgcgt gctggaaccc    1920
ggcctcgtct tctccggtct cggcaaggaa gtcaccgtcg tcgctacca ttccatcttc    1980 gccgatcccg ccaccctgcc acgcgatttc atcatcaccg cagaaagcga ggacggcacc    2040
atcatgggca tcgaacacgc caaggaacca gtggccgccg ttcagttcca cccagaatcc    2100
atcatgaccc tcggtcagga cgccggcatg cgcatgatcg agaacgtcgt ggtgcatctg    2160
acccgcaagg ccaagaccaa ggccgcctga                                    2190
```

<210> SEQ ID NO 76
<211> LENGTH: 2160
<212> TYPE: DNA
<213> ORGANISM: Rhodopseudomonas palustris

<400> SEQUENCE: 76

```
atgaacagga ccgttttctc gcttcccgcg ccagcgact ataagaccgc cgcgggcctc       60
gcggtgacgc gcagcgccca gccttttgcc ggcggccagg cgctcgacga gctgatcgat    120
ctgctcgacc accgccgcgg cgtgatgctg tcgtccggca caaccgtgcc gggccgctac    180
gagagcttcg acctcggctt tgccgatccg ccgctggcgc tcaccactag gccgaaaaaa    240
ttcaccatcg aggcgctcaa tccgcgcggc cgggtgctga tcgcgttcct gtccgacaag    300
cttgaagagc cctgcgtggt ggtggagcag gcctgcgcca ccaagatcag gggccacatc    360
gtccgcggcg aggccccggt cgacgaagaa caacgcaccc gccgcgccag cgcgatctcc    420
ctggtgcgcg cggtgattgc tgccttcgcc tcgccggccg atccgatgct cgggctgtac    480
ggcgccttcg cctacgacct tgtgttccag ttcgaggatc tgaagcagaa gcgtgccccgc    540 gaagccgacc agcgcgacat cgtgctgtac gtgccggatc gcctgctggc ctacgatcgc    600
gccaccggcc gcggcgtcga catttcctac gaattcgcct ggaagggcca gtccaccgcc    660
ggcctgccga acgagaccgc cgagagcgtc tacacccaga ccggcggca gggtttcgcc    720 gaccacgccc cggcgacta tcccaaggtg tcgagaagg cccgcgcggc gttcgcccgc    780
ggcgacctgt cgaggcggt gccgggccag ctgttcggcg agccatgcga gcggtcgccg    840
```

-continued

```
gccgaagtgt tcaagcggtt gtgccggatc aacccgtcgc cctatggcgg cctgctcaat      900
ctcggcgacg gcgaattcct ggtgtcggcc tcgccggaaa tgttcgtccg ctcggacggc      960
cgccggatcg agacctgccc gatctccggc actatcgccc gcggcgtcga tgcgatcagc     1020
gatgctgagc agatccagaa gctcttgaac tccgagaagg acgagttcga gctgaatatg     1080
tgcaccgacg tcgaccgcaa cgacaaggcg cgggtctgcg tgccgggcac gatcaaagtt     1140
ctcgcgcgcc gccagatcga gacctattcg aagctgttcc acaccgtcga tcacgtcgag     1200
ggcatgctgc gaccgggttt cgacgcgctc gacgccttcc tcacccacgc ctgggcggtc     1260
accgtcaccg gcgcgccgaa gctgtgggcg atgcagttcg tcgaggatca cgagcgtagc     1320
ccgcggcgct ggtatgccgg cgcgttcggc gtggtcggct tcgatggctc gatcaacacc     1380
ggcctcacca tccgcaccat ccggatgaag gacggcctcg ccgaagttcg cgtcggcgcc     1440
acctgcctgt cgacagcaa tccggtcgcc gaggacaagg aatgccaggt caaggccgcg      1500
gcactgttcc aggcgctgcg cggcgatccc gccaagccgc tgtcggcggt ggcgccggac     1560
gccactggct cgggcaagaa ggtgctgctg gtcgaccacg acgacagctt cgtgcacatg     1620
ctggcggact atttcaggca ggtcggcgcc caggtcaccg tggtgcgcta cgttcacggc     1680
ctgaagatgc tggccgaaaa cagctatgat cttctggtgc tgtcgcccgg tcccggccgg     1740
ccggaggact tcaagatcaa ggatacgatc gacgccgcgc tcgccaagaa gctgccgatc     1800
ttcggcgtct gcctcggcgt ccaggcgatg gcgaatatt ttggcggtac gctcggccag      1860
ctcgcgcagc cggctcacgg ccgcccgtcg cggattcagg tgcgcggcgg cgcgctgatg     1920
cgcggtctcc cgaacgaggt caccatcggc cgctaccact cgctctatgt cgacatgcgc     1980
gacatgccga aggagctgac cgtcaccgcc tccaccgatg acggcatcgc gatggcgatc     2040
gagcacaaga ccctgccggt cggcggcgtg cagttccacc ccgagtcgct gatgtcgctc     2100
ggcggcgagg tcgggctgcg gatcgtcgaa aacgccttcc ggctcggcca ggcggcctaa     2160
```

<210> SEQ ID NO 77
<211> LENGTH: 733
<212> TYPE: PRT
<213> ORGANISM: Mesorhizobium loti

<400> SEQUENCE: 77

```
Met Glu Thr Ala Met Thr Met Lys Val Leu Glu Asn Gly Ala Glu Ser
  1               5                  10                  15

Phe Val Thr Ala Gly Gly Ile Thr Ile Thr Arg Glu Arg His Asp Arg
             20                  25                  30

Pro Tyr Ala Gly Ala Ile Asp Ala Tyr Val Asp Gly Leu Asn Ser Arg
         35                  40                  45

Arg Gly Ala Val Phe Ser Ser Asn Tyr Glu Tyr Pro Gly Arg Tyr Thr
     50                  55                  60

Arg Trp Asp Thr Ala Ile Ile Asp Pro Pro Leu Val Ile Ser Ala Arg
 65                  70                  75                  80

Gly Arg Ala Met Arg Ile Glu Ala Leu Asn Arg Arg Gly Glu Ala Leu
                 85                  90                  95

Leu Pro Val Ile Gly Lys Thr Leu Gly Gly Leu Ala Asp Ile Thr Ile
            100                 105                 110

Ala Glu Thr Thr Lys Thr Leu Ile Arg Leu Asp Val Ala Lys Pro Gly
        115                 120                 125

Arg Val Phe Thr Glu Glu Glu Arg Ser Arg Val Pro Ser Val Phe Thr
    130                 135                 140
```

-continued

```
Val Leu Arg Ala Ile Thr Ala Leu Phe Lys Thr Asp Glu Asp Ala Asn
145                 150                 155                 160

Leu Gly Leu Tyr Gly Ala Phe Gly Tyr Asp Leu Ser Phe Gln Phe Asp
                165                 170                 175

Pro Val Asp Tyr Lys Leu Glu Arg Lys Pro Ser Gln Arg Asp Leu Val
            180                 185                 190

Leu Phe Leu Pro Asp Glu Ile Leu Val Val Asp His Tyr Ser Ala Lys
        195                 200                 205

Ala Trp Thr Asp Arg Tyr Asp Tyr Ser Gly Glu Gly Phe Ser Thr Glu
    210                 215                 220

Gly Leu Pro Arg Asp Ala Ile Ala Glu Pro Phe Lys Thr Ala Asp Arg
225                 230                 235                 240

Ile Pro Pro Arg Gly Asp His Glu Pro Gly Glu Tyr Ala Asn Leu Val
                245                 250                 255

Arg Arg Ala Met Asp Ser Phe Lys Arg Gly Asp Leu Phe Glu Val Val
            260                 265                 270

Pro Gly Gln Met Phe Tyr Glu Arg Cys Glu Thr Gln Pro Ser Asp Ile
        275                 280                 285

Ser Arg Lys Leu Lys Ser Ile Asn Pro Ser Pro Tyr Ser Phe Phe Ile
    290                 295                 300

Asn Leu Gly Glu Asn Glu Tyr Leu Ile Gly Ala Ser Pro Glu Met Phe
305                 310                 315                 320

Val Arg Val Asn Gly Arg Arg Val Glu Thr Cys Pro Ile Ser Gly Thr
                325                 330                 335

Ile Lys Arg Gly Asp Asp Ala Ile Ser Asp Ser Glu Gln Ile Leu Lys
            340                 345                 350

Leu Leu Asn Ser Lys Lys Asp Glu Ser Glu Leu Thr Met Cys Ser Asp
        355                 360                 365

Val Asp Arg Asn Asp Lys Ser Arg Val Cys Glu Pro Gly Ser Val Arg
    370                 375                 380

Val Ile Gly Arg Arg Gln Ile Glu Met Tyr Ser Arg Leu Ile His Thr
385                 390                 395                 400

Val Asp His Ile Glu Gly Arg Leu Arg Glu Gly Met Asp Ala Phe Asp
                405                 410                 415

Ala Phe Leu Ser His Ala Trp Ala Val Thr Val Thr Gly Ala Pro Lys
            420                 425                 430

Leu Trp Ala Met Arg Phe Ile Glu Gln Asn Glu Lys Ser Pro Arg Ala
        435                 440                 445

Trp Tyr Gly Gly Ala Ile Gly Met Val Asn Phe Asn Gly Asp Met Asn
    450                 455                 460

Thr Gly Leu Thr Leu Arg Thr Ile Arg Ile Lys Asp Gly Ile Ala Glu
465                 470                 475                 480

Val Arg Ala Gly Ala Thr Leu Leu Phe Asp Ser Ile Pro Glu Glu Glu
                485                 490                 495

Glu Ala Glu Thr Glu Leu Lys Ala Ser Ala Met Leu Ser Ala Ile Arg
            500                 505                 510

Asp Ala Lys Thr Gly Asn Ser Ala Ser Thr Glu Arg Thr Thr Ala Arg
        515                 520                 525

Val Gly Asp Gly Val Asn Ile Leu Leu Val Asp His Glu Asp Ser Phe
    530                 535                 540

Val His Thr Leu Ala Asn Tyr Phe Arg Gln Thr Gly Ala Asn Val Ser
545                 550                 555                 560

Thr Val Arg Thr Pro Val Pro Asp Glu Val Phe Glu Arg Leu Lys Pro
```

-continued

```
                565                 570                 575
Asp Leu Val Val Leu Ser Pro Gly Pro Gly Thr Pro Lys Asp Phe Asp
            580                 585                 590

Cys Ala Ala Thr Ile Arg Arg Ala Arg Ala Arg Asp Leu Pro Ile Phe
            595                 600             605

Gly Val Cys Leu Gly Leu Gln Ala Leu Ala Glu Ala Tyr Gly Gly Glu
        610                 615             620

Leu Arg Gln Leu His Ile Pro Met His Gly Lys Pro Ser Arg Ile Arg
625                 630                 635                 640

Val Ser Lys Pro Gly Ile Ile Phe Ser Gly Leu Pro Lys Glu Val Thr
                645                 650                 655

Val Gly Arg Tyr His Ser Ile Phe Ala Asp Pro Val Arg Leu Pro Asp
            660                 665             670

Asp Phe Ile Val Thr Ala Glu Thr Glu Asp Gly Ile Ile Met Ala Phe
            675                 680             685

Glu His Arg Lys Glu Pro Ile Ala Ala Val Gln Phe His Pro Glu Ser
        690                 695             700

Ile Met Thr Leu Gly His Asn Ala Gly Met Arg Ile Ile Glu Asn Ile
705                 710                 715                 720

Val Ala His Leu Pro Arg Lys Ala Lys Glu Lys Ala Ala
                725                 730

<210> SEQ ID NO 78
<211> LENGTH: 732
<212> TYPE: PRT
<213> ORGANISM: Azospirillum brasilense

<400> SEQUENCE: 78

Met Tyr Pro Ala Asp Leu Leu Ala Ser Pro Asp Leu Leu Glu Pro Leu
1               5                   10                  15

Arg Phe Gln Thr Arg Gly Gly Val Thr Val Thr Arg Arg Ala Thr Ala
            20                  25                  30

Leu Asp Pro Arg Thr Ala Leu Asp Pro Val Ile Asp Ala Leu Asp Arg
        35                  40                  45

Arg Arg Gly Leu Leu Ser Ser Gly Val Glu Ala Pro Gly Arg Tyr
    50                  55                  60

Arg Arg His Ala Leu Gly Phe Thr Asp Pro Ala Val Ala Leu Thr Ala
65                  70                  75                  80

Arg Gly Arg Thr Leu Arg Ile Asp Ala Leu Asn Gly Arg Gly Gln Val
                85                  90                  95

Leu Leu Pro Ala Val Ala Glu Ala Leu Arg Gly Leu Glu Ala Leu Ala
            100                 105                 110

Gly Leu Glu Glu Ala Pro Ser Arg Val Thr Ala Ser Ser Ala Ser Pro
        115                 120                 125

Ala Pro Leu Pro Gly Glu Glu Arg Ser Arg Gln Pro Ser Val Phe Ser
    130                 135                 140

Val Leu Arg Ala Val Leu Asp Leu Phe Ala Ala Pro Asp Pro Leu
145                 150                 155                 160

Leu Gly Leu Tyr Gly Ala Phe Ala Tyr Asp Leu Ala Phe Gln Phe Glu
                165                 170                 175

Pro Ile Arg Gln Arg Leu Glu Arg Pro Asp Asp Gln Arg Asp Leu Leu
            180                 185                 190

Leu Tyr Leu Pro Asp Arg Leu Val Ala Leu Asp Pro Ile Ala Gly Leu
        195                 200                 205
```

```
Ala Arg Leu Val Ala Tyr Glu Phe Ile Thr Ala Ala Gly Ser Thr Glu
    210                 215                 220

Gly Leu Glu Cys Gly Gly Arg Asp His Pro Tyr Arg Pro Asp Thr Asn
225                 230                 235                 240

Ala Glu Ala Gly Cys Asp His Ala Pro Gly Asp Tyr Gln Arg Val Val
                245                 250                 255

Glu Ser Ala Lys Ala Ala Phe Arg Arg Gly Asp Leu Phe Glu Val Val
            260                 265                 270

Pro Gly Gln Thr Phe Ala Glu Pro Cys Ala Asp Ala Pro Ser Ser Val
        275                 280                 285

Phe Arg Arg Leu Arg Ala Ala Asn Pro Ala Pro Tyr Glu Ala Phe Val
    290                 295                 300

Asn Leu Gly Arg Gly Glu Phe Leu Val Ala Ser Pro Glu Met Tyr
305                 310                 315                 320

Val Arg Val Ala Gly Gly Arg Val Glu Thr Cys Pro Ile Ser Gly Thr
                325                 330                 335

Val Ala Arg Gly Ala Asp Ala Leu Gly Asp Ala Ala Gln Val Leu Arg
            340                 345                 350

Leu Leu Thr Ser Ala Lys Asp Ala Ala Glu Leu Thr Met Cys Thr Asp
        355                 360                 365

Val Asp Arg Asn Asp Lys Ala Arg Val Cys Glu Pro Gly Ser Val Arg
370                 375                 380

Val Ile Gly Arg Arg Met Ile Glu Leu Tyr Ser Arg Leu Ile His Thr
385                 390                 395                 400

Val Asp His Val Glu Gly Arg Leu Arg Ser Gly Met Asp Ala Leu Asp
                405                 410                 415

Ala Phe Leu Thr His Ser Trp Ala Val Thr Val Thr Gly Ala Pro Lys
            420                 425                 430

Arg Trp Ala Met Gln Phe Leu Glu Asp Thr Glu Gln Ser Pro Arg Arg
        435                 440                 445

Trp Tyr Gly Gly Ala Phe Gly Arg Leu Gly Phe Asp Gly Gly Met Asp
    450                 455                 460

Thr Gly Leu Thr Leu Arg Thr Ile Arg Met Ala Glu Gly Val Ala Tyr
465                 470                 475                 480

Val Arg Ala Gly Ala Thr Leu Leu Ser Asp Ser Asp Pro Asp Ala Glu
                485                 490                 495

Asp Ala Glu Cys Arg Leu Lys Ala Ala Phe Arg Asp Ala Ile Arg
            500                 505                 510

Gly Thr Ala Ala Gly Ala Ala Pro Thr Leu Pro Ala Ala Pro Arg Gly
        515                 520                 525

Gly Glu Gly Arg Arg Val Leu Leu Val Asp His Asp Ser Phe Val
    530                 535                 540

His Thr Leu Ala Asp Tyr Leu Arg Gln Thr Gly Ala Ser Val Thr Thr
545                 550                 555                 560

Leu Arg His Ser His Ala Arg Ala Ala Leu Ala Glu Arg Arg Pro Asp
                565                 570                 575

Leu Val Val Leu Ser Pro Gly Pro Gly Arg Pro Ala Asp Phe Asp Val
            580                 585                 590

Ala Gly Thr Ile Asp Ala Ala Leu Ala Leu Gly Leu Pro Val Phe Gly
        595                 600                 605

Val Cys Leu Gly Leu Gln Gly Met Val Glu Arg Phe Gly Gly Ala Leu
    610                 615                 620

Asp Val Leu Pro Glu Pro Val His Gly Lys Ala Thr Glu Val Arg Val
```

-continued

```
625                 630                 635                 640

Leu Gly Gly Ala Leu Phe Ala Gly Leu Pro Glu Arg Leu Thr Val Gly
                645                 650                 655

Arg Tyr His Ser Leu Val Ala Arg Arg Asp Arg Leu Pro Ala Asp Leu
            660                 665                 670

Thr Val Thr Ala Glu Thr Ala Asp Gly Leu Val Met Ala Val Glu His
        675                 680                 685

Arg Arg Leu Pro Leu Ala Ala Val Gln Phe His Pro Glu Ser Ile Leu
    690                 695                 700

Ser Leu Asp Gly Gly Ala Gly Leu Ala Leu Leu Gly Asn Val Met Asp
705                 710                 715                 720

Arg Leu Ala Ala Gly Ala Leu Thr Asp Ala Ala Ala
                725                 730

<210> SEQ ID NO 79
<211> LENGTH: 731
<212> TYPE: PRT
<213> ORGANISM: Brucella melitensis

<400> SEQUENCE: 79

Met Asn Ala Lys Thr Ala Asp Ser Glu Ile Phe Gln His Glu Thr Ala
 1               5                  10                  15

Gly Gly Ile Ile Val Glu Arg Val Arg His Leu Thr Ala Tyr Lys Gly
            20                  25                  30

Ala Ile Glu Ser Tyr Ile Asp Val Leu Asn Glu Trp Arg Gly Ala Val
        35                  40                  45

Phe Ser Ser Asn Tyr Glu Tyr Pro Gly Arg Tyr Thr Arg Trp Asp Thr
    50                  55                  60

Ala Ile Val Asp Pro Pro Val Val Ile Thr Ser Arg Ala Arg Thr Met
65                  70                  75                  80

Arg Ile Glu Ala Leu Asn Ala Arg Gly Val Ile Leu Leu Arg Pro Ile
                85                  90                  95

Leu Asp Thr Val Lys Ala Leu Ser Glu Val Lys Ile Asp Gln Ser Gly
            100                 105                 110

Glu Asn Arg Ile Asp Leu Thr Ile Val Glu Pro Val Gly Thr Phe Thr
        115                 120                 125

Glu Glu Glu Arg Ser Arg Met Pro Ser Val Phe Thr Val Leu Arg Ala
    130                 135                 140

Ile Val Gly Leu Phe Phe Ser Glu Glu Asp Ala Asn Leu Gly Leu Tyr
145                 150                 155                 160

Gly Ala Phe Gly Tyr Asp Leu Ala Phe Gln Phe Asp Pro Ile Gln Tyr
                165                 170                 175

Lys Leu Lys Arg Pro Asp Asp Gln Arg Asp Leu Val Leu Phe Ile Pro
            180                 185                 190

Asp Glu Ile Phe Val Ala Asp His Tyr Ala Ala Arg Ala Trp Val Asp
        195                 200                 205

Arg Tyr Glu Phe Arg Cys Gly Gly Ser Ser Thr His Gly Leu Asp Arg
    210                 215                 220

Ala Thr Pro Val Val Pro Phe Lys Pro Ser Glu Arg Lys Leu Ala Arg
225                 230                 235                 240

Gly Asp His Asn Pro Gly Glu Tyr Ala Arg Leu Val Glu Arg Ala Lys
                245                 250                 255

Glu Ser Phe Lys Arg Gly Asp Leu Phe Glu Val Val Pro Gly Gln Thr
            260                 265                 270
```

```
Phe Tyr Glu Arg Cys His Thr Ala Pro Ser Glu Ile Phe Arg Arg Leu
        275                 280                 285

Lys Ser Ile Asn Pro Ser Pro Tyr Ser Phe Phe Ile Asn Leu Gly Glu
        290                 295                 300

Ser Glu Tyr Leu Val Gly Ala Ser Pro Glu Met Phe Val Arg Val Asn
305                 310                 315                 320

Gly Arg Arg Ile Glu Thr Cys Pro Ile Ser Gly Thr Ile Lys Arg Gly
                    325                 330                 335

Glu Asp Ala Ile Ser Asp Ser Glu Gln Ile Leu Lys Leu Leu Asn Ser
                340                 345                 350

Lys Lys Asp Glu Ser Glu Leu Thr Met Cys Ser Asp Val Asp Arg Asn
            355                 360                 365

Asp Lys Ser Arg Val Cys Glu Pro Gly Ser Val Arg Val Ile Gly Arg
370                 375                 380

Arg Gln Ile Glu Met Tyr Ser Arg Leu Ile His Thr Val Asp His Ile
385                 390                 395                 400

Glu Gly Arg Leu Arg Asp Gly Met Asp Ala Phe Asp Gly Phe Leu Ser
                405                 410                 415

His Ala Trp Ala Val Thr Val Thr Gly Ala Pro Lys Leu Trp Ala Met
                420                 425                 430

Arg Phe Leu Glu Glu Asn Glu Arg Ser Pro Arg Ala Trp Tyr Gly Gly
            435                 440                 445

Ala Ile Gly Met Met His Phe Asn Gly Asp Met Asn Thr Gly Leu Thr
450                 455                 460

Leu Arg Thr Ile Arg Ile Lys Asp Gly Val Ala Glu Ile Arg Ala Gly
465                 470                 475                 480

Ala Thr Leu Leu Phe Asp Ser Asn Pro Asp Glu Glu Ala Glu Thr
                485                 490                 495

Glu Leu Lys Ala Ser Ala Met Ile Ala Ala Val Arg Asp Ala Gln Lys
                500                 505                 510

Ser Asn Gln Ile Ala Glu Glu Ser Val Ala Ala Lys Val Gly Glu Gly
            515                 520                 525

Val Ser Ile Leu Leu Val Asp His Glu Asp Ser Phe Val His Thr Leu
530                 535                 540

Ala Asn Tyr Phe Arg Gln Thr Gly Ala Lys Val Ser Thr Val Arg Ser
545                 550                 555                 560

Pro Val Ala Glu Glu Ile Phe Asp Arg Val Asn Pro Asp Leu Val Val
                565                 570                 575

Leu Ser Pro Gly Pro Gly Ser Pro Gln Asp Phe Asp Cys Lys Ala Thr
                580                 585                 590

Ile Asp Lys Ala Arg Lys Arg Gln Leu Pro Ile Phe Gly Val Cys Leu
            595                 600                 605

Gly Leu Gln Ala Leu Ala Glu Ala Tyr Gly Gly Ala Leu Arg Gln Leu
610                 615                 620

Arg Val Pro Val His Gly Lys Pro Ser Arg Ile Arg Val Ser Lys Pro
625                 630                 635                 640

Glu Arg Ile Phe Ser Gly Leu Pro Glu Glu Val Thr Val Gly Arg Tyr
                645                 650                 655

His Ser Ile Phe Ala Asp Pro Glu Arg Leu Pro Asp Asp Phe Leu Val
                660                 665                 670

Thr Ala Glu Thr Glu Asp Gly Ile Ile Met Ala Phe Glu His Lys His
            675                 680                 685

Glu Pro Val Ala Ala Val Gln Phe His Pro Glu Ser Ile Met Thr Leu
```

```
                690             695             700
Gly His Asn Ala Gly Met Arg Met Ile Glu Asn Ile Val Thr His Leu
705                 710                 715                 720

Ala Gly Lys His Lys Ala Arg Arg Thr Asn Tyr
                725                 730
```

<210> SEQ ID NO 80
<211> LENGTH: 735
<212> TYPE: PRT
<213> ORGANISM: Nostoc sp.

<400> SEQUENCE: 80

```
Met Ile Ala Asp Ser His Ser Tyr Arg Thr Asn Gly Asn Val Arg Val
  1               5                  10                  15

Ser Arg Ser Ile Thr Gln Val Lys Met Glu Thr Ala Leu Glu Glu Ile
                 20                  25                  30

Leu Phe Tyr Leu Asn Ser Gln Arg Gly Gly Leu Leu Thr Ser Ser Tyr
                 35                  40                  45

Glu Tyr Pro Gly Arg Tyr Lys Arg Trp Ala Ile Gly Phe Val Asn Pro
 50                  55                  60

Pro Val Glu Leu Ser Thr Ser Gly Asn Thr Phe Thr Leu Thr Ala Leu
 65                  70                  75                  80

Asn Glu Arg Gly Tyr Val Leu Leu Pro Val Ile Phe Glu Cys Leu Ser
                 85                  90                  95

Lys Ser Glu Gln Leu Gln Lys Leu Thr Glu His His His Lys Ile Thr
                100                 105                 110

Gly Leu Val Lys Ser Thr Pro Glu Phe Phe Ala Glu Glu Arg Ser
                115                 120                 125

Lys Gln Pro Ser Thr Phe Thr Val Ile Arg Glu Ile Leu His Ile Phe
                130                 135                 140

Ser Ser Gln Glu Asp Glu His Leu Gly Leu Tyr Gly Ala Phe Gly Tyr
145                 150                 155                 160

Asp Leu Val Phe Gln Phe Glu Gln Ile Thr Gln Cys Leu Glu Arg Pro
                165                 170                 175

Gln Asp Gln Arg Asp Leu Val Leu Tyr Leu Pro Asp Glu Leu Ile Val
                180                 185                 190

Val Asp Tyr Tyr Gln Gln Gln Ala Phe Arg Leu Glu Tyr Asp Phe Ile
                195                 200                 205

Thr Ala His Gly Ser Thr Tyr Asp Leu Pro Arg Thr Gly Glu Ser Val
                210                 215                 220

Asp Tyr Arg Gly Gln Cys Leu Thr Pro Pro Gln Asn Ala Asp His Lys
225                 230                 235                 240

Ile Gly Glu Tyr Ala Lys Leu Val Glu Phe Ala Leu Asp Tyr Phe Arg
                245                 250                 255

Arg Gly Asp Leu Phe Glu Val Val Pro Ser Gln Asn Phe Phe Thr Ala
                260                 265                 270

Cys Glu Ala Pro Pro Ser Gln Leu Phe Glu Thr Leu Lys Gln Ile Asn
                275                 280                 285

Pro Ser Pro Tyr Gly Phe Ile Phe Asn Leu Gly Gly Glu Tyr Ile Ile
                290                 295                 300

Gly Ala Ser Pro Glu Met Phe Val Arg Val Gly Arg Arg Val Glu
305                 310                 315                 320

Thr Cys Pro Ile Ser Gly Thr Ile Thr Arg Gly His Asp Ala Ile Asp
                325                 330                 335
```

-continued

```
Asp Ala Val Gln Ile Arg Gln Leu Leu Asn Ser His Lys Asp Glu Ala
                340                 345                 350

Glu Leu Thr Met Cys Thr Asp Val Asp Arg Asn Asp Lys Ser Arg Ile
            355                 360                 365

Cys Glu Pro Gly Ser Val Lys Val Ile Gly Arg Arg Gln Ile Glu Leu
        370                 375                 380

Tyr Ser His Leu Ile His Thr Val Asp His Val Glu Gly Ile Leu Arg
385                 390                 395                 400

Pro Glu Phe Asp Ala Leu Asp Ala Phe Leu Ser His Thr Trp Ala Val
                405                 410                 415

Thr Val Thr Gly Ala Pro Lys Arg Ala Ile Gln Phe Ile Glu Lys
            420                 425                 430

Asn Glu Arg Ser Val Arg Arg Trp Tyr Gly Gly Ala Val Gly Tyr Leu
        435                 440                 445

Asn Phe Asn Gly Asn Leu Asn Thr Gly Leu Ile Leu Arg Thr Ile Arg
450                 455                 460

Leu Gln Asp Ser Ile Ala Glu Val Arg Val Gly Ala Thr Leu Leu Tyr
465                 470                 475                 480

Asp Ser Ile Pro Gln Ala Glu Glu Gln Glu Thr Ile Thr Lys Ala Ala
                485                 490                 495

Ala Ala Phe Glu Thr Ile Arg Arg Ala Lys Gln Ile Asp Pro Gln Ile
            500                 505                 510

Glu Glu Ser Ser Thr Arg Lys Leu Ser Lys Tyr Leu Pro Asp Gly Gln
        515                 520                 525

Ser Gly Lys His Ile Leu Leu Ile Asp His Glu Asp Ser Phe Val His
        530                 535                 540

Thr Leu Ala Asn Tyr Ile Arg Ser Thr Gly Ala Thr Val Thr Thr Leu
545                 550                 555                 560

Arg His Gly Phe Ser Glu Ser Leu Phe Asp Thr Glu Arg Pro Asp Leu
                565                 570                 575

Val Val Leu Ser Pro Gly Pro Gly Arg Pro Ser Glu Phe Lys Val Gln
            580                 585                 590

Glu Thr Val Ala Ala Cys Val Arg Arg Gln Ile Pro Leu Phe Gly Val
        595                 600                 605

Cys Leu Gly Leu Gln Gly Ile Val Glu Ala Phe Gly Gly Glu Leu Gly
        610                 615                 620

Val Leu Asn Tyr Pro Gln His Gly Lys Ser Ser Arg Ile Phe Val Thr
625                 630                 635                 640

Ala Pro Asp Ser Val Met Phe Gln Asp Leu Pro Glu Ser Phe Thr Val
                645                 650                 655

Gly Arg Tyr His Ser Leu Phe Ala Leu Ser Gln Arg Leu Pro Lys Glu
            660                 665                 670

Leu Lys Val Thr Ala Ile Ser Asp Asp Glu Val Ile Met Ala Ile Glu
        675                 680                 685

His Gln Thr Leu Pro Ile Ala Ala Val Gln Phe His Pro Glu Ser Ile
        690                 695                 700

Met Thr Leu Ala Gly Glu Val Gly Leu Met Met Ile Lys Asn Val Val
705                 710                 715                 720

Gln Lys Tyr Thr Gln Ser Gln Gln Ser Thr Val Pro Ile Tyr Asp
                725                 730                 735
```

<210> SEQ ID NO 81
<211> LENGTH: 715
<212> TYPE: PRT

<213> ORGANISM: Nostoc sp.

<400> SEQUENCE: 81

```
Met Arg Val Ser Arg Ser Thr Thr Glu Val Lys Met Asp Thr Ala Leu
 1               5                  10                  15

Asp Glu Ile Leu Phe His Leu Asn Gln Val Arg Gly Gly Leu Leu Thr
             20                  25                  30

Ser Ser Tyr Glu Tyr Pro Gly Arg Tyr Lys Arg Trp Ala Ile Gly Phe
         35                  40                  45

Ile Asn Pro Pro Leu Gln Leu Thr Thr Arg Glu Asn Ala Phe Thr Ile
 50                  55                  60

Ser Ser Leu Asn Pro Arg Gly Gln Val Leu Leu Pro Thr Leu Phe Gln
 65                  70                  75                  80

His Leu Ser Ala Gln Ser Gln Leu Gln Gln Ile Ser Leu Asn His Asp
                 85                  90                  95

Tyr Ile Thr Gly Glu Ile Arg Pro Thr Lys Gln Leu Phe Thr Glu Glu
            100                 105                 110

Gln Arg Ser Lys Gln Pro Ser Ala Phe Thr Val Ile Arg Glu Ile Leu
        115                 120                 125

Gln Ile Phe Ala Ser Asp Glu Asp Glu His Leu Gly Leu Tyr Gly Ala
    130                 135                 140

Phe Gly Tyr Asp Leu Val Phe Gln Phe Glu Pro Ile Pro Gln Lys Ile
145                 150                 155                 160

Ala Arg Pro Ala Asp Gln Arg Asp Leu Val Leu Tyr Leu Pro Asp Glu
                165                 170                 175

Leu Ile Val Val Asp Tyr Tyr Leu Gln Lys Ala Tyr Arg His Gln Tyr
            180                 185                 190

Glu Phe Ala Thr Glu His Gly Asn Thr Glu His Leu Pro Arg Thr Gly
        195                 200                 205

Gln Ser Ile Asp Tyr Gln Gly Lys His Leu Leu Pro Asn Gln Thr Ala
    210                 215                 220

Asp His Gln Pro Gly Glu Tyr Ala Asn Leu Val Glu Gln Ala Leu Asp
225                 230                 235                 240

Tyr Phe Arg Arg Gly Asp Leu Phe Glu Val Val Pro Ser Gln Asn Phe
                245                 250                 255

Phe Thr Ala Cys Glu Gln Ser Pro Ser Gln Leu Phe Gln Thr Leu Arg
            260                 265                 270

Gln Ile Asn Pro Ser Pro Tyr Gly Phe Leu Leu Asn Leu Gly Gly Glu
        275                 280                 285

Tyr Leu Ile Gly Ala Ser Pro Glu Met Phe Val Arg Val Asp Gly Arg
    290                 295                 300

Arg Val Glu Thr Cys Pro Ile Ser Gly Thr Ile Arg Arg Gly Glu Asp
305                 310                 315                 320

Ala Leu Gly Asp Ala Val Gln Ile Arg Gln Leu Leu Asn Ser His Lys
                325                 330                 335

Asp Glu Ala Glu Leu Thr Met Cys Thr Asp Val Asp Arg Asn Asp Lys
            340                 345                 350

Ser Arg Ile Cys Glu Pro Gly Ser Val Arg Val Ile Gly Arg Arg Gln
        355                 360                 365

Ile Glu Leu Tyr Ser His Leu Ile His Thr Val Asp His Val Glu Gly
    370                 375                 380

Ile Leu Arg Pro Glu Phe Asp Ala Leu Asp Ala Phe Leu Ser His Thr
385                 390                 395                 400
```

```
Trp Ala Val Thr Val Thr Gly Ala Pro Lys Arg Ala Ala Met Gln Phe
                    405                 410                 415

Ile Glu Gln His Glu Arg Ser Ala Arg Arg Trp Tyr Gly Gly Ala Val
                420                 425                 430

Gly Tyr Leu Gly Phe Asn Gly Asn Leu Asn Thr Gly Leu Thr Leu Arg
            435                 440                 445

Thr Ile Arg Leu Gln Asp Ser Ile Ala Glu Val Arg Val Gly Ala Thr
        450                 455                 460

Val Leu Tyr Asp Ser Ile Pro Ser Ala Glu Glu Glu Thr Ile Thr
465                 470                 475                 480

Lys Ala Thr Ala Leu Phe Glu Thr Ile Arg Arg His Thr Thr Ala Asn
                485                 490                 495

Lys Thr Gln Gly Asn Asp Ser His Arg Pro Gly Asp Ile Ala His Asn
                500                 505                 510

Lys Arg Ile Leu Leu Ile Asp Tyr Glu Asp Ser Phe Val His Thr Leu
            515                 520                 525

Ala Asn Tyr Ile Arg Thr Thr Gly Ala Thr Val Thr Thr Leu Arg His
        530                 535                 540

Gly Phe Ala Glu Ser Tyr Phe Asp Ala Glu Arg Pro Asp Leu Val Val
545                 550                 555                 560

Leu Ser Pro Gly Pro Gly Arg Pro Ser Asp Phe Arg Val Pro Gln Thr
                565                 570                 575

Val Ala Ala Leu Val Gly Arg Glu Ile Pro Ile Phe Gly Val Cys Leu
                580                 585                 590

Gly Leu Gln Gly Ile Val Glu Ala Phe Gly Gly Glu Leu Gly Val Leu
            595                 600                 605

Asp Tyr Pro Gln His Gly Lys Pro Ala Arg Ile Ser Val Thr Ala Pro
        610                 615                 620

Asp Ser Val Leu Phe Gln Asn Leu Pro Ala Ser Phe Ile Val Gly Arg
625                 630                 635                 640

Tyr His Ser Leu Phe Ala Gln Pro Gln Thr Ile Pro Gly Glu Leu Lys
                645                 650                 655

Val Thr Ala Ile Ser Glu Asp Asn Val Ile Met Ala Ile Glu His Gln
                660                 665                 670

Thr Leu Pro Ile Ala Ala Val Gln Phe His Pro Glu Ser Ile Met Thr
            675                 680                 685

Leu Ala Gly Glu Val Gly Gln Thr Ile Ile Lys Asn Val Val Gln Thr
        690                 695                 700

Tyr Thr Gln Thr Leu Glu Thr Ser Ile Tyr Ser
705                 710                 715

<210> SEQ ID NO 82
<211> LENGTH: 719
<212> TYPE: PRT
<213> ORGANISM: Rhodopseudomonas palustris

<400> SEQUENCE: 82

Met Asn Arg Thr Val Phe Ser Leu Pro Ala Thr Ser Asp Tyr Lys Thr
 1               5                  10                  15

Ala Ala Gly Leu Ala Val Thr Arg Ser Ala Gln Pro Phe Ala Gly Gly
             20                  25                  30

Gln Ala Leu Asp Glu Leu Ile Asp Leu Asp His Arg Arg Gly Val
         35                  40                  45

Met Leu Ser Ser Gly Thr Thr Val Pro Gly Arg Tyr Glu Ser Phe Asp
     50                  55                  60
```

-continued

```
Leu Gly Phe Ala Asp Pro Pro Leu Ala Leu Thr Thr Arg Ala Glu Lys
 65                  70                  75                  80

Phe Thr Ile Glu Ala Leu Asn Pro Arg Gly Arg Val Leu Ile Ala Phe
                 85                  90                  95

Leu Ser Asp Lys Leu Glu Glu Pro Cys Val Val Glu Gln Ala Cys
            100                 105                 110

Ala Thr Lys Ile Arg Gly His Ile Val Arg Gly Glu Ala Pro Val Asp
            115                 120                 125

Glu Glu Gln Arg Thr Arg Arg Ala Ser Ala Ile Ser Leu Val Arg Ala
        130                 135                 140

Val Ile Ala Ala Phe Ala Ser Pro Ala Asp Pro Met Leu Gly Leu Tyr
145                 150                 155                 160

Gly Ala Phe Ala Tyr Asp Leu Val Phe Gln Phe Glu Asp Leu Lys Gln
                165                 170                 175

Lys Arg Ala Arg Glu Ala Asp Gln Arg Asp Ile Val Leu Tyr Val Pro
            180                 185                 190

Asp Arg Leu Leu Ala Tyr Asp Arg Ala Thr Gly Arg Gly Val Asp Ile
        195                 200                 205

Ser Tyr Glu Phe Ala Trp Lys Gly Gln Ser Thr Ala Gly Leu Pro Asn
            210                 215                 220

Glu Thr Ala Glu Ser Val Tyr Thr Gln Thr Gly Arg Gln Gly Phe Ala
225                 230                 235                 240

Asp His Ala Pro Gly Asp Tyr Pro Lys Val Val Glu Lys Ala Arg Ala
                245                 250                 255

Ala Phe Ala Arg Gly Asp Leu Phe Glu Ala Val Pro Gly Gln Leu Phe
            260                 265                 270

Gly Glu Pro Cys Glu Arg Ser Pro Ala Glu Val Phe Lys Arg Leu Cys
        275                 280                 285

Arg Ile Asn Pro Ser Pro Tyr Gly Gly Leu Leu Asn Leu Gly Asp Gly
290                 295                 300

Glu Phe Leu Val Ser Ala Ser Pro Glu Met Phe Val Arg Ser Asp Gly
305                 310                 315                 320

Arg Arg Ile Glu Thr Cys Pro Ile Ser Gly Thr Ile Ala Arg Gly Val
                325                 330                 335

Asp Ala Ile Ser Asp Ala Glu Gln Ile Gln Lys Leu Leu Asn Ser Glu
            340                 345                 350

Lys Asp Glu Phe Glu Leu Asn Met Cys Thr Asp Val Asp Arg Asn Asp
        355                 360                 365

Lys Ala Arg Val Cys Val Pro Gly Thr Ile Lys Val Leu Ala Arg Arg
370                 375                 380

Gln Ile Glu Thr Tyr Ser Lys Leu Phe His Thr Val Asp His Val Glu
385                 390                 395                 400

Gly Met Leu Arg Pro Gly Phe Asp Ala Leu Asp Ala Phe Leu Thr His
                405                 410                 415

Ala Trp Ala Val Thr Val Thr Gly Ala Pro Lys Leu Trp Ala Met Gln
            420                 425                 430

Phe Val Glu Asp His Glu Arg Ser Pro Arg Arg Trp Tyr Ala Gly Ala
        435                 440                 445

Phe Gly Val Val Gly Phe Asp Gly Ser Ile Asn Thr Gly Leu Thr Ile
450                 455                 460

Arg Thr Ile Arg Met Lys Asp Gly Leu Ala Glu Val Arg Val Gly Ala
465                 470                 475                 480
```

-continued

Thr Cys Leu Phe Asp Ser Asn Pro Val Ala Glu Asp Lys Glu Cys Gln
                485                 490                 495

Val Lys Ala Ala Ala Leu Phe Gln Ala Leu Arg Gly Asp Pro Ala Lys
            500                 505                 510

Pro Leu Ser Ala Val Ala Pro Asp Ala Thr Gly Ser Gly Lys Lys Val
            515                 520                 525

Leu Leu Val Asp His Asp Asp Ser Phe Val His Met Leu Ala Asp Tyr
        530                 535                 540

Phe Arg Gln Val Gly Ala Gln Val Thr Val Val Arg Tyr Val His Gly
545                 550                 555                 560

Leu Lys Met Leu Ala Glu Asn Ser Tyr Asp Leu Val Leu Ser Pro
                565                 570                 575

Gly Pro Gly Arg Pro Glu Asp Phe Lys Ile Lys Asp Thr Ile Asp Ala
            580                 585                 590

Ala Leu Ala Lys Lys Leu Pro Ile Phe Gly Val Cys Leu Gly Val Gln
        595                 600                 605

Ala Met Gly Glu Tyr Phe Gly Gly Thr Leu Gly Gln Leu Ala Gln Pro
        610                 615                 620

Ala His Gly Arg Pro Ser Arg Ile Gln Val Arg Gly Gly Ala Leu Met
625                 630                 635                 640

Arg Gly Leu Pro Asn Glu Val Thr Ile Gly Arg Tyr His Ser Leu Tyr
                645                 650                 655

Val Asp Met Arg Asp Met Pro Lys Glu Leu Thr Val Thr Ala Ser Thr
            660                 665                 670

Asp Asp Gly Ile Ala Met Ala Ile Glu His Lys Thr Leu Pro Val Gly
        675                 680                 685

Gly Val Gln Phe His Pro Glu Ser Leu Met Ser Leu Gly Gly Glu Val
        690                 695                 700

Gly Leu Arg Ile Val Glu Asn Ala Phe Arg Leu Gly Gln Ala Ala
705                 710                 715

<210> SEQ ID NO 83
<211> LENGTH: 2160
<212> TYPE: DNA
<213> ORGANISM: Rhodopseudomonas palustris

<400> SEQUENCE: 83
atgaacagga ccgttttctc gcttcccgcg accagcgact ataagaccgc cgcgggcctc      60
gcggtgacgc gcagcgccca gccttttgcc ggcggccagg cgctcgacga gctgatcgat     120
ctgctcgacc accgccgcgg cgtgatgctg tcgtccggca aaccgtgcc gggccgctac     180 gagagcttcg acctcggctt tgccgatccg ccgctggcgc tcaccactag gccgaaaaa     240 ttcaccatcg aggcgctcaa tccgcgcggc cgggtgctga tcgcgttcct gtccgacaag     300
cttgaagagc cctgcgtggt ggtggagcag gcctgcgcca ccaagatcag ggccacatc     360 gtccgcggcg aggccccggt cgacgaagaa caacgcaccc gccgcgccag cgcgatctcc     420
ctggtgcgcg cggtgattgc tgccttcgcc tcgccggccg atccgatgct cgggctgtac     480
ggcgccttcg cctacgacct tgtgttccag ttcgaggatc tgaagcagaa gcgtgcccgc     540
gaagccgacc agcgcgacat cgtgctgtac gtgccggatc gcctgctggc ctacgatcgc     600
gccaccggcc gcggcgtcga catttcctac gaattcgcct ggaagggcca gtccaccgcc     660
ggcctgccga acgagaccgc cgagagcgtc tacacccaga ccggccggca gggtttcgcc     720
gaccacgccc cggcgactta tcccaaggtg gtcgagaagg cccgcgcggc gttcgcccgc     780

-continued

```
ggcgacctgt tcgaggcggt gccgggccag ctgttcggcg agccatgcga gcggtcgccg      840
gccgaagtgt tcaagcggtt gtgccggatc aacccgtcgc cctatggcgg cctgctcaat      900
ctcggcgacg gcgaattcct ggtgtcggcc tcgccggaaa tgttcgtccg ctcggacggc      960
cgccggatcg agacctgccc gatctccggc actatcgccc gcggcgtcga tgcgatcagc     1020
gatgctgagc agatccagaa gctcttgaac tccgagaagg acgagttcga gctgaatatg     1080
tgcaccgacg tcgaccgcaa cgacaaggcg cgggtctgcg tgccgggcac gatcaaagtt     1140
ctcgcgcgcc gccagatcga gacctattcg aagctgttcc acaccgtcga tcacgtcgag     1200
ggcatgctgc gaccgggttt cgacgcgctc gacgccttcc tcacccacgc ctgggcggtc     1260
accgtcaccg gcgcgccgaa gctgtgggcg atgcagttcg tcgaggatca cgagcgtagc     1320
ccgcggcgct ggtatgccgg cgcgttcggc gtggtcggct cgatggctc gatcaacacc      1380 ggcctcacca tccgcaccat ccggatgaag gacggcctcg ccgaagttcg cgtcggcgcc     1440
acctgcctgt cgacagcaa tccggtcgcc gaggacaagg aatgccaggt caaggccgcg      1500
gcactgttcc aggcgctgcg cggcgatccc gccaagccgc tgtcggcggt ggcgccggac     1560
gccactggct cgggcaagaa ggtgctgctg gtcgaccacg acgacagctt cgtgcacatg     1620
ctggcggact atttcaggca ggtcggcgcc caggtcaccg tggtgcgcta cgttcacggc     1680
ctgaagatgc tggccgaaaa cagctatgat cttctggtgc tgtcgcccgg tcccggccgg     1740
ccggaggact tcaagatcaa ggatacgatc gacgccgcgc tcgccaagaa gctgccgatc     1800
ttcggcgtct gcctcggcgt ccaggcgatg gcgaatatt ttggcggtac gctcggccag      1860
ctcgcgcagc cggctcacgg ccgcccgtcg cggattcagg tgcgcggcgg cgcgctgatg     1920
cgcggtctcc cgaacgaggt caccatcggc cgctaccact cgctctatgt cgacatgcgc     1980
gacatgccga aggagctgac cgtcaccgcc tccaccgatg acggcatcgc gatggcgatc     2040
gagcacaaga ccctgccggt cggcggcgtg cagttccacc ccgagtcgct gatgtcgctc     2100
ggcggcgagg tcgggctgcg gatcgtcgaa aacgccttcc ggctcggcca ggcggcctaa     2160
```

<210> SEQ ID NO 84
<211> LENGTH: 2190
<212> TYPE: DNA
<213> ORGANISM: Artificial Sequence
<220> FEATURE:
<223> OTHER INFORMATION: An A. tumefaciens mutant.

<400> SEQUENCE: 84

```
atggtaacga tcattcagga tgacggagcg gagacctacg agacgaaagg cggcatccag       60
gtcagccgaa agcgccggcc caccgattat gccaacgcca tcgataatta catcgaaaag      120
cttgattccc atcgcggcgc gttttttttcg tccaactatg aatatccggg ccgttacacc     180
cgctgggata cggccatcgt cgatccgccg ctcggcattt cctgttttgg ccgcaagatg     240
tggatcgaag cctataatgg ccgcggcgaa gtgctgctcg atttcattac ggaaaagctg     300
aaggcgacac ccgatctcac cctcggcgct tcctcgaccc gccggctcga tcttaccgtc     360
aacgaaccgg accgtgtctt caccgaagaa gaacgctcga aaatcccgac ggtcttcacc     420
gctctcagag ccatcgtcga cctcttctat tcgagcgcgg attcggccat cggcctgttc     480
ggtgccttcg gttacgatct cgccttccag ttcgacgcga tcaagctttc gctgcgcgt      540 ccggaagacc agcgtgacat ggtgctgttt ctgcccgatg aaatcctcgt cgttgatcac     600
tattccgcca aggcctggat cgaccgttac gatttcgaga aggacggcat gacgacggac     660
ggcaaatcct ccgacattac ccccgatccc ttcaagacca ccgataccat cccgcccaag     720
```

-continued

```
ggcgatcacc gtcccggcga atattccgag cttgtggtga aggccaagga aagcttccgc      780
cgcggcgacc tgttcgaggt cgttcccggc cagaaattca tggagcgttg cgaaagcaat      840
ccgtcggcga tttcccgccg cctgaaggcg atcaacccgt cgccctattc cttcttcatc      900
aatctcggcg atcaggaata tctggtcggc gcctcgccgg aaatgttcgt gcgcgtctcc      960
ggccgtcgca tcgagacctg cccgatatca ggcaccatca agcgcggcga cgatccgatt     1020
gccgacagcg agcagatttt gaaactgctc aactcgaaaa aggacgaatc cgaactgacc     1080
atgtgctcgg acgtggaccg caacgacaag agccgcgtct gcgagccggg ttcggtgaag     1140
gtcattggcc gccgccagat cgagatgtat tcacgcctca tccacaccgt cgatcacatc     1200
gaaggccgcc tgcgcgacga tatggacgcc tttgacggtt tcctcagcca cgcctgggcc     1260
gtcaccgtca ccggtgcacc aaagctgtgg gccatgcgct tcatcgaagg tcatgaaaag     1320
agcccgcgcg cctggtatgg cggtgcgatc ggcatggtcg gcttcaacgg cgacatgaat     1380
accggcctga cgctgcgcac catccggatc aaggacggta ttgccgaagt gcgcgccggc     1440
gcgaccctgc tcaatgattc caacccgcag gaagaagaag ccgaaaccga actgaaggcc     1500
tccgccatga tatcagccat tcgtgacgca aaaggcacca actctgccgc caccaagcgt     1560
gatgccgcca agtcggcac cggcgtcaag atcctgctcg tcgaccacga agacagcttc     1620
gtgcacacgc tggcgaatta tttccgccag acgggcgcga cggtctcgac cgtcagatca     1680
ccggtcgcag ccgacgtgtt cgatcgcttc cagccggacc tcgttgtcct gtcgcccgga     1740
cccggcagcc cgacggattt cgactgcaag gcaacgatca aggccgcccg cgcccgcgat     1800
ctgccgatct tcggcgtttg cctcggtctg caggcattgg cagaagccta tggcggcgag     1860
ctgcgccagc ttgctgtgcc catgcacggc aagccttcgc gcatccgcgt gctggaaccc     1920
ggcctcgtct tctccggtct cggcaaggaa gtcacggtcg gtcgttacca ttcgatcttc     1980
gccgatcccg ccaccctgcc gcgtgatttc atcatcaccg cagaaagcga ggacggcacg     2040
atcatgggca tcgaacacgc caaggaaccg gtggccgccg ttcagttcca cccggaatcg     2100
atcatgacgc tcggacagga cgcgggcatg cggatgatcg agaatgtcgt ggtgcatctg     2160
acccgcaagg cgaagaccaa ggccgcgtga                                       2190
```

<210> SEQ ID NO 85
<211> LENGTH: 2190
<212> TYPE: DNA
<213> ORGANISM: Artificial Sequence
<220> FEATURE:
<223> OTHER INFORMATION: An A. tumefaciens mutant.

<400> SEQUENCE: 85

```
atggtaacga tcattcagga tgacggagcg gagacctacg agacgaaagg cggcatccag       60
gtcagccgaa agcgccggcc caccgattat gccaacgcca tcgataatta catcgaaaag      120
cttgattccc atcgcggcgc gtattttcg tccaactatg aatatccggg ccgttacacc       180
cgctgggata cggccatcgt cgatccgccg ctcggcattt cctgttttgg ccgcaagatg      240
tggatcgaag cctataatgg ccgcggcgaa gtgctgctcg atttcattac ggaaaagctg      300
aaggcgacac ccgatctcac cctcggcgct tcctcgaccc gccggctcga tcttaccgtc      360
aacgaaccgg accgtgtctt caccgaagaa gaacgctcga aaatcccgac ggtcttcacc      420
gctctcagag ccatcgtcga cctcttctat tcgagcgcgg attcggccat cggcctgttc      480
ggtgccttcg gttacgatct cgccttccag ttcgacgcga tcaagctttc gctggcgcgt      540
```

-continued

```
ccggaagacc agcgtgacat ggtgctgttt ctgcccgatg aaatcctcgt cgttgatcac      600
tattccgcca aggcctggat cgaccgttac gatttcgaga aggacggcat gacgacggac      660
ggcaaatcct ccgacattac ccccgatccc ttcaagacca ccgataccat cccgcccaag      720
ggcgatcacc gtcccggcga atattccgag cttgtggtga aggccaagga aagcttccgc      780
cgcggcgacc tgttcgaggt cgttcccggc cagaaattca tggagcgttg cgaaagcaat      840
ccgtcggcga tttccgccg cctgaaggcg atcaacccgt cgccctattc cttcttcatc       900
aatctcggcg atcaggaata tctggtcggc gcctcgccgg aaatgttcgt gcgcgtctcc      960
ggccgtcgca tcgagacctg cccgatatca ggcaccatca agcgcggcga cgatccgatt     1020
gccgacagcg agcagatttt gaaactgctc aactcgaaaa aggacgaatc cgaactgacc     1080
atgtgctcgg acgtggaccg caacgacaag agccgcgtct gcgagccggg ttcggtgaag     1140
gtcattggcc gccgccagat cgagatgtat tcacgcctca tccacaccgt cgatcacatc     1200
gaaggccgcc tgcgcgacga tatggacgcc tttgacggtt tcctcagcca cgcctgggcc     1260
gtcaccgtca ccggtgcacc aaagctgtgg gccatgcgct tcatcgaagg tcatgaaaag     1320
agcccgcgcg cctggtatgg cggtgcgatc ggcatggtcg gcttcaacgg cgacatgaat     1380
accggcctga cgctgcgcac catccggatc aaggacggta ttgccgaagt gcgcgccggc     1440
gcgaccctgc tcaatgattc caacccgcag gaagaagaag ccgaaaccga actgaaggcc     1500
tccgccatga tatcagccat cgtgacgca aaaggcacca actctgccgc caccaagcgt      1560
gatgccgcca agtcggcac cggcgtcaag atcctgctcg tcgaccacga agacagcttc      1620
gtgcacacgc tggcgaatta tttccgccag acgggcgcga cggtctcgac cgtcagatca     1680
ccggtcgcag ccgacgtgtt cgatcgcttc cagccggacc tcgttgtcct gtcgcccgga     1740
cccggcagcc cgacggattt cgactgcaag gcaacgatca aggccgcccg cgcccgcgat     1800
ctgccgatct tcggcgtttg cctcggtctg caggcattgg cagaagccta tggcggcgag     1860
ctgcgccagc ttgctgtgcc catgcacggc aagccttcgc gcatccgcgt gctggaaccc     1920
ggcctcgtct tctccggtct cggcaaggaa gtcacggtcg gtcgttacca ttcgatcttc     1980
gccgatcccg ccaccctgcc gcgtgatttc atcatcaccg cagaaagcga ggacggcacg     2040
atcatgggca tcgaacacgc caaggaaccg gtggccgccg ttcagttcca cccggaatcg     2100
atcatgacgc tcggacagga cgcgggcatg cggatgatcg agaatgtcgt ggtgcatctg     2160
acccgcaagg cgaagaccaa ggccgcgtga                                       2190
```

<210> SEQ ID NO 86
<211> LENGTH: 2190
<212> TYPE: DNA
<213> ORGANISM: Artificial Sequence
<220> FEATURE:
<223> OTHER INFORMATION: An A. tumefaciens mutant.

<400> SEQUENCE: 86

```
atggtaacga tcattcagga tgacggagcg gagacctacg agacgaaagg cggcatccag       60
gtcagccgaa agcgccggcc caccgattat gccaacgcca tcgataatta catcgaaaag      120
cttgattccc atcgcggcgc ggttttttcg ttcaactatg aatatccggg ccgttacacc      180
cgctgggata cggccatcgt cgatccgccg ctcggcattt cctgttttgg ccgcaagatg      240
tggatcgaag cctataatgg ccgcggcgaa gtgctgctcg atttcattac ggaaaagctg      300
aaggcgacac ccgatctcac cctcggcgct tcctcgaccc gccggctcga tcttaccgtc      360
aacgaaccgg accgtgtctt caccgaagaa gaacgctcga aaatcccgac ggtcttcacc      420
```

-continued

```
gctctcagag ccatcgtcga cctcttctat tcgagcgcgg attcggccat cggcctgttc      480
ggtgccttcg gttacgatct cgccttccag ttcgacgcga tcaagctttc gctggcgcgt      540
ccggaagacc agcgtgacat ggtgctgttt ctgcccgatg aaatcctcgt cgttgatcac      600
tattccgcca aggcctggat cgaccgttac gatttcgaga aggacggcat gacgacggac      660
ggcaaatcct ccgacattac ccccgatccc ttcaagacca ccgataccat cccgcccaag      720
ggcgatcacc gtcccggcga atattccgag cttgtggtga aggccaagga aagcttccgc      780
cgcggcgacc tgttcgaggt cgttcccggc cagaaattca tggagcgttg cgaaagcaat      840
ccgtcggcga tttccgcccg cctgaaggcg atcaacccgt cgccctattc cttcttcatc      900
aatctcggcg atcaggaata tctggtcggc gcctcgccgg aaatgttcgt gcgcgtctcc      960
ggccgtcgca tcgagacctg cccgatatca ggcaccatca agcgcggcga cgatccgatt     1020
gccgacagcg agcagatttt gaaactgctc aactcgaaaa aggacgaatc cgaactgacc     1080
atgtgctcgg acgtggaccg caacgacaag agccgcgtct gcgagccggg ttcggtgaag     1140
gtcattggcc gccgcagat cgagatgtat tcacgcctca tccacaccgt cgatcacatc     1200
gaaggccgcc tgcgcgacga tatggacgcc tttgacggtt cctcagcca cgcctgggcc     1260 gtcaccgtca ccggtgcacc aaagctgtgg gccatgcgct tcatcgaagg tcatgaaaag     1320
agcccgcgcg cctggtatgg cggtgcgatc ggcatggtcg gcttcaacgg cgacatgaat     1380
accggcctga cgctgcgcac catccggatc aaggacggta ttgccgaagt gcgcgccggc     1440
gcgaccctgc tcaatgattc caacccgcag gaagaagaag ccgaaaccga actgaaggcc     1500
tccgccatga tatcagccat tcgtgacgca aaaggcacca actctgccgc caccaagcgt     1560
gatgccgcca aagtcggcac cggcgtcaag atcctgctcg tcgaccacga agacagcttc     1620
gtgcacacgc tggcgaatta tttccgccag acgggcgcga cggtctcgac cgtcagatca     1680
ccggtcgcag ccgacgtgtt cgatcgcttc cagccggacc tcgttgtcct gtcgcccgga     1740
cccggcagcc cgacggattt cgactgcaag gcaacgatca aggccgcccg cgcccgcgat     1800
ctgccgatct tcggcgtttg cctcggtctg caggcattgg cagaagccta tggcggcgag     1860
ctgcgccagc ttgctgtgcc catgcacggc aagccttcgc gcatccgcgt gctggaaccc     1920
ggcctcgtct tctccggtct cggcaaggaa gtcacggtcg tcgttaccat tcgatcttc     1980 gccgatcccg ccaccctgcc gcgtgatttc atcatcaccg cagaaagcga ggacggcacg     2040
atcatgggca tcgaacacgc caaggaaccg gtggccgcca ttcagttcca cccggaatcg     2100
atcatgacgc tcggacagga cgcgggcatg cggatgatcg agaatgtcgt ggtgcatctg     2160
acccgcaagg cgaagaccaa ggccgcgtga                                      2190
```

<210> SEQ ID NO 87
<211> LENGTH: 2190
<212> TYPE: DNA
<213> ORGANISM: Artificial Sequence
<220> FEATURE:
<223> OTHER INFORMATION: An A. tumefaciens mutant.

<400> SEQUENCE: 87

```
atggtaacga tcattcagga tgacggagcg gagacctacg agacgaaagg cggcatccag       60
gtcagccgaa agcgccggcc caccgattat gccaacgcca tcgataatta catcgaaaag      120
cttgattccc atcgcggcgc ggttttttcg tgcaactatg aatatccggg ccgttacacc      180
cgctgggata cggccatcgt cgatccgccg ctcggcattt cctgtttggg ccgcaagatg      240
```

```
tggatcgaag cctataatgg ccgcggcgaa gtgctgctcg atttcattac ggaaaagctg        300
aaggcgacac ccgatctcac cctcggcgct tcctcgaccc gccggctcga tcttaccgtc        360
aacgaaccgg accgtgtctt caccgaagaa gaacgctcga aaatcccgac ggtcttcacc        420
gctctcagag ccatcgtcga cctcttctat tcgagcgcgg attcggccat cggcctgttc        480
ggtgccttcg gttacgatct cgccttccag ttcgacgcga tcaagctttc gctggcgcgt        540
ccggaagacc agcgtgacat ggtgctgttt ctgcccgatg aaatcctcgt cgttgatcac        600
tattccgcca aggcctggat cgaccgttac gatttcgaga aggacggcat gacgacggac        660
ggcaaatcct ccgacattac ccccgatccc ttcaagacca ccgataccat cccgcccaag        720
ggcgatcacc gtcccggcga atattccgag cttgtggtga aggccaagga aagcttccgc        780
cgcggcgacc tgttcgaggt cgttcccggc cagaaattca tggagcgttg cgaaagcaat        840
ccgtcggcga tttccgcccg cctgaaggcg atcaacccgt cgccctattc cttcttcatc        900
aatctcggcg atcaggaata tctggtcggc gcctcgccgg aaatgttcgt gcgcgtctcc        960
ggccgtcgca tcgagacctg cccgatatca ggcaccatca agcgcggcga cgatccgatt       1020
gccgacagcg agcagatttt gaaactgctc aactcgaaaa aggacgaatc cgaactgacc       1080
atgtgctcgg acgtggaccg caacgacaag agccgcgtct gcgagccggg ttcggtgaag       1140
gtcattggcc gccgccagat cgagatgtat tcacgcctca tccacaccgt cgatcacatc       1200
gaaggccgcc tgcgcgacga tatggacgcc tttgacggtt tcctcagcca cgcctgggcc       1260
gtcaccgtca ccggtgcacc aaagctgtgg gccatgcgct tcatcgaagg tcatgaaaag       1320
agcccgcgcg cctggtatgg cggtgcgatc ggcatggtcg gcttcaacgg cgacatgaat       1380
accgccctga cgctgcgcac catccggatc aaggacggta ttgccgaagt gcgcgccggc       1440
gcgaccctgc tcaatgattc caacccgcag gaagaagaag ccgaaaccga actgaaggcc       1500
tccgccatga tatcagccat tcgtgacgca aaaggcacca actctgccgc caccaagcgt       1560
gatgccgcca aagtcggcac cggcgtcaag atcctgctcg tcgaccacga agacagcttc       1620
gtgcacacgc tggcgaatta tttccgccaa acgggcgcga cggtctcgac cgtcagatca       1680
ccggtcgcag ccgacgtgtt cgatcgcttc cagccggacc tcgttgtcct gtcgcccgga       1740
cccggcagcc cgacggattt cgactgcaag gcaacgatca aggccgcccg cgcccgcgat       1800
ctgccgatct tcggcgtttg cctcggtctg caggcattgg cagaagccta tggcggcgag       1860
ctgcgccagc ttgctgtgcc catgcacggc aagccttcgc gcatccgcgt gctggaaccc       1920
ggcctcgtct tctccggtct cggcaaggaa gtcacggtcg gtcgttacca ttcgatcttc       1980
gccgatcccg ccaccctgcc gcgtgatttc atcatcaccg cagaaagcga ggacggcacg       2040
atcatgggca tcgaacacgc caaggaaccg gtggccgccg ttcagttcca cccggaatcg       2100
atcatgacgc tcggacagga cgcgggcatg cggatgatcg agaatgtcgt ggtgcatctg       2160
acccgcaagg cgaagaccaa ggccgcgtga                                        2190
```

<210> SEQ ID NO 88
<211> LENGTH: 2190
<212> TYPE: DNA
<213> ORGANISM: Artificial Sequence
<220> FEATURE:
<223> OTHER INFORMATION: An A. tumefaciens mutant.

<400> SEQUENCE: 88

```
atggtaacga tcattcagga tgacggagcg gagacctacg agacgaaagg cggcatccag         60
gtcagccgaa agcgccggcc caccgattat gccaacgcca tcgataatta catcgaaaag        120
```

-continued

```
cttgattccc atcgcggcgc ggttttttcg tccttctatg aatatccggg ccgttacacc      180
cgctgggata cggccatcgt cgatccgccg ctcggcattt cctgttttgg ccgcaagatg      240
tggatcgaag cctataatgg ccgcggcgaa gtgctgctcg atttcattac ggaaaagctg      300
aaggcgacac ccgatctcac cctcggcgct tcctcgaccc gccggctcga tcttaccgtc      360
aacgaaccgg accgtgtctt caccgaagaa gaacgctcga aaatcccgac ggtcttcacc      420
gctctcagag ccatcgtcga cctcttctat tcgagcgcgg attcggccat cggcctgttc      480
ggtgccttcg gttacgatct cgccttccag ttcgacgcga tcaagctttc gctggcgcgt      540
ccggaagacc agcgtgacat ggtgctgttt ctgcccgatg aaatcctcgt cgttgatcac      600
tattccgcca aggcctggat cgaccgttac gatttcgaga aggacggcat gacgacggac      660
ggcaaatcct ccgacattac ccccgatccc ttcaagacca ccgataccat cccgcccaag      720
ggcgatcacc gtcccggcga atattccgag cttgtggtga aggccaagga aagcttccgc      780
cgcggcgacc tgttcgaggt cgttcccggc cagaaattca tggagcgttg cgaaagcaat      840
ccgtcggcga tttcccgccg cctgaaggcg atcaacccgt cgccctattc cttcttcatc      900
aatctcggcg atcaggaata tctggtcggc gcctcgccgg aaatgttcgt gcgcgtctcc      960
ggccgtcgca tcgagacctg cccgatatca ggcaccatca agcgcggcga cgatccgatt     1020
gccgacagcg agcagatttt gaaactgctc aactcgaaaa aggacgaatc cgaactgacc     1080
atgtgctcgg acgtgaccg caacgacaag agccgcgtct gcgagccggg ttcggtgaag     1140
gtcattggcc gccgccagat cgagatgtat tcacgcctca tccacaccgt cgatcacatc     1200
gaaggccgcc tgcgcgacga tatggacgcc tttgacggtt tcctcagcca cgcctgggcc     1260
gtcaccgtca ccggtgcacc aaagctgtgg gccatgcgct tcatcgaagg tcatgaaaag     1320
agcccgcgcg cctggtatgg cggtgcgatc ggcatggtcg gcttcaacgg cgacatgaat     1380
accggcctga cgctgcgcac catccggatc aaggacggta ttgccgaagt gcgcgccggc     1440
gcgaccctgc tcaatgattc caacccgcag gaagaagaag ccgaaaccga actgaaggcc     1500
tccgccatga tatcagccat tcgtgacgca aaaggcacca actctgccgc caccaagcgt     1560
gatgccgcca agtcggcac cggcgtcaag atcctgctcg tcgaccacga agacagcttc     1620
gtgcacacgc tggcgaatta ttttccgcca acgggcgcga cggtctcgac cgtcagatca     1680
ccggtcgcag ccgacgtgtt cgatcgcttc cagccggacc tcgttgtcct gtcgcccgga     1740
cccggcagcc cgacggattt cgactgcaag gcaacgatca aggccgcccg cgcccgcgat     1800
ctgccgatct tcggcgtttg cctcggtctg caggcattgg cagaagccta tgcggcgag      1860 ctgcgccagc ttgctgtgcc catgcacggc aagccttcgc gcatccgcgt gctggaaccc     1920
ggcctcgtct tctccggtct cggcaaggaa gtcacggtcg gtcgttacca ttcgatcttc     1980
gccgatcccg ccaccctgcc gcgtgatttc atcatcaccg cagaaagcga ggacggcacg     2040
atcatgggca tcgaacacgc caaggaaccg gtggccgccg ttcagttcca cccggaatcg     2100
atcatgacgc tcggacagga cgcgggcatg cggatgatcg agaatgtcgt ggtgcatctg     2160
acccgcaagg cgaagaccaa ggccgcgtga                                      2190
```

<210> SEQ ID NO 89
<211> LENGTH: 2190
<212> TYPE: DNA
<213> ORGANISM: Artificial Sequence
<220> FEATURE:
<223> OTHER INFORMATION: An A. tumefaciens mutant.

<400> SEQUENCE: 89

```
atggtaacga tcattcagga tgacggagcg gagacctacg agacgaaagg cggcatccag      60
gtcagccgaa agcgccggcc caccgattat gccaacgcca tcgataatta catcgaaaag     120
cttgattccc atcgcggcgc ggttttttcg tccaactatg aatatccggg ccgttacacc     180
cgctgggata cggccatcgt cgatccgccg ctcggcattt cctgttttgg ccgcaagatg     240
tggatcgaag cctataatgg ccgcggcgaa gtgctgctcg atttcattac ggaaaagctg     300
aaggcgacac ccgatctcac cctcggcgct tcctcgaccc gccggctcga tcttaccgtc     360
aacgaaccgg accgtgtctt caccgaagaa gaacgctcga aaatcccgac ggtcttcacc     420
gctctcagag ccatcgtcga cctcttctat tcgagcgcgg attcggccat cggcctgttc     480
ggtgccttcg gttacgatct cgccttccag ttcgacgcga tcaagctttc gctggcgcgt     540
ccggaagacc agcgtgacat ggtgctgttt ctgcccgatg aaatcctcgt cgttgatcac     600
tattccgcca aggcctggat cgaccgttac gatttcgaga aggacggcat gacgacggac     660
ggcaaatcct ccgacattac ccccgatccc ttcaagacca ccgataccat cccgcccaag     720
ggcgatcacc gtcccggcga atattccgag cttgtggtga aggccaagga aagcttccgc     780
cgcggcgacc tgttcgaggt cgttcccggc cagaaattca tggagcgttg cgaaagcaat     840
ccgtcggcga tttcccgccg cctgaaggcg atcaacgcgt cgccctattc cttcttcatc     900
aatctcggcg atcaggaata tctggtcggc gcctcgccgg aaatgttcgt gcgcgtctcc     960
ggccgtcgca tcgagacctg cccgatatca ggcaccatca agcgcggcga cgatccgatt    1020
gccgacagcg agcagatttt gaaactgctc aactcgaaaa aggacgaatc cgaactgacc    1080
atgtgctcgg acgtggaccg caacgacaag agccgcgtct gcgagccggg ttcggtgaag    1140
gtcattggcc gccgccagat cgagatgtat tcacgcctca tccacaccgt cgatcacatc    1200
gaaggccgcc tgcgcgacga tatggacgcc tttgacggtt tcctcagcca cgcctgggcc    1260
gtcaccgtca ccggtgcacc aaagctgtgg gccatgcgct tcatcgaagg tcatgaaaag    1320
agcccgcgcg cctggtatgg cggtgcgatc ggcatggtcg gcttcaacgg cgacatgaat    1380
accggcctga cgctgcgcac catccggatc aaggacggta ttgccgaagt gcgcgccggc    1440
gcgaccctgc tcaatgattc caacccgcag gaagaagaag ccgaaaccga actgaaggcc    1500
tccgccatga tatcagccat tcgtgacgca aaaggcacca actctgccgc caccaagcgt    1560
gatgccgcca agtcggcac cggcgtcaag atcctgctcg tcgaccacga agacagcttc    1620
gtgcacacgc tggcgaatta tttccgccag acgggcgcga cggtctcgac cgtcagatca    1680
ccggtcgcag ccgacgtgtt cgatcgcttc cagccggacc tcgttgtcct gtcgcccgga    1740
cccggcagcc cgacggattt cgactgcaag gcaacgatca aggccgcccg cgcccgcgat    1800
ctgccgatct tcggcgtttg cctcggtctg caggcattgg cagaagccta tggcggcgag    1860
ctgcgccagc ttgctgtgcc catgcacggc aagcttcgc gcatccgcgt gctggaaccc    1920
ggcctcgtct tctccggtct cggcaaggaa gtcacggtcg gtcgttacca ttcgatcttc    1980
gccgatcccg ccaccctgcc gcgtgatttc atcatcaccg cagaaagcga ggacggcacg    2040
atcatgggca tcgaacacgc caaggaaccg gtggccgccg ttcagttcca cccggaatcg    2100
atcatgacgc tcggacagga cgcgggcatg cggatgatca gaatgtcgt ggtgcatctg    2160
acccgcaagg cgaagaccaa ggccgcgtga                                     2190
```

<210> SEQ ID NO 90
<211> LENGTH: 2190

<212> TYPE: DNA
<213> ORGANISM: Artificial Sequence
<220> FEATURE:
<223> OTHER INFORMATION: An A. tumefaciens mutant.

<400> SEQUENCE: 90

| | | | | | |
|---|---|---|---|---|---|
| atggtaacga | tcattcagga | tgacggagcg | gagacctacg | agacgaaagg | cggcatccag | 60 |
| gtcagccgaa | agcgccggcc | caccgattat | gccaacgcca | tcgataatta | catcgaaaag | 120 |
| cttgattccc | atcgcggcgc | ggttttttcg | tccaactatg | aatatccggg | ccgttacacc | 180 |
| cgctgggata | cggccatcgt | cgatccgccg | ctcggcattt | cctgttttgg | ccgcaagatg | 240 |
| tggatcgaag | cctataatgg | ccgcggcgaa | gtgctgctcg | atttcattac | ggaaaagctg | 300 |
| aaggcgacac | ccgatctcac | cctcggcgct | cctcgaccc | gccggctcga | tcttaccgtc | 360 |
| aacgaaccgg | accgtgtctt | caccgaagaa | gaacgctcga | aaatcccgac | ggtcttcacc | 420 |
| gctctcagag | ccatcgtcga | cctcttctat | tcgagcgcgg | attcggccat | cggcctgttc | 480 |
| ggtgccttcg | gttacgatct | cgccttccag | ttcgacgcga | tcaagctttc | gctggcgcgt | 540 |
| ccggaagacc | agcgtgacat | ggtgctgttt | ctgcccgatg | aaatcctcgt | cgttgatcac | 600 |
| tattccgcca | aggcctggat | cgaccgttac | gatttcgaga | aggacggcat | gacgacggac | 660 |
| ggcaaatcct | ccgacattac | ccccgatccc | ttcaagacca | ccgataccat | cccgcccaag | 720 |
| ggcgatcacc | gtcccggcga | atattccgag | cttgtggtga | aggccaagga | aagcttccgc | 780 |
| cgcggcgacc | tgttcgaggt | cgttcccggc | cagaaattca | tggagcgttg | cgaaagcaat | 840 |
| ccgtcggcga | tttcccgccg | cctgaaggcg | atcaacgggt | cgccctattc | cttcttcatc | 900 |
| aatctcggcg | atcaggaata | tctggtcggc | gcctcgccgg | aaatgttcgt | gcgcgtctcc | 960 |
| ggccgtcgca | tcgagacctg | cccgatatca | ggcaccatca | agcgcggcga | cgatccgatt | 1020 |
| gccgacagcg | agcagatttt | gaaactgctc | aactcgaaaa | aggacgaatc | cgaactgacc | 1080 |
| atgtgctcgg | acgtggaccg | caacgacaag | agccgcgtct | gcgagccggg | ttcggtgaag | 1140 |
| gtcattggcc | gccgccagat | cgagatgtat | tcacgcctca | tccacaccgt | cgatcacatc | 1200 |
| gaaggccgcc | tgcgcgacga | tatggacgcc | tttgacggtt | tcctcagcca | cgcctgggcc | 1260 |
| gtcaccgtca | ccggtgcacc | aaagctgtgg | gccatgcgct | tcatcgaagg | tcatgaaaag | 1320 |
| agcccgcgcg | cctggtatgg | cggtgcgatc | ggcatggtcg | gcttcaacgg | cgacatgaat | 1380 |
| accggcctga | cgctgcgcac | catccggatc | aaggacggta | ttgccgaagt | gcgcgccggc | 1440 |
| gcgaccctgc | tcaatgattc | caacccgcag | gaagaagaag | ccgaaaccga | actgaaggcc | 1500 |
| tccgccatga | tatcagccat | cgtgacgca | aaaggcacca | actctgccgc | caccaagcgt | 1560 |
| gatgccgcca | agtcggcac | cggcgtcaag | atcctgctcg | tcgaccacga | agacagcttc | 1620 |
| gtgcacacgc | tggcgaatta | tttccgccag | acgggcgcga | cggtctcgac | cgtcagatca | 1680 |
| ccggtcgcag | ccgacgtgtt | cgatcgcttc | cagccggacc | tcgttgtcct | gtcgcccgga | 1740 |
| cccggcagcc | cgacggattt | cgactgcaag | gcaacgatca | aggccgcccg | cgcccgcgat | 1800 |
| ctgccgatct | tcggcgttg | cctcggtctg | caggcattgg | cagaagccta | tggcggcgag | 1860 |
| ctgcgccagc | ttgctgtgcc | catgcacggc | aagccttcgc | gcatccgcgt | gctggaaccc | 1920 |
| ggcctcgtct | tctccggtct | cggcaaggaa | gtcacggtcg | tcgttacca | ttcgatcttc | 1980 |
| gccgatcccg | ccaccctgcc | gcgtgatttc | atcatcaccg | cagaaagcga | ggacggcacg | 2040 |
| atcatgggca | tcgaacacgc | caaggaaccg | gtgccgccg | ttcagttcca | cccgaatcg | 2100 |
| atcatgacgc | tcggacagga | cgcgggcatg | cggatgatcg | agaatgtcgt | ggtgcatctg | 2160 |

|  |  |
|---|---:|
| acccgcaagg cgaagaccaa ggccgcgtga | 2190 |

<210> SEQ ID NO 91
<211> LENGTH: 2190
<212> TYPE: DNA
<213> ORGANISM: Artificial Sequence
<220> FEATURE:
<223> OTHER INFORMATION: An A. tumefaciens mutant.

<400> SEQUENCE: 91

|  |  |
|---|---:|
| atggtaacga tcattcagga tgacggagcg gagacctacg agacgaaagg cggcatccag | 60 |
| gtcagccgaa agcgccggcc caccgattat gccaacgcca tcgataatta catcgaaaag | 120 |
| cttgattccc atcgcggcgc ggttttttcg tccaactatg aatatccggg ccgttacacc | 180 |
| cgctgggata cggccatcgt cgatccgccg ctcggcattt cctgttttgg ccgcaagatg | 240 |
| tggatcgaag cctataatgg ccgcggcgaa gtgctgctcg atttcattac ggaaaagctg | 300 |
| aaggcgacac ccgatctcac cctcggcgct tcctcgaccc gccggctcga tcttaccgtc | 360 |
| aacgaaccgg accgtgtctt caccgaagaa gaacgctcga aaatcccgac ggtcttcacc | 420 |
| gctctcagag ccatcgtcga cctcttctat tcgagcgcgg attcggccat cggcctgttc | 480 |
| ggtgccttcg gttacgatct cgccttccag ttcgacgcga tcaagctttc gctggcgcgt | 540 |
| ccggaagacc agcgtgacat ggtgctgttt ctgcccgatg aaatcctcgt cgttgatcac | 600 |
| tattccgcca aggcctggat cgaccgttac gatttcgaga aggacggcat gacgacggac | 660 |
| ggcaaatcct ccgacattac ccccgatccc ttcaagacca ccgataccat cccgcccaag | 720 |
| ggcgatcacc gtcccggcga atattccgag cttgtggtga aggccaagga aagcttccgc | 780 |
| cgcggcgacc tgttcgaggt cgttcccggc cagaaattca tggagcgttg cgaaagcaat | 840 |
| ccgtcggcga tttccgccg cctgaaggcg atcaacccgt cgccctattc ctggttcatc | 900 |
| aatctcggcg atcaggaata tctggtcggc gcctcgccgg aaatgttcgt gcgcgtctcc | 960 |
| ggccgtcgca tcgagacctg cccgatatca ggcaccatca agcgcggcga cgatccgatt | 1020 |
| gccgacagcg agcagatttt gaaactgctc aactcgaaaa aggacgaatc cgaactgacc | 1080 |
| atgtgctcgg acgtggaccg caacgacaag agccgcgtct gcgagccggg ttcggtgaag | 1140 |
| gtcattggcc gccgcagat cgagatgtat tcacgcctca tccacaccgt cgatcacatc | 1200 |
| gaaggccgcc tgcgcgacga tatggacgcc tttgacggtt tcctcagcca cgcctgggcc | 1260 |
| gtcaccgtca ccggtgcacc aaagctgtgg gccatgcgct tcatcgaagg tcatgaaaag | 1320 |
| agcccgcgcg cctggtatgg cggtgcgatc ggcatggtcg gcttcaacgg cgacatgaat | 1380 |
| accggcctga cgctgcgcac catccggatc aaggacggta ttgccgaagt gcgcgccggc | 1440 |
| gcgaccctgc tcaatgattc caacccgcag gaagaagaag ccgaaaccga actgaaggcc | 1500 |
| tccgccatga tatcagccat tcgtgacgca aaaggcacca actctgccgc caccaagcgt | 1560 |
| gatgccgcca agtcggcac cggcgtcaag atcctgctcg tcgaccacga agacagcttc | 1620 |
| gtgcacacgc tggcgaatta tttccgccag acgggcgcga cggtctcgac cgtcagatca | 1680 |
| ccggtcgcag ccgacgtgtt cgatcgcttc cagccggacc tcgttgtcct gtcgcccgga | 1740 |
| cccggcagcc cgacggattt cgactgcaag gcaacgatca aggccgcccg cgcccgcgat | 1800 |
| ctgccgatct tcggcgtttg cctcggtctg caggcattgg cagaagccta tggcggcgag | 1860 |
| ctgcgccagc ttgctgtgcc catgcacggc aagccttcgc gcatccgcgt gctggaaccc | 1920 |
| ggcctcgtct tctccggtct cggcaaggaa gtcacggtcg tcgttacca ttcgatcttc | 1980 |
| gccgatcccg ccacccctgcc gcgtgatttc atcatcaccg cagaaagcga ggacggcacg | 2040 |

```
atcatgggca tcgaacacgc caaggaaccg gtggccgccg ttcagttcca cccggaatcg   2100
atcatgacgc tcggacagga cgcgggcatg cggatgatcg agaatgtcgt ggtgcatctg   2160
acccgcaagg cgaagaccaa ggccgcgtga                                    2190

<210> SEQ ID NO 92
<211> LENGTH: 2190
<212> TYPE: DNA
<213> ORGANISM: Artificial Sequence
<220> FEATURE:
<223> OTHER INFORMATION: An A. tumefaciens mutant.

<400> SEQUENCE: 92
atggtaacga tcattcagga tgacggagcg gagacctacg agacgaaagg cggcatccag     60
gtcagccgaa agcgccggcc caccgattat gccaacgcca tcgataatta catcgaaaag    120
cttgattccc atcgcggcgc ggttttaag tccaactatg aatatccggg ccgttacacc     180
cgctgggata cggccatcgt cgatccgccg ctcggcattt cctgttttgg ccgcaagatg    240
tggatcgaag cctataatgg ccgcggcgaa gtgctgctcg atttcattac ggaaaagctg    300
aaggcgacac ccgatctcac cctcggcgct tcctcgaccc gccggctcga tcttaccgtc    360
aacgaaccgg accgtgtctt caccgaagaa gaacgctcga aaatcccgac ggtcttcacc    420
gctctcagag ccatcgtcga cctcttctat tcgagcgcgg attcggccat cggcctgttc    480
ggtgccttcg gttacgatct cgccttccag ttcgacgcga tcaagctttc gctggcgcgt    540
ccggaagacc agcgtgacat ggtgctgttt ctgcccgatg aaatcctcgt cgttgatcac    600
tattccgcca aggcctggat cgaccgttac gatttcgaga aggacggcat gacgacggac    660
ggcaaatcct ccgacattac ccccgatccc ttcaagacca ccgataccat cccgcccaag    720
ggcgatcacc gtcccggcga atattccgag cttgtggtga aggccaagga aagcttccgc    780
cgcggcgacc tgttcgaggt cgttcccggc cagaaattca tggagcgttg cgaaagcaat    840
ccgtcggcga tttccgccg cctgaaggcg atcaacccgt cgccctattc cttcttcatc    900
aatctcggcg atcaggaata tctggtcggc gcctcgccgg aaatgttcgt gcgcgtctcc    960
ggccgtcgca tcgagacctg cccgatatca ggcaccatca agcgcggcga cgatccgatt   1020
gccgacagcg agcagatttt gaaactgctc aactcgaaaa aggacgaatc cgaactgacc   1080
atgtgctcgg acgtggaccg caacgacaag agccgcgtct gcgagccggg ttcggtgaag   1140
gtcattggcc gccgccagat cgagatgtat tcacgcctca tccacaccgt cgatcacatc   1200
gaaggccgcc tgcgcgacga tatggacgcc tttgacggtt tcctcagcca cgcctgggcc   1260
gtcaccgtca ccggtgcacc aaagctgtgg gccatgcgct catcgaaggg tcatgaaaag   1320
agcccgcgcg cctggtatgg cggtgcgatc ggcatggtcg gcttcaacgg cgacatgaat   1380
accgccctga cgctgcgcac catccggatc aaggacggta ttgccgaagt gcgcgccggc   1440
gcgaccctgc tcaatgattc caacccgcag gaagaagaag ccgaaaccga actgaaggcc   1500
tccgccatga tatcagccat tcgtgacgca aaaggcacca actctgccgc caccaagcgt   1560
gatgccgcca aagtcggcac cggcgtcaag atcctgctcg tcgaccacga agacagcttc   1620
gtgcacacgc tggcgaatta tttccgccag acgggcgcga cggtctcgac cgtcagatca   1680
ccggtcgcag ccgacgtgtt cgatcgcttc cagccggacc tcgttgtcct gtcgcccgga   1740
cccggcagcc cgacggattt cgactgcaag gcaacgatca aggccgcccg cgcccgcgat   1800
ctgccgatct tcggcgtttg cctcggtctg caggcattgg cagaagccta tggcggcgag   1860
```

-continued

| | |
|---|---|
| ctgcgccagc ttgctgtgcc catgcacggc aagccttcgc gcatccgcgt gctggaaccc | 1920 |
| ggcctcgtct tctccggtct cggcaaggaa gtcacggtcg gtcgttacca ttcgatcttc | 1980 |
| gccgatcccg ccaccctgcc gcgtgatttc atcatcaccg cagaaagcga ggacggcacg | 2040 |
| atcatgggca tcgaacacgc caaggaaccg gtggccgccg ttcagttcca cccggaatcg | 2100 |
| atcatgacgc tcggacagga cgcgggcatg cggatgatcg agaatgtcgt ggtgcatctg | 2160 |
| acccgcaagg cgaagaccaa ggccgcgtga | 2190 |

<210> SEQ ID NO 93
<211> LENGTH: 2190
<212> TYPE: DNA
<213> ORGANISM: Artificial Sequence
<220> FEATURE:
<223> OTHER INFORMATION: An A. tumefaciens mutant.

<400> SEQUENCE: 93

| | |
|---|---|
| atggtaacga tcattcagga tgacggagcg gagacctacg agacgaaagg cggcatccag | 60 |
| gtcagccgaa agcgccggcc caccgattat gccaacgcca tcgataatta catcgaaaag | 120 |
| cttgattccc atcgcggcgc ggttttttcg tccaactatg aatatccggg ccgttacacc | 180 |
| cgctgggata cggccatcgt cgatccgccg ctcggcattt cctgttttgg ccgcaagatg | 240 |
| tggatcgaag cctataatgg ccgcggcgaa gtgctgctcg atttcattac ggaaaagctg | 300 |
| aaggcgacac ccgatctcac cctcggcgct tcctcgaccc gccggctcga tcttaccgtc | 360 |
| aacgaaccgg accgtgtctt caccgaagaa gaacgctcga aaatcccgac ggtcttcacc | 420 |
| gctctcagag ccatcgtcga cctcttctat tcgagcgcgg attcggccat cggcctgttc | 480 |
| ggtgccttcg gttacgatct cgccttccag ttcgacgcga tcaagctttc gctggcgcgt | 540 |
| ccggaagacc agcgtgacat ggtgctgttt ctgcccgatg aaatcctcgt cgttgatcac | 600 |
| tattccgcca aggcctggat cgaccgttac gatttcgaga aggacggcat gacgacggac | 660 |
| ggcaaatcct ccgacattac ccccgatccc ttcaagacca ccgataccat cccgcccaag | 720 |
| ggcgatcacc gtcccggcga atattccgag cttgtggtga aggccaagga aagcttccgc | 780 |
| cgcggcgacc tgttcgaggt cgttcccggc cagaaattca tggagcgttg cgaaagcaat | 840 |
| ccgtcggcga tttcccgccg cctgaaggcg atcaacccgt cgccctattc cgccttcatc | 900 |
| aatctcggcg atcaggaata tctggtcggc gcctcgccgg aaatgttcgt gcgcgtctcc | 960 |
| ggccgtcgca tcgagacctg cccgatatca ggcaccatca agcgcggcga cgatccgatt | 1020 |
| gccgacagcg agcagatttt gaaactgctc aactcgaaaa aggacgaatc cgaactgacc | 1080 |
| atgtgctcgg acgtggaccg caacgacaag agccgcgtct gcgagccggg ttcggtgaag | 1140 |
| gtcattggcc gccgccagat cgagatgtat tcacgcctca tccacaccgt cgatcacatc | 1200 |
| gaaggccgcc tgcgcgacga tatggacgcc tttgacggtt tcctcagcca cgcctgggcc | 1260 |
| gtcaccgtca ccggtgcacc aaagctgtgg gccatgcgct tcatcgaagg tcatgaaaag | 1320 |
| agcccgcgcg cctggtatgg cggtgcgatc ggcatggtcg gcttcaacgg cgacatgaat | 1380 |
| accgcctga cgctgcgcac catccggatc aaggacggta ttgccgaagt gcgcgccggc | 1440 |
| gcgaccctgc tcaatgattc caacccgcag gaagaagaag ccgaaaccga actgaaggcc | 1500 |
| tccgccatga tatcagccat tcgtgacgca aaaggcacca actctgccgc caccaagcgt | 1560 |
| gatgccgcca agtcggcac cggcgtcaag atcctgctcg tcgaccacga agacagcttc | 1620 |
| gtgcacacgc tggcgaatta tttccgccag acgggcgcga cggtctcgac cgtcagatca | 1680 |
| ccggtcgcag ccgacgtgtt cgatcgcttc cagccggacc tcgttgtcct gtcgcccgga | 1740 |

```
cccggcagcc cgacggattt cgactgcaag gcaacgatca aggccgcccg cgcccgcgat   1800
ctgccgatct tcggcgtttg cctcggtctg caggcattgg cagaagccta tggcggcgag   1860
ctgcgccagc ttgctgtgcc catgcacggc aagccttcgc gcatccgcgt gctggaaccc   1920
ggcctcgtct tctccggtct cggcaaggaa gtcacggtcg gtcgttacca ttcgatcttc   1980
gccgatcccg ccaccctgcc gcgtgatttc atcatcaccg cagaaagcga ggacggcacg   2040
atcatgggca tcgaacacgc caaggaaccg gtggccgccg ttcagttcca cccggaatcg   2100
atcatgacgc tcggacagga cgcgggcatg cggatgatcg agaatgtcgt ggtgcatctg   2160
acccgcaagg cgaagaccaa ggccgcgtga                                    2190

<210> SEQ ID NO 94
<211> LENGTH: 1821
<212> TYPE: DNA
<213> ORGANISM: Oryza sativa

<400> SEQUENCE: 94
atggagtcca tcgccgccgc cacgttcacg ccctcgcgcc tcgccgcccg ccccgccact     60
ccggcggcgg cggcggcccc ggttagagcg agggcggcgg tagcggcagg agggaggagg    120
aggacgagta ggcgcggcgg cgtgaggtgc tccgcgggga agccagaggc aagcgcggtg    180
atcaacggga gcgcggcggc gcgggcggcg gaggaggaca ggaggcgctt cttcgaggcg    240
gcggagcgtg ggagcgggaa gggcaacctg tgcccatgt gggagtgcat cgtctccgac    300
cacctcaccc ccgtgctcgc ctaccgctgc ctcgtcccg aggacaacat ggagacgccc    360
agcttcctct tcgagtccgt cgagcagggg cccgagggca ccaccaacgt cggtcgctat    420
agcatggtgg gagcccaccc agtgatggag gtcgtggcaa aggagcacaa ggtcacaatc    480
atggaccacg agaagggcaa ggtgacggag caggtcgtgg atgatcctat gcagatcccc    540
aggagcatga tggaaggatg gcaccgcag cagatcgatc agctccccga ttccttcacc    600
ggtggatggg tcgggttctt tcctatgat acagtccgtt atgttgaaaa gaagaagctg    660
cccttctccg gtgctcccca ggacgatagg aaccttcctg atgttcacct gggctttat    720 gatgatgttc tcgtcttcga caatgtcgag aagaaagtat atgtcatcca ttgggtaaat    780
cttgatcggc atgcaaccac cgaggatgca ttccaagatg gcaagtcccg gctgaacctg    840
ttgctatcta aagtgcacaa ttcaaatgta cccaagcttt ctccaggatt tgtaaagtta    900
cacactcggc agtttggtac accttttgaac aaatcaacca tgacaagtga tgagtacaag    960
aatgctgtta tgcaggctaa ggagcatatt atggctggtg atattttcca gattgtttta   1020
agccagaggt ttgagaggca gacatacgcc aatccatttg aagtctatcg agctttacga   1080
attgtgaacc caagtccata catggcatat gtacaggcaa gaggctgtgt cctggtagca   1140
tctagtccag aaattcttac tcgtgtgagg aagggtaaaa ttattaaccg tccacttgct   1200
gggactgttc gaaggggcaa gacagagaag gaagatgaaa tgcaagagca caactacta   1260 agtgatgaaa acagtgtgc tgaacatatt atgcttgtag atttgggaag gaatgatgtt   1320
ggaaaggtct ccaaacctgg atctgtgaag gtggagaaat taatgaacat tgaacgctac   1380
tcccatgtca tgcacatcag ttccacggtg agtggagagt tggatgatca tctccaaagt   1440
tgggatgccc tgcgagccgc gttgcctgtt ggaacagtta gtggagcacc aaaggtgaaa   1500
gccatggagc tgatagacga gctagaggtc acaagacgag gaccatacag tggcggcctt   1560
ggagggatat catttgacgg ggacatgctt atcgctcttg cactccgcac cattgtgttc   1620
```

| | |
|---|---|
| tcaacagcgc caagccacaa cacgatgtac tcatacaaag acaccgagag gcgccgggag | 1680 |
| tgggtcgctc accttcaggc tggtgctggc attgtcgctg atagcagccc agacgacgag | 1740 |
| caacgtgaat gcgagaacaa ggcagccgct ctggctcgag ccatcgatct tgctgaatca | 1800 |
| gctttcgtag acaaggaata g | 1821 |

<210> SEQ ID NO 95
<211> LENGTH: 1498
<212> TYPE: DNA
<213> ORGANISM: Oryza sativa

<400> SEQUENCE: 95

| | |
|---|---|
| gaattcaaat tttttatata gagtatttct atacatgaat ttttctaact ttttgttttt | 60 |
| taaaaaaaat ttgtgtggtg tactgtaata ggaagagaag aaggggagga ggaaggaggg | 120 |
| agaagaggga ggagtatatg gggagggggg gatgaactga tcgcccagcg tgatagctgg | 180 |
| cgatcgagca cccattagaa gggcccaata aaccctggat aattgtcatt gagtggcacc | 240 |
| tttcattgag aagacgttat taggaattgt agaagtggat aattatgcta tctgttgtat | 300 |
| tgagtgtcac tgtcaccgat aaagctttgc tggttaatgc attgtatttc tccatcaacg | 360 |
| cttcatgata caatggtatt tggacgtgtt tataaaataa tatacgtata atgtgggtgg | 420 |
| cctagcggcg gccggttaca catagcagcg atcggtccga tgctagtctt cattcattca | 480 |
| ggtatgtatt caggtatcag tgtgtgggtg atagtttttt tttttcgttt ttctagttac | 540 |
| gatatctcat atctcatagt tgtgatctta taaacttttt catgtttatc aatataaatt | 600 |
| tcgtgttatc tagtcgttaa aagaaccgta taatgtggca aaaaaaatgt ataatgtgtc | 660 |
| agagtttgca cgtgtttatc ttgctgcccc gaaacgatta attcagtgat ttggcaacaa | 720 |
| caaaatgtcg tggcggataa gcatatccgt cccaaaagga aaaaagaaa aggaaaaata | 780 |
| atctttagaa ataaagccct tactttttcc aagaagcaga ggtaaccgta gctggtattc | 840 |
| cgcggctaac tcaatcccctt tctctggagt cttggagcgg cacggcggct gcgcacccga | 900 |
| cctcgcccac cacctgctcg gcgaaacgcc cggctcggcc gcgacgtgtc ccaccgcacc | 960 |
| gcgcgcgcac ccgcgcgccc cgagcccctc gccgcctccg cgcgggcgcc gcacctattt | 1020 |
| aaatgcggcc ccgatcccgc attctctcaa ctgcactagt ccccaccaac ggctcggtcc | 1080 |
| agtagagttt atcccccacc tatggccagc ctcgtgctct ccctgcgcat cgcccgttcc | 1140 |
| acgccgccgc tggggctggg cgggggggcga ttccgcggcc gacgaggggc cgtcgcctgc | 1200 |
| cgcgccgcca cgttccagca gctcgacgcc gtcggtgagt ctccgtatca aatgtggggg | 1260 |
| ggcatgtctt ggtttgcgga ttggtgggtt gatttgaatg tgtgttctcg tggccgcagc | 1320 |
| ggtgagggag gaggagtcca agttcaaggc ggggcggcg gagggttgca acatcctgcc | 1380 |
| gctcaagcga tgcatcttct ccgaccacct cacgccggtg ctcgcgtacc gctgcctcgt | 1440 |
| cagggaggac gaccgcgagg cgcccagctt cctgtttgag tccgtcgagc agggatcc | 1498 |

<210> SEQ ID NO 96
<211> LENGTH: 2073
<212> TYPE: DNA
<213> ORGANISM: Zea mays

<400> SEQUENCE: 96

| | |
|---|---|
| gaattccgcc aaatcgggct atagatcaaa cgctgcactg tagggagcgt gaagccagcg | 60 |
| gcgaatggaa tccctagccg ccacctccgt gttcgcgccc tccgcgtcg ccgtcccggc | 120 |
| ggcgcgggcc ctggttaggg cggggacggt ggtaccaacc aggcggacga gcagccggag | 180 |

-continued

```
cggaaccagc ggggtgaaat gctctgctgc cgtgacgccg caggcgagcc cagtgattag      240
caggagcgct gcggcggcga aggcggcgga ggaggacaag aggcggttct tcgaggcggc      300
ggcgcggggg agcgggaagg ggaacctggt gcccatgtgg gagtgcatca agggaacct       360 ggtgcccatg tgggagtgca tcgtgtcgga ccatctcacc cccgtgctcg cctaccgctg      420
cctcgtcccc gaggacaacg tcgacgcccc cagcttcctc ttcgagtccg tcgagcaggg      480
gccccagggc accaccaacg tcggccgcta tagcatggtg ggagcccacc cagtgatgga      540
gattgtggcc aaagaccaca aggttacgat catggaccac gagaagagcc aagtgacaga      600
gcaggtagtg gacgacccga tgcagatccc gaggaccatg atggagggat ggcacccaca      660
gcagatcgac gagctccctg aatccttctc cggtggatgg gttgggttct tttcctatga      720
tacggttagg tatgttgaga agaagaagct accgttctcc agtgctcctc aggacgatag      780
gaaccttcct gatgtgcact tgggactcta tgatgatgtt ctagtcttcg ataatgttga      840
gaagaaagta tatgttatcc attgggtcaa tgtggaccgg catgcatctg ttgaggaagc      900
ataccaagat ggcaggtccc gactaaacat gttgctatct aaagtgcaca attccaatgt      960 cccccacactc tctcctggat tgtgaagct gcacacacgc aagtttggta cacctttgaa     1020
caagtcgacc atgacaagtg atgagtataa gaatgctgtt ctgcaggcta aggaacatat     1080
tatggctggg gatatcttcc agattgtttt aagccagagg ttcgagagac gaacatatgc     1140
caacccattt gaggtttatc gagcattacg gattgtgaat cctagcccat acatggcgta     1200
tgtacaggca agaggctgtg tattggttgc gtctagtcct gaaattctta cacgagtcag     1260
taaggggaag attattaatc gaccacttgc tggaactgtt cgaaggggca agacagagaa     1320
ggaagatcaa atgcaagagc agcaactgtt aagtgatgaa aaacagtgtg ccgagcacat     1380
aatgcttgtg gacttgggaa ggaatgatgt tggcaaggta tccaaaccag gaggatcagt     1440
gaaggtggag aagttgatta ttgagagata ctcccatgtt atgcacataa gctcaacggt     1500
tagtggacag ttggatgatc atctccagag ttgggatgcc ttgagagctg ccttgcccgt     1560
tggaacagtc agtggtgcac caaaggtgaa ggccatggag ttgattgata gttggaagt     1620 tacgaggcga ggaccatata gtggtggtct aggaggaata tcgtttgatg gtgacatgca     1680
aattgcactt tctctccgca ccatcgtatt ctcaacagcg ccgagccaca acacgatgta     1740
ctcatacaaa gacgcagata ggcgtcggga gtgggtcgct catcttcagg ctggtgcagg     1800
cattgttgcc gacagtagcc cagatgacga acaacgtgaa tgcgagaata aggctgctgc     1860
actagctcgg gccatcgatc ttgcagagtc agcttttgtg aacaaagaat agtgtgctat     1920
ggttatcgtt tagttcttgt tcatgtttct tttaccccact ttccgttaaa aaagatgtc     1980 attagtgggt ggagaaaagc aataagactg ttctctagag aaccgaagaa atatggaaat     2040
tgaggttatg gccggaattc ctgcagcccg ggg                                  2073
```

<210> SEQ ID NO 97
<211> LENGTH: 504
<212> TYPE: DNA
<213> ORGANISM: Triticum aestivum

<400> SEQUENCE: 97

```
cccaaacagt ggtggcttag gagggatatc atttgatggt gacatgctta tcgctcttgc       60
tctccgcacc attgtgtttt caacagctcc aagccccaat aggatgtact catacaaaag      120
ctcagatagg ccccgagagt gggttgctca tcttcaggct ggtgcgggca ttgttgctga      180
```

| | |
|---|---|
| tagtatccca gacgatgagc aaaaagaatt tgagaataag gcggctgccc tagctcgggc | 240 |
| aattgatctt gcagagtcgg cttttttaga caaagaatag agtgtctatt aaattatttt | 300 |
| ttttagttgt tcatcatttt tcacccagtt cattttggaa agttgttcat cgttttttca | 360 |
| ccgagttcat attggggaaa aaaagcaata ccgttttgtt gtcctttgaa atgaataaat | 420 |
| ttgagctata ataagatgta ttttgctcat cgggcaaaaa aaaaaaaaaa aatataaaaa | 480 |
| aaaaaaaaaa aaaaaaaaaa aata | 504 |

<210> SEQ ID NO 98
<211> LENGTH: 2161
<212> TYPE: DNA
<213> ORGANISM: Nicotiana tabacum

<400> SEQUENCE: 98

| | |
|---|---|
| gtcaaaaatc cccatttcac cgtttcctcg tttctcctcc tcactaattt tgtctctttc | 60 |
| tcttggtttg ctattgtgct cttgtaggaa tgcagtcgtt acctatctca taccggttgt | 120 |
| ttccggccac ccaccggaaa gttctgccat cgccgtcat ttctagccgg agctcaactt | 180 |
| ctgcacttgc gcttcgtgtc cgtacactac aatgccgctg ccttcactct tcatctctag | 240 |
| ttatggatga ggacaggttc attgaagctt ctaaaagcgg gaacttgatt ccgctgcaca | 300 |
| aaaccatttt ttctgatcat ctgactccgg tgctggctta ccgtgtttg gtgaaagaag | 360 |
| acgaccgtga agctccaagc tttctctttg aatccgttga acctggtttt cgaggttcta | 420 |
| gtgttggtcg ctacagcgtg gtgggggctc aaccatctat ggaaattgtg gctaaggaac | 480 |
| acaatgtgac tatattggac caccacactg gaaaattgac ccagaagact gtccaagatc | 540 |
| ccatgacgat tccgaggagt atttctgagg atggaagcc cagactcatt gatgaacttc | 600 |
| ctgatacctt ttgtggtgga tgggttggtt atttctcata tgacacagtt cggtatgtag | 660 |
| agaacaggaa gttgccattc ctaagggctc cagaggatga ccggaacctt gcagatattc | 720 |
| aattaggact atacgaagat gtcattgtgt ttgatcatgt tgagaagaaa gcacatgtga | 780 |
| ttcactgggt gcagttggat cagtattcat ctcttcctga ggcatatctt gatgggaaga | 840 |
| aacgcttgga aatattagtg tctagagtac aaggaattga gtctccaagg ttatctcccg | 900 |
| gttctgtgga tttctgtact catgcttttg gaccttcatt aaccaaggga acatgacaa | 960 |
| gtgaggagta caagaatgct gtcttacaag caaaggagca cattgctgca ggagacatat | 1020 |
| ttcaaatcgt tttaagtcaa cgctttgaga gaagaacatt tgctgaccca tttgaagtgt | 1080 |
| acagagcatt aagaattgtg aatccaagcc catatatgac ttacatacaa gccagaggct | 1140 |
| gtatttagt tgcatcgagc ccagaaattt tgacacgtgt gaagaagaga gaattgtta | 1200 |
| atcgaccact ggctgggaca agcagaagag ggaagacacc tgatgaggat gtgatgttgg | 1260 |
| aaatgcagat gttaaaagat gagaaacaac gcgcagagca catcatgctg gttgatttag | 1320 |
| gacgaaatga tgtaggaaag gtgtcaaaac ctggttctgt gaatgtcgaa aagctcatga | 1380 |
| gcgttgagcg gtattcccat gtgatgcaca taagctccac ggtctctgga gagttgcttg | 1440 |
| atcatttaac ctgttgggat gcactacgtg ctgcattgcc tgttgggacc gtcagtggag | 1500 |
| caccaaaggt aaaggccatg gagttgattg atcagctaga agtagctcgg agagggcctt | 1560 |
| acagtggtgg gtttggaggc atttcctttt caggtgacat ggacatcgca ctagctctaa | 1620 |
| ggacgatggt attcctcaat ggagctcgtt atgacacaat gtattcatat acagatgcca | 1680 |
| gcaagcgtca ggaatgggtt gctcatctcc aatccgggc tggaattgtg gctgatagta | 1740 |
| atcctgatga ggaacagata gaatgcgaga ataaagtagc cggtctgtgc cgagccattg | 1800 |

-continued

```
acttggccga gtcagctttt gtaaagggaa gacacaaacc gtcagtcaag ataaatggtt    1860
ctgtgccaaa tctattttca agggtacaac gtcaaacatc tgttatgtcg aaggacagag    1920
tacatgagaa aagaaactag cgaatatgaa gatgtacata aattctaaag tggttttctt    1980
gttcagttta atcttttact ggattgagac tgtagttgct gaagatagtt gtttagaatg    2040
accttcattt tggtgttcct gaaaggacag tgcacatata tagcaaattg atcaaatgtt    2100
taatccttgt atgcgggtga gaatcaatgc catcagcaat ttggaaaaaa aaaaaaaaa     2160 a                                                                    2161
```

<210> SEQ ID NO 99
<211> LENGTH: 606
<212> TYPE: PRT
<213> ORGANISM: Oryza sativa

<400> SEQUENCE: 99

```
Met Glu Ser Ile Ala Ala Ala Thr Phe Thr Pro Ser Arg Leu Ala Ala
  1               5                  10                  15

Arg Pro Ala Thr Pro Ala Ala Ala Ala Pro Val Arg Ala Arg Ala
             20                  25                  30

Ala Val Ala Ala Gly Gly Arg Arg Thr Ser Arg Arg Gly Gly Val
         35                  40                  45

Arg Cys Ser Ala Gly Lys Pro Glu Ala Ser Ala Val Ile Asn Gly Ser
     50                  55                  60

Ala Ala Ala Arg Ala Ala Glu Glu Asp Arg Arg Arg Phe Phe Glu Ala
 65                  70                  75                  80

Ala Glu Arg Gly Ser Gly Lys Gly Asn Leu Val Pro Met Trp Glu Cys
                 85                  90                  95

Ile Val Ser Asp His Leu Thr Pro Val Leu Ala Tyr Arg Cys Leu Val
            100                 105                 110

Pro Glu Asp Asn Met Glu Thr Pro Ser Phe Leu Phe Glu Ser Val Glu
        115                 120                 125

Gln Gly Pro Glu Gly Thr Thr Asn Val Gly Arg Tyr Ser Met Val Gly
    130                 135                 140

Ala His Pro Val Met Glu Val Val Ala Lys Glu His Lys Val Thr Ile
145                 150                 155                 160

Met Asp His Glu Lys Gly Lys Val Thr Glu Gln Val Val Asp Asp Pro
                165                 170                 175

Met Gln Ile Pro Arg Ser Met Met Glu Gly Trp His Pro Gln Gln Ile
            180                 185                 190

Asp Gln Leu Pro Asp Ser Phe Thr Gly Gly Trp Val Gly Phe Phe Ser
        195                 200                 205

Tyr Asp Thr Val Arg Tyr Val Glu Lys Lys Leu Pro Phe Ser Gly
    210                 215                 220

Ala Pro Gln Asp Asp Arg Asn Leu Pro Asp Val His Leu Gly Leu Tyr
225                 230                 235                 240

Asp Asp Val Leu Val Phe Asp Asn Val Glu Lys Lys Val Tyr Val Ile
                245                 250                 255

His Trp Val Asn Leu Asp Arg His Ala Thr Thr Glu Asp Ala Phe Gln
            260                 265                 270

Asp Gly Lys Ser Arg Leu Asn Leu Leu Ser Lys Val His Asn Ser
        275                 280                 285

Asn Val Pro Lys Leu Ser Pro Gly Phe Val Lys Leu His Thr Arg Gln
    290                 295                 300
```

-continued

```
Phe Gly Thr Pro Leu Asn Lys Ser Thr Met Thr Ser Asp Glu Tyr Lys
305                 310                 315                 320

Asn Ala Val Met Gln Ala Lys Glu His Ile Met Ala Gly Asp Ile Phe
                325                 330                 335

Gln Ile Val Leu Ser Gln Arg Phe Glu Arg Gln Thr Tyr Ala Asn Pro
            340                 345                 350

Phe Glu Val Tyr Arg Ala Leu Arg Ile Val Asn Pro Ser Pro Tyr Met
        355                 360                 365

Ala Tyr Val Gln Ala Arg Gly Cys Val Leu Val Ala Ser Ser Pro Glu
    370                 375                 380

Ile Leu Thr Arg Val Arg Lys Gly Lys Ile Ile Asn Arg Pro Leu Ala
385                 390                 395                 400

Gly Thr Val Arg Arg Gly Lys Thr Glu Lys Glu Asp Glu Met Gln Glu
                405                 410                 415

Gln Gln Leu Leu Ser Asp Glu Lys Gln Cys Ala Glu His Ile Met Leu
            420                 425                 430

Val Asp Leu Gly Arg Asn Asp Val Gly Lys Val Ser Lys Pro Gly Ser
        435                 440                 445

Val Lys Val Glu Lys Leu Met Asn Ile Glu Arg Tyr Ser His Val Met
    450                 455                 460

His Ile Ser Ser Thr Val Ser Gly Glu Leu Asp Asp His Leu Gln Ser
465                 470                 475                 480

Trp Asp Ala Leu Arg Ala Ala Leu Pro Val Gly Thr Val Ser Gly Ala
                485                 490                 495

Pro Lys Val Lys Ala Met Glu Leu Ile Asp Glu Leu Glu Val Thr Arg
            500                 505                 510

Arg Gly Pro Tyr Ser Gly Gly Leu Gly Gly Ile Ser Phe Asp Gly Asp
        515                 520                 525

Met Leu Ile Ala Leu Ala Leu Arg Thr Ile Val Phe Ser Thr Ala Pro
    530                 535                 540

Ser His Asn Thr Met Tyr Ser Tyr Lys Asp Thr Glu Arg Arg Arg Glu
545                 550                 555                 560

Trp Val Ala His Leu Gln Ala Gly Ile Val Ala Asp Ser Ser
                565                 570                 575

Pro Asp Asp Glu Gln Arg Glu Cys Glu Asn Lys Ala Ala Leu Ala
            580                 585                 590

Arg Ala Ile Asp Leu Ala Glu Ser Ala Phe Val Asp Lys Glu
        595                 600                 605

<210> SEQ ID NO 100
<211> LENGTH: 67
<212> TYPE: PRT
<213> ORGANISM: Oryza sativa

<400> SEQUENCE: 100

Met Cys Val Leu Val Ala Ala Ala Val Arg Glu Glu Glu Ser Lys Phe
1               5                   10                  15

Lys Ala Gly Ala Ala Glu Gly Cys Asn Ile Leu Pro Leu Lys Arg Cys
            20                  25                  30

Ile Phe Ser Asp His Leu Thr Pro Val Leu Ala Tyr Arg Cys Leu Val
        35                  40                  45

Arg Glu Asp Asp Arg Glu Ala Pro Ser Phe Leu Phe Glu Ser Val Glu
    50                  55                  60

Gln Gly Ser
```

<210> SEQ ID NO 101
<211> LENGTH: 525
<212> TYPE: PRT
<213> ORGANISM: Zea mays

<400> SEQUENCE: 101

Met Trp Glu Cys Ile Lys Gly Asn Leu Val Pro Met Trp Glu Cys Ile
1               5                   10                  15

Val Ser Asp His Leu Thr Pro Val Leu Ala Tyr Arg Cys Leu Val Pro
            20                  25                  30

Glu Asp Asn Val Asp Ala Pro Ser Phe Leu Phe Glu Ser Val Glu Gln
        35                  40                  45

Gly Pro Gln Gly Thr Thr Asn Val Gly Arg Tyr Ser Met Val Gly Ala
    50                  55                  60

His Pro Val Met Glu Ile Val Ala Lys Asp His Lys Val Thr Ile Met
65                  70                  75                  80

Asp His Glu Lys Ser Gln Val Thr Glu Gln Val Val Asp Asp Pro Met
                85                  90                  95

Gln Ile Pro Arg Thr Met Met Glu Gly Trp His Pro Gln Gln Ile Asp
            100                 105                 110

Glu Leu Pro Glu Ser Phe Ser Gly Gly Trp Val Gly Phe Phe Ser Tyr
        115                 120                 125

Asp Thr Val Arg Tyr Val Glu Lys Lys Lys Leu Pro Phe Ser Ser Ala
    130                 135                 140

Pro Gln Asp Asp Arg Asn Leu Pro Asp Val His Leu Gly Leu Tyr Asp
145                 150                 155                 160

Asp Val Leu Val Phe Asp Asn Val Glu Lys Lys Val Tyr Val Ile His
                165                 170                 175

Trp Val Asn Val Asp Arg His Ala Ser Val Glu Glu Ala Tyr Gln Asp
            180                 185                 190

Gly Arg Ser Arg Leu Asn Met Leu Leu Ser Lys Val His Asn Ser Asn
        195                 200                 205

Val Pro Thr Leu Ser Pro Gly Phe Val Lys Leu His Thr Arg Lys Phe
    210                 215                 220

Gly Thr Pro Leu Asn Lys Ser Thr Met Thr Ser Asp Glu Tyr Lys Asn
225                 230                 235                 240

Ala Val Leu Gln Ala Lys Glu His Ile Met Ala Gly Asp Ile Phe Gln
                245                 250                 255

Ile Val Leu Ser Gln Arg Phe Glu Arg Arg Thr Tyr Ala Asn Pro Phe
            260                 265                 270

Glu Val Tyr Arg Ala Leu Arg Ile Val Asn Pro Ser Pro Tyr Met Ala
        275                 280                 285

Tyr Val Gln Ala Arg Gly Cys Val Leu Val Ala Ser Pro Glu Ile
    290                 295                 300

Leu Thr Arg Val Ser Lys Gly Lys Ile Ile Asn Arg Pro Leu Ala Gly
305                 310                 315                 320

Thr Val Arg Arg Gly Lys Thr Glu Lys Glu Asp Gln Met Gln Glu Gln
                325                 330                 335

Gln Leu Leu Ser Asp Glu Lys Gln Cys Ala Glu His Ile Met Leu Val
            340                 345                 350

Asp Leu Gly Arg Asn Asp Val Gly Lys Val Ser Lys Pro Gly Gly Ser
        355                 360                 365

```
Val Lys Val Glu Lys Leu Ile Ile Glu Arg Tyr Ser His Val Met His
    370                 375                 380

Ile Ser Ser Thr Val Ser Gly Gln Leu Asp Asp His Leu Gln Ser Trp
385                 390                 395                 400

Asp Ala Leu Arg Ala Ala Leu Pro Val Gly Thr Val Ser Gly Ala Pro
                405                 410                 415

Lys Val Lys Ala Met Glu Leu Ile Asp Lys Leu Glu Val Thr Arg Arg
                420                 425                 430

Gly Pro Tyr Ser Gly Gly Leu Gly Gly Ile Ser Phe Asp Gly Asp Met
                435                 440                 445

Gln Ile Ala Leu Ser Leu Arg Thr Ile Val Phe Ser Thr Ala Pro Ser
    450                 455                 460

His Asn Thr Met Tyr Ser Tyr Lys Asp Ala Asp Arg Arg Arg Glu Trp
465                 470                 475                 480

Val Ala His Leu Gln Ala Gly Ala Gly Ile Val Ala Asp Ser Ser Pro
                485                 490                 495

Asp Asp Glu Gln Arg Glu Cys Glu Asn Lys Ala Ala Ala Leu Ala Arg
                500                 505                 510

Ala Ile Asp Leu Ala Glu Ser Ala Phe Val Asn Lys Glu
                515                 520                 525

<210> SEQ ID NO 102
<211> LENGTH: 92
<212> TYPE: PRT
<213> ORGANISM: Triticum aestivum

<400> SEQUENCE: 102

Pro Asn Ser Gly Gly Leu Gly Gly Ile Ser Phe Asp Gly Asp Met Leu
1               5                   10                  15

Ile Ala Leu Ala Leu Arg Thr Ile Val Phe Ser Thr Ala Pro Ser Pro
                20                  25                  30

Asn Arg Met Tyr Ser Tyr Lys Ser Ser Asp Arg Pro Arg Glu Trp Val
                35                  40                  45

Ala His Leu Gln Ala Gly Ala Gly Ile Val Ala Asp Ser Ile Pro Asp
            50                  55                  60

Asp Glu Gln Lys Glu Phe Glu Asn Lys Ala Ala Ala Leu Ala Arg Ala
65              70                  75                  80

Ile Asp Leu Ala Glu Ser Ala Phe Leu Asp Lys Glu
                85                  90

<210> SEQ ID NO 103
<211> LENGTH: 616
<212> TYPE: PRT
<213> ORGANISM: Nicotiana tabacum

<400> SEQUENCE: 103

Met Gln Ser Leu Pro Ile Ser Tyr Arg Leu Phe Pro Ala Thr His Arg
1               5                   10                  15

Lys Val Leu Pro Phe Ala Val Ile Ser Ser Arg Ser Thr Ser Ala
                20                  25                  30

Leu Ala Leu Arg Val Arg Thr Leu Gln Cys Arg Cys Leu His Ser Ser
            35                  40                  45

Ser Leu Val Met Asp Glu Asp Arg Phe Ile Glu Ala Ser Lys Ser Gly
        50                  55                  60

Asn Leu Ile Pro Leu His Lys Thr Ile Phe Ser Asp His Leu Thr Pro
65              70                  75                  80
```

```
Val Leu Ala Tyr Arg Cys Leu Val Lys Glu Asp Asp Arg Glu Ala Pro
                85                  90                  95

Ser Phe Leu Phe Glu Ser Val Glu Pro Gly Phe Arg Gly Ser Ser Val
            100                 105                 110

Gly Arg Tyr Ser Val Val Gly Ala Gln Pro Ser Met Glu Ile Val Ala
        115                 120                 125

Lys Glu His Asn Val Thr Ile Leu Asp His His Thr Gly Lys Leu Thr
    130                 135                 140

Gln Lys Thr Val Gln Asp Pro Met Thr Ile Pro Arg Ser Ile Ser Glu
145                 150                 155                 160

Gly Trp Lys Pro Arg Leu Ile Asp Glu Leu Pro Asp Thr Phe Cys Gly
                165                 170                 175

Gly Trp Val Gly Tyr Phe Ser Tyr Asp Thr Val Arg Tyr Val Glu Asn
            180                 185                 190

Arg Lys Leu Pro Phe Leu Arg Ala Pro Glu Asp Asp Arg Asn Leu Ala
        195                 200                 205

Asp Ile Gln Leu Gly Leu Tyr Glu Asp Val Ile Val Phe Asp His Val
    210                 215                 220

Glu Lys Lys Ala His Val Ile His Trp Val Gln Leu Asp Gln Tyr Ser
225                 230                 235                 240

Ser Leu Pro Glu Ala Tyr Leu Asp Gly Lys Lys Arg Leu Glu Ile Leu
                245                 250                 255

Val Ser Arg Val Gln Gly Ile Glu Ser Pro Arg Leu Ser Pro Gly Ser
            260                 265                 270

Val Asp Phe Cys Thr His Ala Phe Gly Pro Ser Leu Thr Lys Gly Asn
        275                 280                 285

Met Thr Ser Glu Glu Tyr Lys Asn Ala Val Leu Gln Ala Lys Glu His
    290                 295                 300

Ile Ala Ala Gly Asp Ile Phe Gln Ile Val Leu Ser Gln Arg Phe Glu
305                 310                 315                 320

Arg Arg Thr Phe Ala Asp Pro Phe Glu Val Tyr Arg Ala Leu Arg Ile
                325                 330                 335

Val Asn Pro Ser Pro Tyr Met Thr Tyr Ile Gln Ala Arg Gly Cys Ile
            340                 345                 350

Leu Val Ala Ser Ser Pro Glu Ile Leu Thr Arg Val Lys Lys Arg Arg
        355                 360                 365

Ile Val Asn Arg Pro Leu Ala Gly Thr Ser Arg Arg Gly Lys Thr Pro
    370                 375                 380

Asp Glu Asp Val Met Leu Glu Met Gln Met Leu Lys Asp Glu Lys Gln
385                 390                 395                 400

Arg Ala Glu His Ile Met Leu Val Asp Leu Gly Arg Asn Asp Val Gly
                405                 410                 415

Lys Val Ser Lys Pro Gly Ser Val Asn Val Glu Lys Leu Met Ser Val
            420                 425                 430

Glu Arg Tyr Ser His Val Met His Ile Ser Ser Thr Val Ser Gly Glu
        435                 440                 445

Leu Leu Asp His Leu Thr Cys Trp Asp Ala Leu Arg Ala Ala Leu Pro
    450                 455                 460

Val Gly Thr Val Ser Gly Ala Pro Lys Val Lys Ala Met Glu Leu Ile
465                 470                 475                 480

Asp Gln Leu Glu Val Ala Arg Arg Gly Pro Tyr Ser Gly Gly Phe Gly
                485                 490                 495

Gly Ile Ser Phe Ser Gly Asp Met Asp Ile Ala Leu Ala Leu Arg Thr
```

-continued

```
                500                    505                   510
Met Val Phe Leu Asn Gly Ala Arg Tyr Asp Thr Met Tyr Ser Tyr Thr
        515                     520                 525

Asp Ala Ser Lys Arg Gln Glu Trp Val Ala His Leu Gln Ser Gly Ala
    530                 535                 540

Gly Ile Val Ala Asp Ser Asn Pro Asp Glu Gln Ile Glu Cys Glu
545             550                 555                 560

Asn Lys Val Ala Gly Leu Cys Arg Ala Ile Asp Leu Ala Glu Ser Ala
                565                 570                 575

Phe Val Lys Gly Arg His Lys Pro Ser Val Lys Ile Asn Gly Ser Val
            580                 585                 590

Pro Asn Leu Phe Ser Arg Val Gln Arg Gln Thr Ser Val Met Ser Lys
        595                 600                 605

Asp Arg Val His Glu Lys Arg Asn
    610                 615
```